US008598121B2

(12) United States Patent
Wendt et al.

(10) Patent No.: US 8,598,121 B2
(45) Date of Patent: Dec. 3, 2013

(54) VARIANTS OF C-TYPE NATRIURETIC PEPTIDE

(75) Inventors: Daniel J. Wendt, Walnut Creek, CA (US); Shinong Long, Milpitas, CA (US); Sianna Castillo, San Francisco, CA (US); Christopher P. Price, Kentfield, CA (US); Mika Aoyagi-Scharber, Mill Valley, CA (US); Michel Claude Vellard, San Rafael, CA (US); Augustus O. Okhamafe, Concord, CA (US)

(73) Assignee: Biomarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 13/466,672

(22) Filed: May 8, 2012

(65) Prior Publication Data

US 2012/0316114 A1 Dec. 13, 2012

Related U.S. Application Data

(63) Continuation of application No. 12/784,117, filed on May 20, 2010, now Pat. No. 8,198,242.

(60) Provisional application No. 61/180,112, filed on May 20, 2009, provisional application No. 61/254,563, filed on Oct. 23, 2009.

(51) Int. Cl.
*A61K 38/22* (2006.01)
*A61K 38/00* (2006.01)
*A61K 38/16* (2006.01)
*C12P 21/04* (2006.01)

(52) U.S. Cl.
USPC ....... 514/12.4; 514/16.7; 514/21.3; 435/69.4; 435/69.7; 435/70.1; 530/324

(58) Field of Classification Search
None
See application file for complete search history.

(56) References Cited

U.S. PATENT DOCUMENTS

| | | | |
|---|---|---|---|
| 5,252,714 A | 10/1993 | Harris et al. | |
| 5,352,770 A | 10/1994 | Matsuo | |
| 5,434,133 A | 7/1995 | Tanaka et al. | |
| 5,824,784 A | 10/1998 | Kinstler et al. | |
| 5,846,932 A | 12/1998 | Lowe et al. | |
| 6,020,168 A | 2/2000 | Matsuo et al. | |
| 6,034,231 A | 3/2000 | Tanaka et al. | |
| 6,136,040 A | 10/2000 | Ornitz et al. | |
| 6,265,632 B1 | 7/2001 | Yayon et al. | |
| 6,329,375 B1 | 12/2001 | Tang et al. | |
| 6,344,459 B1 | 2/2002 | Bridges et al. | |
| 6,743,425 B2 | 6/2004 | Nakao | |
| 6,849,714 B1 * | 2/2005 | Bridon et al. | 530/335 |
| 6,861,236 B2 * | 3/2005 | Moll et al. | 435/69.1 |
| 7,276,481 B2 | 10/2007 | Golembo et al. | |
| 2004/0138134 A1 | 7/2004 | Golembo et al. | |
| 2007/0197434 A1 | 8/2007 | Nakao et al. | |
| 2007/0292966 A1 | 12/2007 | Prickett et al. | |
| 2008/0194682 A1 | 8/2008 | Golembo et al. | |

FOREIGN PATENT DOCUMENTS

| | | |
|---|---|---|
| EP | 0466174 A1 | 1/1992 |
| EP | 0497368 A1 | 8/1992 |
| EP | 1743653 A1 | 1/2007 |
| WO | WO-94/20534 A1 | 9/1994 |
| WO | WO-00/61631 | 10/2000 |
| WO | WO-02/074234 A2 | 9/2002 |
| WO | WO-2004/047871 | 6/2004 |
| WO | WO-2009/067639 | 5/2009 |

OTHER PUBLICATIONS

Agoston et al., C-type natriuretic peptide regulates endochondral bone growth through p38 MAP kinase-dependent and -independent pathways, *BMC Dev. Biol.*, 7:18 (2007).
Aigner et al., Apoptosis and cellular vitality: issues in osteoarthritic cartilage degeneration, *Arthritis Rheum.*, 46:1986-96 (2002).
Alfonzo et al., Characterization of a G protein-coupled guanylyl cyclase-B receptor from bovine tracheal smooth muscle, *J. Recept. Signal Transduct. Res.*, 26:269-97 (2006).
Anand-Srivastava et al., Cytoplasmic domain of natriuretic peptide receptor-C inhibits adenylyl cyclase. Involvement of a pertussis toxin-sensitive G protein, *J. Biol. Chem.*, 271:19324-9 (1996).
Bartels et al., Mutations in the transmembrane natriuretic peptide receptor NPR-B impair skeletal growth and cause acromesomelic dysplasia, type Maroteaux, *Am. J. Hum. Genet.*, 75:27-34 (2004).
Barton et al., Endothelium-independent relaxation and hyperpolarization to C-type natriuretic peptide in porcine coronary arteries, *J. Cardiovasc. Pharmacol.*, 31:377-83 (1998).
Bellus et al., Hypochondroplasia: molecular analysis of the fibroblast growth factor receptor 3 gene, *Ann. NY Acad. Sci.*, 785:182-7 (1996).
Bennett et al., Extracellular domain-IgG fusion proteins for three human natriuretic peptide receptors. Hormone pharmacology and application to solid phase screening of synthetic peptide antisera, *J. Biol. Chem.*, 266:23060-7 (1991).
Brandt et al., Neutral endopeptidase regulates C-type natriuretic peptide metabolism but does not potentiate its bioactivity in vivo, *Hypertension*, 30:184-90 (1997).
Caliceti et al., Pharmacokinetic and biodistribution properties of poly(ethylene glycol)-protein conjugates, *Adv. Drug Deliv. Rev.*, 55:1261-77 (2003).
Chauhan et al., Release of C-type natriuretic peptide accounts for the biological activity of endothelium-derived hyperpolarizing factor, *Proc. Natl. Acad. Sci. USA*, 100:1426-31 (2003).
Chen et al., C-type natriuretic peptide: the endothelial component of the natriuretic peptide system, *J. Cardiovasc. Pharmacol.*, Suppl 3:S22-8 (1998).

(Continued)

*Primary Examiner* — Shulamith H Shafer
(74) *Attorney, Agent, or Firm* — Marshall, Gerstein & Borun LLP

(57) ABSTRACT

The present disclosure provides variants of C-type natriuretic peptide (CNP), pharmaceutical compositions comprising CNP variants, and methods of making CNP variants. The CNP variants are useful as therapeutic agents for the treatment of diseases responsive to CNP, including but not limited to bone-related disorders, such as skeletal dysplasias (e.g., achondroplasia), and vascular smooth muscle disorders (e.g., restenosis and arteriosclerosis).

14 Claims, 61 Drawing Sheets

(56) References Cited

OTHER PUBLICATIONS

Chusho et al., Dwarfism and early death in mice lacking C-type natriuretic peptide, *Proc. Natl. Acad. Sci. USA*, 98:4016-21 (2001).
Coffin et al., Abnormal bone growth and selective translational regulation in basic fibroblast growth factor (FGF-2) transgenic mice, *Mol. Biol. Cell*, 6:1861-73 (1995).
Colvin et al., Skeletal overgrowth and deafness in mice lacking fibroblast growth factor receptor 3, *Nat. Genet.*, 12:390-7 (1996).
Cunningham et al., Production of an atrial natriuretic peptide variant that is specific for type A receptor, *EMBO J.*, 13:2508-15 (1994).
Davis, Biochemistry. Mimicking posttranslational modifications of proteins, *Science*, 303:480-2 (2004).
De Plater et al., The natriuretic peptide (OVCNP-39) from platypus (Ornithorhynchus anatinus) venom relaxes the isolated rat uterus and promotes oedema and mast cell histamine release, *Toxicon.*, 36:847-57 (1998).
Furuya et al., C-Type natriuretic peptide is a growth inhibitor of rat vascular smooth muscle cells, Biochem. Biophys. Res. Commun., 177:927-31 (1991).
Furuya et al., Structural requirements of C-type natriuretic peptide for elevation of cyclic GMP in cultured vascular smooth muscle cells, *Biochem. Biophys. Res. Commun.*, 183:964-9 (1992).
Gardner et al., Molecular biology of the natriuretic peptide system: implications for physiology and hypertension, *Hypertension*, 49:419-26 (2007).
Genbank Accession No. NP_002512, natriuretic peptides B preproprotein [*Homo sapiens*], dated Jul. 18, 2010.
Genbank Accession No. NP_006163, atrial natriuretic factor preproprotein [*Homo sapiens*], dated Jul. 18, 2010.
Genbank Accession No. NP_077720, C-type natriuretic peptide precursor [*Homo sapiens*], dated Jul. 18, 2010.
Hama et al., Detection of C-type natriuretic peptide in human circulation and marked increase of plasma CNP level in septic shock patients, *Biochem., Biophys. Res. Commun.*, 198:1177-82 (1994).
He et al., Allosteric activation of a spring-loaded natriuretic peptide receptor dimer by hormone, *Science*, 293:1657-62 (2001).
He et al., Structural determinants of natriuretic peptide receptor specificity and degeneracy, *J. Mol. Biol.*, 361:698-714 (2006).
Hofmann et al., Recent advances in the application of expressed protein ligation to protein engineering, *Curr. Opin. Biotechnol.*, 13:297-303 (2002).
Honing et al., C-Type natriuretic peptide—induced vasodilation is dependent on hyperpolarization in human forearm resistance vessels, *Hypertension*, 37:1179-83 (2001).
Horio et al., Gene expression, secretion, and autocrine action of C-type natriuretic peptide in cultured adult rat cardiac fibroblasts, *Endocrinology*, 144:2279-84 (2003).
Horton et al., Standard growth curves for achondroplasia, *J Pediatr.*, 93:435-8 (1978).
Hunt et al., Bioactivity and metabolism of C-type natriuretic peptide in normal man, *J. Clin. Endocrinol. Metab.*, 78:1428-35 (1994).
Igaki et al., Effects of intravenously administered C-type natriuretic peptide in humans: comparison with atrial natriuretic peptide, *Hypertens. Res.*, 21:7-13 (1998).
Inoue et al., Four functionally distinct C-type natriuretic peptides found in fish reveal evolutionary history of the natriuretic peptide system, *PNAS*, 100:10079-84 (2003).
International Preliminary Report on Patentability for corresponding International Application No. PCT/US08/84270, dated May 25, 2010.
International Preliminary Report on Patentability for corresponding International Application No. PCT/US2010/035586, mailing date Nov. 22, 2011.
International Search Report and Written Opinion for corresponding International Application No. PCT/US2008/084270, dated May 28, 2009.
International Search Report and Written Opinion for corresponding International Application No. PCT/US2010/035586, mailing date Nov. 24, 2010.
Itoh et al., C-type natriuretic peptide ameliorates monocrotaline-induced pulmonary hypertension in rats, *Am. J. Respir. Crit. Care Med.*, 170:1204-11 (2004).
Jin et al., Novel analog of atrial natriuretic peptide selective for receptor-A produces increased diuresis and natriuresis in rats, *J. Clin. Invest.*, 98:969-76 (1996).
Kenny et al., Hydrolysis of human and pig brain natriuretic peptides, urodilatin, C-type natriuretic peptide and some C-receptor ligands by endopeptidase-24.11, *Biochem. J.*, 291 (Pt 1):83-8 (1993).
Klinger et al., C-type natriuretic peptide expression and pulmonary vasodilation in hypoxia-adapted rats, *Am. J. Physiol.*, 275:L645-52 (1998).
Koller et al., Molecular biology of the natriuretic peptides and their receptors, *Circulation*, 86:1081-8 (1992).
Koller et al., Selective activation of the B natriuretic peptide receptor by C-type natriuretic peptide (CNP), *Science*, 252:120-3 (1991).
Krejci et al., Interaction of fibroblast growth factor and C-natriuretic peptide signaling in regulation of chondrocyte proliferation and extracellular matrix homeostasis, *J. Cell Sci.*, 118:5089-100 (2005).
Levin et al., Natriuretic peptides, *N. Engl. J. Med.*, 339:321-8 (1998).
Maack et al., Physiological role of silent receptors of atrial natriuretic factor, *Science*, 238:675-8 (1987).
Maack, Role of atrial natriuretic factor in volume control, *Kidney Int.*, 49:1732-7 (1996).
Matsukawa et al., The natriuretic peptide clearance receptor locally modulates the physiological effects of the natriuretic peptide system, *Proc. Natl. Acad. Sci. USA*, 96:7403-8 (1999).
Melo et al., Chronic regulation of arterial blood pressure by ANP: role of endogenous vasoactive endothelial factors, *Am. J. Physiol.*, 275:H1826-33 (1998).
Murthy et al., Gi-1/Gi-2-dependent signaling by single-transmembrane natriuretic peptide clearance receptor, *Am. J. Physiol. Gastrointest. Liver Physiol.*, 278:G974-80 (2000).
Murthy et al., Identification of the G protein-activating domain of the natriuretic peptide clearance receptor (NPR-C), *J Biol. Chem.*, 274:17587-92 (1999).
Nakao et al., Molecular biology and biochemistry of the natriuretic peptide system. I: Natriuretic peptides, *J. Hypertens.*, 10:907-12 (1992).
Nakao et al., Molecular biology and biochemistry of the natriuretic peptide system. II: Natriuretic peptide receptors, *J. Hypertens.*, 10:1111-4 (1992).
Naski et al., Repression of hedgehog signaling and BMP4 expression in growth plate cartilage by fibroblast growth factor receptor 3, *Development*, 125:4977-88 (1998).
Oefner et al., Structure of human neutral endopeptidase (Neprilysin) complexed with phosphoramidon, *J. Mol. Biol.*, 296:341-9 (2000).
Ogawa et al., Crystal structure of hormone-bound atrial natriuretic peptide receptor extracellular domain: rotation mechanism for transmembrane signal transduction, *J. Biol. Chem.*, 279:28625-31 (2004).
Ohbayashi et al., Neutral Endopeptidase 3.4.24.11 Inhibition Potentiates the Inhibitory Effects of Type-C Natriuretic Peptide on Leukotriene D4-Induced Airway Changes, *Clin. Exp. Pharm. Physiol.*, 25:986-91 (1997).
Okahara et al., Shear stress induces expression of CNP gene in human endothelial cells, *FEBS Lett.*, 373:108-10 (1995).
Olney et al., Heterozygous mutations in natriuretic peptide receptor-B (NPR2) are associated with short stature, *J. Clin. Endocrinol. Metab.*, 91:1229-32 (2006).
Olney, C-type natriuretic peptide in growth: a new paradigm, *Growth Norm. IGF Res.*, 16 Suppl A:S6-14 (2006).
Pagano et al., Cytoplasmic domain of natriuretic peptide receptor C constitutes Gi activator sequences that inhibit adenylyl cyclase activity, *J. Biol. Chem.*, 276:22064-70 (2001).
Pannier et al., Activating Fgfr3 Y367C mutation causes hearing loss and inner ear defect in a mouse model of chondrodysplasia, *Biochim. Biophys. Acta*, 1792:140-7 (2009).
Perlman et al., Glycosylation of an N-terminal extension prolongs the half-life and increases the in vivo activity of follicle stimulating hormone, *J. Clin. Endocrinol. Metab.*, 88:3227-35 (2003).

(56) References Cited

OTHER PUBLICATIONS

Pitkin et al., Charge and lipophilicity govern the pharmacokinetics of glycopeptide antibiotics, *Antimicrob. Agents Chemother.*, 29:440-4 (1986).

Qian et al., Local expression of C-type natriuretic peptide suppresses inflammation, eliminates shear stress-induced thrombosis, and prevents neointima formation through enhanced nitric oxide production in rabbit injured carotid arteries, *Circ. Res.*, 91:1063-9 (2002).

Rose et al., Natriuretic peptide C receptor signalling in the heart and vasculature, *J. Physiol.*, 586:353-66 (2008).

Rousseau et al., Missense FGFR3 mutations create cysteine residues in thanatophoric dwarfism type I (TD1), *Hum. Mol. Genet.*, 5:509-12 (1996).

Rousseau et al., Mutations in the gene encoding fibroblast growth factor receptor-3 in achondroplasia, *Nature*, 371:252-4 (1994).

Sato et al., Therapeutic peptides: technological advances driving peptides into development, *Curr. Opin. Biotechnol.*, 17:638-42 (2006).

Schiller et al., Synthesis and activity profiles of atrial natriuretic peptide (ANP) analogs with reduced ring size, *Biochem. Biophys. Res. Commun.*, 138:880-6 (1986).

Shiang et al., Mutations in the transmembrane domain of FGFR3 cause the most common genetic form of dwarfism, achondroplasia, *Cell*, 78:335-42 (1994).

Sudoh et al., C-type natriuretic peptide (CNP): a new member of natriuretic peptide family identified in porcine brain, *Biochem. Biophys. Res. Commun.*, 168:863-70 (1990).

Suga et al., Receptor selectivity of natriuretic peptide family, atrial natriuretic peptide, brain natriuretic peptide, and C-type natriuretic peptide, *Endocrinology*, 130:229-39 (1992).

Takano et al., Molecular evolution of shark C-type natriuretic peptides, *Zoological Sci.*, 11:451-4 (1994).

Tamura et al., Critical roles of the guanylyl cyclase B receptor in endochondral ossification and development of female reproductive organs, *Proc. Natl. Acad. Sci. USA*, 101:17300-5 (2004).

Tavormina et al., Thanatophoric dysplasia (types I and II) caused by distinct mutations in fibroblast growth factor receptor 3, *Nat. Genet.*, 9:321-8 (1995).

Vehaskari et al., Glomerular charge and urinary protein excretion: effects of systemic and intrarenal polycation infusion in the rat, *Kidney Int.*, 22:127-35 (1982).

Wang et al., A mouse model for achondroplasia produced by targeting fibroblast growth factor receptor 3, *Proc. Natl. Acad. Sci. USA*, 96:4455-60 (1999).

Wang et al., Bone-targeting macromolecular therapeutics, *Adv. Drug Deliv. Rev.*, 57:1049-76 (2005).

Wang et al., Cardiomyocyte-restricted over-expression of C-type natriuretic peptide prevents cardiac hypertrophy induced by myocardial infarction in mice, *Eur. J. Heart Failure*, 9:548-557 (2007).

Wei et al., Vascular actions of C-type natriuretic peptide in isolated porcine coronary arteries and coronary vascular smooth muscle cells, *Biochem. Biophys. Res. Commun.*, 205:765-71 (1994).

Werle et al., Strategies to improve plasma half life time of peptide and protein drugs, *Amino Acids*, 30:351-67 (2006).

Wilkie et al., Functions of fibroblast growth factors and their receptors, *Curr. Biol.*, 5:500-7 (1995).

Wu et al., Furin-mediated processing of Pro-C-type natriuretic peptide, *J. Biol. Chem.*, 278:25847-52 (2003).

Yamashita et al., Concentration of mRNA for the natriuretic peptide receptor-C in hypertrophic chondrocytes of the fetal mouse tibia, *J. Biochem.*, 127:177-9 (2000).

Yasoda et al., Overexpression of CNP in chondrocytes rescues achondroplasia through a MAPK-dependent pathway, *Nat. Med.*, 10:80-6 (2004).

Yeung et al., Binding of CNP-22 and CNP-53 to cultured mouse astrocytes and effects on cyclic GMP, *Peptides*, 17:101-6 (1996).

\* cited by examiner

A.

Coomassie blue stain

B.

Western blot with anti-CNP antibody

A.

Coomassie blue stain          Western blot with anti-CNP antibody

B.

Coomassie blue stain          Western blot with anti-CNP antibody

Bars from left to right:

| 1 | control (no CNP22, no FGF2) |
| 2 | CNP22 (0.2 uM) continuous |
| 3 | CNP22 (0.2 uM) 1 hr once daily |
| 4 | CNP22 (0.2 uM) 2 hr once daily |
| 5 | FGF2 (5 ng/mL) continuous |
| 6 | FGF2 + CNP22 (0.2 uM) continuous |
| 7 | FGF2 + CNP22 (0.2 uM) 1 hr daily |
| 8 | FGF2 + CNP22 (0.2 uM) 2 hr daily |

Cellularity of Proliferating Columns

No treatment

A.

B.

C.

Chondrocyte Hypertrophy

* p < 0.05

* $p < 0.05$

* $p < 0.001$

BMD

A.

BMC

B.

```
                             SEQUENCE LISTING

<160> NUMBER OF SEQ ID NOS: 237

<210> SEQ ID NO 1
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: wtCNP-22
<220> FEATURE:
<221> NAME/KEY: DISULFID
<222> LOCATION: (6)..(22)
<223> OTHER INFORMATION: Cysteines in positions 6 and 22 form cyclic
      domain via disulfide bond

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-17

<400> SEQUENCE: 2

Cys Phe Gly Leu Lys Leu Asp Arg Ile Gly Ser Met Ser Gly Leu Gly
1               5                   10                  15

Cys

<210> SEQ ID NO 3
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-27

<400> SEQUENCE: 3

Gly Ala Asn Lys Lys Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 4
<211> LENGTH: 53
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: MISC_FEATURE
<223> OTHER INFORMATION: CNP-53

<400> SEQUENCE: 4

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
        50

<210> SEQ ID NO 5
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with an amino acid
      sequence derived from a natriuretic polypeptide, a non-natriuretic
      polypeptide
<220> FEATURE:
<221> NAME/KEY: MOD_RES
<222> LOCATION: (22)..(22)
<223> OTHER INFORMATION: Cys is optionally modified with an amino acid
      sequence derived from a natriuretic polypeptide, a non-natriuretic
      polypeptide

<400> SEQUENCE: 5

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is modified with a synthetic or natural
      polymeric group or combination thereof
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid or
      peptidomimetic that does not have a reactive primary amine on a
      side chain, Arg, Gly, 6-hydroxy-norleucine, citrulline (Cit), Gln,
      Glu or Ser
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid or
      peptidomimetic that does not have a reactive primary amine on a
      side chain, Arg, Gly, 6-hydroxy-norleucine, citrulline (Cit), Gln,
      Glu or Ser
<220> FEATURE:
<221> NAME/KEY: MOD_RES
<222> LOCATION: (22)..(22)
<223> OTHER INFORMATION: Cys is optionally modified with a synthetic or
      natural polymeric group or combination thereof

<400> SEQUENCE: 6
```

```
Gly Leu Ser Xaa Gly Cys Phe Gly Leu Xaa Leu Asp Arg Ile Gly Ser
1               5                   10                  15

Met Ser Gly Leu Gly Cys
            20

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Gly Ala Asn Lys Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

Gly Ala Asn Arg Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Gly Ala Asn Pro Arg
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 10

Gly Ala Asn Gln Gln
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 11

Gly Ala Asn Ser Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 12

Gly Ala Asn Arg Gln
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 13

Gly Ala Asn Arg Met
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Gly Ala Asn Arg Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 15

Gly Ala Asn Arg Ser
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 16

Ala Ala Trp Ala Arg Leu Leu Gln Glu His Pro Asn Ala
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 17

Ala Ala Trp Ala Arg Leu Leu Gln Glu His Pro Asn Ala Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 18
```

```
Asp Leu Arg Val Asp Thr Lys Ser Arg Ala Ala Trp Ala Arg
1               5                   10
```

<210> SEQ ID NO 19
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 19

```
Gln Glu His Pro Asn Ala Arg Lys Tyr Lys Gly Ala Asn Lys Lys
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 20

```
Gln Glu His Pro Asn Ala Arg Lys Tyr Lys Gly Ala Asn Arg Arg
1               5                   10                  15
```

<210> SEQ ID NO 21
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 21

```
Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys
            20                  25                  30
```

<210> SEQ ID NO 22
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 22

```
Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Arg Arg
            20                  25                  30
```

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

```
Ser Leu Arg Arg Ser Ser
1               5
```

<210> SEQ ID NO 24
<211> LENGTH: 5
<212> TYPE: PRT
<213> ORGANISM: Artificial Sequence
<220> FEATURE:

<223> OTHER INFORMATION: Synthetic Polypeptide

<400> SEQUENCE: 24

Asn Ser Phe Arg Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 25

Ser Pro Lys Met Val Gln Gly Ser Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 26

Met Val Gln Gly Ser Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Lys Val Leu Arg Arg Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 28

Lys Val Leu Arg Arg His
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 29

Gly Gln His Lys Asp Asp Asn Pro Asn Leu Pro Arg
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 30

Gly Val Pro Gln Val Ser Thr Ser Thr
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31

Gly Glu Arg Ala Phe Lys Ala Trp Ala Val Ala Arg Leu Ser Gln
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 32

Gly Gln Pro Arg Glu Pro Gln Val Tyr Thr Leu Pro Pro Ser
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Amino acid extention

<400> SEQUENCE: 33

Gln Glu His Pro Asn Ala Arg Lys Tyr Lys Gly Ala Asn Lys Lys
1               5                   10                  15

<210> SEQ ID NO 34
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-22 with amino acid extention
<220> FEATURE:
<221> NAME/KEY: MISC_FEATURE
<222> LOCATION: (19)..(19)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Glu or Ser
<220> FEATURE:
<221> NAME/KEY: MISC_FEATURE
<222> LOCATION: (25)..(25)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Glu or Ser
<220> FEATURE:
<221> NAME/KEY: MISC_FEATURE
<222> LOCATION: (37)..(37)
<223> OTHER INFORMATION: Cys is optionally modified with a synthetic,
      natural or combination polymeric group

<400> SEQUENCE: 34

Gln Glu His Pro Asn Ala Arg Lys Tyr Lys Gly Ala Asn Lys Lys Gly
1               5                   10                  15
```

Leu Ser Xaa Gly Cys Phe Gly Leu Xaa Leu Asp Arg Ile Gly Ser Met
            20                  25                  30

Ser Gly Leu Gly Cys
        35

<210> SEQ ID NO 35
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP22 (K4R)

<400> SEQUENCE: 35

Gly Leu Ser Arg Gly Cys Phe Gly Leu Lys Leu Asp Arg Ile Gly Ser
1               5                   10                  15

Met Ser Gly Leu Gly Cys
            20

<210> SEQ ID NO 36
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANRR-CNP22(K4R) - CNP27(Arg4)

<400> SEQUENCE: 36

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANPR-CNP22(K4R) - CNP27(Pro4) - Analog CI

<400> SEQUENCE: 37

Gly Ala Asn Pro Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 38
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: ER-CNP22

<400> SEQUENCE: 38

Glu Arg Gly Leu Ser Lys Gly Cys Phe Gly Leu Lys Leu Asp Arg Ile
1               5                   10                  15

Gly Ser Met Ser Gly Leu Gly Cys

-continued

```
                  20

<210> SEQ ID NO 39
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BA - ER-CNP22(K4R)

<400> SEQUENCE: 39

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 40
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: R-CNP22

<400> SEQUENCE: 40

Arg Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 41
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AZ - R-CNP22(K4R)

<400> SEQUENCE: 41

Arg Gly Leu Ser Arg Gly Cys Phe Gly Leu Lys Leu Asp Arg Ile Gly
1               5                   10                  15

Ser Met Ser Gly Leu Gly Cys
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP22 (K4R)(K10R)

<400> SEQUENCE: 42

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 43
```

```
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP-22 (Cys6-Phe7 variable bond)
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-NH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -C(=O)-N(R)- where R is methyl, ethyl, n-propyl, isopropyl,
      cyclopropyl, n-butyl, isobutyl, sec-butyl or tert-butyl
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -C(=O)-NH-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-S-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-S(O)n where n is 1 or 2
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH2-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH=CH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -C(=O)-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH(CN)-NH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -CH(OH)-CH2-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with -O-C(=O)-NH-
<220> FEATURE:
<221> NAME/KEY: MOD_RES
<222> LOCATION: (6)..(7)
<223> OTHER INFORMATION: Cys6-Phe7 peptide bond (-C(=O)-NH-) replaced
      with NHC(=O)NH-

<400> SEQUENCE: 43

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 44
```

-continued

```
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (7)..(7)
<223> OTHER INFORMATION: Xaa is 3-amino-2-phenylpropionic acid or D-Phe

<400> SEQUENCE: 44

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 45
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CNP22 - modified Cys6
<220> FEATURE:
<221> NAME/KEY: MOD_RES
<222> LOCATION: (6)..(6)
<223> OTHER INFORMATION: Xaa is Cys, homocysteine, penicillamine,
      2-mercaptopropionic acid, or 3-mercaptopropionic acid.

<400> SEQUENCE: 45

Gly Leu Ser Lys Gly Xaa Phe Gly Leu Lys Leu Asp Arg Ile Gly Ser
1               5                   10                  15

Met Ser Gly Leu Gly Cys
            20

<210> SEQ ID NO 46
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with a bone or
      cartilage targeting compound, a biphosphonate, polyAsp, polyGlu,
      osteopontin, osteocalcin, or sialoprotein peptides, polymers, PEG,
      carbohydrates, hydrophobic acids, or amino acids
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid or
      peptidomimetic that does not have a reactive primary amine on a
      side chain, Arg, Gly, 6-hydroxy-norleucine, citrulline (Cit), Gln,
      Ser, or Glu
<220> FEATURE:
<221> NAME/KEY: MOD_RES
<222> LOCATION: (6)..(7)
<223> OTHER INFORMATION: Xaa is Cys with peptide bond isosteres between
      positions 6 and 7
<220> FEATURE:
<221> NAME/KEY: MOD_RES
<222> LOCATION: (7)..(7)
<223> OTHER INFORMATION: Xaa is L-Phe, D-Phe, 3-amino-2-phenylpropionic
      acid, or N-alkylated derivatives of Phe
<220> FEATURE:
<221> NAME/KEY: MOD_RES
<222> LOCATION: (8)..(8)
<223> OTHER INFORMATION: Xaa is Gly, tert-butyl-Gly (tBu-Gly), Thr, Ser,
      Val or Asn
<220> FEATURE:
```

```
<221> NAME/KEY: MOD_RES
<222> LOCATION: (9)..(9)
<223> OTHER INFORMATION: Xaa is Leu, Ser, Thr or peptide bond isosteres
      thereof
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MOD_RES
<222> LOCATION: (11)..(11)
<223> OTHER INFORMATION: Xaa is Leu or peptide bond isosteres thereof
<220> FEATURE:
<221> NAME/KEY: MOD_RES
<222> LOCATION: (14)..(14)
<223> OTHER INFORMATION: Xaa is Ile, tBu-Gly and peptide bond isosteres
      thereof
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Ser, Thr, Arg or peptide
      bond isosteres thereof
<220> FEATURE:
<221> NAME/KEY: MOD_RES
<222> LOCATION: (22)..(22)
<223> OTHER INFORMATION: Cys is optionally modified with a bone or
      cartilage targeting compound, a bisphosphonate, polyAsp, polyGlu,
      osteopontin, osteocalcin or sialoprotein peptides, or amino acid
      sequences derived from non-CNP polypeptides

<400> SEQUENCE: 46

Gly Leu Ser Xaa Gly Xaa Xaa Xaa Xaa Xaa Xaa Asp Arg Xaa Gly Ser
1               5                   10                  15

Xaa Ser Gly Xaa Gly Cys
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with a peptide
      sequence containing one to five amino acids from a natriuretic or
      non-natriuretic polypeptide
<220> FEATURE:
<221> NAME/KEY: MOD_RES
<222> LOCATION: (1)..(1)
<223> OTHER INFORMATION: Gly is optionally modified with a peptide
      sequence containing one to five amino acids from a natriuretic or
      non-natriuretic polypeptide
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid or
      peptidomimetic, Arg, 6-hydroxy-norleucine, citrulline (Cit), Gln,
      Ser, or Glu
<220> FEATURE:
<221> NAME/KEY: MOD_RES
<222> LOCATION: (6)..(6)
<223> OTHER INFORMATION: Xaa is Cys or decarboxy Cys
<220> FEATURE:
<221> NAME/KEY: MOD_RES
<222> LOCATION: (6)..(7)
<223> OTHER INFORMATION: Peptide bond between positions 6 and 7 may be
```

-continued

```
      replaced with -CH2-NH-
<220> FEATURE:
<221> NAME/KEY: MOD_RES
<222> LOCATION: (6)..(7)
<223> OTHER INFORMATION: Peptide bond between positions 6 and 7 may be
      replaced with -C(=O)-N(R)- where R is methyl, ethyl, n-propyl,
      isopropyl, cyclopropyl, n-butyl, isobutyl, sec-butyl or tert-butyl
<220> FEATURE:
<221> NAME/KEY: MOD_RES
<222> LOCATION: (6)..(7)
<223> OTHER INFORMATION: Peptide bond between positions 6 and 7 may be
      replaced with -C(=O)-NH-CH2-
<220> FEATURE:
<221> NAME/KEY: MOD_RES
<222> LOCATION: (6)..(7)
<223> OTHER INFORMATION: Peptide bond between positions 6 and 7 may be
      replaced with -CH2-S-
<220> FEATURE:
<221> NAME/KEY: MOD_RES
<222> LOCATION: (6)..(7)
<223> OTHER INFORMATION: Peptide bond between positions 6 and 7 may be
      replaced with -CH2-S(O)n where n is 1 or 2
<220> FEATURE:
<221> NAME/KEY: MOD_RES
<222> LOCATION: (6)..(7)
<223> OTHER INFORMATION: Peptide bond between positions 6 and 7 may be
      replaced with -CH2-CH2-
<220> FEATURE:
<221> NAME/KEY: MOD_RES
<222> LOCATION: (6)..(7)
<223> OTHER INFORMATION: Peptide bond between positions 6 and 7 may be
      replaced with -CH=CH-
<220> FEATURE:
<221> NAME/KEY: MOD_RES
<222> LOCATION: (6)..(7)
<223> OTHER INFORMATION: Peptide bond between positions 6 and 7 may be
      replaced with -C(=O)-CH2-
<220> FEATURE:
<221> NAME/KEY: MOD_RES
<222> LOCATION: (6)..(7)
<223> OTHER INFORMATION: Peptide bond between positions 6 and 7 may be
      replaced with -CH(CN)-NH-
<220> FEATURE:
<221> NAME/KEY: MOD_RES
<222> LOCATION: (6)..(7)
<223> OTHER INFORMATION: Peptide bond between positions 6 and 7 may be
      replaced with -CH(OH)-CH2-
<220> FEATURE:
<221> NAME/KEY: MOD_RES
<222> LOCATION: (6)..(7)
<223> OTHER INFORMATION: Peptide bond between positions 6 and 7 may be
      replaced with -O-C(=O)-NH-
<220> FEATURE:
<221> NAME/KEY: MOD_RES
<222> LOCATION: (6)..(7)
<223> OTHER INFORMATION: Peptide bond between positions 6 and 7 may be
      replaced with -NHC(=O)NH-
<220> FEATURE:
<221> NAME/KEY: MOD_RES
<222> LOCATION: (7)..(7)
<223> OTHER INFORMATION: Xaa is L-Phe, D-Phe, 3-amino-2-phenylpropionic
      acid, or N-alkylated derivatives of Phe
<220> FEATURE:
<221> NAME/KEY: MOD_RES
<222> LOCATION: (8)..(8)
<223> OTHER INFORMATION: Xaa is Gly, tert-butyl-Gly (tBu-Gly), Val, Ser,
      Thr or Asn
<220> FEATURE:
<221> NAME/KEY: MOD_RES
<222> LOCATION: (9)..(9)
<223> OTHER INFORMATION: Xaa is Leu, Ser, Thr or peptide bond isosteres
      thereof
<220> FEATURE:
<221> NAME/KEY: MOD_RES
<222> LOCATION: (10)..(10)
<223> OTHER INFORMATION: Xaa is Arg, Gly, 6-hydroxy-norleucine,
      citrulline (Cit), Gln, Ser or Glu
<220> FEATURE:
<221> NAME/KEY: MOD_RES
<222> LOCATION: (11)..(11)
```

```
<223> OTHER INFORMATION: Xaa is Leu or peptide isosteres thereof
<220> FEATURE:
<221> NAME/KEY: MOD_RES
<222> LOCATION: (14)..(14)
<223> OTHER INFORMATION: Xaa is Ile, tBu-Gly or peptide isosteres
      thereof
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Ser, Thr, Arg, or peptide
      bond isosteres thereof
<220> FEATURE:
<221> NAME/KEY: MOD_RES
<222> LOCATION: (22)..(22)
<223> OTHER INFORMATION: Cys is optionally modified with a synthetic
      bone targeting compound, a bisphosphonate, polyAsp, polyGlu,
      osteopontin, osteocalcin or sialoprotein peptides, or charged PEG
      molecules

<400> SEQUENCE: 47

Gly Leu Ser Xaa Gly Xaa Xaa Xaa Xaa Xaa Xaa Asp Arg Xaa Gly Ser
1               5                   10                  15

Xaa Ser Gly Xaa Gly Cys
            20

<210> SEQ ID NO 48
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is a synthetic or natural polymeric group
      or combination thereof
<220> FEATURE:
<221> NAME/KEY: MOD_RES
<222> LOCATION: (2)..(2)
<223> OTHER INFORMATION: Xaa is absent or may be one or more amino acids
      from Gly-Leu-Ser-Lys-Gly and/or substitutions at one or more of
      these positions
<220> FEATURE:
<221> NAME/KEY: MOD_RES
<222> LOCATION: (7)..(7)
<223> OTHER INFORMATION: Xaa is Lys, a conservative amino acid
      substitution, any natural or unnatural amino acid or
      peptidomimetic that does have a reactive primary amine on a side
      chain
<220> FEATURE:
<221> NAME/KEY: MOD_RES
<222> LOCATION: (19)..(19)
<223> OTHER INFORMATION: Cys is optionally modified with a synthetic or
      natural polymeric group or a combination thereof

<400> SEQUENCE: 48

Xaa Xaa Cys Phe Gly Leu Xaa Leu Asp Arg Ile Gly Ser Met Ser Gly
1               5                   10                  15

Leu Gly Cys

<210> SEQ ID NO 49
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
```

```
<222> LOCATION: (1)..(1)
<223> OTHER INFORMATION: Xaa is absent or may be a peptide fragment or
      water soluble polymer
<220> FEATURE:
<221> NAME/KEY: MOD_RES
<222> LOCATION: (2)..(2)
<223> OTHER INFORMATION: Xaa is Cys or peptide bond isosteres thereof
<220> FEATURE:
<221> NAME/KEY: MOD_RES
<222> LOCATION: (3)..(3)
<223> OTHER INFORMATION: Xaa is L-Phe, D-Phe, 3-amino-2-phenylpropionic
      acid or N-alkylated derivatives of Phe
<220> FEATURE:
<221> NAME/KEY: MOD_RES
<222> LOCATION: (4)..(4)
<223> OTHER INFORMATION: Xaa is Gly, tert-butyl-Gly (tBu-Gly), Val, Ser,
      Thr or Asn
<220> FEATURE:
<221> NAME/KEY: MOD_RES
<222> LOCATION: (5)..(5)
<223> OTHER INFORMATION: Xaa is Leu, Ser, Thr or N-Me-Leu
<220> FEATURE:
<221> NAME/KEY: MOD_RES
<222> LOCATION: (6)..(6)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MOD_RES
<222> LOCATION: (7)..(7)
<223> OTHER INFORMATION: Xaa is Leu and peptide bond isosteres thereof
<220> FEATURE:
<221> NAME/KEY: MOD_RES
<222> LOCATION: (10)..(10)
<223> OTHER INFORMATION: Xaa is Ile, tBu-Gly or peptide bond isosteres
      thereof
<220> FEATURE:
<221> NAME/KEY: MOD_RES
<222> LOCATION: (13)..(13)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (16)..(16)
<223> OTHER INFORMATION: Xaa is Leu, norleucine (Nle), homoleucine
      (Hleu), Val, tert-butyl-Ala (tBu-Ala), Ser, Thr, Arg or peptide
      bond isosteres thereof
<220> FEATURE:
<221> NAME/KEY: MOD_RES
<222> LOCATION: (18)..(18)
<223> OTHER INFORMATION: Cys is optionally modified with amino acid
      sequences useful in bone/cartilage targeting, polyAsp or polyGlu,
      osteopontin, osteocalcin, sialoprotein or sequences derived from
      NPPC or non-CNP polypeptides

<400> SEQUENCE: 49

Xaa Xaa Xaa Xaa Xaa Xaa Xaa Asp Arg Xaa Gly Ser Xaa Ser Gly Xaa
1               5                   10                  15

Gly Cys

<210> SEQ ID NO 50
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with bone targeting
      compound, moieties to reduce renal clearance, charged PEG
      molecules or hydrophilic polymers
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid, Arg,
```

```
            Gly, 6-hydroxy-norleucine, citrulline (Cit), Gln, Ser or Glu
<220> FEATURE:
<221> NAME/KEY: MOD_RES
<222> LOCATION: (6)..(6)
<223> OTHER INFORMATION: Xaa is Cys or peptide isosteres between
      positions 6 and 7
<220> FEATURE:
<221> NAME/KEY: MOD_RES
<222> LOCATION: (7)..(7)
<223> OTHER INFORMATION: Xaa is L-Phe, D-Phe, 3-amino-2-phenylpropionic
      acid or N-alkylated derivatives of Phe
<220> FEATURE:
<221> NAME/KEY: MOD_RES
<222> LOCATION: (8)..(8)
<223> OTHER INFORMATION: Xaa is Gly, tert-butyl-Gly, Thr, Ser, Val or
      Asn
<220> FEATURE:
<221> NAME/KEY: MOD_RES
<222> LOCATION: (9)..(9)
<223> OTHER INFORMATION: Xaa is Leu, Ser, Thr or peptide bond isosteres
      thereof
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MOD_RES
<222> LOCATION: (11)..(11)
<223> OTHER INFORMATION: Xaa is Leu, Asn or peptide bond isosteres
      thereof
<220> FEATURE:
<221> NAME/KEY: MOD_RES
<222> LOCATION: (14)..(14)
<223> OTHER INFORMATION: Xaa is Ile, tert-butyl-Gly (tBu-Gly), Asn or
      peptide bond isosteres thereof
<220> FEATURE:
<221> NAME/KEY: MOD_RES
<222> LOCATION: (15)..(15)
<223> OTHER INFORMATION: Xaa is Gly, Arg, Ser or Asn
<220> FEATURE:
<221> NAME/KEY: MOD_RES
<222> LOCATION: (17)..(17)
<223> OTHER INFORMATION: Xaa is Met, Val, Asn, beta-Cl-Ala,
      2-aminobutyric acid (Abu) or 2-amino-isobutyric acid (Aib)
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Arg, Thr, Ser or peptide
      bond isoteres thereof
<220> FEATURE:
<221> NAME/KEY: MOD_RES
<222> LOCATION: (22)..(22)
<223> OTHER INFORMATION: Cys is optionally modified with bone targeting
      compound, moieties to reduce renal clearance, charged PEG
      molecules or hydrophilic polymers

<400> SEQUENCE: 50

Gly Leu Ser Xaa Gly Xaa Xaa Xaa Xaa Xaa Xaa Asp Arg Xaa Xaa Ser
1               5                   10                  15

Xaa Ser Gly Xaa Gly Cys
            20

<210> SEQ ID NO 51
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is Arg or Glu

<400> SEQUENCE: 51
```

```
Xaa Leu Ser Lys Gly Cys Phe Gly Leu Lys Leu Asp Arg Ile Gly Ser
1               5                   10                  15

Met Ser Gly Leu Gly Cys
            20
```

<210> SEQ ID NO 52
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (5)..(5)
<223> OTHER INFORMATION: Xaa is Arg, Gln or Ser

<400> SEQUENCE: 52

```
Gly Leu Ser Lys Xaa Cys Phe Gly Leu Lys Leu Asp Arg Ile Gly Ser
1               5                   10                  15

Met Ser Gly Leu Gly Cys
            20
```

<210> SEQ ID NO 53
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (15)..(15)
<223> OTHER INFORMATION: Xaa is Ser, Asn, Arg, or Cit

<400> SEQUENCE: 53

```
Gly Leu Ser Lys Gly Cys Phe Gly Leu Lys Leu Asp Arg Ile Xaa Ser
1               5                   10                  15

Met Ser Gly Leu Gly Cys
            20
```

<210> SEQ ID NO 54
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (19)..(19)
<223> OTHER INFORMATION: Xaa is Ser, Arg, or Asn

<400> SEQUENCE: 54

```
Gly Leu Ser Lys Gly Cys Phe Gly Leu Lys Leu Asp Arg Ile Gly Ser
1               5                   10                  15

Met Ser Xaa Leu Gly Cys
            20
```

<210> SEQ ID NO 55
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (21)..(21)
<223> OTHER INFORMATION: Xaa is Ser, Thr, or Arg

<400> SEQUENCE: 55

```
Gly Leu Ser Lys Gly Cys Phe Gly Leu Lys Leu Asp Arg Ile Gly Ser
1               5                   10                  15

Met Ser Gly Leu Xaa Cys
            20

<210> SEQ ID NO 56
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog A
<220> FEATURE:
<221> NAME/KEY: BINDING
<222> LOCATION: (6)..(6)
<223> OTHER INFORMATION: CH2NH

<400> SEQUENCE: 56

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 57
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analogs B
<220> FEATURE:
<221> NAME/KEY: BINDING
<222> LOCATION: (7)..(7)
<223> OTHER INFORMATION: Xaa replaced with N-Me-Phe

<400> SEQUENCE: 57

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 58
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog F
<220> FEATURE:
<221> NAME/KEY: BINDING
<222> LOCATION: (8)..(8)
<223> OTHER INFORMATION: tBu

<400> SEQUENCE: 58

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 59
<211> LENGTH: 22
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog H
<220> FEATURE:
<221> NAME/KEY: BINDING
<222> LOCATION: (7)..(7)
<223> OTHER INFORMATION: Xaa is replaced with NHCH2-CH(Phe)CO

<400> SEQUENCE: 59

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 60
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BL - CNP37

<400> SEQUENCE: 60

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 61
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CA

<400> SEQUENCE: 61

Ala Ala Trp Ala Arg Leu Leu Gln Glu His Pro Asn Ala Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 62
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CB

<400> SEQUENCE: 62

Ala Ala Trp Ala Arg Leu Leu Gln Glu His Pro Asn Ala Arg Gly Leu
1               5                   10                  15

Ser Lys Gly Cys Phe Gly Leu Lys Leu Asp Arg Ile Gly Ser Met Ser
```

```
                     20                  25                  30

Gly Leu Gly Cys
        35

<210> SEQ ID NO 63
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CC

<400> SEQUENCE: 63

Asp Leu Arg Val Asp Thr Lys Ser Arg Ala Ala Trp Ala Arg Gly Leu
1               5                   10                  15

Ser Lys Gly Cys Phe Gly Leu Lys Leu Asp Arg Ile Gly Ser Met Ser
                20                  25                  30

Gly Leu Gly Cys
        35

<210> SEQ ID NO 64
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANQQ-CNP22

<400> SEQUENCE: 64

Gly Ala Asn Gln Gln Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANRR-CNP22

<400> SEQUENCE: 65

Gly Ala Asn Arg Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 66
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANPR-CNP22

<400> SEQUENCE: 66

Gly Ala Asn Pro Arg Gly Leu Ser Lys Gly Cys Phe Gly Leu Lys Leu
1               5                   10                  15
```

```
Asp Arg Ile Gly Ser Met Ser Gly Leu Gly Cys
            20                  25

<210> SEQ ID NO 67
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANSS-CNP22

<400> SEQUENCE: 67

Gly Ala Asn Ser Ser Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 68
<211> LENGTH: 32
<212> TYPE: PRT
<213> ORGANISM: Artificial Sequene
<220> FEATURE:
<223> OTHER INFORMATION: Sythetic Polypeptide
<220> FEATURE:
<221> NAME/KEY: MISC_FEATURE
<223> OTHER INFORMATION: Analog CD
<220> FEATURE:
<221> NAME/KEY: MOD_RES
<222> LOCATION: (1)..(1)
<223> OTHER INFORMATION: N-terminus BNP tail
<220> FEATURE:
<221> NAME/KEY: MOD_RES
<222> LOCATION: (32)..(32)
<223> OTHER INFORMATION: N-terminus BNP tail

<400> SEQUENCE: 68

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 69
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANQQ-CNP22(K4R) - Analog CH

<400> SEQUENCE: 69

Gly Ala Asn Gln Gln Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: GANSS-CNP22(K4R) - Analog CG
```

-continued

```
<400> SEQUENCE: 70

Gly Ala Asn Ser Ser Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 71
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CS

<400> SEQUENCE: 71

Gly Gln Glu His Pro Asn Ala Arg Lys Tyr Lys Gly Ala Asn Pro Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 72
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CT

<400> SEQUENCE: 72

Gly Gln Glu His Pro Asn Ala Arg Lys Tyr Lys Gly Ala Asn Gln Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 73
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CU

<400> SEQUENCE: 73

Gly Gln Glu His Pro Asn Ala Arg Lys Tyr Lys Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 74
<211> LENGTH: 38
<212> TYPE: PRT
<213> ORGANISM: Artificial Sequence
<220> FEATURE:
```

<223> OTHER INFORMATION: Synthetic Polypeptide
<220> FEATURE:
<221> NAME/KEY: MISC_FEATURE
<223> OTHER INFORMATION: Analog CW

<400> SEQUENCE: 74

Gly Gln Glu His Pro Asn Ala Arg Lys Tyr Lys Gly Ala Asn Lys Pro
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 75
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 75

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 76
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CQ

<400> SEQUENCE: 76

Gly His His Ser His Glu Gln His Pro His Gly Ala Asn Gln Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 77
<211> LENGTH: 38
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CR

<400> SEQUENCE: 77

Gly Ala His His Pro His Glu His Asp Thr His Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

-continued

```
<210> SEQ ID NO 78
<211> LENGTH: 37
<212> TYPE: PRT
<213> ORGANISM: Artificial Sequencce
<220> FEATURE:
<223> OTHER INFORMATION: Synthetic Polypeptide
<220> FEATURE:
<221> NAME/KEY: MISC_FEATURE
<223> OTHER INFORMATION: Analog CX

<400> SEQUENCE: 78

Gly His His Ser His Glu Gln His Pro His Gly Ala Asn Pro Arg Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 79
<211> LENGTH: 36
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CF

<400> SEQUENCE: 79

Gly Gln Pro Arg Glu Pro Gln Val Tyr Thr Leu Pro Pro Ser Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 80
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CY

<400> SEQUENCE: 80

Gly Gln His Lys Asp Asp Asn Pro Asn Leu Pro Arg Gly Ala Asn Pro
1               5                   10                  15

Arg Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 81
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CE

<400> SEQUENCE: 81

Gly Glu Arg Ala Phe Lys Ala Trp Ala Val Ala Arg Leu Ser Gln Gly
1               5                   10                  15
```

```
Leu Ser Lys Gly Cys Phe Gly Leu Lys Leu Asp Arg Ile Gly Ser Met
            20                  25                  30

Ser Gly Leu Gly Cys
            35

<210> SEQ ID NO 82
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CZ

<400> SEQUENCE: 82

Phe Gly Ile Pro Met Asp Arg Ile Gly Arg Asn Pro Arg Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 83
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog DA

<400> SEQUENCE: 83

Gly Lys Arg Thr Gly Gln Tyr Lys Leu Gly Ser Lys Thr Gly Pro Gly
1               5                   10                  15

Pro Lys Gly Leu Ser Lys Gly Cys Phe Gly Leu Lys Leu Asp Arg Ile
            20                  25                  30

Gly Ser Met Ser Gly Leu Gly Cys
            35                  40

<210> SEQ ID NO 84
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CK

<400> SEQUENCE: 84

Gly Gln Pro Arg Glu Pro Gln Val Tyr Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
            35

<210> SEQ ID NO 85
<211> LENGTH: 36
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: Analog CL

<400> SEQUENCE: 85

Gly Val Pro Gln Val Ser Thr Ser Thr Gly Ala Asn Gln Gln Gly Leu
1               5                   10                  15

Ser Arg Gly Cys Phe Gly Leu Lys Leu Asp Arg Ile Gly Ser Met Ser
            20                  25                  30

Gly Leu Gly Cys
        35

<210> SEQ ID NO 86
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CM

<400> SEQUENCE: 86

Gly Gln Pro Ser Ser Ser Ser Gln Ser Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 87
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CN

<400> SEQUENCE: 87

Gly Gln Thr His Ser Ser Gly Thr Gln Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 88
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CO

<400> SEQUENCE: 88

Gly Ser Thr Gly Gln Trp His Ser Glu Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35
```

```
<210> SEQ ID NO 89
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CP

<400> SEQUENCE: 89

Gly Ser Ser Ser Ser Ser Ser Ser Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 90
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with bone targeting
      compound, a bisphosphonates, polyAsp, polyGlu, osteopontin,
      osteocalcin, or sialoprotein peptides, negatively charged PEG
      molecules or natural polymers
<220> FEATURE:
<221> NAME/KEY: MOD_RES
<222> LOCATION: (6)..(6)
<223> OTHER INFORMATION: Xaa is Cys or another natural or unnatural
      amino acid
<220> FEATURE:
<221> NAME/KEY: MOD_RES
<222> LOCATION: (7)..(7)
<223> OTHER INFORMATION: Xaa is Phe or another natural or unnatural
      amino acid
<220> FEATURE:
<221> NAME/KEY: MOD_RES
<222> LOCATION: (8)..(8)
<223> OTHER INFORMATION: Xaa is Gly, a larger natural or unnatural amino
      acid or peptidomimetic
<220> FEATURE:
<221> NAME/KEY: MOD_RES
<222> LOCATION: (22)..(22)
<223> OTHER INFORMATION: Cys is optionally modified with bone targeting
      compound, a bisphosphonates, polyAsp, polyGlu, osteopontin,
      osteocalcin, or sialoprotein peptides, negatively charged PEG
      molecules or natural polymers

<400> SEQUENCE: 90

Gly Leu Ser Lys Gly Xaa Xaa Xaa Leu Lys Leu Asp Arg Ile Gly Ser
1               5                   10                  15

Met Ser Gly Leu Gly Cys
            20

<210> SEQ ID NO 91
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog J
<220> FEATURE:
<221> NAME/KEY: MOD_RES
```

```
<222> LOCATION: (6)..(6)
<223> OTHER INFORMATION: Xaa is CH2-NH
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (20)..(20)
<223> OTHER INFORMATION: N-Me

<400> SEQUENCE: 91

Gly Leu Ser Lys Gly Xaa Phe Gly Leu Lys Leu Asp Arg Ile Gly Ser
1               5                   10                  15

Met Ser Gly Leu Gly Cys
            20

<210> SEQ ID NO 92
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog K
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (20)..(20)
<223> OTHER INFORMATION: N-Me

<400> SEQUENCE: 92

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 93
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog L
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (11)..(11)
<223> OTHER INFORMATION: N-Me
<220> FEATURE:
<221> NAME/KEY: BINDING
<222> LOCATION: (20)..(20)
<223> OTHER INFORMATION: N-Me

<400> SEQUENCE: 93

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 94
<211> LENGTH: 22
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog M
<220> FEATURE:
<221> NAME/KEY: BINDING
<222> LOCATION: (9)..(9)
<223> OTHER INFORMATION: N-Me
<220> FEATURE:
<221> NAME/KEY: BINDING
<222> LOCATION: (11)..(11)
<223> OTHER INFORMATION: N-Me

<400> SEQUENCE: 94

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 95
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog Z

<400> SEQUENCE: 95

Gly Leu Ser Arg Gly Cys Tyr Gly Leu Lys Leu Asp Arg Ile Gly Ser
1               5                   10                  15

Met Ser Gly Leu Gly Cys
            20

<210> SEQ ID NO 96
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AA

<400> SEQUENCE: 96

Gly Leu Ser Arg Gly Cys Phe Val Leu Lys Leu Asp Arg Ile Gly Ser
1               5                   10                  15

Met Ser Gly Leu Gly Cys
            20

<210> SEQ ID NO 97
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AB

<400> SEQUENCE: 97

Gly Leu Ser Arg Gly Cys Phe Ser Leu Lys Leu Asp Arg Ile Gly Ser
1               5                   10                  15

Met Ser Gly Leu Gly Cys
            20
```

<210> SEQ ID NO 98
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AC

<400> SEQUENCE: 98

Gly Leu Ser Arg Gly Cys Phe Thr Leu Lys Leu Asp Arg Ile Gly Ser
1               5                   10                  15

Met Ser Gly Leu Gly Cys
            20

<210> SEQ ID NO 99
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AD

<400> SEQUENCE: 99

Gly Leu Ser Arg Gly Cys Phe Gly Thr Lys Leu Asp Arg Ile Gly Ser
1               5                   10                  15

Met Ser Gly Leu Gly Cys
            20

<210> SEQ ID NO 100
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AE

<400> SEQUENCE: 100

Gly Leu Ser Arg Gly Cys Phe Gly Leu Lys Leu Asp Arg Ile Arg Ser
1               5                   10                  15

Met Ser Gly Leu Gly Cys
            20

<210> SEQ ID NO 101
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AF
<220> FEATURE:
<221> NAME/KEY: MOD_RES
<222> LOCATION: (15)..(15)
<223> OTHER INFORMATION: Xaa is Cit

<400> SEQUENCE: 101

Gly Leu Ser Arg Gly Cys Phe Gly Leu Lys Leu Asp Arg Ile Xaa Ser
1               5                   10                  15

Met Ser Gly Leu Gly Cys
            20

```
<210> SEQ ID NO 102
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AG

<400> SEQUENCE: 102

Gly Leu Ser Arg Gly Cys Phe Gly Leu Lys Leu Asp Arg Ile Gly Ser
1               5                   10                  15

Val Ser Gly Leu Gly Cys
            20

<210> SEQ ID NO 103
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AJ

<400> SEQUENCE: 103

Gly Leu Ser Arg Gly Cys Phe Gly Leu Lys Leu Asp Arg Ile Gly Ser
1               5                   10                  15

Met Ser Gly Val Gly Cys
            20

<210> SEQ ID NO 104
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AK
<220> FEATURE:
<221> NAME/KEY: MOD_RES
<222> LOCATION: (20)..(20)
<223> OTHER INFORMATION: Xaa is tBu-Ala

<400> SEQUENCE: 104

Gly Leu Ser Arg Gly Cys Phe Gly Leu Lys Leu Asp Arg Ile Gly Ser
1               5                   10                  15

Met Ser Gly Xaa Gly Cys
            20

<210> SEQ ID NO 105
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AT

<400> SEQUENCE: 105

Glu Leu Ser Glu Gly Cys Phe Gly Leu Lys Leu Asp Arg Ile Gly Ser
1               5                   10                  15

Met Ser Gly Leu Gly Cys
            20
```

```
<210> SEQ ID NO 106
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AV
<220> FEATURE:
<221> NAME/KEY: MOD_RES
<222> LOCATION: (1)..(1)
<223> OTHER INFORMATION: N-terminus modified with pentanoic acid

<400> SEQUENCE: 106

Glu Leu Ser Glu Gly Cys Phe Gly Leu Lys Leu Asp Arg Ile Gly Ser
1               5                   10                  15

Met Ser Gly Leu Gly Cys
            20

<210> SEQ ID NO 107
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog AW
<220> FEATURE:
<221> NAME/KEY: MOD_RES
<222> LOCATION: (1)..(1)
<223> OTHER INFORMATION: Heptanoic acid modifying N-terminus

<400> SEQUENCE: 107

Glu Leu Ser Glu Gly Cys Phe Gly Leu Lys Leu Asp Arg Ile Gly Ser
1               5                   10                  15

Met Ser Gly Leu Gly Cys
            20

<210> SEQ ID NO 108
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BB
<220> FEATURE:
<221> NAME/KEY: MOD_RES
<222> LOCATION: (1)..(1)
<223> OTHER INFORMATION: N-terminus modified with heptanoic acid

<400> SEQUENCE: 108

Glu Leu Ser Lys Gly Cys Phe Gly Leu Lys Leu Asp Arg Ile Gly Ser
1               5                   10                  15

Met Ser Gly Leu Gly Cys
            20

<210> SEQ ID NO 109
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BC
```

```
<220> FEATURE:
<221> NAME/KEY: MOD_RES
<222> LOCATION: (1)..(1)
<223> OTHER INFORMATION: N-terminus modified with pentanoic acid

<400> SEQUENCE: 109

Glu Leu Ser Lys Gly Cys Phe Gly Leu Lys Leu Asp Arg Ile Gly Ser
1               5                   10                  15

Met Ser Gly Leu Gly Cys
            20

<210> SEQ ID NO 110
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BF
<220> FEATURE:
<221> NAME/KEY: MOD_RES
<222> LOCATION: (10)..(10)
<223> OTHER INFORMATION: Xaa is Cit

<400> SEQUENCE: 110

Gly Leu Ser Arg Gly Cys Phe Gly Leu Xaa Leu Asp Arg Ile Gly Ser
1               5                   10                  15

Met Ser Gly Leu Gly Cys
            20

<210> SEQ ID NO 111
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BG

<400> SEQUENCE: 111

Gly Leu Ser Arg Gly Cys Phe Gly Leu Gln Leu Asp Arg Ile Gly Ser
1               5                   10                  15

Met Ser Gly Leu Gly Cys
            20

<210> SEQ ID NO 112
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BH

<400> SEQUENCE: 112

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 113
<211> LENGTH: 22
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: Analog BJ

<400> SEQUENCE: 113

Gly Leu Ser Arg Gly Cys Phe Gly Leu Lys Leu Asp Arg Ile Asn Ser
1               5                   10                  15

Met Ser Gly Leu Gly Cys
            20

<210> SEQ ID NO 114
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BK

<400> SEQUENCE: 114

Gly Leu Ser Arg Gly Cys Phe Gly Leu Lys Leu Asp Arg Ile Ser Ser
1               5                   10                  15

Met Ser Gly Leu Gly Cys
            20

<210> SEQ ID NO 115
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog N
<220> FEATURE:
<221> NAME/KEY: MISC_FEATURE
<222> LOCATION: (1)..(22)
<223> OTHER INFORMATION: All D-amino acids

<400> SEQUENCE: 115

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 116
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BD
<220> FEATURE:
<221> NAME/KEY: BINDING
<222> LOCATION: (9)..(9)
<223> OTHER INFORMATION: N-Me

<400> SEQUENCE: 116

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 117
```

```
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BN
<220> FEATURE:
<221> NAME/KEY: BINDING
<222> LOCATION: (11)..(11)
<223> OTHER INFORMATION: N-Me

<400> SEQUENCE: 117

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 118
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BE
<220> FEATURE:
<221> NAME/KEY: BINDING
<222> LOCATION: (20)..(20)
<223> OTHER INFORMATION: N-Me

<400> SEQUENCE: 118

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 119
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog V
<220> FEATURE:
<221> NAME/KEY: BINDING
<222> LOCATION: (7)..(7)
<223> OTHER INFORMATION: 3,4-dichloro

<400> SEQUENCE: 119

Gly Leu Ser Gly Gly Cys Phe Gly Leu Lys Leu Asp Arg Ile Gly Ser
1               5                   10                  15

Met Ser Gly Leu Gly Cys
            20

<210> SEQ ID NO 120
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog X
<220> FEATURE:
<221> NAME/KEY: BINDING
<222> LOCATION: (7)..(7)
```

<223> OTHER INFORMATION: 3-methyl

<400> SEQUENCE: 120

Gly Leu Ser Gly Gly Cys Phe Gly Leu Lys Leu Asp Arg Ile Gly Ser
1               5                   10                  15

Met Ser Gly Leu Gly Cys
            20

<210> SEQ ID NO 121
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BP

<400> SEQUENCE: 121

Gly Leu Ser Arg Ser Cys Phe Gly Leu Lys Leu Asp Arg Ile Gly Ser
1               5                   10                  15

Met Ser Gly Leu Gly Cys
            20

<210> SEQ ID NO 122
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BO

<400> SEQUENCE: 122

Gly Leu Ser Arg Arg Cys Phe Gly Leu Lys Leu Asp Arg Ile Gly Ser
1               5                   10                  15

Met Ser Gly Leu Gly Cys
            20

<210> SEQ ID NO 123
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog P

<400> SEQUENCE: 123

Gly Leu Ser Gly Gly Cys Phe Gly Leu Arg Leu Asp Arg Ile Gly Ser
1               5                   10                  15

Met Ser Gly Leu Gly Cys
            20

<210> SEQ ID NO 124
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BY

<400> SEQUENCE: 124

Gly Leu Ser Arg Gly Cys Phe Gly Leu Ser Leu Asp Arg Ile Gly Ser
1               5                   10                  15

Met Ser Gly Leu Gly Cys
            20

<210> SEQ ID NO 125
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BZ

<400> SEQUENCE: 125

Gly Leu Ser Arg Gly Cys Phe Gly Leu Lys Leu Asp Arg Ile Gly Gln
1               5                   10                  15

Met Ser Gly Leu Gly Cys
            20

<210> SEQ ID NO 126
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BX

<400> SEQUENCE: 126

Gly Leu Ser Arg Gly Cys Phe Gly Leu Lys Leu Asp Arg Ile Gly Ser
1               5                   10                  15

Asn Ser Gly Leu Gly Cys
            20

<210> SEQ ID NO 127
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BQ

<400> SEQUENCE: 127

Gly Leu Ser Arg Gly Cys Phe Gly Leu Lys Leu Asp Arg Ile Gly Ser
1               5                   10                  15

Met Ser Ser Leu Gly Cys
            20

<210> SEQ ID NO 128
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BR

<400> SEQUENCE: 128

Gly Leu Ser Arg Gly Cys Phe Gly Leu Lys Leu Asp Arg Ile Gly Ser
1               5                   10                  15

Met Ser Arg Leu Gly Cys

```
                   20

<210> SEQ ID NO 129
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BS

<400> SEQUENCE: 129

Gly Leu Ser Arg Gly Cys Phe Gly Leu Lys Leu Asp Arg Ile Gly Ser
1               5                   10                  15

Met Ser Gly Arg Gly Cys
            20

<210> SEQ ID NO 130
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BT

<400> SEQUENCE: 130

Gly Leu Ser Arg Gly Cys Phe Gly Leu Lys Leu Asp Arg Ile Gly Ser
1               5                   10                  15

Met Ser Gly Leu Ser Cys
            20

<210> SEQ ID NO 131
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BU

<400> SEQUENCE: 131

Gly Leu Ser Arg Gly Cys Phe Gly Leu Lys Leu Asp Arg Ile Gly Ser
1               5                   10                  15

Met Ser Gly Leu Thr Cys
            20

<210> SEQ ID NO 132
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog BW

<400> SEQUENCE: 132

Gly Leu Ser Arg Gly Cys Phe Gly Leu Lys Leu Asp Arg Ile Gly Ser
1               5                   10                  15

Met Ser Gly Leu Arg Cys
            20

<210> SEQ ID NO 133
```

```
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog CJ

<400> SEQUENCE: 133

Arg Ser Ser Cys Phe Gly Gly Arg Ile Asp Arg Ile Gly Ala Cys
1               5                   10                  15

<210> SEQ ID NO 134
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal linked to CNP22 by disuccinimidyl
      glutarate

<400> SEQUENCE: 134

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 135
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal linked to CNP22 by Bis-PEO5

<400> SEQUENCE: 135

Gly Leu Ser Arg Gly Cys Phe Gly Leu Arg Leu Asp Arg Ile Gly Ser
1               5                   10                  15

Met Ser Gly Leu Gly Cys
            20

<210> SEQ ID NO 136
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Analog E
<220> FEATURE:
<221> NAME/KEY: MOD_RES
<222> LOCATION: (7)..(7)
<223> OTHER INFORMATION: Xaa is D-Phe

<400> SEQUENCE: 136

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 137
```

```
<211> LENGTH: 22
<212> TYPE: PRT
<213> ORGANISM: Artificial Sequence
<220> FEATURE:
<223> OTHER INFORMATION: Sythetic Polypeptide
<220> FEATURE:
<221> NAME/KEY: MISC_FEATURE
<223> OTHER INFORMATION: Analog G
<220> FEATURE:
<221> NAME/KEY: MOD_RES
<222> LOCATION: (7)..(7)
<223> OTHER INFORMATION: Xaa is 3-Cl-Phe

<400> SEQUENCE: 137

Gly Leu Ser Lys Gly Cys Xaa Gly Leu Lys Leu Asp Arg Ile Gly Ser
1               5                   10                  15

Met Ser Gly Leu Gly Cys
            20

<210> SEQ ID NO 138
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa comprises one or more amino acids selected
      from Gly-Leu-Ser-Lys-Gly or substitutions at one or more of these
      amino acids and further comprises a hydrophilic or water soluable
      polymer

<400> SEQUENCE: 138

Xaa Cys Phe Gly Leu Lys Leu Asp Arg Ile Gly Ser Met Ser Gly Leu
1               5                   10                  15

Gly Cys

<210> SEQ ID NO 139
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Cys is modified with a natural and/or synthetic
      polymer
<220> FEATURE:
<221> NAME/KEY: MOD_RES
<222> LOCATION: (17)..(17)
<223> OTHER INFORMATION: Cys is modified with a natural and/or synthetic
      polymer

<400> SEQUENCE: 139

Cys Phe Gly Leu Lys Leu Asp Arg Ile Gly Ser Met Ser Gly Leu Gly
1               5                   10                  15

Cys

<210> SEQ ID NO 140
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is modified with a natural and/or synthetic
      polymer
```

```
<220> FEATURE:
<221> NAME/KEY: MOD_RES
<222> LOCATION: (22)..(22)
<223> OTHER INFORMATION: Cys is modified with a natural and/or synthetic
      polymer

<400> SEQUENCE: 140

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 141
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Cys is modified with a natural and/or synthetic
      polymeric group or combination thereof
<220> FEATURE:
<221> NAME/KEY: MOD_RES
<222> LOCATION: (5)..(5)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Glu or Ser
<220> FEATURE:
<221> NAME/KEY: MOD_RES
<222> LOCATION: (17)..(17)
<223> OTHER INFORMATION: Cys is optionally modified with a natural
      and/or synthetic polymeric group or combination thereof

<400> SEQUENCE: 141

Cys Phe Gly Leu Xaa Leu Asp Arg Ile Gly Ser Met Ser Gly Leu Gly
1               5                   10                  15

Cys

<210> SEQ ID NO 142
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Xaa is optionally modified with bone- or
      cartilage-targeting moieties, moieties that reduce renal
      clearance, hydrophilic polymers, carbohydrates, hydrophobic acids
      and combinations thereof
<220> FEATURE:
<221> NAME/KEY: MOD_RES
<222> LOCATION: (2)..(2)
<223> OTHER INFORMATION: Xaa is absent or may comprise 1 to 5 amino
      acids from Gly-Leu-Ser-Lys-Gly, optionally substituted with a
      natural or unnatural amino acid
<220> FEATURE:
<221> NAME/KEY: MOD_RES
<222> LOCATION: (7)..(7)
<223> OTHER INFORMATION: Xaa is Lys, any natural or unnatural amino acid
      or peptidomimetic that does not have a reactive primary amine on a
      side chain
<220> FEATURE:
<221> NAME/KEY: MOD_RES
<222> LOCATION: (19)..(19)
<223> OTHER INFORMATION: Xaa is optionally modified with bone- or
      cartilage-targeting moieties, moieties that reduce renal
      clearance, hydrophilic polymers, carbohydrates, hydrophobic acids
      and combinations thereof

<400> SEQUENCE: 142
```

```
Xaa Xaa Cys Phe Gly Leu Xaa Leu Asp Arg Ile Gly Ser Met Ser Gly
1               5                   10                  15

Leu Gly Cys

<210> SEQ ID NO 143
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Gly is optionally modified with cartilage or
      bone targeting compounds, a bisphosphonate, polyAsp, polyGlu,
      osteopontin peptides, osteocalcin peptides, sialoprotein peptides,
      charged PEG molecules or hydrophilic polymers
<220> FEATURE:
<221> NAME/KEY: MOD_RES
<222> LOCATION: (4)..(4)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: MOD_RES
<222> LOCATION: (6)..(6)
<223> OTHER INFORMATION: Xaa is Cys or peptide isosteres between
      positions 6 and 7
<220> FEATURE:
<221> NAME/KEY: MOD_RES
<222> LOCATION: (7)..(7)
<223> OTHER INFORMATION: Xaa is L-Phe, D-Phe, N-alkylated Phe, or Phe
      analog
<220> FEATURE:
<221> NAME/KEY: MOD_RES
<222> LOCATION: (8)..(8)
<223> OTHER INFORMATION: Xaa is Gly, tert-butyl-Gly, Thr, Ser, Val or
      Asn
<220> FEATURE:
<221> NAME/KEY: MOD_RES
<222> LOCATION: (9)..(9)
<223> OTHER INFORMATION: Xaa is Leu, Ser, Thr or peptide bond isosteres
      thereof
<220> FEATURE:
<221> NAME/KEY: MOD_RES
<222> LOCATION: (10)..(10)
<223> OTHER INFORMATION: Xaa is Lys or a conservative amino acid
      substitution thereof, any natural or unnatural amino acid, Arg,
      Gly, 6-hydroxy-norleucine, citrulline (Cit), Gln, Ser or Glu
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MOD_RES
<222> LOCATION: (15)..(15)
<223> OTHER INFORMATION: Xaa is Gly, Arg, Ser or Asn
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MOD_RES
<222> LOCATION: (20)..(20)
<223> OTHER INFORMATION: Xaa is Leu, norleucine (Nle), homoleucine
      (Hleu), Val, tert-butyl-Ala (tBu-Ala), Arg, Thr, Ser or peptide
      bond isosteres thereof
<220> FEATURE:
<221> NAME/KEY: MOD_RES
<222> LOCATION: (22)..(22)
<223> OTHER INFORMATION: Cys is optionally modified with cartilage or
      bone targeting compounds, a bisphosphonate, polyAsp, polyGlu,
      osteopontin peptides, osteocalcin peptides, sialoprotein peptides,
```

-continued charged PEG molecules or hydrophilic polymers

<400> SEQUENCE: 143

Gly Leu Ser Xaa Gly Xaa Xaa Xaa Xaa Xaa Asp Arg Xaa Xaa Ser
1               5                   10                  15

Xaa Ser Gly Xaa Gly Cys
            20

<210> SEQ ID NO 144
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 144

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35

<210> SEQ ID NO 145
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 145

Pro Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 146
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 146

Leu Arg Val Asp Thr Lys Ser Arg Ala Ala Trp Ala Arg Leu Leu Gln
1               5                   10                  15

Glu His Pro Asn Ala Arg Lys Tyr Lys Gly Ala Asn Lys Lys Gly Leu
            20                  25                  30

Ser Lys Gly Cys Phe Gly Leu Lys Leu Asp Arg Ile Gly Ser Met Ser
        35                  40                  45

Gly Leu Gly Cys
    50

<210> SEQ ID NO 147
<211> LENGTH: 51
<212> TYPE: PRT
<213> ORGANISM: Artificial Sequence
<220> FEATURE:
<223> OTHER INFORMATION: Synthetic Polypeptide

<400> SEQUENCE: 147

```
Arg Val Asp Thr Lys Ser Arg Ala Ala Trp Ala Arg Leu Leu Gln Glu
1               5                   10                  15

His Pro Asn Ala Arg Lys Tyr Lys Gly Ala Asn Lys Lys Gly Leu Ser
            20                  25                  30

Lys Gly Cys Phe Gly Leu Lys Leu Asp Arg Ile Gly Ser Met Ser Gly
        35                  40                  45

Leu Gly Cys
    50
```

<210> SEQ ID NO 148
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 148

```
Val Asp Thr Lys Ser Arg Ala Ala Trp Ala Arg Leu Leu Gln Glu His
1               5                   10                  15

Pro Asn Ala Arg Lys Tyr Lys Gly Ala Asn Lys Lys Gly Leu Ser Lys
            20                  25                  30

Gly Cys Phe Gly Leu Lys Leu Asp Arg Ile Gly Ser Met Ser Gly Leu
        35                  40                  45

Gly Cys
    50
```

<210> SEQ ID NO 149
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 149

```
Asp Thr Lys Ser Arg Ala Ala Trp Ala Arg Leu Leu Gln Glu His Pro
1               5                   10                  15

Asn Ala Arg Lys Tyr Lys Gly Ala Asn Lys Lys Gly Leu Ser Lys Gly
            20                  25                  30

Cys Phe Gly Leu Lys Leu Asp Arg Ile Gly Ser Met Ser Gly Leu Gly
        35                  40                  45

Cys
```

<210> SEQ ID NO 150
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 150

```
Thr Lys Ser Arg Ala Ala Trp Ala Arg Leu Leu Gln Glu His Pro Asn
1               5                   10                  15

Ala Arg Lys Tyr Lys Gly Ala Asn Lys Lys Gly Leu Ser Lys Gly Cys
            20                  25                  30

Phe Gly Leu Lys Leu Asp Arg Ile Gly Ser Met Ser Gly Leu Gly Cys
        35                  40                  45
```

<210> SEQ ID NO 151
<211> LENGTH: 47
<212> TYPE: PRT
<213> ORGANISM: Artificial Sequence
<220> FEATURE:

<223> OTHER INFORMATION: Synthetic Polypeptide

<400> SEQUENCE: 151

Lys Ser Arg Ala Ala Trp Ala Arg Leu Leu Gln Glu His Pro Asn Ala
1               5                   10                  15

Arg Lys Tyr Lys Gly Ala Asn Lys Lys Gly Leu Ser Lys Gly Cys Phe
            20                  25                  30

Gly Leu Lys Leu Asp Arg Ile Gly Ser Met Ser Gly Leu Gly Cys
        35                  40                  45

<210> SEQ ID NO 152
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 152

Ser Arg Ala Ala Trp Ala Arg Leu Leu Gln Glu His Pro Asn Ala Arg
1               5                   10                  15

Lys Tyr Lys Gly Ala Asn Lys Lys Gly Leu Ser Lys Gly Cys Phe Gly
            20                  25                  30

Leu Lys Leu Asp Arg Ile Gly Ser Met Ser Gly Leu Gly Cys
        35                  40                  45

<210> SEQ ID NO 153
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 153

Arg Ala Ala Trp Ala Arg Leu Leu Gln Glu His Pro Asn Ala Arg Lys
1               5                   10                  15

Tyr Lys Gly Ala Asn Lys Lys Gly Leu Ser Lys Gly Cys Phe Gly Leu
            20                  25                  30

Lys Leu Asp Arg Ile Gly Ser Met Ser Gly Leu Gly Cys
        35                  40                  45

<210> SEQ ID NO 154
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 154

Ala Ala Trp Ala Arg Leu Leu Gln Glu His Pro Asn Ala Arg Lys Tyr
1               5                   10                  15

Lys Gly Ala Asn Lys Lys Gly Leu Ser Lys Gly Cys Phe Gly Leu Lys
            20                  25                  30

Leu Asp Arg Ile Gly Ser Met Ser Gly Leu Gly Cys
        35                  40

<210> SEQ ID NO 155
<211> LENGTH: 43
<212> TYPE: PRT
<213> ORGANISM: Artificial Sequence
<220> FEATURE:
<223> OTHER INFORMATION: Synthetic Polypeptide

<400> SEQUENCE: 155

```
Ala Trp Ala Arg Leu Leu Gln Glu His Pro Asn Ala Arg Lys Tyr Lys
1               5                   10                  15

Gly Ala Asn Lys Lys Gly Leu Ser Lys Gly Cys Phe Gly Leu Lys Leu
            20                  25                  30

Asp Arg Ile Gly Ser Met Ser Gly Leu Gly Cys
            35                  40
```

<210> SEQ ID NO 156
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 156

```
Trp Ala Arg Leu Leu Gln Glu His Pro Asn Ala Arg Lys Tyr Lys Gly
1               5                   10                  15

Ala Asn Lys Lys Gly Leu Ser Lys Gly Cys Phe Gly Leu Lys Leu Asp
            20                  25                  30

Arg Ile Gly Ser Met Ser Gly Leu Gly Cys
            35                  40
```

<210> SEQ ID NO 157
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 157

```
Ala Arg Leu Leu Gln Glu His Pro Asn Ala Arg Lys Tyr Lys Gly Ala
1               5                   10                  15

Asn Lys Lys Gly Leu Ser Lys Gly Cys Phe Gly Leu Lys Leu Asp Arg
            20                  25                  30

Ile Gly Ser Met Ser Gly Leu Gly Cys
            35                  40
```

<210> SEQ ID NO 158
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 158

```
Arg Leu Leu Gln Glu His Pro Asn Ala Arg Lys Tyr Lys Gly Ala Asn
1               5                   10                  15

Lys Lys Gly Leu Ser Lys Gly Cys Phe Gly Leu Lys Leu Asp Arg Ile
            20                  25                  30

Gly Ser Met Ser Gly Leu Gly Cys
            35                  40
```

<210> SEQ ID NO 159
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 159

```
Leu Leu Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
```

```
                    20                  25                  30

Ser Met Ser Gly Leu Gly Cys
        35

<210> SEQ ID NO 160
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 160

Leu Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
                20                  25                  30

Met Ser Gly Leu Gly Cys
        35

<210> SEQ ID NO 161
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 161

Glu His Pro Asn Ala Arg Lys Tyr Lys Gly Ala Asn Lys Lys Gly Leu
1               5                   10                  15

Ser Lys Gly Cys Phe Gly Leu Lys Leu Asp Arg Ile Gly Ser Met Ser
                20                  25                  30

Gly Leu Gly Cys
        35

<210> SEQ ID NO 162
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 162

His Pro Asn Ala Arg Lys Tyr Lys Gly Ala Asn Lys Lys Gly Leu Ser
1               5                   10                  15

Lys Gly Cys Phe Gly Leu Lys Leu Asp Arg Ile Gly Ser Met Ser Gly
                20                  25                  30

Leu Gly Cys
        35

<210> SEQ ID NO 163
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 163

Pro Asn Ala Arg Lys Tyr Lys Gly Ala Asn Lys Lys Gly Leu Ser Lys
1               5                   10                  15

Gly Cys Phe Gly Leu Lys Leu Asp Arg Ile Gly Ser Met Ser Gly Leu
                20                  25                  30

Gly Cys
```

<210> SEQ ID NO 164
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 164

Asn Ala Arg Lys Tyr Lys Gly Ala Asn Lys Lys Gly Leu Ser Lys Gly
1               5                   10                  15

Cys Phe Gly Leu Lys Leu Asp Arg Ile Gly Ser Met Ser Gly Leu Gly
            20                  25                  30

Cys

<210> SEQ ID NO 165
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 165

Ala Arg Lys Tyr Lys Gly Ala Asn Lys Lys Gly Leu Ser Lys Gly Cys
1               5                   10                  15

Phe Gly Leu Lys Leu Asp Arg Ile Gly Ser Met Ser Gly Leu Gly Cys
            20                  25                  30

<210> SEQ ID NO 166
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 166

Arg Lys Tyr Lys Gly Ala Asn Lys Lys Gly Leu Ser Lys Gly Cys Phe
1               5                   10                  15

Gly Leu Lys Leu Asp Arg Ile Gly Ser Met Ser Gly Leu Gly Cys
            20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 167

Lys Tyr Lys Gly Ala Asn Lys Lys Gly Leu Ser Lys Gly Cys Phe Gly
1               5                   10                  15

Leu Lys Leu Asp Arg Ile Gly Ser Met Ser Gly Leu Gly Cys
            20                  25                  30

<210> SEQ ID NO 168
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 168

Tyr Lys Gly Ala Asn Lys Lys Gly Leu Ser Lys Gly Cys Phe Gly Leu
1               5                   10                  15

Lys Leu Asp Arg Ile Gly Ser Met Ser Gly Leu Gly Cys

```
           20                  25

<210> SEQ ID NO 169
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 169

Lys Gly Ala Asn Lys Lys Gly Leu Ser Lys Gly Cys Phe Gly Leu Lys
 1               5                  10                  15

Leu Asp Arg Ile Gly Ser Met Ser Gly Leu Gly Cys
            20                  25

<210> SEQ ID NO 170
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 170

Gly Ala Asn Lys Lys Gly Leu Ser Lys Gly Cys Phe Gly Leu Lys Leu
 1               5                  10                  15

Asp Arg Ile Gly Ser Met Ser Gly Leu Gly Cys
            20                  25

<210> SEQ ID NO 171
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 171

Ala Asn Lys Lys Gly Leu Ser Lys Gly Cys Phe Gly Leu Lys Leu Asp
 1               5                  10                  15

Arg Ile Gly Ser Met Ser Gly Leu Gly Cys
            20                  25

<210> SEQ ID NO 172
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 172

Asn Lys Lys Gly Leu Ser Lys Gly Cys Phe Gly Leu Lys Leu Asp Arg
 1               5                  10                  15

Ile Gly Ser Met Ser Gly Leu Gly Cys
            20                  25

<210> SEQ ID NO 173
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 173

Lys Lys Gly Leu Ser Lys Gly Cys Phe Gly Leu Lys Leu Asp Arg Ile
 1               5                  10                  15

Gly Ser Met Ser Gly Leu Gly Cys
```

```
<210> SEQ ID NO 174
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 174

Lys Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 175
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 175

Leu Ser Lys Gly Cys Phe Gly Leu Lys Leu Asp Arg Ile Gly Ser Met
1               5                   10                  15

Ser Gly Leu Gly Cys
            20

<210> SEQ ID NO 176
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 176

Ser Lys Gly Cys Phe Gly Leu Lys Leu Asp Arg Ile Gly Ser Met Ser
1               5                   10                  15

Gly Leu Gly Cys
            20

<210> SEQ ID NO 177
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 177

Lys Gly Cys Phe Gly Leu Lys Leu Asp Arg Ile Gly Ser Met Ser Gly
1               5                   10                  15

Leu Gly Cys

<210> SEQ ID NO 178
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 178

Gly Cys Phe Gly Leu Lys Leu Asp Arg Ile Gly Ser Met Ser Gly Leu
1               5                   10                  15

Gly Cys
```

<210> SEQ ID NO 179
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 179

Gly Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 180
<211> LENGTH: 53
<212> TYPE: PRT
<213> ORGANISM: Artificial Sequence
<220> FEATURE:
<223> OTHER INFORMATION: Synthetic Polypeptide

<400> SEQUENCE: 180

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Asn
        35                  40                  45

Ser Gly Leu Gly Cys
    50

<210> SEQ ID NO 181
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 181

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
        35

<210> SEQ ID NO 182
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 182

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Asn
            20                  25                  30

Ser Gly Leu Gly Cys

<210> SEQ ID NO 183
<211> LENGTH: 38
<212> TYPE: PRT
<213> ORGANISM: Artificial Sequence
<220> FEATURE:
<223> OTHER INFORMATION: Sythetic Polypeptide

<400> SEQUENCE: 183

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
        35

<210> SEQ ID NO 184
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 184

Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25

<210> SEQ ID NO 185
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 185

Pro Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 186
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 186

Pro Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 187

<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 187

Pro Asn Ala Arg Lys Tyr Lys Gly Ala Asn Lys Lys Gly Leu Ser Lys
1               5                   10                  15

Gly Cys Phe Gly Leu Lys Leu Asp Arg Ile Gly Ser Met Ser Gly Leu
            20                  25                  30

Gly Cys

<210> SEQ ID NO 188
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 188

Pro Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 189
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 189

Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 190
<211> LENGTH: 54
<212> TYPE: PRT
<213> ORGANISM: Artificial Sequence
<220> FEATURE:
<223> OTHER INFORMATION: Synthetic Polypeptide

<400> SEQUENCE: 190

Met Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 191
<211> LENGTH: 39
<212> TYPE: PRT
<213> ORGANISM: Artificial Sequence
<220> FEATURE:
<223> OTHER INFORMATION: Synthetic Polypeptide

```
<400> SEQUENCE: 191

Met Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 192
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 192

Met Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 193
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 193

Met Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 194
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 194

Met Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 195
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 195

Met Gly Ser Ser His His His His His His Ser Ser Gly Leu Val Pro
1               5                   10                  15

Arg Gly Ser His Thr Gly Asp Asp Asp Asp Lys His Met Asp
```

20                  25                  30

<210> SEQ ID NO 196
<211> LENGTH: 142
<212> TYPE: PRT
<213> ORGANISM: Artificial Sequence
<220> FEATURE:
<223> OTHER INFORMATION: Synthetic Polypeptide

<400> SEQUENCE: 196

Met Val Leu Thr Lys Lys Leu Gln Asp Leu Val Arg Glu Val Cys
1               5                   10                  15

Pro Asn Glu Gln Leu Asp Glu Asp Val Glu Glu Met Leu Leu Gln Ile
            20                  25                  30

Ala Asp Asp Phe Ile Glu Ser Val Val Thr Ala Ala Cys Gln Leu Ala
        35                  40                  45

Arg His Arg Lys Ser Ser Thr Leu Glu Val Lys Asp Val Gln Leu His
    50                  55                  60

Leu Glu Arg Gln Trp Asn Met Trp Ile Met Gly Ser His His His
65                  70                  75                  80

His His His Ser Ser Gly Leu Val Pro Arg Gly Ser His Thr Gly Asp
                85                  90                  95

Asp Asp Asp Lys His Met Asp Pro Gly Gln Glu His Pro Asn Ala Arg
            100                 105                 110

Lys Tyr Lys Gly Ala Asn Lys Lys Gly Leu Ser Lys Gly Cys Phe Gly
        115                 120                 125

Leu Lys Leu Asp Arg Ile Gly Ser Met Ser Gly Leu Gly Cys
    130                 135                 140

<210> SEQ ID NO 197
<211> LENGTH: 72
<212> TYPE: PRT
<213> ORGANISM: Artificial Sequence
<220> FEATURE:
<223> OTHER INFORMATION: Synthetic Polypeptide

<400> SEQUENCE: 197

Val Leu Thr Lys Lys Leu Gln Asp Leu Val Arg Glu Val Cys Pro
1               5                   10                  15

Asn Glu Gln Leu Asp Glu Asp Val Glu Glu Met Leu Leu Gln Ile Ala
            20                  25                  30

Asp Asp Phe Ile Glu Ser Val Val Thr Ala Ala Cys Gln Leu Ala Arg
        35                  40                  45

His Arg Lys Ser Ser Thr Leu Glu Val Lys Asp Val Gln Leu His Leu
    50                  55                  60

Glu Arg Gln Trp Asn Met Trp Ile
65                  70

<210> SEQ ID NO 198
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 198

Pro Gly Gln Glu His Pro Asn Ala Arg
1               5

<210> SEQ ID NO 199
<211> LENGTH: 30

```
<212> TYPE: PRT
<213> ORGANISM: Artificial Sequence
<220> FEATURE:
<223> OTHER INFORMATION: Synthetic Polypeptide

<400> SEQUENCE: 199

Lys Tyr Lys Gly Ala Asn Lys Lys Gly Leu Ser Lys Gly Cys Phe Gly
1               5                   10                  15

Leu Lys Leu Asp Arg Ile Gly Ser Met Ser Gly Leu Gly Cys
            20                  25                  30

<210> SEQ ID NO 200
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 200

Gly Ala Asn Lys Pro
1               5

<210> SEQ ID NO 201
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 201

Gly Ala Asn Pro Lys
1               5

<210> SEQ ID NO 202
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 202

Gly Ala Asn Pro Gln
1               5

<210> SEQ ID NO 203
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 203

Gly Ala Asn Gln Lys
1               5

<210> SEQ ID NO 204
<211> LENGTH: 41
<212> TYPE: PRT
<213> ORGANISM: Triakis scyllium

<400> SEQUENCE: 204

Arg Leu Leu Lys Asp Leu Ser Asn Asn Pro Leu Arg Phe Arg Gly Arg
1               5                   10                  15

Ser Lys Lys Gly Pro Ser Arg Gly Cys Phe Gly Val Lys Leu Asp Arg
            20                  25                  30

Ile Gly Ala Met Ser Gly Leu Gly Cys
```

<210> SEQ ID NO 205
<211> LENGTH: 39
<212> TYPE: PRT
<213> ORGANISM: Triakis scyllium

<400> SEQUENCE: 205

Leu Lys Asp Leu Ser Asn Asn Pro Leu Arg Phe Arg Gly Arg Ser Lys
1               5                   10                  15

Lys Gly Pro Ser Arg Gly Cys Phe Gly Val Lys Leu Asp Arg Ile Gly
            20                  25                  30

Ala Met Ser Gly Leu Gly Cys
        35

<210> SEQ ID NO 206
<211> LENGTH: 38
<212> TYPE: PRT
<213> ORGANISM: Triakis scyllium

<400> SEQUENCE: 206

Lys Asp Leu Ser Asn Asn Pro Leu Arg Phe Arg Gly Arg Ser Lys Lys
1               5                   10                  15

Gly Pro Ser Arg Gly Cys Phe Gly Val Lys Leu Asp Arg Ile Gly Ala
            20                  25                  30

Met Ser Gly Leu Gly Cys
        35

<210> SEQ ID NO 207
<211> LENGTH: 22
<212> TYPE: PRT
<213> ORGANISM: Triakis scyllium

<400> SEQUENCE: 207

Gly Pro Ser Arg Gly Cys Phe Gly Val Lys Leu Asp Arg Ile Gly Ala
1               5                   10                  15

Met Ser Gly Leu Gly Cys
            20

<210> SEQ ID NO 208
<211> LENGTH: 41
<212> TYPE: PRT
<213> ORGANISM: Lamna ditropis

<400> SEQUENCE: 208

Arg Leu Leu Lys Asp Leu Ser Asn Asn Pro Leu Arg Phe Lys Gly Arg
1               5                   10                  15

Ser Lys Lys Gly Pro Ser Arg Gly Cys Phe Gly Val Lys Leu Asp Arg
            20                  25                  30

Ile Gly Ala Met Ser Gly Leu Gly Cys
        35                  40

<210> SEQ ID NO 209
<211> LENGTH: 39
<212> TYPE: PRT
<213> ORGANISM: Lamna ditropis

<400> SEQUENCE: 209

Leu Lys Asp Leu Ser Asn Asn Pro Leu Arg Phe Lys Gly Arg Ser Lys
1               5                   10                  15

Lys Gly Pro Ser Arg Gly Cys Phe Gly Val Lys Leu Asp Arg Ile Gly
            20                  25                  30

```
Ala Met Ser Gly Leu Gly Cys
        35

<210> SEQ ID NO 210
<211> LENGTH: 38
<212> TYPE: PRT
<213> ORGANISM: Lamna ditropis

<400> SEQUENCE: 210

Lys Asp Leu Ser Asn Asn Pro Leu Arg Phe Lys Gly Arg Ser Lys Lys
1               5                   10                  15

Gly Pro Ser Arg Gly Cys Phe Gly Val Lys Leu Asp Arg Ile Gly Ala
            20                  25                  30

Met Ser Gly Leu Gly Cys
        35

<210> SEQ ID NO 211
<211> LENGTH: 29
<212> TYPE: PRT
<213> ORGANISM: Lamna ditropis

<400> SEQUENCE: 211

Phe Lys Gly Arg Ser Lys Lys Gly Pro Ser Arg Gly Cys Phe Gly Val
1               5                   10                  15

Lys Leu Asp Arg Ile Gly Ala Met Ser Gly Leu Gly Cys
            20                  25

<210> SEQ ID NO 212
<211> LENGTH: 22
<212> TYPE: PRT
<213> ORGANISM: Lamna ditropis

<400> SEQUENCE: 212

Gly Pro Ser Arg Gly Cys Phe Gly Val Lys Leu Asp Arg Ile Gly Ala
1               5                   10                  15

Met Ser Gly Leu Gly Cys
            20

<210> SEQ ID NO 213
<211> LENGTH: 41
<212> TYPE: PRT
<213> ORGANISM: Squalus acanthias

<400> SEQUENCE: 213

Arg Leu Leu Gln Asp Leu Ser Asn Asn Pro Leu Arg Phe Lys Gly Arg
1               5                   10                  15

Ser Lys Lys Gly Pro Ser Arg Ser Cys Phe Gly Leu Lys Leu Asp Arg
            20                  25                  30

Ile Gly Ala Met Ser Gly Leu Gly Cys
        35                  40

<210> SEQ ID NO 214
<211> LENGTH: 22
<212> TYPE: PRT
<213> ORGANISM: Squalus acanthias

<400> SEQUENCE: 214

Gly Pro Ser Arg Ser Cys Phe Gly Leu Lys Leu Asp Arg Ile Gly Ala
1               5                   10                  15

Met Ser Gly Leu Gly Cys
            20
```

<210> SEQ ID NO 215
<211> LENGTH: 22
<212> TYPE: PRT
<213> ORGANISM: Oryzias latipes

<400> SEQUENCE: 215

Gly Trp Asn Arg Gly Cys Phe Gly Leu Lys Leu Asp Arg Ile Gly Ser
1               5                   10                  15

Met Ser Gly Leu Gly Cys
            20

<210> SEQ ID NO 216
<211> LENGTH: 24
<212> TYPE: PRT
<213> ORGANISM: Oryzias latipes

<400> SEQUENCE: 216

Pro Met Val Ala Gly Gly Cys Phe Gly Met Lys Met Asp Arg Ile
1               5                   10                  15

Gly Ser Ile Ser Gly Leu Gly Cys
            20

<210> SEQ ID NO 217
<211> LENGTH: 27
<212> TYPE: PRT
<213> ORGANISM: Arothron maculatus

<400> SEQUENCE: 217

Gly Arg Ser Ser Met Val Gly Gly Arg Gly Cys Phe Gly Met Lys Ile
1               5                   10                  15

Asp Arg Ile Gly Ser Ile Ser Gly Leu Gly Cys
            20                  25

<210> SEQ ID NO 218
<211> LENGTH: 22
<212> TYPE: PRT
<213> ORGANISM: Oryzias latipes

<400> SEQUENCE: 218

Gly Gly Met Arg Ser Cys Phe Gly Val Arg Leu Glu Arg Ile Gly Ser
1               5                   10                  15

Phe Ser Gly Leu Gly Cys
            20

<210> SEQ ID NO 219
<211> LENGTH: 22
<212> TYPE: PRT
<213> ORGANISM: Arothron maculatus

<400> SEQUENCE: 219

Gly Gly Leu Arg Ser Cys Phe Gly Val Arg Leu Ala Arg Ile Gly Ser
1               5                   10                  15

Phe Ser Gly Leu Gly Cys
            20

<210> SEQ ID NO 220
<211> LENGTH: 25
<212> TYPE: PRT
<213> ORGANISM: Oryzias latipes

<400> SEQUENCE: 220

Gly Gly Ser Thr Ser Arg Ser Gly Cys Phe Gly His Lys Met Asp Arg
1               5                   10                  15

```
Ile Gly Thr Ile Ser Gly Met Gly Cys
            20                  25

<210> SEQ ID NO 221
<211> LENGTH: 24
<212> TYPE: PRT
<213> ORGANISM: Arothron maculatus

<400> SEQUENCE: 221

Gly Gly Ser Ser Arg Ser Gly Cys Phe Gly His Lys Met Asp Arg Ile
1               5                   10                  15

Gly Thr Ile Ser Gly Met Gly Cys
            20

<210> SEQ ID NO 222
<211> LENGTH: 39
<212> TYPE: PRT
<213> ORGANISM: Ornithorhynchus anatinus

<400> SEQUENCE: 222

Leu Leu His Asp His Pro Asn Pro Arg Lys Tyr Lys Pro Ala Asn Lys
1               5                   10                  15

Lys Gly Leu Ser Lys Gly Cys Phe Gly Leu Lys Leu Asp Arg Ile Gly
            20                  25                  30

Ser Thr Ser Gly Leu Gly Cys
            35

<210> SEQ ID NO 223
<211> LENGTH: 22
<212> TYPE: PRT
<213> ORGANISM: Ornithorhynchus anatinus

<400> SEQUENCE: 223

Gly Leu Ser Lys Gly Cys Phe Gly Leu Lys Leu Asp Arg Ile Gly Ser
1               5                   10                  15

Thr Ser Gly Leu Gly Cys
            20

<210> SEQ ID NO 224
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 224

Gly Leu Ser Lys Gly Cys Phe Gly Leu Lys Leu Asp Arg Ile Gly Ala
1               5                   10                  15

Met Ser Gly Leu Gly Cys
            20

<210> SEQ ID NO 225
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 225

Gly Leu Ser Lys Gly Cys Phe Gly Leu Lys Leu Asp Arg Ile Gly Ser
1               5                   10                  15

Gln Ser Gly Leu Gly Cys
            20
```

<210> SEQ ID NO 226
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 226

```
Gly Leu Ser Lys Gly Cys Phe Gly Leu Lys Leu Asp Arg Ile Gly Ser
1               5                   10                  15

Ala Ser Gly Leu Gly Cys
            20
```

<210> SEQ ID NO 227
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 227

```
Ser Leu Arg Arg Ser Ser Cys Phe Gly Leu Lys Leu Asp Arg Ile Gly
1               5                   10                  15

Ser Met Ser Gly Leu Gly Cys
            20
```

<210> SEQ ID NO 228
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 228

```
Gly Leu Ser Lys Gly Cys Phe Gly Leu Lys Leu Asp Arg Ile Gly Ser
1               5                   10                  15

Met Ser Gly Leu Gly Cys Asn Ser Phe Arg Tyr
            20                  25
```

<210> SEQ ID NO 229
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 229

```
Cys Phe Gly Leu Lys Leu Asp Arg Ile Gly Ser Gln Ser Gly Leu Gly
1               5                   10                  15

Cys Asn Ser Phe Arg Tyr
            20
```

<210> SEQ ID NO 230
<211> LENGTH: 5
<212> TYPE: PRT
<213> ORGANISM: Artificial Sequence
<220> FEATURE:
<223> OTHER INFORMATION: Sythetnic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 230

```
Ile Glu Gly Arg Xaa
1               5
```

```
<210> SEQ ID NO 231
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 231

Asp Asp Asp Asp Lys Xaa
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 232

Glu Xaa Xaa Tyr Xaa Gln Gly
1               5

<210> SEQ ID NO 233
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 233

Val Asp Asp Arg
1

<210> SEQ ID NO 234
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 234

Gly Ser Asp Arg
1

<210> SEQ ID NO 235
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 235

Ile Thr Asp Arg
1
```

```
<210> SEQ ID NO 236
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 236

Pro Gly Asp Arg
1

<210> SEQ ID NO 237
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 237

Ala Phe Leu Gly Pro Gly Asp Arg
1               5
```

VARIANTS OF C-TYPE NATRIURETIC PEPTIDE

CROSS-REFERENCE TO RELATED APPLICATIONS

The present application claims the priority and benefit of U.S. Provisional Application No. 61/254,563, filed on Oct. 23, 2009, and U.S. Provisional Application No. 61/180,112, filed on May 20, 2009, the disclosure of each of which is incorporated herein by reference in its entirety.

FIELD OF THE DISCLOSURE

The field of the disclosure relates, in general, to variants of C-type natriuretic peptide (CNP), compositions comprising CNP variants, methods of making CNP variants, and methods of using CNP variants to treat disorders responsive to CNP, including but not limited to bone-related disorders such as skeletal dysplasias (e.g., achondroplasia) and vascular smooth muscle disorders.

BACKGROUND OF THE DISCLOSURE

The natriuretic peptide family consists of three structurally related peptides: atrial natriuretic peptide (ANP) (Genbank Accession No. NP_006163, for the ANP precursor protein, NPPA), brain natriuretic peptide (BNP) (GenBank Accession No. NP_002512, for the BNP precursor protein, NPPB), and C-type natriuretic peptide (CNP) (Biochem. Biophys. Res. Commun., 168: 863-870 (1990) (GenBank Accession No. NP_077720, for the CNP precursor protein, NPPC) (J. Hypertens., 10: 907-912 (1992)). These small, single chain peptides (ANP, BNP, CNP) have a 17-amino acid loop structure (Levin et al., N. Engl. J. Med., 339: 863-870 (1998)) and have important roles in multiple biological processes. ANP and BNP bind to and activate the natriuretic peptide receptor A (NPR-A), also termed guanalyl cyclase A (GC-A), resulting in higher intracellular cyclic guanosine monophosphate (cGMP) levels. Likewise, CNP interacts with NPR-B (GC-B) to stimulate the generation of cGMP (J. Hypertens., 10: 1111-1114 (1992)). A third type of receptor, NPR-C, binds each of the natriuretic peptides with high affinity and functions primarily to capture the peptides from the extracellular compartment and deposit the peptides into lysosomes, where they are degraded (Science, 238: 675-678 (1987)). ANP and BNP are produced primarily within the muscle cells of the heart, and are believed to have important roles in cardiovascular homeostasis (Science, 252: 120-123 (1991)). CNP is expressed more widely, including in the central nervous system, reproductive tract, bone and endothelium of blood vessels (Hypertension, 49: 419-426 (2007)).

In humans, CNP is initially produced from the natriuretic peptide precursor C(NPPC) gene as a single chain 126-amino acid pre-pro polypeptide (Biochem. Biophys. Res. Commun., 168: 863-870 (1990)). Removal of the signal peptide yields pro-CNP, and further cleavage by the endoprotease furin generates an active 53-amino acid peptide (CNP-53), which is secreted and cleaved again by an unknown enzyme to produce the mature 22-amino acid peptide (CNP-22) (Wu, J. Biol. Chem. 278: 25847-852 (2003)). CNP-53 and CNP-22 differ in their distribution, with CNP-53 predominating in tissues, while CNP-22 is mainly found in plasma and cerebrospinal fluid (J. Alfonzo, Recept. Signal. Transduct. Res., 26: 269-297 (2006)). The predominant CNP form in cartilage is unknown. Both CNP-53 and CNP-22 bind similarly to NPR-B. Furthermore, they both induce cGMP production in a dose-dependent and similar fashion (V T Yeung, Peptides, 17: 101-106 (1996)).

Natural CNP gene and polypeptide have been previously described. U.S. Pat. No. 5,352,770 discloses isolated and purified CNP-22 from porcine brain identical in sequence to human CNP and its use in treating cardiovascular indications. U.S. Pat. No. 6,034,231 discloses the human gene and polypeptide of proCNP (126 amino acids) and the human CNP-53 gene and polypeptide.

Clearance of CNP from the extracellular space occurs through the action of membrane-bound neutral endopeptidase (NEP), which rapidly degrades CNP (Biochem. J., 291 (Pt 1): 83-88 (1993)), and through NPR-C, which binds to and deposits CNP into lysosomes, where CNP is degraded. CNP has been shown to have an in vivo half-life of 2.6 min in the normal human (J. Clin. Endocrinol. Metab., 78: 1428-35 (1994)). The low plasma concentration of CNP (J. Bone Moner. Res., 19 (Suppl. 1) S20 (2004)) and its co-expression with NPR-B in a number of tissues suggests that CNP functions primarily through an autocrine/paracrine mechanism.

As stated above, CNP binds to and activates natriuretic peptide receptor B (NPR-B), also termed guanylyl cyclase B (GC-B), resulting in higher intracellular cyclic guanosine monophosphate (cGMP) levels. Downstream signaling mediated by cGMP generation influences a diverse array of biological processes that include endochondral ossification. Accordingly, elevated or depressed levels of any of the components in this pathway may lead to aberrant bone growth. For example, knockout of either CNP or NPR-B in mouse models results in animals having a dwarfed phenotype with shorter long bones and vertebrae. Mutations in human NPR-B that block proper CNP signaling have been identified and result in dwarfism (Olney, et al., J. Clin. Endocrinol. Metab. 91(4): 1229-1232 (2006); Bartels, et al., Am. J. Hum. Genet. 75: 27-34 (2004)). In contrast, mice engineered to produce elevated levels of CNP display elongated long bones and vertebrae.

Achondroplasia is a result of an autosomal dominant mutation in the gene for fibroblast growth factor receptor 3 (FGFR-3), which causes an abnormality of cartilage formation. FGFR-3 normally has a negative regulatory effect on chondrocyte growth, and hence bone growth. In achondroplasia, the mutated form of FGFR-3 is constitutively active, which leads to severely shortened bones. Both chondrocyte proliferation and differentiation appear to be disturbed, leading to remarkably short growth plate cartilage (P. Krejci et al., J. Cell Sci. 118: 5089-5100 (2005)). Endochondral ossification is the process that governs longitudinal long-bone growth. There are four zones of the growth plate—resting, proliferative, hypertrophic and zone of calcification. In the growth plate, NPR-B is expressed by proliferative cells while NPR-C is expressed by hypertrophic cells (Yamashite et al., J. Biochem. 127: 177-179 (2000)). In normal endochondral bone growth, chondrocytes organize in columns and proliferate in the proliferative zone of the growth plate. These columns are disorganized in achondroplasia patients. Additionally, the hypertrophic zone is where the cells become large and eventually apoptose (lyse), leading to osteocyte invasion and mineralization. The hypertrophic chondrocytes and the overall size of the zone are much smaller in achondroplasia patients than in normal patients. CNP is an agonist for NPR-B, a positive regulator of chondrocyte and bone growth. Downstream signaling of CNP/NPR-B inhibits the FGFR-3 pathway at the level of mitogen-activated protein kinase (MAP K). Inhibition at MAP K promotes proliferation and differentiation of the chondrocytes in the proliferative and hypertrophic zones of the growth plate, resulting in bone growth.

In humans activating mutations of FGFR-3 are the primary cause of genetic dwarfism. Mice having activated FGFR-3 serve as a model of achondroplasia, the most common form of the skeletal dysplasias, and overexpression of CNP rescues these animals from dwarfism. Accordingly, CNP and functional variants of CNP are potential therapeutics for treatment of the various skeletal dysplasias.

Therapeutic use of CNP is currently limited by its short plasma half-life, which has been shown to be 2.6 minutes in vivo in humans (J. Clin. Endocrinol. Metab., 78: 1428-35 (1994)). To increase CNP concentration above intrinsic levels (about 5 pM) typically found in human plasma, continuous infusion has been necessary in all human and animal studies using systemically administered CNP. A CNP variant having a longer in vivo serum half-life and exhibiting similar or improved activity to that of wild-type CNP is important for a sustainable therapeutic strategy. Two mechanisms by which the half-life of CNP is reduced in human plasma are degradation by neutral endopeptidase (NEP) and clearance by natriuretic peptide receptor C(NPR-C) (Growth Horm. & IGF Res., 16: S6-S14 (2006)). Modifications of peptides reportedly can improve resistance to endopeptidase and exopeptidase cleavage (Amino Acids, 30: 351-367 (2006); Curr. Opin. Biotech., 17: 638-642 (2006)).

The biological activities of various analogs and derivatives of CNP have been evaluated. By substituting S-methyl Cys in place of both $Cys_6$ and $Cys_{22}$, cyclization of the peptide via a Cys6-Cys22 disulfide linkage was reportedly shown to be important for the activity of CNP in stimulating cGMP formation (Biochem. Biophys. Res. Comm., 183: 964-969 (1992), also using alanine scanning to identify amino acids important for CNP functionality). A significant additional enhancement of activity reportedly results from the combined presence of the amino acids $Leu_9$, $Lys_{10}$, and $Leu_{11}$. U.S. Pat. No. 5,434,133 describes CNP analogs comprising CNP-22 with substitutions at amino acid position 6, 7, 9, 11, or 22, wherein the amino acid is selected from Cys or Pmp (pentacyclomercaptopropionic acid) at position 6, Phe, 4-chloro-Phe, 4-fluoro-Phe, 4-nitro-Phe, or Cha (3-cyclohexyl-Ala) at position 7, Gly, Val, Aib, or tLeu at position 9, Leu or Ile at position 11, and Cys or Pmp at position 22.

U.S. Patent Publication No. 2004/0138134 (now U.S. Pat. No. 7,276,481) describes CNP variants comprising amino acids $Cys_6$ to $Cys_{22}$ of CNP-22 ("CNP-17") which include at least one substitution for another natural amino acid at position 9, 10, 11, 16, 17, 19, or 20, CNP variants with insertions and deletions, such as addition of a His residue at the reported primary site of NEP cleavage, between $Cys_6$ and $Phe_7$, and methods of using such variants for increasing the size of a bone growth plate in abnormal bone and elongation of an abnormal bone. However, no significant gains in activity as measured by cGMP production were obtained for these variants, and activity was diminished for nearly all of the variants, as observed in an in vitro cell-based method (Example 7). Further no supportive data, such as for example in vitro stability or in vivo determination of improved pharmacokinetics (PK) were provided to substantiate the asserted NEP resistance and NPR-C resistance of the CNP analogs. U.S. Pat. No. 6,743,425 discloses substances for treating achondroplasia which activate NPR-B/GC-B and are peptides or low molecular weight compounds, including the C-type natriuretic peptides CNP-22 and CNP-53. PCT Publication No. WO 94/20534 discloses a chimera of CNP-22 and the 5-amino acid C-terminus of ANP designated as the vasonatrin peptide (VNP), a limited number of amino acid substitutions and cyclic chimeric peptides that result from formation of a disulfide or double bond.

Approaches for improving the half-life of other natriuretic peptide family members include decreasing the affinity of ANP for NPR-C (U.S. Pat. No. 5,846,932), utilizing pentapeptide antagonists of NPR-C (WO 00/61631), and co-administering NEP inhibitors such as thiorphan and candoxatril (Clin. Exp. Pharma. Physiol., 25: 986-991 (1997), Hyperten., 30: 184-190 (1997)). WO 2004/047871 describes conjugates of BNP and BNP variants to polyalkylene glycol moieties, sugar moieties, polysorbate moieties, polycationic moieties, and other hydrophilic polymer moieties that reportedly exhibit improved half-life in circulation and reportedly are useful for the treatment of acute congestive heart failure.

There have been no published reports, however, on a successful strategy for making CNP resistant to NEP while retaining its functionality.

SUMMARY OF THE DISCLOSURE

The present disclosure relates to variants of C-type natriuretic peptide (CNP) which are useful in the treatment of bone-related disorders (e.g., achondroplasia) and vascular smooth muscle disorders. The disclosure encompasses CNP variants having increased serum half-life, e.g. as a result of reduced ability to bind to neutral endopeptidase (NEP), greater resistance to proteolysis by NEP and/or reduced affinity to the clearance natriuretic peptide receptor C(NPR-C), while retaining the functionality of CNP.

The wild-type sequence of human CNP-22 (referred to herein as "hCNP22", "wtCNP22" or "CNP22") is set forth below:

```
                                          (SEQ ID NO: 1)
(N-terminus) Gly₁-Leu₂-Ser₃-Lys₄-Gly₅-Cys₆-Phe₇-
Gly₈-Leu₉-Lys₁₀-Leu₁₁-Asp₁₂-Arg₁₃-Ile₁₄-Gly₁₅-
Ser₁₆-Met₁₇-Ser₁₈-Gly₁₉-Leu₂₀-Gly₂₁-Cys₂₂.
```

Positions 6 to 22 of CNP22 form a cyclic domain by means of a disulfide bond between Cys6 and Cys22. The 17-amino acid cyclic structure has been shown to be important for binding of CNP to NPR-B (Schiller, Biochem. Biophys. Res. Commun., 138: 880-886 (1986)). The amino acid sequence of positions 6 to 22 of CNP22 is referred to herein as "CNP17" (SEQ ID NO: 2).

CNP is susceptible to NEP cleavage at a number of sites: Cys6-Phe7, Gly8-Leu9, Lys10-Leu11, Arg13-Ile14, Ser16-Met17 and Gly19-Leu20. In one embodiment, the disclosure encompasses a CNP variant that is (1) modified to increase its overall size or molecular weight, e.g., to a range from about 2.6 kDa or 2.8 kDa to about 4 kDa, 4.2 kDa, 4.4 kDa, 4.6 kDa, 4.8 kDa, 5 kDa, 5.2 kDa, 5.4 kDa, 5.6 kDa, 5.8 kDa, 6 kDa, 6.2 kDa, 6.4 kDa, or to about 7 kDa, 7.2 kDa or about 8.2 kDa, and/or (2) modified at certain amino acid positions to reduce its susceptibility to NEP cleavage at 1, 2, 3, 4, 5 or all 6 of the sites listed above. The size or molecular weight of the CNP variant can be increased by various means, e.g., by conjugating additional amino acids and/or other kinds of chemical (e.g., natural or synthetic polymeric) groups to the peptide sequence at, e.g., the N-terminus, the C-terminus and/or side chain(s), and/or by using natural amino acids, unnatural amino acids, or peptidomimetics with bulkier side chains. The CNP variant is optionally further conjugated to other functional or structural moieties. Optionally in combination with any of the embodiments described herein, mutation(s) (e.g., substitution(s), addition(s), and/or deletion(s))

may be introduced to certain position(s) of CNP22 to reduce the CNP variants' affinity to NPR-C. Further modifications may be made without affecting NEP resistance or CNP activity, e.g., conservative substitutions, or other modifications known in the art.

In one embodiment, the CNP variant is represented by the general formula: (x)-Gly$_1$-Leu$_2$-Ser$_3$-Lys$_4$-Gly$_5$-Cys$_6$-Phe$_7$-Gly$_8$-Leu$_9$-Lys$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 5), wherein:

the CNP variant comprises one or more modified amino acids, which may result in modified peptide bonds (e.g., through use of peptide bond isosteres), at a position corresponding to one or more of the following CNP residues: Gly1, Lys4, Gly5, Cys6, Phe7, Gly8, Leu9, Lys10, Leu11, Ile14, Gly15, Ser16, Met17, Gly19, Leu20 and Gly21; and (x) and (z) independently may be absent or may be an amino acid sequence derived from a natriuretic polypeptide (e.g., NPPC, ANP, BNP) or a non-natriuretic polypeptide (e.g., human serum albumin (HSA), IgG, etc.).

In an embodiment, the CNP variant includes: (1) a modification at an amino acid position corresponding to one of positions 6, 7 or 8 (Cys6, Phe7 or Gly8) of CNP22, (2) optionally deletion, addition and/or substitution of any or all of the amino acids at positions 1-5 (Gly1, Leu2, Ser3, Lys4, and Gly5) and (3) optionally up to 1, 2, 3, 4, 5, 6, 7, 8, 9 or 10 further modifications (deletions, additions and/or substitutions) at positions corresponding to positions 6-22, of which 1, 2, 3, 4, 5, 6, 7, 8, 9 or 10 may be conservative substitutions or other substitutions described herein or known in the art.

It is understood that a reference to a particular amino acid position by number (e.g. position 7 of CNP22) refers to the corresponding amino acid position in any CNP variant, even if the number of the position in that CNP variant has changed due to preceding insertions or deletions. For example, a reference to "position 7" or "Phe7" would mean the corresponding position 2 for a CNP variant in which the first five amino acids had been deleted. Similarly, a reference to "position 7" would mean the corresponding position 8 for a CNP variant in which one amino acid had been added to the N-terminus.

In any of the embodiments described herein, the CNP variant may be cyclized through a covalent bond between positions corresponding to 6 and 22 of CNP22. It is contemplated that the covalent bond is formed using any methods known in the art. In another embodiment, the CNP variant may be cyclized through a covalent bond formed between an amino acid at or toward the N-terminus and an amino acid at or toward the C-terminus (referred to as "terminal" amino acids for this purpose) of the peptide. In one embodiment, the covalent bond is formed between the side chains of the two terminal amino acids or the amino acids at positions corresponding to 6 and 22 of CNP22. In another embodiment, the covalent bond is formed between the side chain of one terminal amino acid and the terminal group of the other terminal amino acid, or between the terminal groups of each terminal amino acid. For example, head-to-tail, side chain-to-side chain, side chain-to-head, or side chain-to-tail bonds are possible for the covalent bond formed between the terminal amino acids or between the amino acids at positions corresponding to 6 and 22 of CNP22.

In one embodiment, the disclosure provides a CNP variant having reduced affinity to NEP, and/or greater resistance to cleavage by NEP and/or increased in vivo serum half-life, while retaining functionality of CNP (e.g., stimulation of cGMP production). NEP preferably recognizes substrates smaller than about 3 kDa, due to the limited size of its active site cavity (Oefner, J. Mol. Biol., 296: 341-349 (2000)). In an embodiment, the CNP variants are modified to increase their overall molecular weight to a range from about 2.6 or 2.8 kDa to about 4, 4.6, 5, 5.2, 5.8, 6, 6.4 or 7 kDa, e.g., by adding about 0.6 to about 5 kDa of amino acids, hydrophilic or water-soluble polymers, hydrophobic acids (including fatty acids), and/or carbohydrates. In specific exemplary embodiments, the CNP variants have a molecular weight between about 2.6 kDa and about 7 kDa, or between about 2.8 kDa and 6 kDa, or between about 2.8 kDa and about 5.8 kDa. In certain embodiments, at least about 0.6, 0.8, 1, 1.2, 1.4, 1.6 or 1.8 kDa, or up to 2, 2.2, 2.4, 2.6, 2.8, 3, 3.2, 3.4, 3.6, 3.8, 4, 4.2, 4.4, 4.6, 4.8 or 5 kDa are added, to increase the total molecular weight of the CNP variant, e.g., to a range from about 2.6 or 2.8 kDa up to about 4 kDa, 4.2 kDa, 4.4 kDa, 4.6 kDa, 4.8 kDa, 5 kDa, 5.2 kDa, 5.4 kDa, 5.6 kDa, 5.8 kDa, 6 kDa, 6.2 kDa, 7.2 kDa, 8.2 kDa or higher. In some embodiments, such CNP variants comprise an amino acid sequence at least about 70%, 75%. 80%, 85%, 90%, or 95% identical or homologous to amino acids 6-22 of CNP22. In other embodiments, such CNP variants comprise a substitution, insertion or deletion of 1, 2, 3, 4, 5, 6 or 7 amino acids with another natural or unnatural amino acid or peptidomimetic. While both conservative and non-conservative substitutions or insertions are envisioned at any position, introduction of modifications may commence, e.g., by conservative substitutions in regions that have been identified in the art as involved in CNP activity or NPR-B binding, while non-conservative substitutions may be made in those regions that have been previously shown to be tolerant of modification.

In another embodiment, the CNP variants comprise a CNP having an intact cyclized portion between Cys6 and Cys22, and N-terminal and/or C-terminal tails that contain about 1-40, 1-20, 5-40, 5-35, 10-35, 15-35, 5-31, 10-31, or 15-31 amino acids and are fragments derived from a CNP polypeptide and/or a non-CNP polypeptide. In an embodiment, such CNP variants have a molecular weight in a range from about 2.8 kDa to about 4, 4.6, 5, 5.2, 5.8, 6, 6.4 or 7 kDa. Non-limiting examples of such CNP variants include wild-type CNP22 or CNP22 with one or more amino acid substitutions (e.g., a K4R substitution), having an N-terminal and/or C-terminal extension derived from natriuretic peptide precursor sequences (e.g., ANP, BNP or CNP) from human or other species, a natriuretic peptide precursor C (NPPC) variant with amino acid substitutions, additions and/or deletions (e.g., the CNP variants may be truncations of CNP-53 which result in peptides with a molecular weight between about 2.8 kDa and 5.8 kDa), or other non-CNP polypeptides such as, e.g., serum albumin or IgG protein (e.g., the CNP variants may be CNP chimeras containing fragments of serum albumin or IgG from human or other species).

In one embodiment, CNP variants having a total mass characterized by the ranges described generally herein, e.g., from about 2.6 kDa or 2.8 kDa to about 6 or 7 kDa, designed for increased resistance to NEP degradation, are represented by the general formula:

(x)-Gly$_1$-Leu$_2$-Ser$_3$-(b)$_4$-Gly$_5$-Cys$_6$-Phe$_7$-Gly$_8$-Leu$_9$-(h)$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 6), wherein:

(x) is a synthetic or natural polymeric group, or a combination thereof, wherein a non-limiting example of a synthetic polymeric group is polyethylene glycol (PEG, also called polyethylene oxide (PEO)), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histidine-rich glycoproteins, fibronectin, fibrinogen, zinc finger-containing polypeptides, osteocrin or fibroblast growth factor 2 (FGF2);

(z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG); and (b) and (h) independently may each be the wild type Lys at that position or may be replaced with a conservative amino acid substitution or any natural or unnatural amino acid or peptidomimetic that does not have a reactive primary amine on a side chain, including but not limited to Arg, Gly, 6-hydroxy-norleucine, citrulline (Cit), Gln, Glu or Ser. In one embodiment, (b) is Arg. In another embodiment, for improved NEP resistance, (b) is not Gly. In yet another embodiment, (h) is not Arg.

Non-limiting examples of amino acid sequences derived from NPPC or variants thereof include:

Arg,

Glu-Arg,

```
                                            (SEQ ID NO: 7)
Gly-Ala-Asn-Lys-Lys, (SEQ ID NO: 8)
Gly-Ala-Asn-Arg-Arg, (SEQ ID NO: 9)
Gly-Ala-Asn-Pro-Arg, (SEQ ID NO: 10)
Gly-Ala-Asn-Gln-Gln, (SEQ ID NO: 11)
Gly-Ala-Asn-Ser-Ser, (SEQ ID NO: 12)
Gly-Ala-Asn-Arg-Gln, (SEQ ID NO: 13)
Gly-Ala-Asn-Arg-Met, (SEQ ID NO: 14)
Gly-Ala-Asn-Arg-Thr, (SEQ ID NO: 15)
Gly-Ala-Asn-Arg-Ser, (SEQ ID NO: 16)
Ala-Ala-Trp-Ala-Arg-Leu-Leu-Gln-Glu-His-Pro-Asn-
Ala, (SEQ ID NO: 17)
Ala-Ala-Trp-Ala-Arg-Leu-Leu-Gln-Glu-His-Pro-Asn-
Ala-Arg, (SEQ ID NO: 18)
Asp-Leu-Arg-Val-Asp-Thr-Lys-Ser-Arg-Ala-Ala-Trp-
Ala-Arg, (SEQ ID NO: 19)
Gln-Glu-His-Pro-Asn-Ala-Arg-Lys-Tyr-Lys-Gly-Ala-
Asn-Lys-Lys, (SEQ ID NO: 20)
Gln-Glu-His-Pro-Asn-Ala-Arg-Lys-Tyr-Lys-Gly-Ala-
Asn-Arg-Arg, (SEQ ID NO: 21)
Asp-Leu-Arg-Val-Asp-Thr-Lys-Ser-Arg-Ala-Ala-Trp-
Ala-Arg-Leu-Leu-Gln-Glu-His-Pro-Asn-Ala-Arg-Lys-
Tyr-Lys-Gly-Ala-Asn-Lys-Lys, and
                                            (SEQ ID NO: 22)
Asp-Leu-Arg-Val-Asp-Thr-Lys-Ser-Arg-Ala-Ala-Trp-
Ala-Arg-Leu-Leu-Gln-Glu-His-Pro-Asn-Ala-Arg-Lys-
Tyr-Lys-Gly-Ala-Asn-Arg-Arg.
```

Non-limiting examples of amino acid sequences derived from non-CNP polypeptides such as, e.g., ANP, BNP, serum albumin and IgG include:

```
                                            (SEQ ID NO: 23)
Ser-Leu-Arg-Arg-Ser-Ser;

(SEQ ID NO: 24)
Asn-Ser-Phe-Arg-Tyr;

(SEQ ID NO: 25)
Ser-Pro-Lys-Met-Val-Gln-Gly-Ser-Gly;

(SEQ ID NO: 26)
Met-Val-Gln-Gly-Ser-Gly;

(SEQ ID NO: 27)
Lys-Val-Leu-Arg-Arg-Tyr;

(SEQ ID NO: 28)
Lys-Val-Leu-Arg-Arg-His;

(SEQ ID NO: 29)
Gly-Gln-His-Lys-Asp-Asp-Asn-Pro-Asn-Leu-Pro-Arg;

(SEQ ID NO: 30)
Gly-Val-Pro-Gln-Val-Ser-Thr-Ser-Thr;

(SEQ ID NO: 31)
Gly-Glu-Arg-Ala-Phe-Lys-Ala-Trp-Ala-Val-Ala-Arg-
Leu-Ser-Gln;
and
                                            (SEQ ID NO: 32)
Gly-Gln-Pro-Arg-Glu-Pro-Gln-Val-Tyr-Thr-Leu-Pro-
Pro-Ser.
```

In an embodiment, the N-terminus and/or C-terminus of CNP22 or a variant thereof independently may be conjugated to an amino acid extension containing 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids. In one embodiment, the amino acid extension is derived from NPPC, CNP53, ANP or BNP. In a specific embodiment, the amino acid extension is Gln-Glu-His-Pro-Asn-Ala-Arg-Lys-Tyr-Lys-Gly-Ala-Asn-Lys-Lys (SEQ ID NO: 33). In a related embodiment, this 15-amino acid extension is added to the N-terminus to provide a CNP variant of the formula Gln-Glu-His-Pro-Asn-Ala-Arg-Lys-Tyr-Lys-Gly-Ala-Asn-Lys-Lys-Gly$_1$-Leu$_2$-Ser$_3$-(b)$_4$-Gly$_5$-Cys$_6$-Phe$_7$-Gly$_8$-Leu$_9$-(h)$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 34).

In one embodiment, the CNP variants comprise wtCNP22 or a variant thereof (e.g., one having addition(s), deletion(s), and/or substitution(s) such as, e.g., a K4R substitution) (SEQ ID NO: 35) conjugated at the N-terminus and/or C-terminus to a hydrophilic polymer (e.g., PEG) to increase their overall molecular size to a range from about 2.6 kDa or 2.8 kDa to about 4, 5, 6 or 7 kDa. Such CNP variants are optionally further conjugated at the N-terminus and/or C-terminus to a polymeric group comprising, e.g., amino acids, carbohydrates, hydrophobic acids and/or phospholipids, a non-limiting example of which is an N-terminal amino acid extension containing 1 to 35, or 5 to 31, amino acids. In an embodiment, a hydrophilic polymeric (e.g., PEG) moiety of at least about 0.4, 0.6, 0.8, 1, 1.2, 1.4, 1.6 or 1.8 kDa, or up to about 2, 2.2, 2.4, 2.6, 2.8, 3, 3.2, 3.4, 3.6, 3.8, 4, 4.2, 4.4, 4.6, 4.8 or 5 kDa, is added to the N-terminus and/or C-terminus of wtCNP22 or a variant thereof.

As shown herein, conjugation of a hydrophilic or water-soluble PEG (or PEO) polymer of about 0.6 kDa or more to CNP22 or variants thereof generally increases resistance to NEP cleavage markedly. However, addition of PEG, even as small as 0.6 kDa, to wtCNP22 may reduce CNP functionality (e.g., stimulation of cGMP signaling), and addition of greater than about 2 or 3 kDa of PEG to CNP22 or variants thereof may reduce CNP functional activity in a size-dependent manner. But CNP functionality (at least comparable to that of wtCNP22) is retained when a PEG (or PEO) polymer of about 0.6 kDa to about 1.2 kDa, or potentially to about 2 kDa, is conjugated to a CNP variant having an N-terminal amino acid extension in which at least one relatively large amino acid that may potentially be positively charged under physiological conditions (e.g., arginine) immediately precedes the position corresponding to Gly1 of CNP22, such as, e.g., GANRR-CNP22(K4R) (SEQ ID NO: 36), GANPR-CNP22(K4R) (SEQ ID NO: 37), ER-CNP22 (SEQ ID NO: 38), ER-CNP22 (K4R) (SEQ ID NO: 39), R-CNP22 (SEQ ID NO: 40) and R-CNP22(K4R) (SEQ ID NO: 41).

Accordingly, in one embodiment, PEGylated CNP variants comprise at the N-terminus of CNP22 or a variant thereof (e.g., one having a K4R substitution) an amino acid extension containing at least 1, 2, 3, 4 or 5 amino acids, wherein the PEG polymer is conjugated to the N-terminus of the amino acid-extended CNP variant to result in a total mass characterized by the ranges described generally herein, e.g., from about 2.6 kDa or 2.8 kDa to about 6 or 7 kDa for increased resistance to NEP cleavage. In an embodiment, for enhanced CNP functionality, such pegylated, amino acid-extended CNP variants contain at least one relatively large natural or unnatural amino acid that may potentially be positively charged under physiological conditions, immediately preceding the position corresponding to Gly1 of CNP22. In a specific embodiment, the pegylated, amino acid-extended CNP variants contain at least one arginine residue immediately preceding the position corresponding to Gly1 of CNP22.

In addition to CNP variants conjugated at the N-terminus and/or C-terminus to a hydrophilic or water-soluble polymer such as, e.g., PEG (or PEO), the disclosure encompasses CNP variants conjugated to such a polymer at an internal site. For purposes of brevity here, PEG (or PEO) will be used as a representative example of a hydrophilic or water-soluble polymer. Various sites of PEGylation of a CNP variant are possible, including but not limited to: (1) PEGylation only at the N-terminus; (2) PEGylation only at the C-terminus; (3) PEGylation only at an internal site (e.g., Lys4); (4) PEGylation at both the N-terminus and the C-terminus; (5) PEGylation at the N-terminus and an internal site; and (6) PEGylation at the C-terminus and an internal site. For increased resistance to NEP degradation and retention of CNP functionality, in certain embodiments the total mass of PEGylated CNP variants is characterized by the ranges described generally herein, e.g., in the range from about 2.6 kDa or 2.8 kDa to about 4, 5, 6 or 7 kDa. In a particular embodiment, CNP17, CNP22, CNP37 (defined below) or variants thereof (including those having amino acid additions, substitutions and/or deletions) are PEGylated only at the N-terminus. In another embodiment, the CNP variants are PEGylated only at an internal site (e.g., Lys4). In yet another embodiment, the CNP variants are PEGylated at the N-terminus and an internal site (e.g., Lys4). In still another embodiment, for better functionality the CNP variants are not PEGylated at a site (e.g., Lys10) within the cyclic domain (corresponding to Cys6 to Cys22 of CNP22). To prevent PEGylation at an internal site, Lys4 and/or Lys10 can be substituted with a natural or unnatural amino acid or peptidomimetic that does not contain a reactive primary amino group on a side chain, such as, e.g., Gly, Ser, Arg, Asn, Gln, Asp, Glu or citrulline (Cit). In a particular embodiment, Lys4 and/or Lys10 are replaced with Arg. In another embodiment, Lys10 is not replaced with Arg.

The disclosure contemplates use of hydrophilic or water soluble polymers (e.g., PEG molecules) that may vary in type (e.g., homopolymer or copolymer; random, alternating or block copolymer; linear or branched; monodispersed or polydispersed), linkage (e.g., hydrolysable or stable linkage such as, e.g., amide, imine, aminal, alkylene, or ester bond), conjugation site (e.g., at the N-terminus and/or C-terminus, preferably not at any of the residues in the cyclized region of CNP (corresponding to residues 6-22 of CNP22)), and length (e.g., from about 0.2, 0.4 or 0.6 kDa to about 2, 3, 4 or 5 kDa). The hydrophilic or water-soluble polymer can be conjugated to the CNP peptide by means of N-hydroxy succinimide (NHS)- or aldehyde-based chemistry or other chemistry, as is known in the art. Such CNP variants can be generated using, e.g., wtCNP-22 (2.2 kDa), CNP-17 retaining only the cyclized region (residues 6-22) of wtCNP22, CNP variants having an amino acid extension at the N-terminus and/or C-terminus of CNP22, or variants with amino acid substitutions, additions and/or deletions, for example, GANRR-CNP22(K4R) (SEQ ID NO: 36), GANPR-CNP22(K4R) (SEQ ID NO: 37), R-CNP22 (SEQ ID NO: 40), R-CNP22(K4R) (SEQ ID NO: 41), ER-CNP22 (SEQ ID NO: 38) and ER-CNP22(K4R) (SEQ ID NO: 39). In an embodiment, the PEG-CNP variants having a total mass characterized by the ranges described generally herein, e.g., from about 2.6 kDa or 2.8 kDa to about 6 or 7 kDa, contain a monodispersed, linear PEG (or PEO) group conjugated at the N-terminus and/or C-terminus via NHS- or aldehyde-based chemistry, or a two-arm or three-arm branched PEG group conjugated at the N-terminus and/or C-terminus via NHS-based chemistry. The disclosure further contemplates negatively charged PEG-CNP variants designed for reduced renal clearance, including but not limited to carboxylated, sulfated and phosphorylated compounds.

In a related embodiment, the disclosure contemplates PEG-CNP conjugates comprising NHS- or aldehyde-based PEG of the formula $(CH_2CH_2O)_n$, wherein n is an integer from 12 to 50, and the PEG polymer is up to about 2.5 kDa in molecular weight. In a specific embodiment, n is 12 or 24. In an embodiment, the terminal hydroxyl group of the PEG polymer is capped with a non-reactive group. In a particular embodiment, the capping group is an alkyl group, e.g., a lower alkyl group such as methyl.

In an additional embodiment, the PEG polymers or derivatives thereof have a polymer number-average molecular weight in the range from about 0.4 kDa to about 2.5 kDa or from about 0.6 kDa to about 1.5 kDa.

In a further embodiment, the wtCNP or CNP variant peptide is conjugated to a moiety including, e.g., bisphosphonates, carbohydrates, hydrophobic acids (including fatty acids) or amino acid sequences. Such amino acid sequences include for example polyAsp or polyGlu useful in bone/cartilage targeting, or can be derived from bone proteins with elucidated bone-targeting domains or derivatives thereof, such as for example fusion proteins or peptide sequences of osteopontin, osteocalcin, sialoprotein, etc. In embodiments described herein where CNP22 or a variant thereof is attached to a bone- or cartilage-targeting moiety, such a moiety is designed to promote getting the modified CNP peptide to chondrocytes of bone growth plates, where the peptide can bind and activate NPR-B on the chondrocytes.

In another embodiment, the disclosure provides CNP variants with a peptide bond that is less susceptible to cleavage by peptidases including NEP. The disclosure encompasses a CNP variant comprising at least one modified residue at a site of endopeptidase cleavage. In one embodiment, the Cys6-Phe7 peptide bond (—C(=O)—NH—) at an NEP cleavage site in CNP can be replaced with anyone of the following peptide-bond isosteres:

—CH$_2$—NH—,
—C(=O)—N(R)—, where the amide group is alkylated with any of the following R groups: methyl, ethyl, n-propyl, isopropyl, cyclopropyl, n-butyl, isobutyl, sec-butyl or tert-butyl,
—C(=O)—NH—CH$_2$—,
—CH$_2$—S—,
—CH$_2$—S(O)$_n$—, where n is 1 or 2,
—CH=CH—,
—C(=O)—CH$_2$—,
—CH(CN)—NH—,
—CH(OH)—CH$_2$—,
—O—C(=O)—NH—, and
—NHC(=O)NH—.

In another embodiment, Phe7 is substituted with its enantiomer D-Phe. In yet another embodiment, D-enantiomers are introduced to one or more, up to all 22, positions within wtCNP-22. In a further embodiment, a beta amino acid such as 3-amino-2-phenylpropionic acid is substituted for Phe7, which increases the length of the backbone while reducing the length of the side chain. In yet another embodiment, the disclosure contemplates Cys analogs at the Cys6 position including but not limited to homocysteine, penicillamine, 2-mercaptopropionic acid, and 3-mercaptopropionic acid.

Even in the presence of a NEP-resistant bond between Cys6 and Phe7, other peptide bonds can be hydrolyzed by NEP, including Gly8-Leu9, Lys10-Leu11, Arg13-Ile14, Ser16-Met17 and Gly19-Leu20. Accordingly, the disclosure encompasses CNP analogs containing peptide bond isosteres at multiple locations in the backbone of the CNP analogs. In one embodiment, CNP analogs or variants comprise modifications at more than one peptidase cleavage site. In a further embodiment, such variant comprises a CNP with substitutions at amino acid residues important in binding to the NEP active site, thereby increasing resistance to NEP degradation. One or more NEP-binding residues, including but not limited to Gly8, Gly15, Ser18, Gly19 and/or Gly21, are replaced with larger-size natural or unnatural amino acid residues to reduce affinity to the NEP active site. In yet another embodiment, one or more hydrophobic residues essential in NEP recognition, including but not limited to Phe7, Leu9, Leu11, Ile14, Met17 and Leu20, are substituted with natural or unnatural amino acids and/or peptidomimetics that decrease NEP binding. In yet another embodiment, one to five of the first five amino acids of CNP can be deleted or substituted with any other natural amino acids or unnatural amino acids or peptidomimetics, or one or more natural or unnatural amino acids or peptidomimetics can be added to any one or to all of the first five positions of CNP.

In a further embodiment, the CNP variants have a total mass characterized by the ranges described generally herein, e.g., from about 2.6 kDa or 2.8 kDa to about 6 or 7 kDa for increased resistance to NEP, and are represented by the formula:

(x)-Gly$_1$-Leu$_2$-Ser$_3$-(a)$_4$-Gly$_5$-(b)$_6$-(c)$_7$-(d)$_8$-(e)$_9$-(f)$_{10}$-(g)$_{11}$-Asp$_{12}$-Arg$_{13}$-(h)$_{14}$-Gly$_{15}$-Ser$_{16}$-(i)$_{17}$-Ser$_{18}$-Gly$_{19}$-(j)$_{20}$-Gly$_{21}$-Cys$_{22}$-(z) (SEQ ID NO: 46), wherein:

(x) may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone proteins with elucidated bone-targeting domains, such as, e.g., fusion proteins or peptide sequences of osteopontin, osteocalcin, sialoprotein, etc.; polymeric or non-polymeric molecules that reduce renal clearance such as, e.g., charged PEG molecules; and extensions comprising, e.g., polymers (e.g., PEGs), carbohydrates, hydrophobic acids (including fatty acids), and/or amino acids, and wherein such amino acid extensions can contain, e.g., from 1 to 31, or 1 to 35, or 5 to 35, or 10 to 35, or 15 to 35 amino acid residues, and can be derived from NPPC, ANP, BNP, other non-CNP (poly)peptides such as, e.g., serum albumin or IgG, or variants of the aforementioned polypeptides having substitutions, additions and/or deletions, or combinations thereof;

(z) may be absent or may be selected from the group consisting of amino acid sequences useful in bone or cartilage targeting such as for example polyAsp and polyGlu, amino acid sequences from bone-targeting domains of bone proteins such as, e.g., osteopontin, osteocalcin and sialoprotein, and amino acid sequences derived from non-CNP (poly)peptides such as, e.g., ANP or BNP;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide-bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched C$_{1-6}$ alkyl, straight or branched C$_{1-6}$ alkoxy, straight or branched halo-C$_{1-6}$ alkyl, C$_{3-10}$ cycloalkyl, heterocyclyl, C$_{6-14}$ aryl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Thr, Ser, Val and Asn;

(e) is selected from the group consisting of Leu, Ser, Thr and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly, and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In one embodiment, the CNP variants comprise a modification at one or more of positions 6, 7, 8, 9, 10, 11, 13, 14, 16, 17, 19 and/or 20, and may optionally have modifications at any of the other positions disclosed herein.

In embodiments described herein where CNP22 or variants thereof can be attached to a hydrophobic acid, the CNP peptides can be attached to one or hydrophobic acids. Non-limiting examples of hydrophobic acids include straight-chain or branched, saturated or unsaturated $C_5$-$C_{12}$ carboxylic acids (e.g., pentanoic acid, heptanoic acid, etc.) and natural fatty acids. The hydrophobic acids can be attached to the N-terminus, the C-terminus, and/or the side chain of one or more amino acid residues. In one embodiment, the hydrophobic acids are conjugated to the N-terminus. In an embodiment, conjugation of CNP22 or a variant thereof to a hydrophobic acid is designed, inter alia, to promote non-specific interaction between the modified CNP peptide and serum albumin, thereby increasing the size of the CNP peptide and protecting it from cleavage by proteases such as, e.g., NEP. The interaction between the hydrophobic acid-conjugated CNP peptide and albumin is designed to be not too strong, so that the modified CNP peptide can diffuse through cartilage, get to chondrocytes of bone growth plates, and bind and activate NPR-B.

In a further embodiment, the disclosure provides CNP variants that in vitro or in vivo stimulate the production of at least about 50%, 60%, 70%, 80%, 90%, 100%, 110%, 120%, 130%, 140% or 150% of the cGMP level produced under the same concentration of wtCNP22 (e.g., 1 uM), comprise at least one modified amino acid at position (b)$_6$, (c)$_7$ and/or (d)$_8$, and are represented by the general formula:

(x)-Gly$_1$-Leu$_2$-Ser$_3$-(a)$_4$-Gly$_5$-(b)$_6$-(c)$_7$-(d)$_8$-(e)$_9$-(f)$_{10}$-(g)$_{11}$-Asp$_{12}$-Arg$_{13}$-(h)$_{14}$-Gly$_{15}$-Ser$_{16}$-(i)$_{17}$-Ser$_{18}$-Gly$_{19}$-(j)$_{20}$-Gly$_{21}$-Cys$_{22}$-(z) (SEQ ID NO: 47), wherein:

(x) may be absent or may be a peptide sequence containing one to five amino acids which is derived from a natriuretic polypeptide (e.g. NPPC, CNP, ANP or BNP) or a non-natriuretic polypeptide as described herein (e.g., HSA, IgG, a bone-targeting protein, etc.);

(z) may be absent or may be selected from the group consisting of synthetic bone-targeting compounds such as, e.g., bisphosphonates; amino acid sequences useful in bone/cartilage targeting such as, e.g., polyAsp and polyGlu; bone proteins with bone-targeting domains and derivatives thereof, such as fusion proteins or peptides sequences of osteopontin, osteocalcin, and sialoprotein; molecules that reduce renal clearance, such as, e.g., charged PEGs; and molecules that increase resistance of CNP to NEP-mediated degradation, as described herein;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) may be Cys or descarboxy cysteine, or the (b)$_6$-(c)$_7$ peptide bond (—C(=O)—NH—) may be replaced with any one of the following peptide bond isosteres:

—CH$_2$—NH—,
—C(=O)—N(R)—, where the amide group is alkylated with any of the following R groups: methyl, ethyl, n-propyl, isopropyl, cyclopropyl, n-butyl, isobutyl, sec-butyl or tert-butyl,
—C(=O)—NH—CH$_2$—,
—CH$_2$—S—,
—CH$_2$—S(O)$_n$—, where n is 1 or 2,
—CH$_2$—CH$_2$—,
—CH=CH—,
—C(=O)—CH$_2$—,
—CH(CN)—NH—,
—CH(OH)—CH$_2$—,
—O—C(=O)—NH—, or
—NHC(=O)NH—;

(c) is selected from the group consisting of L-Phe; D-Phe; 3-amino-2-phenylpropionic acid; peptide bond isosteres of Phe such as N-alkylated derivatives of Phe wherein the N-alkyl group is selected from the group consisting of methyl, ethyl, n-propyl, isopropyl, cyclopropyl, n-butyl, isobutyl, sec-butyl and tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Val, Ser, Thr and Asn;

(e) is selected from the group consisting of Leu, Ser, Thr, and peptide-bond isosteres such as, e.g., N-Me-Leu;

(f) is any natural or unnatural amino acid or peptidomimetic that does not have a reactive primary amino group on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In a further embodiment, the disclosure encompasses CNP variants that in vitro or in vivo stimulate the production of at least about 50%, 60%, 70%, 80%, 90%, 100%, 110%, 120%, 130%, 140% or 150% of the cGMP level produced under the same concentration of wtCNP22 (e.g., 1 uM), have a total mass characterized by the ranges described generally herein, e.g., from about 2.6 kDa or 2.8 kDa to about 6 or 7 kDa for increased resistance to NEP degradation, and are represented by the general formula:

(x)-(y)-Cys$_6$-Phe$_7$-Gly$_8$-Leu$_9$-(h)$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 48), wherein:

(x) is a synthetic or natural polymeric group, or a combination thereof, wherein a non-limiting example of a synthetic polymeric group is polyethylene glycol (PEG), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histidine-rich glycoproteins, fibronectin, fibrinogen, zinc finger-containing polypeptides, osteocrin or FGF2;

(y) may be absent or may be one or more amino acids from $Gly_1$-$Leu_2$-$Ser_3$-$Lys_4$-$Gly_5$ (corresponding to positions 1 to 5 of CNP22) (SEQ ID NO: 1) and/or substitutions at one or more of those positions using natural or unnatural amino acids (e.g., K4R substitution);

(h) may be the wild-type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (h) is not Arg; and (z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG).

In an embodiment, (x), (y) and (z) together contain from about 10 to about 40, or from about 15 to about 35 amino acids. In another embodiment, (x) is an amino acid sequence comprising from 1 to 40 amino acids, or from 1 to 20 amino acids.

Further contemplated are CNP variants that in vitro or in vivo stimulate the production of at least about 50%, 60%, 70%, 80%, 90%, 100%, 110%, 120%, 130%, 140% or 150% of the cGMP level produced under the same concentration of wtCNP22 (e.g., 1 uM), and comprise the sequence:

(y)-$Cys_6$-$Phe_7$-$Gly_8$-$Leu_9$-$Lys_{10}$-$Leu_{11}$-$Asp_{12}$-$Arg_{13}$-$Ile_{14}$-$Gly_{15}$-$Ser_{16}$-$Met_{17}$-$Ser_{18}$-$Gly_{19}$-$Leu_{20}$-$Gly_{21}$-$Cys_{22}$ (SEQ ID NO: 138), wherein:

(y) comprises one or more amino acids selected from $Gly_1$-$Leu_2$-$Ser_3$-$Lys_4$-$Gly_5$ (SEQ ID NO: 1) and/or substitutions at one or more of those positions using natural or unnatural amino acids (e.g., K4R substitution), and further comprises a hydrophilic or water soluble polymer of molecular weight from about 0.6 kDa to about 5 kDa. In an embodiment, the hydrophilic or water-soluble polymer is conjugated to the N-terminus of such amino acid-extended CNP variant. In a particular embodiment, the hydrophilic or water-soluble polymer is PEG (or PEO).

In yet another embodiment, the disclosure provides CNP variants that in vitro or in vivo stimulate the production of at least about 50%, 60%, 70%, 80%, 90%, 100%, 110%, 120%, 130%, 140% or 150% of the cGMP level produced under the same concentration of wtCNP22 (e.g. 1 uM), wherein the CNP variants comprise an N-terminal and/or C-terminal peptide extension containing from 1 to 15 amino acids, and are conjugated to a hydrophilic or water soluble polymer. In an embodiment, the peptide extension contains from 5 to 10 amino acids. In a specific embodiment, the peptide extension contains 5 amino acids. In another specific embodiment, the hydrophilic or water-soluble polymer is PEG (or PEO).

In a still further embodiment, the CNP variants of the disclosure in vitro or in vivo stimulate the production of at least about 50%, 60%, 70%, 80%, 90%, 100%, 110%, 120%, 130%, 140% or 150% of the cGMP level produced under the same concentration of wtCNP22 (e.g. 1 uM), and comprise at least a 15 amino acid fragment derived from natriuretic peptide precursor C(NPPC), wherein the fragment is at least 70% homologous to a sequence from wild type NPPC containing the same number of amino acid residues.

In still another embodiment, the CNP variants have a total mass characterized by the ranges described generally herein, e.g., from about 2.6 kDa or 2.8 kDa to about 6 or 7 kDa for increased NEP resistance, and are represented by the formula:
(x)-$(b)_6$-$(c)_7$-$(d)_8$-$(e)_9$-$(f)_{10}$-$(g)_{11}$-$Asp_{12}$-$Arg_{13}$-$(h)_{14}$-$Gly_{15}$-$Ser_{16}$-$(i)_{17}$-$Ser_{18}$-$Gly_{19}$-$(j)_{20}$-$Gly_{21}$-$Cys_{22}$-(z) (SEQ ID NO: 49), wherein:

(x) may be absent (i.e., the N-terminus ends with an —$NH_2$ group) or may be selected from the group consisting of a sequence of 1, 2, 3, 4 or 5 amino acids from the peptide $Gly_1$-$Leu_2$-$Ser_3$-$Lys_4$-$Gly_5$ (SEQ ID NO: 1); amino acid sequences useful in bone/cartilage targeting such as for example polyAsp or polyGlu; bone-targeting domains from bone proteins such as for example osteopontin, osteocalcin or sialoprotein; molecules that reduce renal clearance such as hydrophilic or water-soluble polymers, including but not limited to charged PEG molecules; and moieties comprising PEG, carbohydrates, hydrophobic acids, amino acids, or combinations thereof, wherein such moieties can be amino acid extensions including but not limited to amino acid sequences derived from NPPC or non-CNP (poly)peptides such as, e.g., BNP, ANP, serum albumin or IgG;

(z) may be absent or may be selected from the group consisting of amino acid sequences useful in bone/cartilage targeting such as for example polyAsp or polyGlu; amino acid sequences derived from bone-targeting proteins, such as for example osteopontin, osteocalcin or sialoprotein; and amino acid sequences derived from NPPC or non-CNP (poly)peptides, as described herein;

(b) is selected from the group consisting of Cys and peptide bond isosteres between Cys6 and Phe7 such as, e.g., Cys-$CH_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Val, Ser, Thr and Asn;

(e) is selected from the group consisting of Leu, Ser, Thr, and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In a further embodiment, the CNP variants have a total mass characterized by the ranges described generally herein, e.g., from about 2.6 kDa or 2.8 kDa to about 6 or 7 kDa for increased NEP resistance, and are represented by the formula:

(x)-Gly$_1$-Leu$_2$-Ser$_3$-(a)$_4$-Gly$_5$-(b)$_6$-(c)$_7$-(d)$_8$-(e)$_9$-(f)$_{10}$-(g)$_{11}$-Asp$_{12}$-Arg$_{13}$-(h)$_{14}$-(i)$_{15}$-Ser$_{16}$-(j)$_{17}$-Ser$_{18}$-Gly$_{19}$-(k)$_{20}$-Gly$_{21}$-Cys$_{22}$-(z) (SEQ ID NO: 50), wherein:

(x) and (z) independently may be absent or may be selected from the group consisting of synthetic bone-targeting compounds such as, e.g., bisphosphonates; amino acid sequences useful in bone/cartilage targeting such as for example polyAsp or polyGlu; amino acid sequences derived from bone-targeting domains of bone proteins and derivatives thereof, such as for example fusion proteins or peptide sequences of osteopontin, osteocalcin, sialoprotein, etc.; moieties that reduce renal clearance, including but not limited to hydrophilic or water-soluble polymers such as, e.g., charged PEG molecules; and moieties comprising, e.g., hydrophilic polymers (e.g., PEG), carbohydrates, hydrophobic acids, and/or amino acids;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched C$_{1-6}$ alkyl, straight or branched C$_{1-6}$ alkoxy, straight or branched halo-C$_{1-6}$ alkyl, C$_{3-10}$ cycloalkyl, C$_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly, Thr, Ser, Val and Asn;

(e) is selected from the group consisting of Leu, Ser, Thr, and peptide bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu, Asn, and peptide bond isosteres such as, e.g., N-Me-Leu;

(h) is selected from the group consisting of Ile, tert-butyl-Gly (tBu-Gly), Asn, and peptide bond isosteres such as, e.g., N-Me-Ile;

(i) is selected from the group consisting of Gly, Arg, Ser and Asn;

(j) is selected from the group consisting of Met, Val, Asn, beta-Cl-Ala, 2-aminobutyric acid (Abu) and 2-amino-isobutyric acid (Aib); and (k) is selected from the group consisting of Leu, norleucine (Nle), homoleucine (Hleu), Val, tert-butyl-Ala (tBu-Ala), Arg, Thr, Ser, and peptide bond isosteres such as, e.g., N-Me-Leu.

In a further embodiment, the CNP variants can have amino acid substitution(s) at one or more of any of positions 1 to 22 of CNP22. In one embodiment, Gly1 is substituted with Arg or Glu. In another embodiment, Lys4 is replaced with Arg. In still another embodiment, Gly5 is substituted with Arg, Gln or Ser. In yet another embodiment, Gly15 is substituted with Ser, Asn, Arg or Cit. In a further embodiment, Gly19 is substituted with Ser, Arg or Asn. In yet another embodiment, Gly21 is substituted with Ser, Thr, or Arg.

In one embodiment, the CNP variant is selected from the group consisting of GLSKGC(CH$_2$NH)FGLKLDRIGSMS-GLGC (formed using descarboxy-Cys) (SEQ ID NO: 56), GLSKGC-(N-Me-Phe)-GLKLDRIGSMSGLGC (SEQ ID NO: 57), GLSKGC-(D-Phe)-GLKLDRIGSMSGLGC(SEQ ID NO:136), GLSKGCF-(tBuG)-LKLDRIGSMSGLGC (SEQ ID NO: 58), GLSKGC-(3-Cl-Phe)-GLKLDRIGSMS-GLGC (SEQ ID NO:137), and GLSKGC-[NHCH$_2$CH(Ph)CO]-GLKLDRIGSMSGLGC (formed using 3-amino-2-phenylpropionic acid) (SEQ ID NO: 59). In a further embodiment, a disulfide bond exists between Cys6, descarboxy-Cys or another sulfhydryl-containing cysteine analog at the Cys6 position, and Cys22 of any CNP variant described herein.

In another embodiment, the CNP variants contain an amino acid extension at the N-terminus and/or C-terminus of CNP22 or CNP17, including but not limited to:

```
                                        (SEQ ID NO: 4)
DLRVDTKSRAAWARLLQEHPNARKYKGANKKGLSKGCFGLKLDRIGSMS
GLGC (CNP-53);

(SEQ ID NO: 60)
QEHPNARKYKGANKKGLSKGCFGLKLDRIGSMSGLGC
(CNP-37, Analog BL);

(SEQ ID NO: 61)
AAWARLLQEHPNAGLSKGCFGLKLDRIGSMSGLGC (Analog CA);

(SEQ ID NO: 62)
AAWARLLQEHPNARGLSKGCFGLKLDRIGSMSGLGC (Analog CB);

(SEQ ID NO: 63)
DLRVDTKSRAAWARGLSKGCFGLKLDRIGSMSGLGC (Analog CC);

(SEQ ID NO: 40)
RGLSKGCFGLKLDRIGSMSGLGC;

(SEQ ID NO: 38)
ERGLSKGCFGLKLDRIGSMSGLGC;

(SEQ ID NO: 64)
GANQQGLSKGCFGLKLDRIGSMSGLGC;

(SEQ ID NO: 65)
GANRRGLSKGCFGLKLDRIGSMSGLGC;
```

```
                                    (SEQ ID NO: 66)
GANPRGLSKGCFGLKLDRIGSMSGLGC;

(SEQ ID NO: 67)
GANSSGLSKGCFGLKLDRIGSMSGLGC;

(SEQ ID NO: 144)
GHKSEVAHRFKGANKKGLSKGCFGLKLDRIGSMSGLGC
(sometimes designated "CNP27-HSA" or "HSA-CNP27"
in the Examples and figures);

(SEQ ID NO: 68)
SPKMVQGSG-CNP17-KVLRRH (Analog CD) (CNP17 having
N-terminal and C-terminal tails derived from BNP).
```

In a further embodiment, the CNP variants have a K4R substitution at position 4 of CNP22. Non-limiting examples of CNP(K4R) variants include:

```
                                    ((SEQ ID NO: 36)
    GANRRGLSRGCFGLKLDRIGSMSGLGC (Analog AY);

(SEQ ID NO: 37)
    GANPRGLSRGCFGLKLDRIGSMSGLGC (Analog CI);

(SEQ ID NO: 41)
    RGLSRGCFGLKLDRIGSMSGLGC (Analog AZ);

(SEQ ID NO: 39)
    ERGLSRGCFGLKLDRIGSMSGLGC (Analog BA);

(SEQ ID NO: 69)
    GANQQGLSRGCFGLKLDRIGSMSGLGC (Analog CH);
    and (SEQ ID NO: 70)
    GANSSGLSRGCFGLKLDRIGSMSGLGC (Analog CG).
```

In one embodiment, CNP variants having a PEG (or PEO) moiety and an amino acid extension at the N-terminus contain arginine at the position immediately preceding the position corresponding to Gly1 of CNP22. Such PEGylated CNP variants are designed for increased resistance to NEP degradation, reduced binding to serum albumin, and enhanced CNP functional activity (e.g., activation of cGMP signaling). Non-limiting examples of PEGylated CNP variants include PEO24-GANRR-CNP22(K4R) (SEQ ID NO: 36), PEO12-GANRR-CNP22(K4R) (SEQ ID NO: 36), PEO24-GANRR-CNP22(SEQ ID NO: 65), PEO12-GANRR-CNP22(SEQ ID NO: 65), PEO24-GANPR-CNP22(K4R) (SEQ ID NO: 37), PEO12-GANPR-CNP22(K4R) (SEQ ID NO: 37), PEO24-GANPR-CNP22(SEQ ID NO: 37), PEO12-GANPR-CNP22 (SEQ ID NO: 66), PEO24-GANQQ-CNP22(SEQ ID NO: 64), PEO12-GANQQ-CNP22(SEQ ID NO: 64), PEO24-ER-CNP22(K4R) (SEQ ID NO: 39), PEO12-ER-CNP22(K4R) (SEQ ID NO: 39), PEO24-ER-CNP22(SEQ ID NO: 38), PEO12-ER-CNP22(SEQ ID NO: 38), PEO24-R-CNP22 (K4R) (SEQ ID NO: 41), PEO12-R-CNP22(K4R) (SEQ ID NO: 41), PEO24-R-CNP22(SEQ ID NO: 40), and PEO12-R-CNP22(SEQ ID NO: 40), wherein PEO24 is a monodispersed 1.2 kDa PEG polymer and PEO12 is a monodispersed 0.6 kDa PEG polymer. In an embodiment, the PEG (or PEO) polymer is attached to the N-terminus of the CNP variants.

Additional CNP variants include, but are not limited to, derivatives of CNP37 having mutation(s) at the furin cleavage site (underlined), designed to improve in vivo resistance to the furin protease, and/or having glycine (underlined) preceding glutamine, designed to prevent pyroglutamine formation, including but not limited to:

```
                                    (SEQ ID NO: 71)
GQEHPNARKYKGANPKGLSKGCFGLKLDRIGSMSGLGC (An. CS);

(SEQ ID NO: 72)
GQEHPNARKYKGANQKGLSKGCFGLKLDRIGSMSGLGC (An. CT);

(SEQ ID NO: 73)
GQEHPNARKYKGANQQGLSKGCFGLKLDRIGSMSGLGC (An. CU);

(SEQ ID NO: 74)
GQEHPNARKYKGANKPGLSKGCFGLKLDRIGSMSGLGC (An. CW);

(SEQ ID NO: 75)
GQEHPNARKYKGANKKGLSKGCFGLKLDRIGSMSGLGC
(Gly-CNP37, An. DB);

(SEQ ID NO: 145)
PGQEHPNARKYKGANKKGLSKGCFGLKLDRIGSMSGLGC
(Pro-Gly-CNP37).
```

In another embodiment, the CNP variants are chimera comprising CNP22 and an N-terminal peptide fragment, including but not limited to:

```
                                    (SEQ ID NO: 76)
GHHSHEQHPHGANQQGLSKGCFGLKLDRIGSMSGLGC (Analog CQ)
(histidine-rich glycoprotein (HRGP) fragment-
CNP22 chimera);

(SEQ ID NO: 77)
GAHHPHEHDTHGANQQGLSKGCFGLKLDRIGSMSGLGC (Analog CR)
(HRGP fragment-CNP22 chimera);

(SEQ ID NO: 78)
GHHSHEQHPHGANPRGLSKGCFGLKLDRIGSMSGLGC (Analog CX)
(HRGP fragment-CNP22 chimera);

(SEQ ID NO: 79)
GQPREPQVYTLPPSGLSKGCFGLKLDRIGSMSGLGC (Analog CF)
(IgG1(Fc) fragment-CNP22 chimera);

(SEQ ID NO: 80)
GQHKDDNPNLPRGANPRGLSKGCFGLKLDRIGSMSGLGC (Analog
CY) (human serum albumin (HSA) fragment-CNP22
chimera);

(SEQ ID NO: 81)
GERAFKAWAVARLSQGLSKGCFGLKLDRIGSMSGLGC (Analog CE)
(HSA fragment-CNP22 chimera);

(SEQ ID NO: 82)
FGIPMDRIGRNPRGLSKGCFGLKLDRIGSMSGLGC (Analog CZ)
(osteocrin "NPR C inhibitor" fragment-CNP22
chimera);
and (SEQ ID NO: 83)
GKRTGQYKLGSKTGPGPKGLSKGCFGLKLDRIGSMSGLGC
(Analog DA) (FGF2 "heparin-binding domain"
fragment-CNP22 chimera).
```

In a further embodiment, the CNP variants are chimera comprising an N-terminal peptide fragment and CNP22 in which arginine is substituted for Lys4 of CNP22 ("CNP22 (K4R)"), including but not limited to:

```
                                    (SEQ ID NO: 84)
GQPREPQVYTGANQQGLSRGCFGLKLDRIGSMSGLGC (Analog CK)
(IgG1(Fc) fragment-CNP22(K4R) chimera);

(SEQ ID NO: 85)
GVPQVSTSTGANQQGLSRGCFGLKLDRIGSMSGLGC (Analog CL)
(HSA fragment-CNP22(K4R) chimera)
```

```
                                              (SEQ ID NO: 86)
GQPSSSSQSTGANQQGLSRGCFGLKLDRIGSMSGLGC
(Analog CM) (fibronectin fragment-CNP22(K4R)
chimera);

(SEQ ID NO: 87)
GQTHSSGTQSGANQQGLSRGCFGLKLDRIGSMSGLGC
(Analog CN) (fibrinogen fragment-CNP22(K4R)
chimera);

(SEQ ID NO: 88)
GSTGQWHSESGANQQGLSRGCFGLKLDRIGSMSGLGC
(Analog CO) (fibrinogen fragment-CNP22(K4R)
chimera);
and (SEQ ID NO: 89)
GSSSSSSSSSGANQQGLSRGCFGLKLDRIGSMSGLGC
(Analog CP) (zinc finger fragment-CNP22(K4R)
chimera).
```

In yet another embodiment, the CNP variants are chimera, or fusion proteins, comprising a CNP peptide or variant, and a cleavable peptide or protein, or peptide tag. Exemplary cleavable proteins or peptides include, but are not limited to, histidine (e.g., hexa-His) tags; TAF12: human transcription factor TAF12; KSI: ketosteroid isomerase; MBP: maltose-binding protein; β-Gal: β-galactosidase; GST: glutathione-S-transferase; Trx: thioredoxin; CBD: chitin binding domain; BMPM: BMP-2 mutation, SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly(Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and fragments thereof.

In yet another embodiment, the CNP variant may be a monomer or a dimer. In a related embodiment the monomers of dimeric CNP variants can be attached N-terminus to N-terminus via a linker or no linker, N-terminus to C-terminus via a linker or no linker, or C-terminus to C-terminus via a linker or no linker.

Chimera comprising an IgG fragment and CNP22 or a variant thereof are designed for, inter alia, increased resistance to NEP degradation and reduced binding to serum albumin. CNP chimera comprising a surface fragment of HSA are designed for, inter alia, reduced immunogenicity and reduced binding to serum albumin. HRGP-CNP22 and HRGP-CNP22(K4R) chimera containing a cationic, histidine-rich, non-lysine, non-arginine sequence at the N-terminus are designed for, inter alia, increased stability to proteases. Chimera containing an osteocrin fragment are designed to release, upon protease (e.g., furin) cleavage, the osteocrin fragment at bone growth plates, where the fragment would inhibit the clearance receptor NPR-C. With respect to chimera comprising an FGF2 heparin-binding fragment, heparin binding to the fragment is designed to protect the chimera from degradation, thereby providing a longer serum half-life. Chimera containing a fibronectin, fibrinogen, or zinc-finger fragment are designed for reduced binding to serum albumin, among other advantageous features.

Not intending to be bound by theory, a CNP variant of molecular weight from about 2.6 kDa or 2.8 kDa to about 6 or 7 kDa which has increased resistance to NEP degradation and has similar or improved functionality (e.g., binding to NPR-B and stimulation of cGMP signaling) as compared to wtCNP22, may be more effective if it does not bind tightly to plasma proteins such as serum albumin. A CNP variant that does not bind tightly to plasma proteins (e.g., serum albumin) may be more effective in diffusing through cartilage, getting to chondrocytes of bone growth plates, and binding to and activating NPR-B for cGMP signaling. In one embodiment, CNP variants designed for reduced binding to plasma proteins (e.g., serum albumin) are chimeras comprising CNP22 or a variant thereof and a peptide fragment from IgG. In another embodiment, CNP variants designed for reduced binding to plasma proteins are chimeras comprising CNP22 or CNP22(K4R) and a fragment from a polypeptide (e.g., IgG, HSA, fibronectin, fibrinogen, a zinc finger-containing polypeptide, etc.). In yet another embodiment, CNP variants designed for reduced binding to plasma proteins comprise CNP22 or a variant thereof conjugated to a hydrophilic or water-soluble polymer. In one embodiment, the hydrophilic or water-soluble polymer is PEG (or PEO). In another embodiment, the hydrophilic or water-soluble polymer (e.g., PEG) is functionalized with one or more functional groups that impart a negative charge to the polymer under physiological conditions, such as, e.g, carboxyl, sulfate or phosphate groups, or a combination thereof.

In any of the embodiments disclosed herein, the CNP variants may have substantially the same or better biological activity than wild-type CNP22. For example, the CNP variants may retain at least 50%, 60%, 70%, 80%, 90%, 95% or more of the activity of wild-type CNP22, or may have greater activity than CNP22, e.g., with respect to interaction with NPR-B (GC-B) to stimulate the generation of cGMP. Alternatively, or in addition, the CNP variants may retain at least 50%, 60%, 70%, 80%, 90%, 95% or more of the activity of wild-type CNP22, or may have greater activity than CNP22, with respect to regulating endochondral bone growth and chondrocyte activity, including but not limited to chondrocyte proliferation, chondrocyte differentiation, inhibition of the mitogen activated protein (MAP) kinase/MEK (Raf-1) kinase signaling pathway, and promoting endochondral ossification. In any of the embodiments described herein, the CNP variants may comprise an amino acid sequence that is at least 40%, 50%, 60%, 70%, 80%, 90%, 95% or more identical or homologous to amino acids 6-22 or 1-22 of wild-type CNP22.

In a further embodiment, the disclosure provides variants of CNP22 having less affinity to the NPR-C clearance receptor while retaining the ability to bind and activate NPR-B. The present disclosure encompasses variants that were, or can be, generated from a homology-based structural model of the NPR-B/CNP complex as described in the Detailed Description. In another embodiment, the CNP variants have substitution(s) at one or more Gly sites at positions 1, 5, 8, 15, 19 and 21, to reduce conformational flexibility, which may increase their specificity for binding to NPR-B over NPR-C. Variants of CNP having potentially reduced affinity to the NPR-C include but are not limited to those having one or more of the following substitutions: G1R, G1E, G5R, G5Q, G5S, F7Y, G8T, G8S, G8V, G8N, L9S, L9T, K10Cit, K10Q, K10S, I14N, G15R, G15S, G15N, G15Cit, S16Q, M17V, M17N, G19S, G19R, G19N, L20V, L20R, L20T, L20S, G21S, G21T and G21R.

In yet another embodiment, the CNP variants have a modification and/or substitution at one or more of positions 5, 7, 8, 9, 10, 14, 15, 16, 17, 19, 20 and 21, and may optionally have modifications and/or substitutions at any of the other positions disclosed herein. In a further embodiment, the CNP variants can optionally have conjugation(s) or extension(s), e.g., at the N- and/or C-terminus to facilitate bone/cartilage targeting, reduce renal clearance, and/or increase resistance to NEP degradation. Such conjugation(s) or extension(s) can comprise molecules or sequences formed or derived from, e.g., polyAsp, polyGlu, bone- or cartilage-targeting peptides, osteopontin, osteocalcin, sialoprotein, PEGs, carbohydrates, hydrophobic acids, NPPC or non-CNP (poly)peptides, or combinations thereof.

In still another embodiment, the CNP variants are prepared by standard solid-phase peptide synthesis methods with natural or unnatural amino acid(s) or peptidomimetic(s) being substituted and/or added where appropriate. In another embodiment, the CNP variants are produced by recombinant synthesis processes, e.g., via fusion proteins containing a tag or carrier protein, wherein use of the tag or carrier protein facilitates, e.g., detection, isolation and/or purification of the fusion protein, and selective chemical or proteolytic cleavage of the tag or carrier protein from the fusion protein provides the target CNP variant. In a further embodiment, PEGylation of the CNP variants occurs following, or part of, chemical or biological synthesis with the conjugation reaction being performed by NHS- or aldehyde-based chemistry or other chemistry known in the art. In another embodiment, the CNP variants comprise a disulfide bond. In a related embodiment, the disulfide bond forms a cyclic peptide. In a particular embodiment, the disulfide bond is formed between cysteine residues at positions corresponding to positions 6 and 22 of CNP22.

It is further contemplated that the CNP variants can be conjugated to a hydrophobic polymeric or non-polymeric moiety, such as, e.g., heptanoic acid, pentanoic acid, or fatty acids. The hydrophobic moiety can be conjugated to the side chain of an amino acid residue, including but not limited to a lysine, a serine, a cysteine or a threonine, or can be attached to the N-terminus and/or C-terminus of the CNP variant.

In an embodiment, the CNP variants as described herein have a pI in the range from about 8 to about 10.5 or from about 8.5 to about 10.

In a further embodiment, the disclosure provides a pharmaceutical composition comprising a CNP variant, optionally another biologically active agent, and optionally a pharmaceutically acceptable excipient, carrier or diluent. In some embodiments, the compositions are sterile pharmaceutical compositions suitable for parenteral injection. In some embodiments, the compositions comprise substantially pure CNP variant, e.g. at least about 90% or 95% pure. In some embodiments, the compositions contain less than about 5%, 4%, 3%, 2%, 1% or 0.5% contaminants, such as other human proteins, porcine proteins, or CNP53 or fragments thereof (other than the desired CNP variant). In certain embodiments, the sterile composition is administered to a subject for treating or preventing any of the CNP-responsive conditions or disorders disclosed herein.

CNP variants of the disclosure advantageously retain CNP activity and exhibit increased serum half-life. Retention of CNP activity can be shown, for example, as retention of desired in vivo biological effect, or retention of at least about 50%, 60%, 70%, 80%, 90%, 95% or at least about 100% of the cGMP stimulating activity of CNP22, under the same concentration (e.g., 1 uM of CNP peptide or greater than the ED80). In some embodiments, CNP variants exhibit at least about 1.5-fold, 2-fold, 3-fold, 4-fold, 5-fold, 10-fold, 15-fold, 20-fold, 25-fold, 30-fold, 35-fold or 40-fold increase in serum half-life compared to CNP22.

In a related embodiment, the CNP variants described herein have increased NEP resistance and exhibit increased half-life compared to wild-type CNP22. In one embodiment, the half-life of the CNP variants is increased by about 20%, 30%, 40%, 50%, 60%, 70%, 80%, 90%, 95%, 96%, 97%, 98%, 99% or about 100% compared to wild-type CNP22.

In certain embodiments, the CNP variants described herein increase cGMP production in vitro, increase cGMP production in vivo, increase in vivo the level of one or more biomarkers associated with cartilage or bone formation or growth, increase resistance to NEP cleavage in vitro, increase plasma or serum half-life in vivo, increase bioavailability in vivo, or increase the length of particular bones in vivo, or effect combinations of such increases, by about 1.5-fold, about 2-fold, about 2.5-fold, about 3-fold, about 3.5-fold, about 4-fold, about 4.5-fold, or about 5-fold or more compared to wild-type CNP22.

In yet another embodiment, the disclosure provides methods of treating conditions or disorders responsive to CNP, comprising administering a therapeutically effective amount of a CNP variant or a composition comprising the same to a subject in need thereof. In one embodiment, disorders responsive to CNP are disorders of bone growth, including but not limited to skeletal dysplasias and inherited skeletal malformations such as disorders associated with fibroblast growth factor receptor 3 (FGFR-3) mutations. In a specific embodiment, the disorder associated with FGFR-3 mutation(s) is achondroplasia. In another embodiment, the disorders responsive to CNP are disorders associated with vascular smooth muscle cells and tissues. In a further embodiment, the CNP variants are useful for increasing the size of the growth plate of a bone (e.g., a limb bone). In another embodiment, the CNP variants are useful for elongating a bone or increasing long bone growth. In still another embodiment, the CNP variants are useful for enhancing matrix production, proliferation and differentiation of chondrocytes.

In certain embodiments, the CNP variants described herein are administered at a dose in the range from about 5 or 10 nmol/kg to about 300 nmol/kg, or from about 20 nmol/kg to about 200 nmol/kg. In some embodiments, the CNP variants are administered at a dose of about 5, 10, 15, 20, 25, 30, 35, 40, 45, 50, 55, 60, 65, 70, 75, 80, 85, 90, 95, 100, 125, 150, 175, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variants are administered at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750 or 800 ug/kg, or about 1 mg/kg, 1.25 mg/kg, 1.5 mg/kg, 2 mg/kg or other dose deemed appropriate by the treating physician. The doses of CNP variants described herein can be administered according to the dosing frequency/frequency of administration described herein, including without limitation daily, 2 or 3 times per week, weekly, every 2 weeks, every 3 weeks, monthly, etc.

In another embodiment, the CNP variants are administered in a single treatment or in multiple doses. The multiple doses may be administered daily, or in multiple doses over the course of treatment. In certain embodiments, it is contemplated that the CNP variant is administered, in a single dose or in multiple doses, daily, every other day, every 3 days, 2 times per week, 3 times per week, weekly, bi-weekly, every 3 weeks, monthly, every 6 weeks, every 2 months, every 3 months or as deemed appropriate by a treating physician.

In certain embodiments, administration of the CNP variant is adjusted to allow for periods of growth (e.g., chondrogenesis), followed by a recovery period (e.g., osteogenesis). For example, the CNP variant may be administered subcutaneously, intravenously, or by another mode daily or multiple times per week for a period of time, followed by a period of no treatment, then the cycle is repeated. In some embodiments, the initial period of treatment (e.g., administration of the CNP variant daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

In additional embodiments, the disclosure provides a method of treating a CNP-responsive condition or disorder, comprising administering a CNP peptide or variant to a subject, and monitoring the level of at least one bone- or cartilage-associated biomarker in the subject (e.g., in a biological sample from the subject), wherein an increase or decrease in the level of the bone- or cartilage-associated biomarker indicates a therapeutic effect of the CNP peptide or variant on the subject. In some embodiments, when the level of a biomarker increases in association with bone or cartilage formation or growth, an increase in the level of that biomarker indicates a therapeutic effect of the CNP peptide or variant on the subject. In other embodiments, when the level of a biomarker decreases in association with bone or cartilage formation or growth, a decrease in the level of that biomarker indicates a therapeutic effect of the CNP peptide or variant on the subject.

In further embodiments, the therapeutic method further comprises adjusting the amount (or dose) or frequency of administration of the CNP peptide or variant, wherein:
(i) the amount (or dose) or frequency of administration of the CNP peptide or variant is increased if the level of the at least one bone- or cartilage-associated biomarker is below a target level, where the level of the biomarker increases in association with bone or cartilage formation or growth; or
(ii) the amount (or dose) or frequency of administration of the CNP peptide or variant is decreased if the level of the at least one bone- or cartilage-associated biomarker is above a target level, where the level of the biomarker increases in association with bone or cartilage formation or growth; or
(iii) the amount (or dose) or frequency of administration of the CNP peptide or variant is increased if the level of the at least one bone- or cartilage-associated biomarker is above a target level, where the level of the biomarker decreases in association with bone or cartilage formation or growth; or
(iv) the amount (or dose) or frequency of administration of the CNP peptide or variant is decreased if the level of the at least one bone- or cartilage-associated biomarker is below a target level, where the level of the biomarker decreases in association with bone or cartilage formation or growth.

It is contemplated that the target level of a biomarker refers to the level or range of levels of the biomarker that is associated with therapeutic effect in the subject and/or beneficial effect in alleviating or ameliorating symptoms of the disorder or condition. In certain embodiments, a level of a biomarker above or below a target level may be deleterious to the subject.

In other embodiments, the disclosure contemplates a method for assessing the effect of administration of a CNP peptide or variant on bone or cartilage formation or growth. In one embodiment, the method provides for assaying or measuring the level of at least one bone- or cartilage-associated biomarker in a subject that has been administered a CNP peptide or variant in order to assess the effect of the CNP peptide or variant on bone and cartilage formation and growth in vivo. In a related embodiment, an increase in the level of the at least one bone- or cartilage-associated biomarker may indicate that administration of a CNP peptide or variant has a positive effect on bone or cartilage formation or growth and is a useful treatment for skeletal dysplasias and other bone- or cartilage-related diseases or disorders associated with decreased CNP activity. Exemplary bone- or cartilage-associated biomarkers include, but are not limited to, CNP (e.g., endogenous level of CNP-22 or CNP-53), cGMP, osteocalcin, proliferating cell nuclear antigen (PCNA), propeptides of type I procollagen (PINP) and fragments thereof, collagen type I and fragments thereof, propeptides of collagen type II and fragments thereof, collagen type II and fragments thereof, aggrecan chondroitin sulfate, and alkaline phosphatase.

In further embodiments, the disclosure contemplates a method for assessing the effect of a CNP peptide or variant on the level of at least one bone- or cartilage-associated biomarker in a subject, comprising assaying or measuring the level of the bone- or cartilage-associated biomarker in a biological sample from a subject that has been administered a CNP peptide or variant. In some embodiments, the method further comprises administering the CNP peptide or variant to the subject before assaying or measuring the level of the bone- or cartilage-associated biomarker.

In certain embodiments, the at least one bone- or cartilage-associated biomarker is selected from the group consisting of CNP (e.g., endogenous level of CNP-22 or CNP-53), cGMP, propeptides of collagen type II and fragments thereof, collagen type II and fragments thereof, osteocalcin, proliferating cell nuclear antigen (PCNA), propeptides of type I procollagen (PINP) and fragments thereof, collagen type I and fragments thereof, aggrecan chondroitin sulfate, and alkaline phosphatase.

In some embodiments of methods (e.g., therapeutic, diagnostic and assay methods) relating to bone- or cartilage-associated biomarkers, the CNP peptide or variant is CNP-22, CNP-53, or any of the CNP peptides and variants described herein. In certain embodiments of such methods, the CNP peptide or variant is not CNP-22 or CNP-53.

In other embodiments, the disclosure provides a method for recombinant production of a CNP variant, comprising culturing in a medium a host cell comprising a polynucleotide encoding a CNP variant peptide linked to a polynucleotide encoding a cleavable peptide or protein, under conditions that result in expression of a fusion polypeptide encoded by the polynucleotides. In a related embodiment, the host cell is transformed with an expression vector comprising a polynucleotide encoding a CNP variant peptide linked to a polynucleotide encoding a cleavable peptide or protein.

In one embodiment, the vector is a plasmid. In still another embodiment, the plasmid is selected from the group consisting of pET-21a, pJexpress, pET-31b, pET-15b, pET-32a, pET-41a, pMAL, pQE-30, pET-SUMO, pET-22b, and pTYB11.

In certain embodiments, the cleavable peptide or protein comprises a polypeptide that is selected from the group consisting of a histidine tag, human transcription factor TAF12, ketosteroid isomerase, maltose-binding protein, β-galactosidase, glutathione-S-transferase, thioredoxin, chitin binding domain, and BMP-2 mutation, or fragments thereof.

In a related embodiment, the cleavable peptide or protein is cleaved by a cleaving agent. In some embodiments, the cleaving agent is selected from the group consisting of formic acid, cyanogen bromide (CNBr), hydroxylamine, protein self cleavage, Factor Xa, enterokinase, ProTEV, and SUMO protease. Additional exemplary cleaving agents include, but are not limited to, palladium, clostripain, thrombin, chymotrypsin, trypsin, trypsin-like proteases, carboxypeptidase, enteropeptidase, Kex 2 protease, Omp T protease, subtilisin, V8 protease, HIV protease, rhinovirus protease, furilisin protease, IgA proteases, human Pace protease, collagenase, Nia protease, poliovirus 2Apro protease, poliovirus 3C protease, genenase, furin, elastase, Proteinase K, pepsin, rennin (chymosin), microbial aspartic proteases, papain, calpain, chymopapain, ficin (ficain), bromelain (bromelase), cathespisin B, caspases, thermolysin, Endoprotease Arg-C, Endoprotease Glu-C, Endoprotease Lys-C, kallikrein, and plasmin.

In certain embodiments, the fusion polypeptide is expressed as a soluble protein or as an inclusion body. In a related embodiment, the disclosure contemplates isolating the expressed fusion polypeptide from the host cell or culture medium. In a further embodiment, the isolated fusion polypeptide is contacted with a cleaving agent as described herein.

In one embodiment, the disclosure provides a bacterial host cell comprising an expression vector, said vector comprising a polynucleotide encoding a CNP variant peptide linked to a polynucleotide encoding a cleavable peptide or protein. In some embodiments, the cleavable peptide or protein is selected from the group consisting of a histidine tag, human transcription factor TAF12, ketosteroid isomerase, maltose-binding protein, β-galactosidase, glutathione-S-transferase, thioredoxin, chitin binding domain, and BMP-2 mutation, or fragments thereof.

In another embodiment, the host cell is a bacteria, such as E. coli. In a related embodiment, the E. coli cell is selected from the group consisting of BL21(DE3), BL21(DE3)pLysS, BL21(DE3)pGro7, ArcticExpress(DE3), C41 [also called C41(DE3)], C43 [also called C43(DE3)], Origami B(DE3), Origami B(DE3)pLysS, KRX, and Tuner(DE3). In still a further embodiment, the host cell comprises a vector as described above. In some embodiments, the host cell is transformed with the vector prior to cell culture.

In certain embodiments, it is contemplated that the host cell is cultured in a medium under conditions suitable for expression of a fusion polypeptide encoded by the polynucleotides. In one embodiment, the fusion polypeptide is expressed as a soluble protein or as inclusion body. In a related embodiment, the expressed fusion polypeptide is isolated from the host cell or culture medium. In still another embodiment, the isolated fusion polypeptide is contacted with a cleaving agent as described herein.

76E-H show that liver (E), heart (F), lung (G) and brain (H) tissues did not exhibit appreciable cGMP secretion in response to Gly-CNP37 relative to vehicle control at the studied time points.

Figure 82:
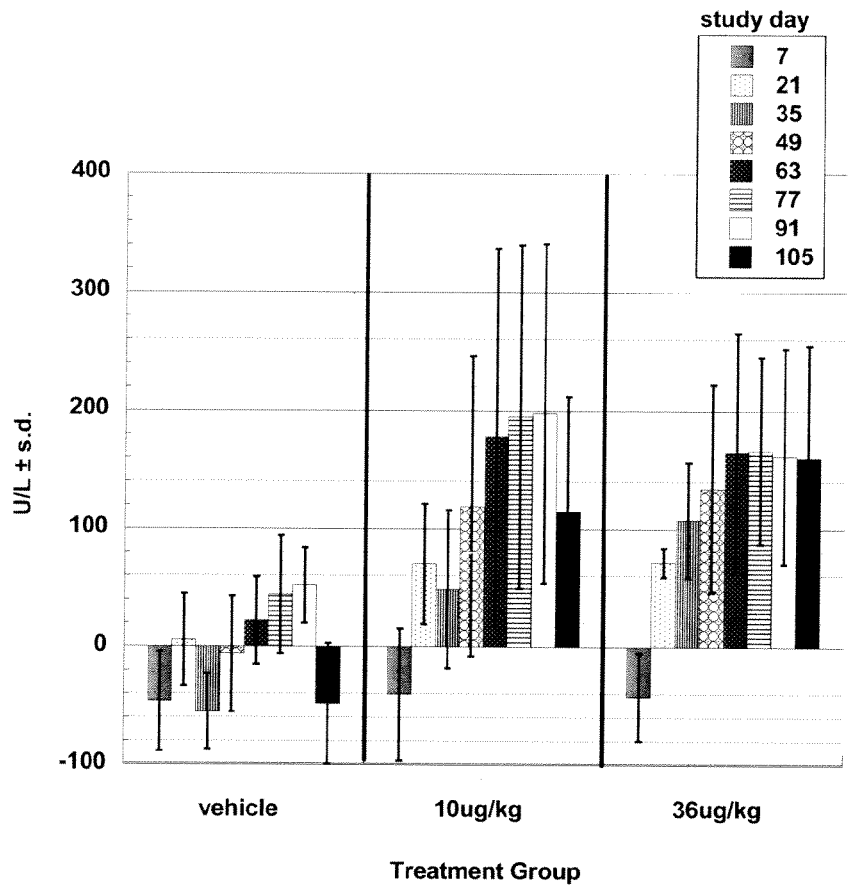

FIGS. 77-82 show results from an on-going study in normal juvenile cynomolgus monkeys subcutaneously injected daily with vehicle or 10 or 36 ug/kg of Pro-Gly-CNP37. Both doses of Pro-Gly-CNP37 have increased growth plate width (FIG. 77), increased right and left tibia lengths (FIGS. 78A and B), increased leg length (FIG. 79), increased arm length (FIG. 80), increased body length (FIG. 81), and increased the serum level of alkaline phosphatase (FIG. 82).

Figure 83:
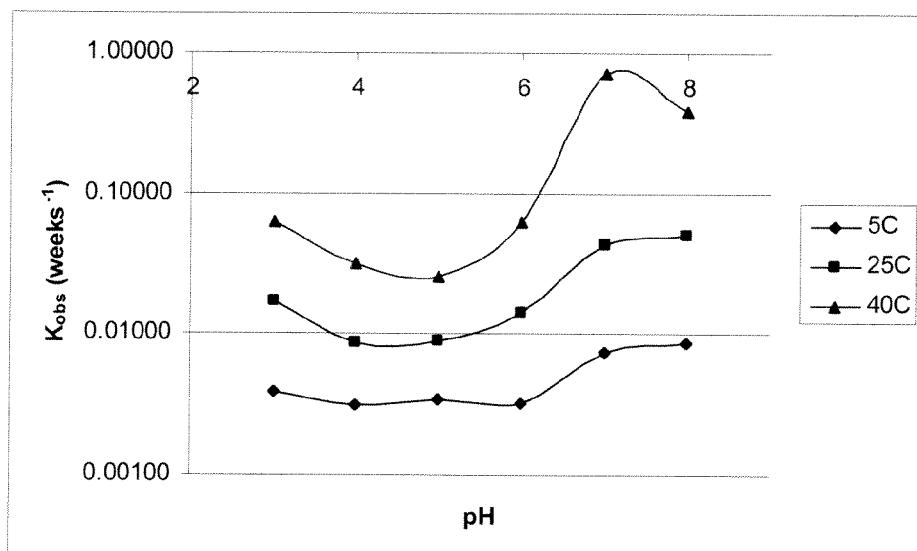

FIG. 83 depicts the observed plot of degradation rate constant ($K_{obs}$) vs. pH at pH 3-8 and 5° C., 25° C. and 40° C. for Gly-CNP37 formulations.

DETAILED DESCRIPTION OF THE DISCLOSURE

The present disclosure relates to novel variants of CNP having reduced affinity to NEP and/or NPR-C, and reduced susceptibility to cleavage by NEP and/or clearance by NPR-C, pharmaceutical compositions comprising such CNP variants, and methods of using such CNP variants to treat disorders responsive to CNP, including but not limited to bone-related disorders such as achondroplasia and disorders associated with vascular smooth muscle cells and tissues.

A. Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

The terms "ambient temperature" and "room temperature" are used interchangeably herein and refer to the temperature of the surrounding environment (e.g., the room in which a reaction is conducted or a composition is stored). In certain embodiments, ambient temperature or room temperature is a range from about 15° C. to about 28° C., or from about 15° C. to about 25° C., or from about 20° C. to about 28° C., or from about 20° C. to about 25° C., or from about 22° C. to about 28° C., or from about 22° C. to about 25° C. In other embodiments, ambient temperature or room temperature is about 15° C., 16° C., 17° C., 18° C., 19° C., 20° C., 21° C., 22° C., 23° C., 24° C., 25° C., 26° C., 27° C. or 28° C.

Definition of standard chemistry terms may be found in reference works, including Carey and Sundberg, Advanced Organic Chemistry, 3$^{rd}$ Edition, Vols. A and B (Plenum Press, New York 1992). The practice of the present disclosure may employ, unless otherwise indicated, certain conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., 4$^{th}$ Edition, 2004); Sambrook, et al., Molecular Cloning: A Laboratory Manual (2$^{nd}$ Edition, 1989); Methods In Enzymology (S. Colowick and N. Kaplan eds., Academic Press, Inc.); Remington's Pharmaceutical Sciences, 18$^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

"Polypeptide" and "protein" refer to a polymer composed of amino acid residues, related naturally occurring structural variants, and synthetic non-naturally occurring analogs thereof, linked via peptide bonds or peptide bond isosteres. Synthetic polypeptides can be synthesized, for example, using an automated polypeptide synthesizer. The terms "polypeptide" and "protein" are not limited to a minimum length of the product. The term "protein" typically refers to large polypeptides. The term "peptide" typically refers to short polypeptides. Thus, peptides, oligopeptides, dimers, multimers, and the like, are included within the definition. Both full-length proteins and fragments thereof are encompassed by the definition. The terms "polypeptide" and "protein" also include postexpression modifications of the polypeptide or protein, for example, glycosylation, acetylation, phosphorylation and the like. Furthermore, for purposes of the present disclosure, a "polypeptide" can include "modifications," such as deletions, additions, substitutions (which may be conservative in nature or may include substitutions with any of the 20 amino acids that are commonly present in human proteins, or any other naturally or non-naturally-occurring or atypical amino acids), and chemical modifications (e.g., addition of or substitution with peptidomimetics), to the native sequence. These modifications may be deliberate, as through site-directed mutagenesis, or through chemical modification of amino acids to remove or attach chemical moieties, or may be accidental, such as through mutations arising with hosts that produce the proteins or through errors due to PCR amplification.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to substitution of an amino acid in a polypeptide with a functionally, structurally or chemically similar natural or unnatural amino acid. In one embodiment, the following groups each contain natural amino acids that are conservative substitutions for one another:

(1), Alanine (A) Serine (S), Threonine (T);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V); and
(6) Phenylalanine (F), Tyrosine (Y), Tryptophan (W).

In another embodiment, the following groups each contain natural amino acids that are conservative substitutions for one another:

(1) Glycine (G), Alanine (A);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V), Alanine (A);
(6) Phenylalanine (F), Tyrosine (Y), Tryptophan (W); and
(7) Serine (S), Threonine (T), Cysteine (C).

In a further embodiment, amino acids may be grouped as set out below.

(1) hydrophobic: Met, Ala, Val, Leu, Ile, Phe, Trp;
(2) neutral hydrophilic: Cys, Ser, Thr, Asn, Gln;
(3) acidic: Asp, Glu;
(4) basic: His, Lys, Arg;
(5) residues that influence backbone orientation: Gly, Pro; and
(6) aromatic: Trp, Tyr, Phe, His.

In one embodiment, the peptides or polypeptides described herein are generated via recombinant means, using a polynucleotide encoding a CNP variant. The disclosure thus encompasses polynucleotides encoding any of the CNP variants described herein, host cells or vectors comprising such polynucleotides, optionally linked to expression control sequences, and methods of using such polynucleotides, vectors or host cells to produce CNP variants of the disclosure. CNP variants expressed by such polynucleotides may be produced by methods including growing host cells in culture medium under conditions suitable for expression of the polynucleotide encoding a CNP variant, and isolating the expression product from the host cells or culture medium. Actual expression products may vary slightly from the encoded protein product depending on any post-translational processing.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), the nucleotide sequence also encompasses an RNA sequence (i.e., A, U, G, C) in which "U" replaces "T." "cDNA" refers to a DNA that is complementary or identical to an mRNA, in either single stranded or double stranded form.

"Expression control sequence" refers to a nucleotide sequence that regulates the expression of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Chimera" as used herein refers to a polynucleotide or polypeptide comprising at least two heterologous polynucleotide or polypeptide sequences (i.e. derived from different sources or not associated with each other as a naturally-occurring sequence) which are directly or indirectly attached or linked together using techniques commonly known in the art, e.g., recombinant expression or chemical crosslinking. In one embodiment, the heterologous sequence can comprise a protein or peptide directly or indirectly linked to a CNP peptide or variant, including proteins or peptides which are cleavable from the CNP peptide or variant. In a related embodiment, CNP variants are chimera as described herein.

In certain embodiments, chimeras include CNP fusion proteins comprising a cleavable carrier protein or peptide tag. The term "cleavable carrier protein" or "cleavable peptide tag" refers to a peptide or polypeptide sequence that may be fused, directly or indirectly via a linker, to a heterologous polypeptide sequence, and is removable from the heterologous sequence using an agent that cleaves or separates the cleavable peptide or polypeptide from the heterologous polypeptide or protein. In some embodiments, the cleavable carrier protein or peptide tag improves generation, purification and/or detection of the fusion protein or the heterologous polypeptide. Exemplary cleavable carrier proteins and peptide tags include, but are not limited to, human transcription factor TAF12 (TAF12), ketosteroid isomerase (KSI), maltose-binding protein (MBP), β-galactosidase (β-Gal), glutathione-S-transferase (GST), thioredoxin (Trx), chitin-binding domain (CBD), BMP-2 mutation (BMPM), SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly (Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and fragments thereof.

A "cleaving agent" is an agent that is useful to cleave or separate, e.g., a cleavable peptide or polypeptide from a heterologous polypeptide or protein. Exemplary cleaving agents include, but are not limited to, palladium, cyanogen bromide (CNBr), formic acid, hydroxylamine, clostripain, thrombin, chymotrypsin, trypsin, trypsin-like proteases, carboxypeptidase, enterokinase (enteropeptidase), Kex 2 protease, Omp T protease, Factor Xa protease, subtilisin, proTEV, SUMO protease, V8 protease, HIV protease, rhinovirus protease, furilisin protease, IgA proteases, human Pace protease, collagenase, Nia protease, poliovirus 2Apro protease, poliovirus 3C protease, genenase, furin, elastase, Proteinase K, pepsin, rennin (chymosin), microbial aspartic proteases, papain, calpain, chymopapain, ficin (ficain), bromelain (bromelase), cathespisin B, caspases, thermolysin, Endoprotease Arg-C, Endoprotease Glu-C, Endoprotease Lys-C, kallikrein, and plasmin.

The terms "identical" and percent "identity", in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical", in the context of two nucleic acids or polypeptides, generally refers to two or more sequences or subsequences that have at least 40%, 50%, 60%, 70%, 80%, 90%, 95%, or 98% nucleotide or amino acid residue identity, when compared and aligned for maximum correspondence, as measured using one of the following sequence comparison algorithms or by visual inspection. In certain embodiments, the substantial homology or identity exists over regions of the sequences that are at least about 25, 50, 100 or 150 residues in length. In another embodiment, the sequences are substantially homologous or identical over the entire length of either or both comparison biopolymers.

For sequence comparison, typically one sequence acts as a reference sequence, to which test sequences are compared. When using a sequence comparison algorithm, test and reference sequences are inputted into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math., 2: 482 (1981), by the homology alignment algorithm of Needleman & Wunsch, J. Mol. Biol., 48: 443 (1970), by the search for similarity method of Pearson & Lipman, Proc. Natl. Acad. Sci. USA, 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a useful algorithm is PILEUP, which uses a simplification of the progressive alignment method of Feng & Doolittle, J. Mol. Evol., 35: 351-360 (1987) and is similar to the method described by Higgins & Sharp, CABIOS, 5: 151-153 (1989). Another algorithm useful for generating multiple alignments of sequences is Clustal W (Thompson et al., Nucleic Acids Research, 22: 4673-4680 (1994)). An example of an algorithm that is suitable for determining percent sequence identity and sequence similarity is the BLAST algorithm (Altschul et al., J. Mol. Biol., 215: 403-410 (1990); Henikoff & Henikoff, Proc. Natl. Acad. Sci. USA, 89: 10915 (1989); Karlin & Altschul, Proc. Natl. Acad. Sci. USA, 90: 5873-5787 (1993)). Software for performing BLAST analyses is publicly available through the National Center for Biotechnology Information.

A further indication that two nucleic acid sequences or polypeptides are substantially homologous or identical is that the polypeptide encoded by the first nucleic acid is immunologically cross reactive with the polypeptide encoded by the second nucleic acid, as described below. Thus, a polypeptide is typically substantially identical to a second polypeptide, for example, where the two polypeptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. In one embodiment, a substantially pure composition means that the species of interest comprises at least about 70%, 75%, 80%, 85%, 90%, 95%, 98% or more of the macromolecular species present in the composition on a molar or weight basis. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In an embodiment, the compounds of the disclosure are substantially pure or isolated. In another embodiment, the compounds of the disclosure are substantially pure or isolated with respect to the macromolecular starting materials used in their production. In yet another embodiment, the pharmaceutical compositions of the disclosure comprise a substantially pure or isolated CNP variant admixed with one or more pharmaceutically acceptable excipients, carriers or diluents, and optionally with another biologically active agent.

"Naturally occurring" as applied to an object refers to the fact that the object can be found in nature. For example, a polypeptide or polynucleotide sequence that is present in an organism (including viruses) and which has not been intentionally modified by man in the laboratory is naturally occurring. In one embodiment, a "naturally occurring" substance is of human origin.

"Wild-type" (wt) is a term referring to the natural form, including sequence, of a polynucleotide, polypeptide or protein in a species. A wild-type form is distinguished from a mutant form of a polynucleotide, polypeptide or protein arising from genetic mutation(s).

In one embodiment, a first polypeptide that is an "analog" or "variant" or "derivative" of a second polypeptide is a polypeptide having at least about 50%, 60% or 70% sequence homology, but less than 100% sequence homology, with the second polypeptide. Such analogs, variants or derivatives may be comprised of non-naturally occurring amino acid residues, including without limitation, homoarginine, ornithine, penicillamine, and norvaline, as well as naturally occurring amino acid residues. Such analogs, variants or derivatives may also be composed of one or a plurality of D-amino acid residues, and may also contain peptidomimetics or peptide bond isosteres such as non-peptide linkages between two or more amino acid or peptidomimetic residues. In another embodiment, a first polypeptide is an "analog", "variant" or "derivative" of a second polypeptide if the first polypeptide is not a known cleavage product of the second polypeptide or is not a known precursor of the second polypeptide, even if the first polypeptide has 100% sequence homology to the second polypeptide or has a wild-type sequence.

In an embodiment, the term "derived from" as used herein refers to a polypeptide or peptide sequence that is based on a wild type or naturally occurring polypeptide or peptide sequence and can have one or more deletions, additions, and/or substitutions with natural amino acids, unnatural amino acids or peptidomimetics. In one embodiment, the derivative sequence shares at least about 40%, 50%, 60% or 70%, but less than 100%, sequence similarity to the wild-type or naturally occurring sequence. In another embodiment, the derivative may be a fragment of a polypeptide, wherein the fragment is substantially homologous (e.g., at least about 70%, 75%, 80%, 85%, 90%, or 95% homologous) to the wild-type polypeptide over a length of at least about 5, 10, 15, 20, 25, 30, 35, 40, 45 or 50 amino acids. In still another embodiment, a polypeptide is "derived from" a wild-type polypeptide if it has a moiety (e.g., a polymer such as, e.g., PEG) directly or indirectly attached to it which is not present on the wild-type polypeptide, even if both polypeptides share 100% homology in their amino acid sequence.

As used herein, an "NPPC-derived" polypeptide refers to a polypeptide derived from the natriuretic peptide precursor C(NPPC) polypeptide, which is a single chain 126-amino acid pre-pro polypeptide, and which upon cleavage ultimately results in wtCNP22. Removal of the signal peptide from NPPC yields pro-CNP, and further cleavage by the endoprotease furin generates an active 53-amino acid peptide (CNP-53), which is secreted and cleaved again by an unknown enzyme to produce the mature 22-amino acid peptide (CNP, or CNP-22). Therefore, CNP22 itself is an "NPPC-derived" polypeptide by virtue of being derived from NPPC. In one embodiment, an NPPC-derived polypeptide is at least about 40%, 50%, 60%, 70%, 75%, 80%, 85%, 90%, or 95% homologous to the wild type NPPC over the same number of amino acid residues. It is further contemplated that an NPPC-derived peptide may comprise from about 1 to about 53, or 1 to 37, or 1 to 35, or 1 to 31, or 1 to 27, or 1 to 22, or to 35, or about 15 to about 37 residues of the NPPC polypeptide. In one embodiment, an NPPC-derived peptide may comprise a sequence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acids derived from the NPPC polypeptide.

The term "effective amount" means a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health. An appropriate "effective" amount in any individual case may be determined by one of ordinary skill in the art using routine experimentation. It will be understood that the specific dose level and frequency of dosage for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex, and diet of the patient; and the severity of the particular condition.

"Treatment" refers to prophylactic treatment or therapeutic treatment or diagnostic treatment. In certain embodiments, "treatment" refers to administration of a compound or composition to a subject for therapeutic, prophylactic or diagnostic purposes.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective.

The compounds of the disclosure may also be given as a therapeutic treatment or for diagnosis.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Bone- or cartilage-associated biomarker" or "bone- or cartilage-associated marker" refers to a growth factor, enzyme, protein, or other detectable biological substance or moiety whose level is increased or decreased in association with, e.g., cartilage turnover, cartilage formation, cartilage growth, bone resorption, bone formation, bone growth, or combinations thereof. Such biomarkers may be measured before, during and/or after administration of a CNP variant as described herein. Exemplary bone- or cartilage-associated biomarkers include, but are not limited to, CNP, cGMP, propeptides of collagen type II and fragments thereof, collagen type II and fragments thereof, propeptides of collagen type I and fragments thereof, collagen type 1 and fragments thereof, osteocalcin, proliferating cell nuclear antigen (PCNA), aggrecan chondroitin sulfate, and alkaline phosphatase. Cartilage- and bone-associated biomarkers can be measured in any appropriate biological sample, including but not limited to tissues, blood, serum, plasma, cerebrospinal fluid, synovial fluid and urine. In some embodiments, the biomarkers are measured in blood, plasma or serum from animals undergoing efficacy/pharmacodynamic in vivo studies and/or from the conditioned media of ex vivo studies.

In certain embodiments, the level of at least one bone- or cartilage-associated biomarker is measured and the amount or frequency of administration of CNP variant administered to a subject can be adjusted according to the level of the biomarker measured. In some embodiments, the level of biomarker is "below a target level" or "above a target level." A target level of a biomarker is a level or range of levels of the biomarker at which a therapeutic effect is observed in the subject receiving the CNP variant. In certain embodiments, the target level of a biomarker for a subject having a CNP-responsive disorder or condition is the level or range of levels of the biomarker observed in a normal, non-affected subject. In other embodiments, to indicate a therapeutic effect, the target level of a biomarker need not be equivalent to the level or range of levels of the biomarker observed in a normal subject, but can be within, e.g., 100%, 90%, 80%, 70%, 60%, 50%, 40%, 30%, 20%, 10% or 5% of the "normal" level or range of levels of the biomarker observed in a non-affected subject.

For example, if the level of a biomarker increases in association with bone or cartilage formation or growth, the target level of the biomarker indicating a therapeutic effect may be higher than the level of the biomarker in patients suffering from a CNP-responsive disorder who have not been administered a CNP variant, and may optionally be lower than the "normal" level(s), at about the "normal" level(s), or above the "normal" level(s) of the biomarker in subjects not suffering from that disorder. In one embodiment, if the level of a biomarker is below a target level, it indicates an inadequate therapeutic effect, which may require an increase in the amount or frequency of administration of CNP variant administered. In a related embodiment, if the biomarker is above a target level, it indicates that more CNP variant than necessary has been administered, which may require a decrease in the amount or frequency of administration of the CNP variant administered.

As another example, if the level of a biomarker decreases in association with bone or cartilage formation or growth, the target level of the biomarker indicating a therapeutic effect may be lower than the level of the biomarker in patients suffering from a CNP-responsive disorder who have not been administered a CNP variant, and may optionally be higher than the "normal" level(s), at about the "normal" level(s), or below the "normal" level(s) of the biomarker in subjects not suffering from that disorder. In such a case, the converse of the above adjustments in CNP variant amount and frequency of administration may apply.

"Pharmaceutical composition" refers to a composition suitable for pharmaceutical use in subject animal, including humans and mammals. A pharmaceutical composition comprises a therapeutically effective amount of a CNP variant, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

By "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

The term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

"Physiological conditions" refer to conditions in the body of an animal (e.g., a human). Physiological conditions include, but are not limited to, body temperature and an aqueous environment of physiologic ionic strength, pH and enzymes. Physiological conditions also encompass conditions in the body of a particular subject which differ from the "normal" conditions present in the majority of subjects, e.g., which differ from the normal human body temperature of approximately 37° C. or differ from the normal human blood pH of approximately 7.4.

By "physiological pH" or a "pH in a physiological range" is meant a pH in the range of approximately 7.0 to 8.0 inclusive, more typically in the range of approximately 7.2 to 7.6 inclusive.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

The terms "polyethylene glycol", "PEG", "polyethylene oxide" and "PEO" are used interchangeably herein unless indicated otherwise. A CNP peptide (CNP22 or a variant thereof) conjugated via an amino group to a "PEOn" polymer associated with the number n, in general has the formula: $CH_3-[-O-CH_2CH_2-]_n-C(=O)-NHR$, where n is the number of ethylene oxide units and R denotes the rest of the peptide. The "PEOn" polymer can optionally have an alkylene group, $(CH_2)_m$, where m is an integer from 1 to 5, between the carbonyl carbon and the repeating ethylene oxide units. Such a "PEOn" (e.g., PEO12 or PEO24) polymer is monodispersed, i.e., is a single discrete polymer of a particular molecular weight. Similarly, a CNP peptide conjugated via an amino group to a "PEGnK" polymer associated with the number nK, in general has the formula: $CH_3-[-O-CH_2CH_2-]_p-C(=O)-NHR$, where p is an integer greater than 1. The "PEGnK" polymer also can optionally have an alkylene group, $(CH_2)_m$, where m is an integer from 1 to 5, between the carbonyl carbon and the repeating ethylene oxide units. However, such a "PEGnK" (e.g., PEG1K, PEG2K, PEG5K or PEG20K) polymer is polydispersed, i.e., contains a mixture of polymers having a distribution of molecular weights, where the number nK denotes the polymer number-average molecular weight ($M_n$) in kilo Daltons. For example, "PEG2K" conjugated to a CNP peptide denotes a polydispersed PEG polymer having a polymer number-average molecular weight of around 2 kDa.

When a range of the mass of a polymer (e.g., PEG) is given (e.g., in units of kDa), the range refers to a range of polymer number-average molecular weights, not to a range of molecular weights of multiple polymers in a polydispersed mixture, unless expressly indicated otherwise.

The term "halogen", "halide" or "halo" refers to fluorine, chlorine, bromine, and/or iodine.

The term "alkyl" refers to a linear or branched saturated monovalent hydrocarbon radical, wherein the alkyl may optionally be substituted with one or more substituents Q as described herein. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, including n-propyl and isopropyl), butyl (including all isomeric forms, including n-butyl, isobutyl, sec-butyl and tert-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkoxy" refers to an —O-alkyl group. In certain embodiments, an alkoxy group may optionally be substituted with one or more substituents Q as described herein.

The term "haloalkyl" refers to an alkyl group that is substituted with one or more halide atoms. In certain embodiments, a haloalkyl group is substituted with one, two, three, four, five or six halide atoms. In certain embodiments, a haloalkyl group may optionally be substituted with one or more additional substituents Q as described herein.

The term "cycloalkyl" refers to a cyclic saturated bridged and/or non-bridged monovalent hydrocarbon radical, which may be optionally substituted with one or more substituents Q as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "heterocyclyl" or "heterocyclic" refers to a monocyclic non-aromatic ring system or a multicyclic ring system that contains at least one non-aromatic ring, wherein one or more of the non-aromatic ring atoms are heteroatoms independently selected from O, S, or N, and the remaining non-aromatic ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclic groups include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, a heterocyclic group may optionally be substituted with one or more substituents Q as described herein.

The term "aryl" refers to a monocyclic aromatic group or a multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where at least one of the rings is aromatic and the others may be saturated, partially unsaturated, or aromatic, for example, dihydronaphthyl, indenyl, indanyl, and tetrahydronaphthyl (tetralinyl). In certain embodiments, an aryl group may optionally be substituted with one or more substituents Q as described herein.

The term "heteroaryl" refers to a monocyclic aromatic group or a multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, a heteroaryl group may optionally be substituted with one or more substituents Q as described herein.

The term "optionally substituted" is intended to mean that a group, including alkyl, alkoxy, haloalkyl, cycloalkyl, heterocyclyl, aryl and heteroaryl, may be substituted with one or more substituents Q (in one embodiment, one, two, three or four substituents Q), where each Q is independently selected from the group consisting of cyano, halo, oxo, nitro, $C_{1-6}$ alkyl, $C_{1-6}$ alkoxy, halo-$C_{1-6}$ alkyl, $C_{3-7}$ cycloalkyl, heterocyclyl, $C_{6-14}$ aryl, heteroaryl, —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^f$, —N$R^e$C(O)O$R^f$, —N$R^e$C(O)N$R^fR^g$, —N$R^e$C(=N$R^h$)N$R^fR^g$, —N$R^e$S(O)$R^f$, —N$R^e$S(O)$_2R^f$, —N$R^e$S(O)N$R^fR^g$, —N$R^e$S(O)$_2$N$R^fR^g$, —S$R^e$, —S(O)$R^e$, —S(O)$_2R^e$, and —S(O)$_2$N$R^fR^g$, wherein each $R^e$, $R^f$, $R^g$, and $R^h$ is independently hydrogen, $C_{1-6}$ alkyl, $C_{3-7}$ cycloalkyl, heterocyclyl, $C_{6-14}$ aryl, or heteroaryl; or $R^f$ and $R^g$, together with the N atom to which they are attached, form heterocyclyl.

B. CNP Variants

The use of CNP22 as a therapeutic is limited by its short half-life in plasma (J. Clin. Endocrinol. Metab., 78: 1428-35 (1994)). In human plasma, the concentration of CNP22 typically is less than five picomolar. CNP22 is degraded and cleared from circulation by NEP and NPR-C in humans (Growth Hormone & IGF Res., 16: S6-S14). In all human and animal studies using systemically administered CNP22, continuous infusion has been used to increase the CNP22 concentration in the subjects. A CNP peptide having a longer half-life and at least a similar level of functionality would be beneficial to a CNP-based therapeutic strategy. CNP variants are also disclosed in related International Application No. PCT/US08/84270, specifically incorporated herein by reference.

The present disclosure provides CNP variants which have reduced affinity to NEP and/or NPR-C, and reduced susceptibility to cleavage by NEP and/or clearance by NPR-C, but which have substantially similar or better functionality than wild-type CNP22. Reduced susceptibility of CNP variants to cleavage by NEP and/or clearance by NPR-C would increase the plasma or serum half-life of the variants, thereby increasing the opportunity for the variants to distribute to the target tissues and sites and effectuate the desired pharmacological effects. In certain embodiments, the CNP variants described herein have reduced susceptibility to cleavage by NEP and/or clearance by NPR-C in vitro or in vivo by at least about 1.5-fold, 2-fold, 2.5-fold, 3-fold, 3.5-fold, 4-fold, 4.5-fold, or 5-fold compared to wtCNP22, and have increased plasma or serum half-life in vivo by at least about 1.5-fold, 2-fold, 2.5-fold, 3-fold, 3.5-fold, 4-fold, 4.5-fold, or 5-fold compared to wtCNP22, while retaining at least about 50%, 60%, 70%, 80%, 90% or 100% of the functionality of wtCNP22, or having at least about 1.5-fold, 2-fold, 2.5-fold, 3-fold, 3.5-fold, 4-fold, 4.5-fold, or 5-fold greater functionality than wtCNP22. CNP functionality can be evaluated in terms of, e.g., the level of one or more biomarkers (e.g., cGMP) associated with cartilage or bone formation or growth in an in vitro or in vivo study, the length of particular bones in an ex vivo or in vivo study, etc.

Natural substrates of NEP are small and natriuretic peptides (about 2.2 to about 3.2 kDa) are the largest of the natural substrates. According to X-ray crystallographic analyses, the NEP active-site is buried deep inside a central cavity, effectively restricting the size of substrate molecules to no more than about 3 kDa (Oefner et al., J. Mol. Biol., 296: 341-349 (2000)). Based on NPR-B signaling studies, variants of CNP-22, such as CNP-17 (retaining only the cyclic domain, Cys6-Cys22, of CNP22) and CNP-53 (CNP-22 with a 31-amino acid extension at the N-terminus), can still bind and activate NPR-B similarly to the 2.2 kDa wtCNP-22. Accordingly, the disclosure encompasses CNP variants conjugated to a natural (e.g., peptide) and/or synthetic (e.g., PEG) polymer at the N-terminus and/or C-terminus of CNP22 or variants thereof, which exhibit increased NEP resistance but retain the ability to bind and activate the NPR-B signaling receptor.

In one embodiment, the disclosure encompasses CNP variants represented by the general formula:

(x)-$Cys_6$-$Phe_7$-$Gly_8$-$Leu_9$-$Lys_{10}$-$Leu_{11}$-$Asp_{12}$-$Arg_{13}$-$Ile_{14}$-$Gly_{15}$-$Ser_{16}$-$Met_{17}$-$Ser_{18}$-$Gly_{19}$-$Leu_{20}$-$Gly_{21}$-$Cys_{22}$-(z) (SEQ ID NO:139), or (x)-$Gly_1$-$Leu_2$-$Ser_3$-$Lys_4$-$Gly_5$-$Cys_6$-$Phe_7$-$Gly_8$-$Leu_9$-$Lys_{10}$-$Leu_{11}$-$Asp_{12}$-$Arg_{13}$-$Ile_{14}$-$Gly_{15}$-$Ser_{16}$-$Met_{17}$-$Ser_{18}$-$Gly_{19}$-$Leu_{20}$-$Gly_{21}$-$Cys_{22}$-(z) (SEQ ID NO:140), wherein:

(x) and (z) each independently are a natural polymer (e.g., a peptide sequence containing at least one amino acid) and/or a synthetic polymer (e.g., PEG) as described herein, such that the total mass of the CNP variant is characterized by the ranges described generally herein, e.g., in the range from about 2.6 kDa or 2.8 kDa to about 6 or 7 kDa. In one embodiment, the residues from Cys6 to Cys22 form a cyclic portion. In an embodiment, (x) and/or (z) comprise an amino acid extension derived from NPPC or a non-CNP polypeptide (e.g., ANP, BNP, IgG, etc.), wherein the extension contains 1 to 40, 1 to 35, 1 to 31, 5 to 35, 5 to 31 or 5 to 15 amino acids. In another embodiment, the CNP variants comprise one or more modifications and/or substitutions with another natural amino acid, an unnatural amino acid, a peptidomimetic and/or a peptide bond isostere at one or more of the following positions of CNP22: Gly1, Lys4, Gly5, Cys6, Phe7, Gly8, Leu9, Lys10, Leu11, Ile14, Gly15, Ser16, Met17, Gly19, Leu20 and Gly21.

In another embodiment, CNP variants having a total mass characterized by the ranges described generally herein, e.g., from about 2.6 kDa or 2.8 kDa to about 6 or 7 kDa, designed for increased resistance to NEP degradation, are represented by the general formula:

(x)-$Cys_6$-$Phe_7$-$Gly_8$-$Leu_9$-(h)$_{10}$-$Leu_{11}$-$Asp_{12}$-$Arg_{13}$-$Ile_{14}$-$Gly_{15}$-$Ser_{16}$-$Met_{17}$-$Ser_{18}$-$Gly_{19}$-$Leu_{20}$-$Gly_{21}$-$Cys_{22}$-(z) (SEQ ID NO: 141), or (x)-$Gly_1$-$Leu_2$-$Ser_3$-(b)$_4$-$Gly_5$-$Cys_6$-$Phe_7$-$Gly_8$-$Leu_9$-(h)$_{10}$-$Leu_{11}$-$Asp_{12}$-$Arg_{13}$-$Ile_{14}$-$Gly_{15}$-$Ser_{16}$-$Met_{17}$-$Ser_{18}$-$Gly_{19}$-$Leu_{20}$-$Gly_{21}$-$Cys_{22}$-(z) (SEQ ID NO: 6), wherein:

(x) is a synthetic or natural polymeric group, or a combination thereof, wherein a non-limiting example of a synthetic polymeric group is PEG (or PEO), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histidine-rich glycoproteins, fibronectin, fibrinogen, zinc finger-containing polypeptides, osteocrin or fibroblast growth factor 2 (FGF2);

(z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG); and (b) and (h) independently may be the wild type Lys at that position or may be replaced with a conservative amino acid substitution or any natural or unnatural amino acid or peptidomimetic that does not have a reactive primary amine on a side chain, including but not limited to Arg, Gly, 6-hydroxy-norleucine, citrulline (Cit), Gln, Glu or Ser. In one embodiment, (b) is Arg. In another embodiment, for improved NEP resistance, (b) is not Gly. In yet another embodiment, (h) is not Arg.

Non-limiting examples of amino acid sequences derived from NPPC or variants thereof include:

Arg,

Glu-Arg,

Gly-Ala-Asn-Lys-Lys, (SEQ ID NO: 7)

Gly-Ala-Asn-Arg-Arg, (SEQ ID NO: 8)

Gly-Ala-Asn-Pro-Arg, (SEQ ID NO: 9)

-continued

Gly-Ala-Asn-Gln-Gln, (SEQ ID NO: 10)

Gly-Ala-Asn-Ser-Ser, (SEQ ID NO: 11)

Gly-Ala-Asn-Arg-Gln, (SEQ ID NO: 12)

Gly-Ala-Asn-Arg-Met, (SEQ ID NO: 13)

Gly-Ala-Asn-Arg-Thr, (SEQ ID NO: 14)

Gly-Ala-Asn-Arg-Ser, (SEQ ID NO: 15)

Ala-Ala-Trp-Ala-Arg-Leu-Leu-Gln-Glu-His-Pro-Asn-Ala, (SEQ ID NO: 16)

Ala-Ala-Trp-Ala-Arg-Leu-Leu-Gln-Glu-His-Pro-Asn-Ala-Arg, (SEQ ID NO: 17)

Asp-Leu-Arg-Val-Asp-Thr-Lys-Ser-Arg-Ala-Ala-Trp-Ala-Arg, (SEQ ID NO: 18)

Gln-Glu-His-Pro-Asn-Ala-Arg-Lys-Tyr-Lys-Gly-Ala-Asn-Lys-Lys, (SEQ ID NO: 19)

Gln-Glu-His-Pro-Asn-Ala-Arg-Lys-Tyr-Lys-Gly-Ala-Asn-Arg-Arg, (SEQ ID NO: 20)

Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Lys-Lys, (SEQ ID NO: 21)
and Asp-Leu-Arg-Val-Asp-Thr-Lys-Ser-Arg-Ala-Ala-Trp-Ala-Arg-Leu-Leu-Gln-Glu-His-Pro-Asn-Ala-Arg-Lys-Tyr-Lys-Gly-Ala-Asn-Arg-Arg. (SEQ ID NO: 22)

Non-limiting examples of amino acid sequences derived from non-CNP polypeptides such as, e.g., ANP, BNP, serum albumin and IgG include:

Ser-Leu-Arg-Arg-Ser-Ser; (SEQ ID NO: 23)

Asn-Ser-Phe-Arg-Tyr; (SEQ ID NO: 24)

Ser-Pro-Lys-Met-Val-Gln-Gly-Ser-Gly; (SEQ ID NO: 25)

Met-Val-Gln-Gly-Ser-Gly; (SEQ ID NO: 26)

Lys-Val-Leu-Arg-Arg-Tyr; (SEQ ID NO: 27)

Lys-Val-Leu-Arg-Arg-His; (SEQ ID NO: 28)

Gly-Gln-His-Lys-Asp-Asp-Asn-Pro-Asn-Leu-Pro-Arg; (SEQ ID NO: 29)

Gly-Val-Pro-Gln-Val-Ser-Thr-Ser-Thr; (SEQ ID NO: 30)

Gly-Glu-Arg-Ala-Phe-Lys-Ala-Trp-Ala-Val-Ala-Arg-Leu-Ser-Gln; (SEQ ID NO: 31)

Gly-Gln-Pro-Arg-Glu-Pro-Gln-Val-Tyr-Thr-Leu-Pro-Pro-Ser. (SEQ ID NO: 32)

In an embodiment, the N-terminal (x) group and/or the C-terminal (z) group of any of the CNP variants having an (x) and/or (z) group, as described herein, independently comprise an amino acid sequence that contains a small number of, if any, acidic natural or unnatural amino acids (e.g., Asp or Glu). In another embodiment, (x) and/or (z) are enriched in basic natural or unnatural amino acids (e.g., Lys, Arg or His) to maintain an alkaline pI similar to the pI of CNP22 (pI 8.9). In one embodiment, the pI of the CNP variants is in the range from about 8 to about 10.5, designed so that the CNP variants can diffuse more readily through the extracellular matrix surrounding chondrocytes of bone growth plates. In narrower embodiments, the pI of the CNP variants is from about 8.5 to about 10.5, or from about 8.5 to about 10, or from about 9 to about 10.

In yet another embodiment, (x) and/or (z) are enriched in polar natural or unnatural amino acids, designed for increased aqueous solubility. In still another embodiment, (x) and/or (z) contain a small number of, if any, hydrophobic natural or unnatural amino acids (e.g., Ala, Val, Leu, Ile or Met).

In a further embodiment, the N-terminus of the CNP variants terminates in at least one glycine residue, designed for increased serum half-life. In a related embodiment, to prevent pyroglutamine formation, the N-terminus of CNP variants terminates in a glycine residue if it would otherwise terminate in glutamine. In one embodiment, the (x) group contains an amino acid extension whose N-terminus terminates in at least one glycine residue. In another embodiment, (x) and/or (z) do not contain two adjacent basic natural or unnatural amino acids (e.g., Lys-Lys or Arg-Arg), designed to reduce susceptibility to cleavage by the protease furin. In an embodiment, (x) does not contain two adjacent basic amino acids immediately preceding the position corresponding to Gly1 of CNP22.

In still another embodiment, the (x) group and/or the (z) group of the CNP variants comprise an amino acid sequence derived from NPPC (e.g., derived from CNP53). In an embodiment, (x) comprises an amino acid sequence derived from the N-terminal tail of ANP or BNP. In another embodiment, (z) comprises an amino acid sequence derived from the C-terminal tail of ANP or BNP. In a further embodiment, (x) and/or (z) comprise an amino acid sequence derived from a non-natriuretic polypeptide such as, e.g., IgG, human serum albumin (HSA), histidine-rich glycoproteins, fibronectin, fibrinogen, zinc finger-containing polypeptides, FGF-2, and bone-targeting proteins (e.g., osteocrin, osteopontin, osteocalcin, and sialoprotein).

In any embodiment described herein in which CNP22 or a variant thereof can have an N-terminal (x) group and/or a C-terminal (z) group, (x) and/or (z) independently can contain an amino acid sequence derived from the functional domain of a bone morphogenetic protein (BMP). An N-terminal and/or C-terminal amino acid extension derived from the functional domain of a BMP can increase the NEP resistance, and hence the serum half-life of the CNP variant, by increasing the total mass of the CNP variant to characterized by the ranges described generally herein, e.g., a range from about 2.6 kDa or 2.8 kDa to about 6 or 7 kDa. In addition, since certain BMPs are growth factors and cytokines that induce the formation of bone and cartilage, a fragment derived from the functional domain of a BMP can promote chondrocyte, cartilage or bone growth by a mechanism distinct from activation of the guanylyl cyclase function of NPR-B by the cyclic domain of CNP22 or a variant thereof. Non-limiting examples of BMPs that promote bone formation and development, cartilage formation and development, and/or osteoblast differentiation include BMP1, BMP2, BMP3, BMP5, BMP7 and BMP8a. In an embodiment, the N-terminus and/or C-terminus of CNP22 or a variant thereof independently are conjugated to an amino acid sequence derived from the last 140 amino acids in the C-terminal portion of BMP1, BMP2, BMP3, BMP5, BMP7 or BMP8a.

In one embodiment, the CNP variants contain an amino acid extension at the N-terminus and/or C-terminus of CNP22 or CNP17, including but not limited to:

```
                                              (SEQ ID NO: 4)
DLRVDTKSRAAWARLLQEHPNARKYKGANKKGLSKGCFGLKLDRIGSMS
GLGC (CNP-53);

(SEQ ID NO: 60)
QEHPNARKYKGANKKGLSKGCFGLKLDRIGSMSGLGC
(CNP-37, Analog BL);

(SEQ ID NO: 61)
AAWARLLQEHPNAGLSKGCFGLKLDRIGSMSGLGC (Analog CA);

(SEQ ID NO: 62)
AAWARLLQEHPNARGLSKGCFGLKLDRIGSMSGLGC (Analog CB);

(SEQ ID NO: 63)
DLRVDTKSRAAWARGLSKGCFGLKLDRIGSMSGLGC (Analog CC);

(SEQ ID NO: 40)
RGLSKGCFGLKLDRIGSMSGLGC;

(SEQ ID NO: 38)
ERGLSKGCFGLKLDRIGSMSGLGC;

(SEQ ID NO: 64)
GANQQGLSKGCFGLKLDRIGSMSGLGC;

(SEQ ID NO: 65)
GANRRGLSKGCFGLKLDRIGSMSGLGC;

(SEQ ID NO: 66)
GANPRGLSKGCFGLKLDRIGSMSGLGC;

(SEQ ID NO: 67)
GANSSGLSKGCFGLKLDRIGSMSGLGC;

(SEQ ID NO: 144)
GHKSEVAHRFKGANKKGLSKGCFGLKLDRIGSMSGLGC;
and (SEQ ID NO: 68)
SPKMVQGSG-CNP17-KVLRRH (Analog CD) (CNP17 having
N-terminal and C-terminal tails derived from BNP).
```

In another embodiment, the CNP variants have a K4R substitution at position 4 of CNP22. Non-limiting examples of CNP(K4R) variants include:

```
                                             (SEQ ID NO: 36)
    GANRRGLSRGCFGLKLDRIGSMSGLGC (Analog AY);

(SEQ ID NO: 37)
    GANPRGLSRGCFGLKLDRIGSMSGLGC (Analog CI);

(SEQ ID NO: 41)
    RGLSRGCFGLKLDRIGSMSGLGC (Analog AZ);

(SEQ ID NO: 39)
    ERGLSRGCFGLKLDRIGSMSGLGC (Analog BA);

(SEQ ID NO: 69)
    GANQQGLSRGCFGLKLDRIGSMSGLGC (Analog CH);
and (SEQ ID NO: 70)
    GANSSGLSRGCFGLKLDRIGSMSGLGC (Analog CG).
```

In further embodiments, the CNP variants are chimeras comprising CNP22, or a variant thereof having amino acid addition(s), deletion(s) and/or substitution(s), and a peptide fragment derived from a polypeptide or protein other than CNP, or the whole non-CNP polypeptide or protein, to the N-terminus of the CNP peptide, wherein CNP22 or the variant thereof may optionally have an N-terminal amino acid extension of one or more amino acid residues. In certain embodiments, the CNP chimeras comprise CNP22 or a variant thereof that has an N-terminal amino acid extension of one or more amino acid residues. In certain embodiments, the CNP chimeras contain lysine-lysine (KK) residues or GANKK residues immediately preceding the first position of CNP22 (Gly in the case of CNP22) or a variant thereof. In other embodiments, the CNP chimeras contain one or two residues different from lysine-lysine immediately preceding the first position of CNP22 or a variant thereof. Non-limiting examples of residues that can immediately precede the first position of CNP22 or a variant thereof include KP, PK, PR, PQ, QK, QQ, RR, SS, GANKP(SEQ ID NO: 200), GANPK (SEQ ID NO: 201), GANPR (SEQ ID NO: 9), GANPQ (SEQ ID NO: 202), GANQK (SEQ ID NO: 203), GANQQ (SEQ ID NO: 10), GANRR (SEQ ID NO: 8), and GANSS (SEQ ID NO: 11).

In another embodiment, the CNP variants are chimera comprising CNP22 and an N-terminal peptide fragment, including but not limited to:

```
                                             (SEQ ID NO: 76)
GHHSHEQHPHGANQQGLSKGCFGLKLDRIGSMSGLGC (Analog CQ)
(histidine-rich glycoprotein (HRGP) fragment-CNP22
chimera);

(SEQ ID NO: 77)
GAHHPHEHDTHGANQQGLSKGCFGLKLDRIGSMSGLGC (Analog CR)
(HRGP fragment-CNP22 chimera);

(SEQ ID NO: 78)
GHHSHEQHPHGANPRGLSKGCFGLKLDRIGSMSGLGC (Analog CX)
(HRGP fragment-CNP22 chimera);

(SEQ ID NO: 79)
GQPREPQVYTLPPSGLSKGCFGLKLDRIGSMSGLGC (Analog CF)
(IgG₁(F_c) fragment-CNP22 chimera);

(SEQ ID NO: 80)
GQHKDDNPNLPRGANPRGLSKGCFGLKLDRIGSMSGLGC
(Analog CY) (human serum albumin (HSA) fragment-
CNP22 chimera);

(SEQ ID NO: 81)
GERAFKAWAVARLSQGLSKGCFGLKLDRIGSMSGLGC
(Analog CE) (HSA fragment-CNP22 chimera);

(SEQ ID NO: 82)
FGIPMDRIGRNPRGLSKGCFGLKLDRIGSMSGLGC (Analog CZ)
(osteocrin "NPR C inhibitor" fragment-CNP22
chimera);
and (SEQ ID NO: 83)
GKRTGQYKLGSKTGPGPKGLSKGCFGLKLDRIGSMSGLGC
(Analog DA) (FGF2 "heparin-binding domain"
fragment-CNP22 chimera).
```

In yet another embodiment, the CNP variants are chimera comprising an N-terminal peptide fragment and CNP22 in which arginine is substituted for Lys4 of CNP22 ("CNP22 (K4R)"), including but not limited to:

```
                                              (SEQ ID NO: 84)
GQPREPQVYTGANQQGLSRGCFGLKLDRIGSMSGLGC (Analog CK)
(IgG₁(F_c) fragment-CNP22(K4R) chimera);

(SEQ ID NO: 85)
GVPQVSTSTGANQQGLSRGCFGLKLDRIGSMSGLGC (Analog CL)
(HSA fragment-CNP22(K4R) chimera);

(SEQ ID NO: 86)
GQPSSSSQSTGANQQGLSRGCFGLKLDRIGSMSGLGC (Analog
CM) (fibronectin fragment-CNP22(K4R) chimera);

(SEQ ID NO: 87)
GQTHSSGTQSGANQQGLSRGCFGLKLDRIGSMSGLGC (Analog
CN) (fibrinogen fragment-CNP22(K4R) chimera);

(SEQ ID NO: 88)
GSTGQWHSESGANQQGLSRGCFGLKLDRIGSMSGLGC (Analog
CO) (fibrinogen fragment-CNP22(K4R) chimera);
and (SEQ ID NO: 89)
GSSSSSSSSSGANQQGLSRGCFGLKLDRIGSMSGLGC (Analog
CP) (zinc finger fragment-CNP22(K4R) chimera).
```

Chimera comprising IgG and CNP22 or a variant thereof are designed for, inter alia, increased resistance to NEP degradation and reduced binding to serum albumin. CNP chimera comprising a surface fragment of HSA are designed for, inter alia, reduced immunogenicity and reduced binding to serum albumin. HRGP-CNP22 and HRGP-CNP22(K4R) chimera containing a cationic, histidine-rich, non-lysine, non-arginine sequence at the N-terminus are designed for, inter alia, increased stability to proteases. Chimera containing an osteocrin fragment are designed to release, upon protease (e.g., furin) cleavage, the osteocrin fragment at bone growth plates, where the fragment would inhibit the clearance receptor NPR-C. With respect to chimera comprising an FGF2 heparin-binding fragment, heparin binding to the fragment is designed to protect the chimera from degradation, thereby providing a longer serum half-life. Chimera containing a fibronectin, fibrinogen, or zinc-finger fragment are designed for reduced binding to serum albumin, among other features.

Not intending to be bound by theory, a CNP variant of molecular weight from about 2.6 or 2.8 kDa to about 6 or 7 kDa which has increased resistance to NEP degradation and has similar or improved functionality (e.g., binding to NPR-B and stimulation of cGMP signaling) as compared to wtCNP22, may be more effective if it does not bind tightly to plasma proteins such as serum albumin. A CNP variant that does not bind tightly to plasma proteins (e.g., serum albumin) may be more effective in diffusing through cartilage, getting to chondrocytes of bone growth plates, and binding to and activating NPR-B for cGMP signaling. In one embodiment, CNP variants designed for reduced binding to plasma proteins (e.g., serum albumin) are chimeras comprising CNP22 or a variant thereof and a peptide fragment from IgG. In another embodiment, CNP variants designed for reduced binding to plasma proteins are chimeras comprising CNP22 or CNP22(K4R) and a fragment from a polypeptide (e.g., IgG, HSA, fibronectin, fibrinogen, a zinc finger-containing polypeptide, etc.). In yet another embodiment, CNP variants designed for reduced binding to plasma proteins comprise CNP22 or a variant thereof conjugated to a hydrophilic or water-soluble polymer. In one embodiment, the hydrophilic or water-soluble polymer is PEG (or PEO). In another embodiment, the hydrophilic or water-soluble polymer (e.g., PEG) is functionalized with one or more functional groups that impart a negative charge to the polymer under physiological conditions, such as, e.g, carboxyl, sulfate or phosphate groups, or a combination thereof.

In a further embodiment, CNP variants of the disclosure include truncated CNP peptides ranging from human CNP-17 (hCNP-17) to human CNP-53 (hCNP-53), and having wild-type amino acid sequences derived from hCNP-53. Such truncated CNP peptides include:

```
                                              (SEQ ID NO: 4)
DLRVDTKSRAAWARLLQEHPNARKYKGANKKGLSKGCFGLKLDRIGSMSG
LGC (CNP-53);

(SEQ ID NO: 146)
LRVDTKSRAAWARLLQEHPNARKYKGANKKGLSKGCFGLKLDRIGSMSGL
GC (CNP-52);

(SEQ ID NO: 147)
RVDTKSRAAWARLLQEHPNARKYKGANKKGLSKGCFGLKLDRIGSMSGL
GC (CNP-51);

(SEQ ID NO: 148)
VDTKSRAAWARLLQEHPNARKYKGANKKGLSKGCFGLKLDRIGSMSGLGC
(CNP-50);

(SEQ ID NO: 149)
DTKSRAAWARLLQEHPNARKYKGANKKGLSKGCFGLKLDRIGSMSGLGC
(CNP-49);

(SEQ ID NO: 150)
TKSRAAWARLLQEHPNARKYKGANKKGLSKGCFGLKLDRIGSMSGLGC
(CNP-48);

(SEQ ID NO: 151)
KSRAAWARLLQEHPNARKYKGANKKGLSKGCFGLKLDRIGSMSGLGC
(CNP-47);

(SEQ ID NO: 152)
SRAAWARLLQEHPNARKYKGANKKGLSKGCFGLKLDRIGSMSGLGC
(CNP-46);

(SEQ ID NO: 153)
RAAWARLLQEHPNARKYKGANKKGLSKGCFGLKLDRIGSMSGLGC
(CNP-45);

(SEQ ID NO: 154)
AAWARLLQEHPNARKYKGANKKGLSKGCFGLKLDRIGSMSGLGC
(CNP-44);

(SEQ ID NO: 155)
AWARLLQEHPNARKYKGANKKGLSKGCFGLKLDRIGSMSGLGC
(CNP-43);

(SEQ ID NO: 156)
WARLLQEHPNARKYKGANKKGLSKGCFGLKLDRIGSMSGLGC
(CNP-42);

(SEQ ID NO: 157)
ARLLQEHPNARKYKGANKKGLSKGCFGLKLDRIGSMSGLGC
(CNP-41);

(SEQ ID NO: 158)
RLLQEHPNARKYKGANKKGLSKGCFGLKLDRIGSMSGLGC (CNP-40);

(SEQ ID NO: 159)
LLQEHPNARKYKGANKKGLSKGCFGLKLDRIGSMSGLGC (CNP-39);

(SEQ ID NO: 160)
LQEHPNARKYKGANKKGLSKGCFGLKLDRIGSMSGLGC (CNP-38);

(SEQ ID NO: 60)
QEHPNARKYKGANKKGLSKGCFGLKLDRIGSMSGLGC (CNP-37);

(SEQ ID NO: 161)
EHPNARKYKGANKKGLSKGCFGLKLDRIGSMSGLGC (CNP-36);
```

HPNARKYKGANKKGLSKGCFGLKLDRIGSMSGLGC (CNP-35); (SEQ ID NO: 162)

PNARKYKGANKKGLSKGCFGLKLDRIGSMSGLGC (CNP-34); (SEQ ID NO: 163)

NARKYKGANKKGLSKGCFGLKLDRIGSMSGLGC (CNP-33); (SEQ ID NO: 164)

ARKYKGANKKGLSKGCFGLKLDRIGSMSGLGC (CNP-32); (SEQ ID NO: 165)

RKYKGANKKGLSKGCFGLKLDRIGSMSGLGC (CNP-31); (SEQ ID NO: 166)

KYKGANKKGLSKGCFGLKLDRIGSMSGLGC (CNP-30); (SEQ ID NO: 167)

YKGANKKGLSKGCFGLKLDRIGSMSGLGC (CNP-29); (SEQ ID NO: 168)

KGANKKGLSKGCFGLKLDRIGSMSGLGC (CNP-28); (SEQ ID NO: 169)

GANKKGLSKGCFGLKLDRIGSMSGLGC (CNP-27); (SEQ ID NO: 170)

ANKKGLSKGCFGLKLDRIGSMSGLGC (CNP-26); (SEQ ID NO: 171)

NKKGLSKGCFGLKLDRIGSMSGLGC (CNP-25); (SEQ ID NO: 172)

KKGLSKGCFGLKLDRIGSMSGLGC (CNP-24); (SEQ ID NO: 173)

KGLSKGCFGLKLDRIGSMSGLGC (CNP-23); (SEQ ID NO: 174)

GLSKGCFGLKLDRIGSMSGLGC (CNP-22); (SEQ ID NO: 1)

LSKGCFGLKLDRIGSMSGLGC (CNP-21); (SEQ ID NO: 175)

SKGCFGLKLDRIGSMSGLGC (CNP-20); (SEQ ID NO: 176)

KGCFGLKLDRIGSMSGLGC (CNP-19); (SEQ ID NO: 177)

GCFGLKLDRIGSMSGLGC (CNP-18); (SEQ ID NO: 178)
and

CFGLKLDRIGSMSGLGC (CNP-17). (SEQ ID NO: 2)

In certain embodiments, CNP variants do not include CNP-17, CNP-22 or CNP-53.

In another embodiment, the truncated CNP peptides ranging from hCNP-17 to hCNP-53 can contain amino acid addition(s), deletion(s) and/or substitution(s) with natural or unnatural amino acid(s) or peptidomimetic(s) (e.g., peptide bond isostere(s)), as described herein, at any one or more of the amino acid positions of the particular truncated CNP peptides. In yet another embodiment, the truncated CNP peptides having wild-type sequences or amino acid addition(s), deletion(s) and/or substitution(s), can be conjugated at the N-terminus, C-terminus and/or internal site(s) to any of the moieties described herein, including but not limited to bone- or cartilage-targeting moieties (e.g., bisphosphonates, bone- or cartilage-targeting peptide sequences (e.g., polyAsp, polyGlu), peptide sequences derived from bone-targeting domains of bone proteins (e.g., osteopontin, osteocalcin, sialoprotein)), peptide sequences derived from the functional domains of bone morphogenetic proteins (e.g., BMP2, BMP3, BMP5, BMP7, BMP8a), peptide sequences derived from natriuretic polypeptides (e.g., NPPC, ANP, BNP), peptide sequences derived from polypeptides of non-natriuretic origin (e.g., serum albumin, IgG, histidine-rich glycoproteins, fibronectin, fibrinogen, zinc finger-containing polypeptides, FGF-2, osteocrin), moieties that reduce renal clearance (e.g., negatively charged PEG moieties), hydrophilic polymers (e.g., PEG), carbohydrates (e.g., carbohydrates recognized by receptors on the surface of cells at bone growth plates), hydrophobic acids (e.g., $C_5$-$C_{12}$ carboxylic acids, natural fatty acids), phospholipids, and combinations thereof. In an embodiment, the truncated CNP peptides having wild-type sequences or amino acid addition(s), deletion(s) and/or substitution(s), and optionally conjugated to one or more moieties at the N-terminus, C-terminus and/or internal site(s), have a total mass characterized by the ranges described generally herein, e.g., from about 2.6 kDa or 2.8 kDa to about 6 or 7 kDa.

In a further embodiment, the CNP variants are derivatives of CNP37, which is QEHPNARKYKGANKK-CNP22 (SEQ ID NO: 60). The CNP37 variants can contain amino acid addition(s), deletion(s), and/or substitution(s) with natural or unnatural amino acid(s) or peptidomimetic(s) (e.g., peptide bond isostere(s)) at any one or more of the 37 positions of CNP37. Non-limiting examples of substitutions that can be made in CNP37, based on the numbering of CNP22, include K4R, G5S, G5R, G8S, K10R, G15S, S16Q, M17N, G19R, and combinations thereof. In an embodiment, the CNP37 derivatives contain a substitution of Met17 to a natural (e.g., asparagine) or unnatural amino acid or peptidomimetic, designed in part to avoid oxidation of the sulfur atom of methionine. In another embodiment, the CNP37 variants contain substitution(s) of Lys8, Lys10, Lys14 and/or Lys15 (based on numbering from the N-terminus of CNP37) to non-basic natural or unnatural amino acid(s) or peptiomimetic(s), designed in part to reduce albumin binding.

In addition or alternatively to amino acid addition(s), deletion(s) and/or substitution(s), the CNP37 derivatives can be conjugated at the N-terminus, C-terminus, and/or an internal site to any of the moieties described herein, including but not limited to bone- or cartilage-targeting moieties (e.g., bone-targeting peptide domains), moieties that reduce renal clearance (e.g., negatively charged PEG moieties), hydrophilic polymers (e.g., PEG), amino acid sequences comprising one or more amino acids (e.g., osteocrin "NPR-C inhibitor" fragment), carbohydrates (e.g., carbohydrates recognized by receptors on the surface of cells at bone growth plates), hydrophobic acids (e.g., $C_5$-$C_{12}$ carboxylic acids and natural fatty acids), and combinations thereof.

In one embodiment, the CNP variants are modified CNP37 peptides having mutation(s)/substitution(s) at the furin cleavage site (underlined), designed to improve in vivo resistance to the furin protease, and/or containing glycine (underlined) at the N-terminus, designed to improve plasma stability and prevent pyroglutamine formation. Such CNP37 variants include but are not limited to:

GQEHPNARKYKGANPKGLSKGCFGLKLDRIGSMSGLGC (An. CS); (SEQ ID NO: 71)

GQEHPNARKYKGANQKGLSKGCFGLKLDRIGSMSGLGC (An. CT); (SEQ ID NO: 72)

GQEHPNARKYKGANQQGLSKGCFGLKLDRIGSMSGLGC (An. CU); (SEQ ID NO: 73)

GQEHPNARKYKGANKPGLSKGCFGLKLDRIGSMSGLGC (An. CW); (SEQ ID NO: 74)

GQEHPNARKYKGANKKGLSKGCFGLKLDRIGSMSGLGC
(Gly-CNP37, An. DB);
and (SEQ ID NO: 75)

PGQEHPNARKYKGANKKGLSKGCFGLKLDRIGSMSGLGC
(Pro-Gly-CNP37) (SEQ ID NO: 145)

In a further embodiment, the CNP variants of the disclosure include CNP peptides and variants thereof that can be produced by the fusion protein process described herein. Non-limiting examples of CNP variants that can be produced by the fusion protein process described herein, using chemical or proteolytic cleavage or protein self-cleavage, include:

GDLRVDTKSRAAWARLLQEHPNARKYKGANKKGLSKGCFGLKLDRIGSMSGLGC (Gly-wtCNP53); (SEQ ID NO: 179)

GQEHPNARKYKGANKKGLSKGCFGLKLDRIGSMSGLGC (Gly-wtCNP37); (SEQ ID NO: 75)

QEHPNARKYKGANKKGLSKGCFGLKLDRIGSMSGLGC (wtCNP37); (SEQ ID NO: 60)

GHKSEVAHRFK-GANKKGLSKGCFGLKLDRIGSMSGLGC (HSA fragment-wtCNP27); (SEQ ID NO: 144)

GANRRGLSRGCFGLKLDRIGSMSGLGC [CNP27(K4,5,9R)]; (SEQ ID NO: 36)

DLRVDTKSRAAWARLLQEHPNARKYKGANKKGLSKGCFGLKLDRIGSNSGLGC [CNP53(M48N)]; (SEQ ID NO: 180)

GQEHPNARKYKGANKKGLSKGCFGLKLDRIGSNSGLGC [Gly-CNP37(M32N)]; (SEQ ID NO: 181)

QEHPNARKYKGANKKGLSKGCFGLKLDRIGSNSGLGC [CNP37(M32N)]; (SEQ ID NO: 182)

GHKSEVAHRFK-GANKKGLSKGCFGLKLDRIGSNSGLGC [HSA-CNP27(M22N)]; (SEQ ID NO: 183)

GANRRGLSRGCFGLKLDRIGSNSGLGC [CNP27(K4,5,9R,M22N)]; (SEQ ID NO: 184)

PDLRVDTKSRAAWARLLQEHPNARKYKGANKKGLSKGCFGLKLDRIGSMSGLGC (Pro-wtCNP53); (SEQ ID NO: 185)

PGQEHPNARKYKGANKKGLSKGCFGLKLDRIGSMSGLGC (Pro-Gly-wtCNP37); (SEQ ID NO: 145)

PQEHPNARKYKGANKKGLSKGCFGLKLDRIGSMSGLGC (Pro-wtCNP37); (SEQ ID NO: 186)

PNARKYKGANKKGLSKGCFGLKLDRIGSMSGLGC (wtCNP34); (SEQ ID NO: 187)

P-GHKSEVAHRFK-GANKKGLSKGCFGLKLDRIGSMSGLGC (Pro-HSA-wtCNP27); (SEQ ID NO: 188)

PGANRRGLSRGCFGLKLDRIGSMSGLGC [Pro-CNP27(K4,5,9R)]; (SEQ ID NO: 189)

MDLRVDTKSRAAWARLLQEHPNARKYKGANKKGLSKGCFGLKLDRIGSMSGLGC (Met-wtCNP53); (SEQ ID NO: 190)

MGQEHPNARKYKGANKKGLSKGCFGLKLDRIGSMSGLGC (Met-Gly-wtCNP37); (SEQ ID NO: 191)

MQEHPNARKYKGANKKGLSKGCFGLKLDRIGSMSGLGC (Met-wtCNP37); (SEQ ID NO: 192)

M-GHKSEVAHRFK-GANKKGLSKGCFGLKLDRIGSMSGLGC (Met-HSA-wtCNP27); (SEQ ID NO: 193)

MGANRRGLSRGCFGLKLDRIGSMSGLGC [Met-CNP27(K4,5,9R)]. (SEQ ID NO: 194)

Other CNP variants, including truncated CNP peptides ranging from hCNP-17 to hCNP-53 and having wild-type sequences or amino acid addition(s), deletion(s) and/or substitution(s), can also be produced by the fusion protein process described herein, so long as the intended site of chemical or proteolytic cleavage of the fusion protein is not present within the amino acid sequence of the target CNP variant itself. As a non-limiting example, the fusion protein process described herein can be employed to produce truncated wtCNP34 using formic acid cleavage.

In additional embodiments, for any of the CNP peptides and CNP variants described herein that have asparagine (Asn/N) residue(s) and/or glutamine (Gln/Q) residue(s), whether they have a wild-type sequence or a non-natural amino acid sequence, any Asn residue(s) and/or any Gln residue(s) can independently be substituted with any other natural or unnatural amino acids, including conservative substitutions such as Asn to Gln. Such substitution(s) are designed in part to minimize or avoid any potential deamidation of asparagine and/or glutamine. Non-limiting examples of CNP peptides and variants in which any Asn residue(s) and/or any Gln residue(s) can independently be substituted with any other natural or unnatural amino acids, including conservative substitutions such as Asn to Gln, include wtCNP34, wtCNP37, Gly-wtCNP37, Pro-wtCNP37, Pro-Gly-wtCNP37, GHKSE-VAHRFK-wtCNP27 (SEQ ID NO: 144), Pro-GHKSE-VAHRFK-wtCNP27 (SEQ ID NO: 188), PEO12-GANRR-CNP22(K4R) (SEQ ID NO: 36), and PEO24-GANRR-CNP22(K4R) (SEQ ID NO: 36). In certain embodiments, an asparagine residue of the CNP peptides and CNP variants described herein is not substituted with glutamine, aspartic acid or glutamic acid. In certain embodiments, a glutamine residue of the CNP peptides and CNP variants described herein is not substituted with asparagine, aspartic acid or glutamic acid. As a non-limiting example, asparagine residues 7 and/or 15 of Pro-Gly-wtCNP37 (PGQEHP NARKYKGANKKGLSKGCFGLKLDRIGSMSGLGC) (SEQ ID NO: 145) can independently be substituted with any other natural or unnatural amino acids, including glutamine, to avoid any potential deamidation of the asparagine residue(s) to aspartic acid or isoaspartic acid. In certain embodiments, asparagine residues 7 and/or 15 of Pro-Gly-wtCNP37 are not substituted with glutamine, aspartic acid or glutamic acid.

It is understood, however, that the present disclosure encompasses CNP variants in which any one or more, up to all, residues susceptible to deamidation or a deamidation-like reaction (e.g., isomerization) may be converted to other residue(s) via deamidation or a deamidation-like reaction to any extent, up to 100% conversion per converted residue. In certain embodiments, the disclosure encompasses CNP variants in which:

(1) any one or more, up to all, asparagine (Asn/N) residues may be converted to aspartic acid or aspartate, and/or to isoaspartic acid or isoaspartate, via deamidation up to about 5%, 10%, 20%, 30%, 40%, 50%, 60%, 70%, 80%, 90% or 100% conversion per converted residue; or (2) any one or more, up to all, glutamine (Gln/Q) residues may be converted to glutamic acid or glutamate, and/or to isoglutamic acid or isoglutamate, via deamidation up to about 5%, 10%, 20%, 30%, 40%, 50%, 60%, 70%, 80%, 90% or 100% conversion per converted residue; or (3) any one or more, up to all, aspartic acid or aspartate (Asp/D) residues may be converted to isoaspartic acid or isoaspartate via a deamidation-like reaction (also called isomerization) up to about 5%, 10%, 20%, 30%, 40%, 50%, 60%, 70%, 80%, 90% or 100% conversion per converted residue; or (4) any one or more, up to all, glutamic acid or glutamate (Glu/E) residues may be converted to isoglutamic acid or isoglutamate via a deamidation-like reaction (also called isomerization) up to about 5%, 10%, 20%, 30%, 40%, 50%, 60%, 70%, 80%, 90% or 100% conversion per converted residue; or (5) a combination of the above.

As a non-limiting example, the disclosure encompasses CNP variants in which any one or more, up to all, asparagine, glutamine, aspartic acid, and/or glutamic acid residues of Pro-Gly-wtCNP37 [PGQEHPNARKYKGANKKGLSKGCFGLKLDRIGSMSGLGC] (SEQ ID NO: 145) may be converted to (1) aspartic acid/aspartate and/or isoaspartic acid/isoaspartate, (2) glutamic acid/glutamate and/or isoglutamic acid/isoglutamate, (3) isoaspartic acid/isoaspartate, and/or (4) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue, as described above.

As a further example, the disclosure encompasses CNP variants in which any one or more, up to all, asparagine and/or aspartic acid residues of Pro-Gly-wtCNP37 [PGQEHPNARKYKGANKKGLSKGCFGLKLDRIGSMSGLGC] (SEQ ID NO: 145) may be converted to (1) aspartic acid/aspartate and/or isoaspartic acid/isoaspartate, and/or (2) isoaspartic acid/isoaspartate, respectively, via deamidation or a deamidation-like reaction up to about 5%, 10%, 20%, 30%, 40%, 50%, 60%, 70%, 80%, 90% or 100% conversion per converted residue.

As another example, the present disclosure encompasses CNP variants in which any one or more, up to all, asparagine, glutamine, aspartic acid, and/or glutamic acid residues of Gly-wtCNP37 [GQEHPNARKYKGANKKGLSKGCFGLKLDRIGSMSGLGC (SEQ ID NO: 75)] may be converted to (1) aspartic acid/aspartate and/or isoaspartic acid/isoaspartate, (2) glutamic acid/glutamate and/or isoglutamic acid/isoglutamate, (3) isoaspartic acid/isoaspartate, and/or (4) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

As yet another example, the disclosure encompasses CNP variants in which any one or more, up to all, asparagine, glutamine, aspartic acid, and/or glutamic acid residues of wtCNP37 [QEHPNARKYKGANKKGLSKGCFGLKLDRIGSMSGLGC (SEQ ID NO: 60)] may be converted to (1) aspartic acid/aspartate and/or isoaspartic acid/isoaspartate, (2) glutamic acid/glutamate and/or isoglutamic acid/isoglutamate, (3) isoaspartic acid/isoaspartate, and/or (4) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

As a further example, the present disclosure encompasses CNP variants in which any one or more, up to all, asparagine, aspartic acid, and/or glutamic acid residues of an HSA-wtCNP27 chimera, GHKSEVAHRFKGANKKGLSKGCFGLKLDRIGSMSGLGC (SEQ ID NO: 144), may be converted to (1) aspartic acid/aspartate and/or isoaspartic acid/isoaspartate, (2) isoaspartic acid/isoaspartate, and/or (3) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

As a still further example, the disclosure encompasses CNP variants in which any one or more, up to all, asparagine, aspartic acid, and/or glutamic acid residues of a Pro-HSA-wtCNP27 chimera, PGHKSEVAHRFKGANKKGLSKGCFGLKLDRIGSMSGLGC (SEQ ID NO: 188), may be converted to (1) aspartic acid/aspartate and/or isoaspartic acid/isoaspartate, (2) isoaspartic acid/isoaspartate, and/or (3) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

In addition, the present disclosure encompasses CNP variants in which any one or more, up to all, methionine (Met/M) residues may be oxidized to any chemically feasible oxidized form (e.g., sulfoxide and/or sulfone) up to about 5%, 10%, 20%, 30%, 40%, 50%, 60%, 70%, 80%, 90% or 100% transformation per oxidized residue.

In another embodiment, the CNP variants comprise CNP22 or variants thereof conjugated at the N-terminus and/or C-terminus to moiet(ies) that facilitate translocation of the variants across a cell membrane or cell barrier. In one embodiment, the CNP variants are conjugated at the N-terminus and/or C-terminus to peptide sequence(s) that facilitate transport of the variants across a cell membrane or cell barrier, including via active peptide transporters.

In a further embodiment, the N-terminus and/or C-terminus of CNP22 or a variant thereof are conjugated to chemical moieties such as, e.g., natural and/or synthetic polymers, to increase the total mass of the modified CNP peptide to the ranges described generally herein, e.g., a range from about 2.6 or 2.8 kDa to about 6 or 7 kDa. In one embodiment, the chemical moieties are biocompatible hydrophilic or water-soluble natural (e.g., peptides, carbohydrates) or synthetic (e.g., PEG (or PEO)) polymers.

In a particular embodiment, the N-terminus and/or C-terminus of CNP22 or a variant thereof are conjugated to PEG (or PEO) polymers to result in a total mass characterized by the ranges described generally herein, e.g., from about 2.6 or 2.8 kDa to about 6 or 7 kDa. Pegylation of CNP22 or a variant thereof is designed, inter alia, to reduce immunogenicity and improve half-life by reducing renal clearance and increasing protease resistance. A PEG moiety can be attached to the N- and/or C-terminus of CNP22 or any variant described herein, including but not limited to CNP-17 (the Cys6-Cys22 cyclized portion of CNP22), CNP37, and variants of CNP17, CNP22 or CNP37 having N- and/or C-terminal amino acid extension(s), amino acid substitution(s) and/or amino acid deletion(s). In an embodiment, the Lys4 and/or Lys10 residues of CNP17, CNP22 or CNP37, or variants thereof, are substituted with a natural or unnatural amino acid (e.g., Arg, Gly, Ser, Gln, Glu or Cit) or peptidomimetic that does not contain a reactive primary amine on a side chain, to preclude any potential PEGylation of these lysine residues. In one embodiment, the Lys4 and/or Lys10 residues of the CNP peptides are substituted with Arg. In another embodiment, the Lys10 residue is not substituted with Arg.

In a further embodiment, CNP variants (including CNP22 and variants thereof) having a PEG (or PEO) moiety and an amino acid extension at the N-terminus contain arginine at the position immediately preceding the position corresponding to Gly1 of CNP22. Such PEGylated CNP variants are designed for increased resistance to NEP degradation, reduced binding to serum albumin, and enhanced CNP functional activity (e.g., activation of cGMP signaling). Non-limiting examples of PEGylated CNP variants include PEO24-GANRR-CNP22(K4R) (SEQ ID NO: 36), PEO12-GANRR-CNP22(K4R) (SEQ ID NO: 36), PEO24-GANRR-CNP22(SEQ ID NO: 36), PEO12-GANRR-CNP22(SEQ ID NO: 36), PEO24-GANPR-CNP22(K4R) (SEQ ID NO: 37), PEO12-GANPR-CNP22(K4R) (SEQ ID NO: 37), PEO24-GANPR-CNP22(SEQ ID NO: 37), PEO12-GANPR-CNP22 (SEQ ID NO: 37), PEO24-GANQQ-CNP22(SEQ ID NO: 64), PEO12-GANQQ-CNP22(SEQ ID NO: 64), PEO24-ER-CNP22(K4R) (SEQ ID NO: 39), PEO12-ER-CNP22(K4R) (SEQ ID NO: 39), PEO24-ER-CNP22(SEQ ID NO: 39), PEO12-ER-CNP22(SEQ ID NO: 39), PEO24-R-CNP22 (K4R) (SEQ ID NO: 41), PEO12-R-CNP22(K4R) (SEQ ID NO: 41), PEO24-R-CNP22(SEQ ID NO: 41), and PEO12-R-CNP22(SEQ ID NO: 41), wherein PEO24 is a monodispersed 1.2 kDa PEG polymer and PEO12 is a monodispersed 0.6 kDa PEG polymer. In one embodiment, the PEG (or PEO) polymer is conjugated to the N-terminus of the CNP variants.

The disclosure contemplates use of hydrophilic or water soluble polymers (e.g., PEG) that can vary in type (e.g., homopolymer or copolymer; random, alternating or block copolymer; linear or branched; monodispersed or polydispersed), linkage (e.g., hydrolysable or stable linkage such as, e.g., amide, imine, aminal, alkylene, or ester bond), conjugation site (e.g., at the N-terminus and/or C-terminus, preferably not at any of the residues in the cyclized region of CNP (corresponding to residues 6-22 of CNP22)), and length (e.g., from about 0.2, 0.4 or 0.6 kDa to about 2, 3, 4 or 5 kDa). The hydrophilic or water-soluble polymer can be conjugated to the CNP peptide by means of N-hydroxy succinimide (NHS)- or aldehyde-based chemistry or other chemistry, as is known in the art. Such CNP variants can be generated using, e.g., wtCNP22 (2.2 kDa), CNP17 retaining only the cyclized region (residues 6-22) of wtCNP22, CNP variants having an amino acid extension at the N-terminus and/or C-terminus of CNP22 or CNP17, or variants having amino acid substitutions, additions and/or deletions such as, e.g., GANRR-CNP22(K4R) (SEQ ID NO: 36), GANPR-CNP22(K4R) (SEQ ID NO: 37), R-CNP22(SEQ ID NO: 40), R-CNP22 (K4R) (SEQ ID NO: 41), ER-CNP22(SEQ ID NO: 38) and ER-CNP22(K4R) (SEQ ID NO: 39). In an embodiment, the PEG-CNP variants having a total mass characterized by the ranges described generally herein, e.g., from about 2.6 or 2.8 kDa to about 6 or 7 kDa, contain a monodispersed, linear PEG (or PEO) moiety conjugated at the N-terminus and/or C-terminus via NHS- or aldehyde-based chemistry, or a two-arm or three-arm branched PEG moiety conjugated at the N-terminus and/or C-terminus via NHS-based chemistry. The disclosure also encompasses negatively charged PEG-CNP variants designed for reduced renal clearance, including but not limited to carboxylated, sulfated and phosphorylated compounds (Caliceti, Adv. Drug Deliv. Rev., 55: 1261-77 (2003); Perlman, J. Clin. Endo. Metab., 88: 3227-35 (2003); Pitkin, Antimicrob. Ag. Chemo., 29: 440-444 (1986); Vehaskari, Kidney Int'l, 22: 127-135 (1982)). In one embodiment, the PEG (or PEO) moiety contains carboxyl group(s), sulfate group(s), and/or phosphate group(s).

In another embodiment, the PEG (or PEO) moieties conjugated to the N-terminus, C-terminus and/or internal site(s) of CNP variants described herein contain one or more functional groups that are positively charged under physiological conditions. Such PEG moieties are designed, inter alia, to improve distribution of such PEGylated CNP variants to cartilage tissues. In one embodiment, such PEG moieties contain one or more primary, secondary or tertiary amino groups, quaternary ammonium groups, and/or other amine-containing (e.g., urea) groups.

In an embodiment, the disclosure encompasses CNP22 or variants thereof conjugated via NHS- or aldehyde-based chemistry to PEG (or PEO) of the formula $(CH_2CH_2O)_n$, wherein n is an integer from about 6 to about 100, and the PEG polymer is from about 0.3 kDa to about 5 kDa. In another embodiment, n is an integer from about 12 to about 50, and the PEG polymer is from about 0.6 kDa to about 2.5 kDa. In yet another embodiment, n is from about 12 to about 24, and the PEG polymer is from about 0.6 kDa to about 1.2 kDa. In still another embodiment, the terminal hydroxyl group of the PEG polymer is capped with a non-reactive group. In a particular embodiment, the end-capping group is an alkyl group, e.g., a lower alkyl group such as methyl.

In a further embodiment, the disclosure provides CNP variants having one or more peptide bonds or peptide bond isosteres that have reduced susceptibility to cleavage by peptidases including neutral endopeptidase (NEP). NEP is a membrane-bound zinc-dependent endopeptidase that cleaves a substrate peptide bond at the amino end of large hydrophobic residues. Thus, modification of a peptide bond at a cleavage site for NEP to an unnatural peptide or non-peptide bond may preclude or decrease the efficiency of NEP cleavage.

For ANP and CNP, NEP cleavage is reported to occur first at the Cys6-Phe7 bond within the cyclized region, then elsewhere throughout the remainder of the structures. For BNP, cleavage is reported to occur first at the peptide N-terminus, then within the cyclic structure. Although the primary NEP cleavage site on CNP is reported to be the Cys6-Phe7 bond, when wtCNP22 was exposed to NEP digestion for 2.5 minutes in vitro, all possible sites were unexpectedly hydrolyzed, with the Cys6-Phe7 and Gly8-Leu9 peptide bonds being slightly most labile, as described in Example 2.

Substrate specificity of NEP is primarily determined by two substrate-binding subsites, S1' and S2' (Oefner et al., J. Mol. Biol. 296:341-349 (2000)). The S1' site accepts a large hydrophobic P1' residue of which the N-terminal peptide bond is subjected to hydrolysis (e.g., Phe, Leu, Be and Met). The S2' site generally prefers a smaller residue, termed P2' (e.g., Gly or Ser). In the case of CNP, Phe7 is reported to be the preferred P1' residue for the NEP S1' site, while Gly8 is the preferred P2' residue for the S2' site. Because these two subsites can together accommodate only a certain total side chain size, any increase in the total size of the P1'-P2' residues of CNP can potentially disrupt NEP binding. For example, addition of a chloride atom at the 3-position of the P1' Phe7 aromatic ring (i.e., 3-Cl-Phe7) can potentially modify (e.g., destabilize) interactions between CNP and the NEP cleavage sites, for example at the S1' subsite. Addition of a tertiary butyl group to the smaller P2' residue Gly8 (i.e., tBu-Gly8) can potentially disrupt the interaction between CNP and the S2' subsite.

Accordingly, in one embodiment, CNP variants of the disclosure include CNP having an increase in the size of the P1'-P2' residues, such as Phe7-Gly8, to interfere with substrate recognition at the active site, thereby reducing susceptibility to NEP cleavage. Natural amino acids, unnatural amino acids and/or peptidomimetic moieties are substituted for one or more large P1' hydrophobic residues, including but not limited to Phe7, Leu9, Leu11, Ile14, Met17 and Leu20, and/or for one or more smaller P2' residues, including but not limited to Cys6, Gly8, Gly15, Ser16 and Gly19.

The disclosure encompasses CNP variants comprising at least one modified amino acid and/or at least one modified peptide bond, at at least one residue involved in substrate recognition and/or cleavage by NEP, wherein the modified amino acids and modified peptide bonds can be natural amino acids, unnatural amino acids, peptidomimetics and/or peptide bond isosteres. In one embodiment, the NEP cleavage site on CNP between Cys6 and Phe7 is modified. In a related embodiment, the peptide bond (—C(═O)—NH—) between Cys6 and Phe7 is replaced with one of the following peptide bond isosteres:

—CH$_2$—NH—,
—C(═O)—N(R)—, where the amide group is alkylated with any of the following R groups: methyl, ethyl, n-propyl, isopropyl, cyclopropyl, n-butyl, isobutyl, sec-butyl or tert-butyl,
—C(═O)—NH—CH$_2$—,
—CH$_2$—S—,
—CH$_2$—S(O)$_n$—, where n is 1 or 2,
—CH$_2$—CH$_2$—,
—CH═CH—,
—C(═O)—CH$_2$—,
—CH(CN)—NH—,
—CH(OH)—CH$_2$—,
—O—C(═O)—NH—, or
—NHC(═O)NH—.

In another embodiment, the CNP variants are represented by the formula:

(x)-Gly$_1$-Leu$_2$-Ser$_3$-Lys$_4$-Gly$_5$-(b)$_6$-(c)$_7$-(d)$_8$-Leu$_9$-Lys$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys$_{22}$-(z) (SEQ ID NO: 90), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins such as, e.g., osteopontin, osteocalcin, and sialoprotein (Wang et al., Adv. Drug Delivery Rev., 57: 1049-76 (2005)); polymeric and non-polymeric molecules that reduce renal clearance such as, e.g., negatively charged PEGs; and natural polymers (e.g., those containing amino acids, fatty acids and/or carbohydrates) and synthetic polymers (e.g., PEGs) that increase resistance of the CNP variant to NEP degradation by increasing the total mass of the CNP variant to the ranges described generally herein, e.g., from about 2.6 or 2.8 kDa to about 6 or 7 kDa;

(b) and (c) may be the wild-type Cys6 and Phe7, another natural amino acid or an unnatural amino acid, or may contain a peptide bond isostere as described herein to increase resistance to NEP cleavage; and (d) may be the wild-type Gly8, or may be a larger natural or unnatural (e.g., t-Bu-Gly) amino acid or peptidomimetic to reduce binding to NEP.

In one embodiment, such CNP variants contain at least one modified amino acid at (b), (c) and/or (d).

Other peptide bonds within CNP may be cleaved even if CNP22 or a variant thereof has an NEP-resistant peptide bond or peptide bond isostere at Cys6-Phe7, including the Gly8-Leu9, Lys10-Leu11, Arg13-Ile14, Ser16-Met17, and Gly19-Leu20 bonds. Therefore, the disclosure encompasses CNP variants having peptide bond isostere(s) at one or more other NEP cleavages sites in addition to the Cys6-Phe7 bond, wherein the peptide bond isosteres include those described herein.

In another embodiment, the disclosure encompasses CNP variants having a cysteine analog at Cys6 and/or Cys22, including but not limited to homocysteine, penicillamine, 2-mercaptopropionic acid, and 3-mercaptopropionic acid. In an embodiment, such CNP variants have a cyclic domain formed by a disulfide bond between the wild-type Cys6 or analog and Cys22 or analog.

In yet another embodiment, one or more residues of CNP22 or a variant thereof, up to all the residues, are substituted with a D-amino acid. Substitution of an L-amino acid with a D-amino acid essentially moves the side chain about 120 degrees from its original position, thereby potentially disrupting the binding of the CNP peptide to NEP. In a specific embodiment, L-Phe at Phe7 is substituted with its D-enantiomer, D-Phe.

In still another embodiment, a beta amino acid such as, e.g., 3-amino-2-phenylpropionic acid (or 2-phenyl-beta-alanine), replaces the wild-type alpha-amino acid Phe7. Use of a beta-amino acid effectively increases the peptide backbone length by one methylene unit. Protease resistance can result from the change in substrate conformation or the increased distance between amino acid side chains.

Non-limiting examples of variants of CNP22 having an unnatural alpha-amino acid, a beta-amino acid or a peptide bond isostere include:

```
                                     (SEQ ID NO: 56)
GLSKGC(CH2NH)FGLKLDRIGSMSGLGC (Analog A), (SEQ ID NO: 57)
GLSKGC-(N-Me-Phe)-GLKLDRIGSMSGLGC (Analog B), (SEQ ID NO: 136)
GLSKGC-(D-Phe)-GLKLDRIGSMSGLGC (Analog E), (SEQ ID NO: 58)
GLSKGCF-(tBu-Gly)-LKLDRIGSMSGLGC (Analog F), (SEQ ID NO: 137)
GLSKGC-(3-Cl-Phe)-GLKLDRIGSMSGLGC (Analog G),
and (SEQ ID NO: 59)
GLSKGC-[NHCH2CH(Ph)CO]-GLKLDRIGSMSGLGC (Analog H,
formed using 3-amino-2-phenylpropionic acid).
```

In a further embodiment, the CNP variants have a total mass characterized by the ranges described generally herein, e.g., from about 2.6 or 2.8 kDa to about 6 or 7 kDa, designed for increased resistance to NEP degradation, and are represented by the formula:

(x)-Gly$_1$-Leu$_2$-Ser$_3$-(a)$_4$-Gly$_5$-(b)$_6$-(c)$_7$-(d)$_8$-(e)$_9$-(f)$_{10}$-(g)$_{11}$-Asp$_{12}$-Arg$_{13}$-(h)$_{14}$-Gly$_{15}$-Ser$_{16}$-(i)$_{17}$-Ser$_{18}$-Gly$_{19}$-(j)$_{20}$-Gly$_{21}$-Cys$_{22}$-(z) (SEQ ID NO: 46), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins such as, e.g., osteopontin, osteocalcin, and sialoprotein; polymeric and non-polymeric moieties that reduce renal clearance such as, e.g., negatively charged PEGs; polymers containing, e.g., amino acids, hydrophobic acids, and/or carbohydrates; and synthetic hydrophilic polymers such as, e.g., PEGs;

(a) may be the wild-type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide-bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched C$_{1-6}$ alkyl, straight or branched C$_{1-6}$ alkoxy, straight or branched halo-C$_{1-6}$ alkyl, C$_{3-10}$ cycloalkyl, heterocyclyl, C$_{6-14}$ aryl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Thr, Ser, Val and Asn;

(e) is selected from the group consisting of Leu, Ser, Thr and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly, and peptide-bond isosteres such as, e.g., N-Me-Ile;

(i) is selected from the group consisting of Met, Val, Asn, beta-Cl-Ala, 2-aminobutyric acid (Abu) and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In another embodiment, the CNP variants have a total mass characterized by the ranges described generally herein, e.g., from about 2.6 or 2.8 kDa to about 6 or 7 kDa, designed for increased resistance to NEP cleavage, and are represented by the formula:

(x)-Gly$_1$-Leu$_2$-Ser$_3$-(a)$_4$-Gly$_5$-(b)$_6$-(c)$_7$-(d)$_8$-(e)$_9$-(f)$_{10}$-(g)$_{11}$-Asp$_{12}$-Arg$_{13}$-(h)$_{14}$-(i)$_{15}$-Ser$_{16}$-(j)$_{17}$-Ser$_{18}$-Gly$_{19}$-(k)$_{20}$-Gly$_{21}$-Cys$_{22}$-(z) (SEQ ID NO:143), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins and derivatives thereof, such as, e.g., fusion proteins or peptide sequences of osteopontin, osteocalcin, sialoprotein, etc.; moieties that reduce renal clearance, including but not limited to hydrophilic or water-soluble polymers such as, e.g., charged PEG molecules; and moieties comprising, e.g., PEGs, amino acids, carbohydrates, and/or hydrophobic acids;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser or Glu, wherein in one embodiment (a) is Arg;

(b) is selected from the group consisting of Cys and peptide bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched C$_{1-6}$ alkyl, straight or branched C$_{1-6}$ alkoxy, straight or branched halo-C$_{1-6}$ alkyl, C$_{3-10}$ cycloalkyl, C$_{6-14}$ aryl, heterocyclyl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly, Thr, Ser, Val and Asn;

(e) is selected from the group consisting of Leu, Ser, Thr, and peptide bond isosteres such as, e.g., N-Me-Leu;

(f) is selected from the group consisting of Lys, Arg, Gly, 6-hydroxy-norleucine, citrulline (Cit), Gln and Ser;

(g) is selected from the group consisting of Leu, Asn, and peptide bond isosteres such as, e.g., N-Me-Leu;

(h) is selected from the group consisting of Ile, tert-butyl-Gly (tBu-Gly), Asn, and peptide bond isosteres such as, e.g., N-Me-Ile;

(i) is selected from the group consisting of Gly, Arg, Ser and Asn;

(j) is selected from the group consisting of Met, Val, Asn, beta-Cl-Ala, 2-aminobutyric acid (Abu) and 2-amino-isobutyric acid (Aib); and (k) is selected from the group consisting of Leu, norleucine (Nle), homoleucine (Hleu), Val, tert-butyl-Ala (tBu-Ala), Arg, Thr, Ser, and peptide bond isosteres such as, e.g., N-Me-Leu.

To improve the delivery of the CNP variants to the target sites of bone-related disorders (e.g., skeletal dysplasias), the CNP variants can be attached (e.g., at the N-terminus and/or C-terminus) to bone- or cartilage-targeting moieties. Non-limiting examples of bone- or cartilage-targeting moieties include bisphosphonates; hydroxyapatite; glucosamine; collagen (e.g., collagen type X); polyAsp; polyGlu; and amino acid sequences derived from bone-targeting domains of bone proteins such as, e.g., osteocrin, osteopontin, osteocalcin, and sialoprotein.

In addition to being less susceptible to NEP cleavage, the CNP variants potentially have reduced affinity to the NPR-C clearance receptor, while retaining CNP functionality. Besides NEP-mediated degradation, the half-life of CNP22 is influenced by the clearance receptor, NPR-C, which shares 58% sequence homology with the extracellular peptide-binding domain of NPR-B. CNP22 binds tightly to not only NPR-B (7-30 pM affinity), but also NPR-C (11-140 pM)

(Bennett, B. D. et al., J. Biol. Chem., 266: 23060-67 (1991); Koller K. J. & Goeddel, D. V., Circulation, 86: 1081-88 (1992); Suga, S. et al., Endocrinology, 130: 229-39 (1992)). Even though the NPR-B crystal structure has yet to be reported, sequence homology as well as similarities between the NPR-C and NPR-A crystal structures (He, X.-L. et al., Science, 293(5535): 1657-62 (2001); Ogawa, H. et al., J. Biol. Chem., 279(27): 28625-31 (2004); He, X.-L., J. Mol. Biol., 361(4): 698-714 (2006)) suggest that NPR-B likely assumes a similar overall structural fold.

Therefore, an NPR-B homology model was built based on structure-based sequence alignment and crystallographic structures of the following related systems: CNP bound to NPR-C, ANP bound to NPR-A, and ANP bound to NPR-C (He, X.-L. et al., Science, 293(5535): 1657-62 (2001); Ogawa, H. et al., J. Biol. Chem., 279(27): 28625-31 (2004); He, X.-L., J. Mol. Biol., 361(4): 698-714 (2006)). Based on observations that the receptor appears to determine the bound peptide conformation, and that NPR-B most closely resembles NPR-A with respect to primary structure and functional properties, the NPR-B/CNP homology model was built with the NPR-A/ANP crystal structure as a model. Published signaling data of CNP variants (U.S. Pat. No. 5,434,133 and US Patent Application Publication No. 2004/0138134 A1), and of functional ANP variants that no longer bind to NPR-C (Cunningham, EMBO 13(11) 2508-15, 1994) were used to refine and interpret the NPR-B/CNP model.

The present disclosure encompasses CNP variants designed for improved NPR-B selectivity based on a homology-based structural model of the NPR-B/CNP complex. Combining the experimental and computational structure data of natriuretic peptides bound to the various receptors with the published functional data, CNP variants were generated that continue to bind to NPR-B, but can potentially have reduced affinity to the NPR-C clearance receptor. For example, NPR-C has a unique insertion in a loop structure in the peptide-binding site, placing its loop residues closer to such peptide residues as CNP Gly8 (or ANP Gly9), compared to respective loop residues in NPR-A and NPR-B. Earlier studies indicated that the G9T mutation in ANP contributes to reduce affinity to NPR-C, thereby improving NPR-A selectivity (Cunningham, EMBO J., 13(11): 2508-15 (1994)). Accordingly, CNP variants were generated to replace the corresponding Gly8 residue with a larger residue (Ser, Val, Thr or Asn) to disrupt the CNP binding to NPR-C without affecting its binding to NPR-B. Further, one or more mutations were introduced at the C-terminal end of CNP, encompassing Gly15 to Gly21, which is predicted to interact with receptor-specific residues, based on the detailed structural analyses of the receptor/peptide complexes. For example, a G19R mutation in CNP22 does not result in a significant loss of NPR-B signaling activity. This mutation, however, cannot be modeled into the available crystal structure of NPR-C/CNP without altering the conformations of neighboring residues. These observations suggest that the G19R mutation may selectively disrupt the binding of CNP to a particular receptor, such as NPR-C.

In an embodiment, the CNP variants have substitution(s) at one or more Gly sites at positions 1, 5, 8, 15, 19 and 21, to reduce conformational flexibility and thereby increase receptor specificity. Comparative analyses of crystal structures of ANP bound to NPR-C and NPR-A (Ogawa, H. et al., J. Biol. Chem., 279: 28625-31 (2004); He, X.-L., J. Mol. Biol., 361: 698-714 (2006)) indicate that the conformational flexibility of ANP may play an important role in determining the receptor selectivity.

In one embodiment, functional CNP variants with potentially reduced affinity to NPR-C have one or more of the following amino acid substitutions: G1R, G1E, G5R, G5Q, G5S, F7Y, G8T, G8S, G8V, G8N, L9S, L9T, K10Cit, K10Q, K10S, I14N, G15R, G15S, G15N, G15Cit, S16Q, M17V, M17N, G19S, G19R, G19N, L20V, L20R, L20T, L20S, G21S, G21T and G21R. In an embodiment, the CNP variants have multipoint substitutions at positions 1, 5, 7, 8, 9, 10, 14, 15, 16, 17, 19, 20 and/or 21, and may optionally have modifications at any of the other positions in the peptide sequence of the variant.

In a further embodiment, the CNP variants described herein may be conjugated to moieties, up to a total mass characterized by the ranges described generally herein, e.g., from about 2.6 or 2.8 kDa to about 6 or 7 kDa, at the N-terminus, the C-terminus and/or an internal site, to facilitate bone/cartilage targeting, reduce NPR-C and renal clearance, increase resistance to NEP degradation, and/or improve CNP functionality. In one embodiment, the CNP variants are not conjugated to a polymeric moiety at a site within the cyclic region (corresponding to Cys6 to Cys22 of CNP22). Non-limiting examples of polymeric or non-polymeric moieties that can be conjugated to the CNP variants include synthetic bone-targeting compounds such as, e.g., bisphosphonates; bone/cartilage targeting peptide sequences such as, e.g., polyAsp and polyGlu; peptide sequences derived from bone-targeting domains of bone proteins such as, e.g., osteopontin, osteocalcin and sialoprotein; peptide sequences derived from the functional domains of bone morphogenetic proteins such as, e.g., BMP2, BMP3, BMP5, BMP7 and BMP8a; peptide sequences derived from polypeptides of natriuretic origin such as, e.g., NPPC, ANP and BNP; other natural polymeric or non-polymeric moieties such as, e.g., carbohydrates, fatty acids and phospholipids; biocompatible synthetic hydrophilic polymers such as, e.g., PEG (or PEO); hydrophobic polymeric or non-polymeric moieties such as, e.g., heptanoic acid and pentanoic acid; and combinations thereof.

The CNP variants described herein can have substantially similar or better functional activity than CNP22, e.g., with respect to stimulation of cGMP production and signaling. In one embodiment, the CNP variants in vitro or in vivo stimulate the production of at least about 50% of the cGMP level produced under the same concentration of wtCNP22 (e.g., 1 uM). In certain embodiments, the CNP variants retain at least about 50%, 60%, 70%, 80%, 90%, 95% or 100% of the cGMP-stimulation activity of wild-type CNP22 in vitro or in vivo. In another embodiment, the CNP variants have improved cGMP-stimulation activity compared to CNP22. In certain embodiments, the CNP variants in vitro or in vivo stimulate the production of at least about 110%, 120%, 130%, 140%, 150%, 200%, 250%, 300%, 350%, 400%, 450%, 500% or more of the cGMP level produced under the same concentration of wtCNP22 (e.g., 1 uM).

Optionally excluded from the present disclosure are any of the natriuretic (e.g., CNP) peptides, fragments and variants specifically disclosed, and any of the natriuretic (e.g., CNP) peptides, fragments and variants actually produced, in any of the prior publications referenced herein, including but not limited to, U.S. Pat. Nos. 5,434,133, 6,034,231, 6,020,168, 6,743,425, 7,276,481, WO 94/20534, WO 02/047871, WO 2005/098490, WO 2004/047871, EP 0497368, EP 0466174, and Furuya et al., Biochem. Biophys. Res. Comm. 183: 964-969 (1992)). All such documents are incorporated by reference herein in their entirety.

In one embodiment, the present disclosure optionally excludes all known wild-type CNP-53, wild-type CNP-22, wild-type CNP-17, wild-type BNP, and wild-type ANP of human origin and non-human origin. For example, in an embodiment the disclosure optionally excludes human CNP-17, human CNP-22, chicken CNP-22 (corresponding to hCNP-22(Leu9Val)), trout and eel CNP-22 (corresponding to hCNP-22(Leu2Trp, Ser3Asn, Lys4Arg)), frog CNP22-I (corresponding to hCNP-22(Leu2Tyr, Lys4Arg, Leu9Val, Ser16Ala, Met17Phe)), frog CNP22-II (corresponding to hCNP-22(Leu2Thr, Ser16Ala)), human CNP-53, and pig and rat CNP-53 (corresponding to hCNP-53(Gln17His, Ala28Gly)). In another embodiment, the disclosure optionally excludes fragments of NPPC, proCNP and CNP-53 which are produced by proteolytic cleavage in vivo in humans and non-human animals. In yet another embodiment, optionally excluded from the disclosure are the following truncated fragments of wild-type human CNP-53: CNP-50, CNP-46, CNP-44, CNP-39, CNP-30, CNP-29, CNP-28, CNP-27 and CNP-26.

In a further embodiment, the present disclosure optionally excludes CNP peptides and fragments thereof isolated or sought from the shark species *Triakis scyllia* and *Scyliorhinus canicula* (see, e.g., M. Takano et al., Zool. Sci., 11: 451-454 (1994)), including:

```
                                              (SEQ ID NO: 204)
RLLKDLSNNPLRFRGRSKKGPSRGCFGVKLDRIGAMSGLGC
(CNP-41);

(SEQ ID NO: 205)
LKDLSNNPLRFRGRSKKGPSRGCFGVKLDRIGAMSGLGC (CNP-39);

(SEQ ID NO: 206)
KDLSNNPLRFRGRSKKGPSRGCFGVKLDRIGAMSGLGC (CNP-38);
and (SEQ ID NO: 207)
GPSRGCFGVKLDRIGAMSGLGC (CNP-22).
```

In another embodiment, optionally excluded from the disclosure are CNP peptides and fragments thereof isolated or sought from the shark species *Lamna ditropis* (see, e.g., M. Takano et al., Zool. Sci., 11: 451-454 (1994)), including:

```
                                              (SEQ ID NO: 208)
RLLKDLSNNPLRFKGRSKKGPSRGCFGVKLDRIGAMSGLGC
(CNP-41);

(SEQ ID NO: 209)
LKDLSNNPLRFKGRSKKGPSRGCFGVKLDRIGAMSGLGC (CNP-39);

(SEQ ID NO: 210)
KDLSNNPLRFKGRSKKGPSRGCFGVKLDRIGAMSGLGC (CNP-38);

(SEQ ID NO: 211)
FKGRSKKGPSRGCFGVKLDRIGAMSGLGC (CNP-29);
and (SEQ ID NO: 212)
GPSRGCFGVKLDRIGAMSGLGC (CNP-22).
```

In still another embodiment, optionally excluded from the disclosure are CNP peptides and fragments thereof isolated from the shark species *Squalus acanthias* (see, e.g., M. Takano et al., Zool. Sci., 11: 451-454 (1994)), including:

```
                                              (SEQ ID NO: 213)
RLLQDLSNNPLRFKGRSKKGPSRSCFGLKLDRIGAMSGLGC
(CNP-41);
and (SEQ ID NO: 214)
GPSRSCFGLKLDRIGAMSGLGC (CNP-22).
```

In a further embodiment, the present disclosure optionally excludes CNP peptides isolated from medaka and puffer fish, designated "CNP-1", "CNP-2", "CNP-3" and "CNP-4" in K. Inoue et al., Proc. Nat. Acad. Sci., 100(17): 10079-10084 (2003):

```
                                              (SEQ ID NO: 215)
GWNRGCFGLKLDRIGSMSGLGC (medaka and puffer fish
CNP-1);

(SEQ ID NO: 216)
PMVAGGGCFGMKMDRIGSISGLGC (medaka CNP-2);

(SEQ ID NO: 217)
GRSSMVGGRGCFGMKIDRIGSISGLGC (puffer fish CNP-2);

(SEQ ID NO: 218)
GGMRSCFGVRLERIGSFSGLGC (medaka CNP-3);

(SEQ ID NO: 219)
GGLRSCFGVRLARIGSFSGLGC (puffer fish CNP-3);

(SEQ ID NO: 220)
GGSTSRSGCFGHKMDRIGTISGMGC (medaka CNP-4);
and (SEQ ID NO: 221)
GGSSRSGCFGHKMDRIGTISGMGC (puffer fish CNP-4).
```

In a still further embodiment, optionally excluded from the disclosure are CNP-39 isolated from platypus venom and the CNP-22 fragment thereof, designated "ovCNP-39" and "ovCNP-39(18-39)" in G. de Plater et al., Toxicon., 36(6): 847-857 (1998):

```
                                              (SEQ ID NO: 222)
LLHDHPNPRKYKPANKKGLSKGCFGLKLDRIGSTSGLGC
(ovCNP-39);
and (SEQ ID NO: 223)
GLSKGCFGLKLDRIGSTSGLGC (ovCNP-39(18-39).
```

In another embodiment, the present disclosure optionally excludes the following peptides as specifically disclosed in US 2007/0197434:

```
                                              (SEQ ID NO: 224)
Gly-Leu-Ser-Lys-Gly-Cys-Phe-Gly-Leu-Lys-Leu-Asp-
Arg-Ile-Gly-Ala-Met-Ser-Gly-Leu-Gly-Cys;

(SEQ ID NO: 225)
Gly-Leu-Ser-Lys-Gly-Cys-Phe-Gly-Leu-Lys-Leu-Asp-
Arg-Ile-Gly-Ser-Gln-Ser-Gly-Leu-Gly-Cys;

(SEQ ID NO: 226)
Gly-Leu-Ser-Lys-Gly-Cys-Phe-Gly-Leu-Lys-Leu-Asp-
Arg-Ile-Gly-Ser-Ala-Ser-Gly-Leu-Gly-Cys;

(SEQ ID NO: 227)
Ser-Leu-Arg-Arg-Ser-Ser-Cys-Phe-Gly-Leu-Lys-Leu-
Asp-Arg-Ile-Gly-Ser-Met-Ser-Gly-Leu-Gly-Cys;

(SEQ ID NO: 228)
Gly-Leu-Ser-Lys-Gly-Cys-Phe-Gly-Leu-Lys-Leu-Asp-
Arg-Ile-Gly-Ser-Met-Ser-Gly-Leu-Gly-Cys-Asn-Ser-
Phe-Arg-Tyr;
and (SEQ ID NO: 229)
Cys-Phe-Gly-Leu-Lys-Leu-Asp-Arg-Ile-Gly-Ser-Gln-
Ser-Gly-Leu-Gly-Cys-Asn-Ser-Phe-Arg-Tyr.
```

In yet another embodiment, the disclosure optionally excludes peptides of SEQ ID NO:10, disclosed generically in US 2007/0197434, wherein such peptides are CNP-17 variants having certain natural amino acid substitution(s) at position(s) 4, 5, 6, 11, 12, 14 and/or 15. In still another embodiment, optionally excluded from the disclosure are peptides corresponding to hCNP-53(Ser47Ala), hCNP-53 (Met48Gln), hCNP-53(Met48Ala), and hCNP-53(C-term.)-Asn-Ser-Phe-Arg-Tyr.

In an embodiment, the present disclosure optionally excludes the peptides of SEQ ID NOs 1-4 and 6-71 as specifically disclosed in U.S. Pat. No. 7,276,481. In another embodiment, the disclosure optionally excludes peptides of SEQ ID NO 5, disclosed generically in U.S. Pat. No. 7,276,481, wherein such peptides are variants of CNP17 having at least one natural amino acid substitution at Leu9, Lys10, Leu11, Ser16, Met17, Gly19, and/or Leu20. In still another embodiment, optionally excluded are CNP17 variants in which CNP17 or variants thereof contain N-Me-Phe7, or N-Me-Phe7 and N-Me-Leu11. In a further embodiment, the disclosure optionally excludes CNP17 variants of SEQ ID NO 5, as disclosed in U.S. Pat. No. 7,276,481, which are fused or conjugated to growth hormone (GH), insulin-like growth factor 1 (IGF-1), or thyroid hormone (TH). In yet another embodiment, optionally excluded are CNP22 variants in which CNP22 is fused to GH, IGF-1 or TH, or attached to GH, IGF-1 or TH via a linker (e.g., a peptide linker). In still another embodiment, optionally excluded are CNP17 variants in which CNP17 or variants thereof are conjugated to biotin or fluorescein at the N-terminus or the C-terminus.

In a further embodiment, the present disclosure optionally excludes the peptides of Compound Nos. 1-27, and SEQ ID NOs 1-17, 22-24, 30, 31 and 40-42 as specifically disclosed in U.S. Pat. No. 5,434,133. In another embodiment, the disclosure optionally excludes peptides of SEQ ID NOs 18-21 and 25-29, disclosed generically in U.S. Pat. No. 5,434,133. In still another embodiment, the disclosure optionally excludes the peptides of SEQ ID NOs 1-4 and 9 as specifically disclosed in WO 94/20534.

In some embodiments, however, the disclosure still encompasses methods of use of the natriuretic (e.g., CNP) peptides, fragments and variants optionally excluded herein, as well as pharmaceutical compositions (including sterile pharmaceutical compositions) comprising such natriuretic (e.g., CNP) peptides, fragments and variants.

C. Synthesis and Purification of CNP Variants

In some embodiments, the CNP variants described herein are produced by recombinant expression, using certain techniques known in the art in certain embodiments. See, e.g., Sambrook, Fritsch & Maniatis, Molecular Cloning: A Laboratory Manual, Second Edition. Cold Spring Harbor Laboratory Press (Cold Spring Harbor, N.Y. (1989)); DNA Cloning: A Practical Approach, Volumes I and II, D. N. Glover, Ed. (1985); and Current Protocols in Molecular Biology, John Wiley & Sons, Inc. (1994).

In certain embodiments, the CNP variants described herein are produced by a recombinant process that comprises culturing in a medium a host cell comprising a first polynucleotide encoding a CNP variant polypeptide linked to a second polynucleotide encoding a cleavable peptide or protein under conditions that result in expression of a fusion polypeptide encoded by the polynucleotides, wherein the fusion polypeptide comprises the CNP variant polypeptide directly linked to the cleavable peptide or protein or indirectly linked thereto via a linker. In some embodiments, the host cell is transformed with an expression vector comprising the polynucleotide encoding the CNP variant polypeptide linked to the polynucleotide encoding the cleavable peptide or protein. In certain embodiments, the fusion polypeptide is expressed as a soluble protein or as an inclusion body. The expressed fusion polypeptide can be isolated from the host cell or culture medium, and the isolated fusion polypeptide can be contacted with a cleaving agent to release the CNP variant.

Host cells used to produce CNP variants can be bacterial, yeast, insect, non-mammalian vertebrate, or mammalian cells. Bacterial cells include without limitation E. coli cell lines and strains. Non-limiting examples of E. coli cell lines and strains include BL21, BL21(DE3), BL21(DE3)pLysS, BL21(DE3)pGro7, ArcticExpress(DE3), C41 [also called C41(DE3)], C43 [also called C43(DE3)], Origami B(DE3), Origami B(DE3)pLysS, KRX, and Tuner(DE3). In an embodiment, CNP variants and CNP fusion proteins are produced using BL21(DE3) cells. Mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), chondrocytes and other bone-derived cells, and precursors of these somatic cell types. Host cells containing the CNP variant DNA or RNA are cultured under conditions appropriate for growth of the cells, expression of the DNA or RNA and identification/selection of cells expressing the CNP variant.

In some embodiments, the host cells are grown or cultured for a time period at a temperature from about 10° C. to about 40° C., or from about 20° C. to about 40° C., or from about 30° C. to about 40° C. In certain embodiments, the host cells are grown or cultured for a time period at about 20° C., 22° C., 25° C., 28° C., 30° C., 35° C. or 37° C. In certain embodiments, the host cells are grown or cultured for a time period at about 35° C. or 37° C.

Recombinant polynucleotides encoding CNP variant polypeptides (including CNP fusion proteins) are expressed in an expression vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, including without limitation cosmids, plasmids (e.g., naked or contained in liposomes) and viruses that incorporate the recombinant polynucleotide. The expression vector is inserted into an appropriate host cell, via transformation or transfection, for expression of the polynucleotide encoding the polypeptide (see, e.g., Sambrook et al. (supra)).

Non-limiting examples of expression vectors contemplated for production of CNP variants, including cleavable CNP fusion proteins, include pJexpress, pJexpress401, pJexpress404, pET-15b, pET-21a, pET-22b, pET-31b, pET-32a, pET-41a, pMAL, pMAL-c2X, pQE-30, pET-SUMO, and pTYB11. Expression of particular constructs can generate soluble CNP variants (including CNP fusion proteins) or insoluble CNP variants (including CNP fusion proteins) in the form of inclusion bodies.

In some embodiments, expression of the polynucleotide(s) encoding a CNP variant or CNP fusion protein is enhanced using an isopropyl β-D-1-thiogalactopyranoside (IPTG)-inducible vector. In some embodiments, the host cells are grown or cultured for a time period at a temperature from about 10° C. to about 40° C., or from about 20° C. to about 40° C., or from about 30° C. to about 40° C., in the presence of IPTG. In certain embodiments, the host cells are grown or cultured for a time period at about 20° C., 22° C., 25° C., 28° C., 30° C., 35° C. or 37° C. in the presence of IPTG. In certain embodiments, the host cells are grown or cultured for a time period at about 35° C. or 37° C. in the presence of 1 mM IPTG.

In further embodiments, the host cells are cultured with IPTG at a concentration from about 0.4 mM to about 2 mM, or from about 0.4 mM to about 1.5 mM, or from about 0.4 mM to about 1 mM. In certain embodiments, the IPTG is at a concentration of about 0.4, 0.5, 0.6, 0.7, 0.8, 0.9, 1, 1.1, 1.2, 1.3, 1.4, 1.5, 1.6, 1.7, 1.8, 1.9 or 2 mM. In an embodiment, the concentration of IPTG is about 1 mM.

In certain embodiments, the CNP variants described herein are recombinantly expressed as fusion proteins comprising a CNP variant polypeptide and a cleavable carrier protein or cleavable tag (e.g., peptide tag), wherein the fusion protein comprises the CNP variant polypeptide directly linked to the cleavable carrier protein or tag or indirectly linked thereto via a linker. Use of a carrier protein or tag facilitates, e.g., detection, isolation and/or purification of the fusion protein. Cleavable carrier proteins and tags include, but are not limited to, histidine (e.g., hexa-His) tags; human transcription factor TAF12 (TAF12), TAF12 fragments, TAF12 histone fold domain, mutants of TAF12 and fragments thereof, TAF12(C/A), TAF12(D/E), TAF12(4D/4E), TAF12(6D/6E), TAF12 (10D/10E), TAF12(C/A & D/E), TAF12(C/A & 4D/4E), TAF12(C/A & 6D/6E), TAF12(C/A & 10D/10E); ketosteroid isomerase (KSI); maltose-binding protein (MBP); β-galactosidase (β-Gal); glutathione-S-transferase (GST); thioredoxin (Trx); chitin binding domain (CBD); BMP-2, BMP-2 mutants, BMP-2(C/A); SUMO; and mutants and fragments thereof.

An expression construct can express a fusion protein comprising a CNP variant and a carrier protein or tag. The tag can be an amino acid sequence that confers a useful property to the fusion protein. In one embodiment, the tag is a ligand-binding domain that can be used to purify the fusion protein by applying the fusion protein to separation media containing the ligand. For example, a fusion protein comprising a glutathione-S-transferase (GST) domain can be applied to a chromatographic column containing glutathione-linked separation media. As another example, a fusion protein comprising maltose-binding protein (MBP) as a tag can be applied to separation media containing maltose. As a further example, a fusion protein comprising a polyhistidine tag may be applied to a nickel column, whereby chelation of the polyhistidine tag to the nickel column facilitates purification of the fusion protein. In another embodiment, the tag is a ligand. For example, a fusion protein can comprise glutathione as a tag and be applied to a chromatographic column containing glutathione-S-transferase-linked separation media. Non-limiting examples of carrier proteins and tags for use in fusion proteins include human transcription factor TAF12 (TAF12), ketosteroid isomerase (KSI), maltose-binding protein (MBP), β-galactosidase (β-Gal), glutathione-S-transferase (GST), thioredoxin (Trx), chitin-binding domain (CBD), BMP-2 mutation (BMPM), SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, poly(His), poly(Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and mutants and fragments thereof.

To generate the target CNP variant, the carrier protein or tag can be cleaved from the fusion protein by means of chemical cleavage, protease cleavage, or protein self-cleavage. Exemplary chemical and proteolytic cleavage agents (cleavage sites in parenthesis) include, but are not limited to, formic acid (Asp-Pro), cyanogen bromide (CNBr) (Met-X), hydroxylamine (Asn-Gly), Factor Xa (IEGR-X) (SEQ ID NO: 230), Enterokinase (DDDDK-X) (SEQ ID NO: 231), ProTEV (EXXYXQ-G) (SEQ ID NO: 232), and SUMO protease. Due to the nature of the particular kinds of chemical cleavage, cleavage using formic acid may generate Pro-CNP, CNBr may generate CNP having Met-to-Asn substitution, and hydroxylamine may generate Gly-CNP. Alternatively, chemical or protease cleavage may be avoided by using particular constructs (e.g., pET-21a-CNP) that express CNP variants not as fusion proteins. Expression of pET-21a-CNP may produce Met-CNP. Or certain fusion proteins (e.g., those containing intein-CBD) can undergo self-cleavage to generate CNP.

In further embodiments, a fusion protein comprises a cleavable peptide linker between a CNP variant and a carrier protein or tag (e.g., peptide tag). In certain embodiments, the cleavable peptide linker is selected from the group consisting of Asp-Pro, Asn-Gly, Met-X, Val-Asp-Asp-Arg (SEQ ID NO: 233), Gly-Ser-Asp-Arg (SEQ ID NO: 234), Ile-Thr-Asp-Arg (SEQ ID NO: 235), Pro-Gly-Asp-Arg (SEQ ID NO: 236), Ile-Glu-Gly-Arg-X (SEQ ID NO: 230), Asp-Asp-Asp-Asp-Lys-X (SEQ ID NO: 231), Glu-X-X-Tyr-X-Gln-Gly (SEQ ID NO: 232), Ala-Phe-Leu-Gly-Pro-Gly-Asp-Arg (SEQ ID NO: 237), and MGSSHHHHHHSSGLVPRGSHTGD-DDDKHMD (pET-15b linker) (SEQ ID NO: 95), where X denotes an amino acid. In some embodiments, the cleavable peptide linker is cleaved by a cleaving agent selected from the group consisting of palladium, cyanogen bromide (CNBr), formic acid, hydroxylamine, clostripain, thrombin, chymotrypsin, trypsin, trypsin-like proteases, carboxypeptidase, enterokinase (enteropeptidase), Kex 2 protease, Omp T protease, Factor Xa protease, subtilisin, proTEV, SUMO protease, V8 protease, HIV protease, rhinovirus protease, furilisin protease, IgA proteases, human Pace protease, collagenase, Nia protease, poliovirus 2Apro protease, poliovirus 3C protease, genenase, furin, elastase, Proteinase K, pepsin, rennin (chymosin), microbial aspartic proteases, papain, calpain, chymopapain, ficin (ficain), bromelain (bromelase), cathespisin B, caspases, thermolysin, Endoprotease Arg-C, Endoprotease Glu-C, Endoprotease Lys-C, kallikrein, and plasmin.

In certain embodiments, the cleavable carrier protein, tag (e.g., peptide tag) or peptide linker is cleaved using formic acid to release the CNP variant from the fusion protein. In some embodiments, the formic acid is at a concentration from about 1% to about 20%, or from about 1% to about 15%, or from about 2% to about 15%, or from about 1% to about 10%, or from about 2% to about 10%, or from about 1% to about 5%, or from about 2% to about 5%. In certain embodiments, the formic acid is at a concentration of about 1%, 2%, 3%, 4%, 5%, 6%, 7%, 8%, 9%, 10%, 11%, 12%, 13%, 14% or 15%. In certain embodiments, the formic acid is at a concentration of about 2%, 5% or 10%.

In further embodiments, cleavage of the CNP fusion protein in the presence of formic acid is conducted at a temperature from about 20° C. to about 80° C., or from about 30° C. to about 75° C., or from about 40° C. to about 75° C., or from about 50° C. to about 75° C., or from about 50° C. to about 70° C., or from about 55° C. to about 70° C., or from about 50° C.

to about 60° C. In some embodiments, cleavage in the presence of formic acid is conducted at about 20° C., 22° C., 25° C., 30° C., 35° C., 37° C., 40° C., 42° C., 45° C., 50° C., 55° C., 60° C., 65° C., 70° C., 75° C. or 80° C. In certain embodiments, cleavage in the presence of formic acid is conducted at about 50° C., 55° C., 60° C., 65° C. or 70° C. In certain embodiments, cleavage in the presence of formic acid is conducted at about 55° C. or 70° C.

In additional embodiments, cleavage of the CNP fusion protein in the presence of formic acid is performed for a time period from about 3 hr to about 48 hr, or from about 5 hr to about 48 hr, or from about 5 hr to about 36 hr, or from about 5 hr to about 24 hr, or from about 5 hr to about 18 hr, or from about 20 hr to about 24 hr, or for about 6 hr to about 10 hr. In certain embodiments, cleavage in the presence of formic acid is performed for about 5 hr, 6 hr, 12 hr, 15 hr, 18 hr, 20 hr or 24 hr.

In some embodiments, cleavage of the CNP fusion protein is conducted in the presence of about 2%, 5% or 10% formic acid at about 55° C. for about 20 hr to about 36 hr, or at about 60° C. for about 15 hr to about 24 hr, or at about 65° C. for about 10 hr to about 21 hr, or at about 70° C. for about 6 hr to about 18 hr. In certain embodiments, cleavage of the CNP fusion protein is conducted in the presence of about 2% formic acid at about 55° C. for about 20 hr to about 24 or 36 hr, or at about 60° C. for about 15 hr to about 24 hr, or at about 65° C. for about 10 hr to about 18 hr, or at about 70° C. for about 6 hr to about 10 hr.

The present disclosure provides mild conditions for cleavage of CNP fusion proteins using formic acid to afford high yields of CNP variants. The conditions described herein for fusion protein cleavage using formic acid are also suitable for cleavage of fusion proteins comprising polypeptides or proteins other than CNP, where the fusion proteins contain an Asp-Pro peptide bond.

In further embodiments, soluble CNP fusion proteins or CNP fusion protein inclusion bodies are treated with a buffer and/or a detergent prior to chemical cleavage (e.g., using formic acid) or proteolytic cleavage of the CNP fusion protein. Non-limiting examples of buffers include B-PER II; diluted B-PER II (e.g., 1/20 dilution); B-PER; B-PER phosphate buffer; buffers containing Tris (e.g., 25 mM Tris, pH 7.5); buffers containing Tris and NaCl (e.g., 25 mM Tris, 150 mM NaCl, pH 7.9); and PBS. In an embodiment, the buffer is B-PER II. Non-limiting examples of detergents include octylsucrose, Triton X-100, Tween-20, NP-40, and CA-630. The detergent can be in a buffer (e.g., 1% detergent in 25 mM Tris buffer, pH 7.5). In certain embodiments, the detergent is Triton X-100 or CA-630.

It is understood that any of the methods and conditions described above may be used in combination with any of the other methods and conditions described above to generate a CNP variant disclosed herein.

In other embodiments, the CNP variants described herein are synthesized using a peptide synthesizer and purified according to methods known in the art, e.g., according to the methods of Atherton and Sheppard, *Solid Phase Peptide Synthesis: a Practical Approach*, IRL Press (Oxford, England (1989)).

Peptides can be synthesized based on, e.g., the following peptide sequence of CNP: $G^1LS(K$ or $R)GC^6F^7G^8L(K$ or $R$ or Nle or 6-OH-Nle)$LDRIGSMSGLGC^{22}$.

Exemplary CNP variants include but are not limited to:

Analog A (GLSKGC(CH2NH)FGLKLDRIGSMSGLGC) (SEQ ID NO: 56) was made by converting the backbone "—C═O" group of $C^6$ to a "—CH$_2$" group;

Analog B (GLSKGC(N—Me—Phe)GLKLDRIGSMSGLGC) (SEQ ID NO: 57) was made by converting the backbone "—NH" group of $F^7$ to an "—N—CH$_3$" group;

Analog E (GLSKGC(D-Phe)GLKLDRIGSMSGLGC) (SEQ ID NO: 136) was made using D-Phe at $F^7$;

Analog F (GLSKGCF(tBu-Gly)LKLDRIGSMSGLGC) (SEQ ID NO: 58) was made using a tertiary-butyl-Gly at $G^8$;

Analog G (GLSKGC(3-Cl-Phe)GLKLDRIGSMSGLGC) (SEQ ID NO: 137) was made by adding a chloride atom to a meta position of the phenyl ring of $F^7$ (similar variants can be generated by making ortho, meta and/or para substitutions of the phenyl ring of Phe7 with Cl, F, Br, OH and/or CH$_3$); and Analog H (GLSKGC[NHCH$_2$CH(Ph)CO]GLKLDRIGSMSGLGC) (SEQ ID NO: 59) was made using (±)-3-(amino)-2-phenylpropionic acid at $F^7$.

Examples of CNP variants having, e.g., amino acid extensions, substitutions with natural or unnatural amino acids or peptide bond isosteres, and/or conjugations to polymers or hydrophobic moieties, include without limitation:

Analog J (SEQ ID NO: 91)
C6—CH2—NH, N—Me-L9, N—Me-L20

Analog K (SEQ ID NO: 92)
N—Me-L9, N—Me-L20

Analog L (SEQ ID NO: 93)
N—Me-L9, N—Me-L11, N—Me-L20

Analog M (SEQ ID NO: 94)
N—Me-L9, N—Me-L11

Analog Z (SEQ ID NO: 95)
K4R, F7Y

Analog AA (SEQ ID NO: 96)
K4R, G8V

Analog AB (SEQ ID NO: 97)
K4R, G8S

Analog AC (SEQ ID NO: 98)
K4R, G8T

Analog AD (SEQ ID NO: 99)
K4R, L9T

Analog AE (SEQ ID NO: 100)
K4R, G15R

Analog AF (SEQ ID NO: 101)
K4R, G15Cit

```
Analog AG
                                           (SEQ ID NO: 102)
K4R, M17V Analog AH
                                           (SEQ ID NO: 35)
K4R Analog AJ
                                           (SEQ ID NO: 103)
K4R, L20V Analog AK
                                           (SEQ ID NO: 104)
K4R, L20t-Bu-Ala Analog AT
                                           (SEQ ID NO: 105)
G1E, K4E Analog AV
                                           (SEQ ID NO: 106)
G1E, K4E - pentanoic acid (attached at the
N-terminus)

Analog AW
                                           (SEQ ID NO: 107)
G1E, K4E - heptanoic acid (attached at the
N-terminus)

Analog AX
                                             (SEQ ID NO: 2)
CNP17 (delta N-term)

Analog AY
                                            (SEQ ID NO: 36)
GANRR-CNP22(K4R)

Analog AZ
                                            (SEQ ID NO: 41)
R-CNP22(K4R)

Analog BB
                                           (SEQ ID NO: 108)
G1E - heptanoic acid (attached at the
N-terminus)

Analog BC
                                           (SEQ ID NO: 109)
G1E - pentanoic acid (attached at the
N-terminus)

Analog BF
                                           (SEQ ID NO: 110)
K4R, K10Cit Analog BG
                                           (SEQ ID NO: 111)
K4R, K10Q Analog BH
                                           (SEQ ID NO: 112)
K4R, K10R Analog BJ
                                           (SEQ ID NO: 113)
K4R, G15N Analog BK
                                           (SEQ ID NO: 114)
K4R, G15S Analog BL
                                            (SEQ ID NO: 60)
CNP-37
                                             (SEQ ID NO: 4)
CNP-53

Analog CA
                                            (SEQ ID NO: 61)
AAWARLLQEHPNA-CNP22

Analog CB
                                            (SEQ ID NO: 62)
AAWARLLQEHPNAR-CNP22

Analog CC
                                            (SEQ ID NO: 63)
DLRVDTKSRAAWAR-CNP22

Analog CD
                                            (SEQ ID NO: 68)
SPKMVQGSG-CNP17-KVLRRH (N- and C-terminal
BNP tails)

Analog CE
                                            (SEQ ID NO: 81)
GERAFKAWAVARLSQ-CNP22 (HSA-CNP22)

Analog CF
                                            (SEQ ID NO: 79)
GQPREPQVYTLPPS-CNP22
PEG(24K)-CNP22
PEG(20K)-CNP22
PEG(5K)-CNP22
PEG(2K)-CNP22
PEG(2K)-CNP17

(SEQ ID NO: 36)
PEG(1K)-GANRR-CNP22(K4R)
PEG(1K)-CNP22
PEO4-(PEO12)3(branched)-CNP22
PEO12-CNP22

(SEQ ID NO: 36)
PEO12-GANRR-CNP22(K4R)

(SEQ ID NO: 36)
PEO24-GANRR-CNP22(K4R);
and

SEQ ID NOs: 1 to 6 and 34 to 144, and variants
thereof that comprise up to 1, 2, 3, 4, or 5
further modifications.
```

In one embodiment, the CNP variants are cyclized via formation of a disulfide bond between $Cys^6$ and $Cys^{22}$. $Cys^6$ can be a cysteine analog such as, e.g., homocysteine or penicillamine. In a further embodiment, the CNP variants can be cyclized by a covalent bond formed head-to-tail, side chain-to-side chain, side chain-to-head, or side chain-to-tail. In an embodiment, the covalent bond is formed between an amino acid at or toward the N-terminus and an amino acid at or toward the C-terminus of the peptide (referred to as "terminal" amino acids in this context). In another embodiment, the covalent bond is formed between the side chains of the two terminal amino acids. In yet another embodiment, the covalent bond is formed between the side chain of one terminal amino acid and the terminal group of the other terminal amino acid, or between the terminal groups of the two terminal amino acids.

Head-to-tail cyclization of the terminal amine to the terminal carboxyl group can be carried out using a number of methods, e.g., using p-nitrophenyl ester, 2,4,5-trichlorophenyl ester, pentafluorophenyl ester, the azide method, the mixed anhydride method, HATU, a carbodimide (e.g., DIC, EDC or DCC) with a catalyst such as HOBt, HONSu or HOAt, or on-resin cyclization.

In addition, the cyclic structure can be formed via a bridging group involving the side chains of amino acid residues of the CNP variant and/or the terminal amino acid residues. A bridging group is a chemical moiety that allows cyclization of two portions of the peptide. Non-limiting examples of bridging groups include amides, thioethers, thioesters, disulfides, ureas, carbamates, sulfonamides, and the like. A variety of methods are known in the art for incorporation of units having such bridging groups. For example, a lactam bridge (i.e., a cyclic amide) can be formed between the N-terminal amino group or an amino group on a side chain and the C-terminal carboxylic acid or a carboxyl group on a side chain, e.g., the side chain of lysine or ornithine and the side chain of glutamic acid or aspartic acid. A thioester can be formed between the C-terminal carboxyl group or a carboxyl group on a side chain and the thiol group on the side chain of cysteine or a cysteine analog.

Alternatively, a cross link can be formed by incorporating a lanthionine (thio-dialanine) residue to link alanine residues that are covalently bonded together by a thioether bond. In another method, a cross-linking agent, such as a dicarboxylic acid (e.g., suberic acid (octanedioic acid)), can link the functional groups of amino acid side chains, such as free amino, hydroxyl, and thiol groups.

Enzyme-catalyzed cyclization can also be used. For example, it has been reported that the thioesterase domain of tyrocidine synthetase can be used to cyclize a thioester precursor, a subtilisin mutant can be utilized to cyclize peptide glycolate phenylalanylamide esters, and the antibody ligase 16G3 can be employed to cyclize a p-nitrophenylester. For a review of peptide cyclization, see Davies, J. Peptide Sci., 9: 471-501 (2003), incorporated herein by reference in its entirety.

In certain embodiments, the final cyclized product has a purity of at least about 70%, 75%, 80%, 85%, 90%, 95%, 96%, 97%, 98%, or at least about 99%.

D. Chemically Modified CNP Variants

Chemical modification of CNP22 or variants thereof can potentially impart advantageous properties to the modified CNP peptides, such as increased stability and half-life and reduced immunogenicity (for a general discussion of chemical modification of therapeutic proteins, see Pharmazie, 57(1): 5-29 (2002)). For example, attaching natural or synthetic, polymeric or non-polymeric moieties (e.g., PEG) to CNP peptides, to increase the total mass of the CNP peptides to the ranges described generally herein, e.g., a range from about 2.6 or 2.8 kDa to about 6 or 7 kDa, can reduce the susceptibility of the modified peptides to in vivo cleavage by exopeptidases and/or endopeptidases (e.g., NEP). In addition to PEGylation, glycosylation and other chemical derivatization procedures, e.g., modification by phosphorylation, amidation, carboxylation, acetylation, methylation, and creation of acid-addition salts, amides, esters and N-acyl derivatives, may also mask potentially immunogenic regions and/or proteolytically sensitive regions (Science, 303: 480-482 (2004)).

Examples of chemical modifications include, without limitation, the polymer addition method of Bednarsaki and the cross-linking method of Altus Corporation for improving stability and protease resistance and reducing immunogenicity. Bednarsaki showed that polymer addition can improve protein temperature stability (J. Am. Chem. Soc., 114(1): 378-380 (1992)), and Altus Corporation found that glutaraldehyde cross-linking can improve enzyme stability.

Chemical modification of polypeptides can be performed in a non-specific fashion (leading to mixtures of derivatized species) or in a site-specific fashion (e.g., based on wild-type macromolecule reactivity-directed derivatization and/or site-selective modification using a combination of site-directed mutagenesis and chemical modification) or, alternatively, using expressed protein ligation methods (Curr. Opin. Biotechnol., 13(4): 297-303 (2002)).

Pegylated CNP Variants

In one embodiment, for increased stability (e.g., resistance to NEP degradation), CNP22 or variants thereof (including those having amino acid additions, substitutions and/or deletions) are conjugated to hydrophilic, natural or synthetic polymers, to increase the total mass of the modified CNP peptides to a range from about 2.6 kDa or 2.8 kDa to about 4, 5, 6, 7 or higher kDa. In certain embodiments, the added hydrophilic polymers have a total mass of about 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, or about 5 kDa.

In an embodiment, the hydrophilic polymers are water-soluble so that the CNP peptides conjugated thereto do not precipitate out in an aqueous (e.g., physiological) environment. Further, the hydrophilic polymers are biocompatible, i.e., do not cause injury, toxicity or an immunological reaction in vivo.

The hydrophilic polymers can be branched or unbranched. In one embodiment, the hydrophilic polymers are not branched.

Various sites of conjugation of CNP22 or variants thereof to a hydrophilic polymer are possible, including but not limited to: (1) only at the N-terminus; (2) only at the C-terminus; (3) only at an internal site (e.g., Lys4); (4) at both the N-terminus and the C-terminus; (5) at the N-terminus and an internal site; and (6) at the C-terminus and an internal site. In one embodiment, CNP22 or variants thereof are conjugated to a hydrophilic polymer only at the N-terminus. In another embodiment, conjugation is only at an internal site (e.g., Lys4). In yet another embodiment, conjugation is at the N-terminus and an internal site (e.g., Lys4). In still another embodiment, for better functionality the CNP peptides are not conjugated to a hydrophilic polymer at a site (e.g., Lys10) within the cyclic domain (corresponding to Cys6 to Cys22 of CNP22). If conjugation to a hydrophilic polymer is based on bond formation with a reactive primary amino group on the CNP peptide, conjugation at an internal site (e.g., Lys4 and/or Lys10) can be prevented by substitution of Lys4 and/or Lys10 with a natural or unnatural amino acid or peptidomimetic that does not contain a reactive primary amino group on a side chain, such as, e.g., Gly, Ser, Arg, Asn, Gln, Asp, Glu or citrulline (Cit). In a particular embodiment, Lys4 and/or Lys10 are replaced with Arg. In another embodiment, Lys10 is not replaced with Arg.

Non-limiting examples of hydrophilic polymers include polymers formed from carboxylic acid-bearing monomers (e.g., methacrylic acid (MA) and acrylic acid (AA)), polyvinyl alcohols, polymers formed from hydroxyl-bearing monomers (e.g., hydroxyethyl methacrylate (HEMA), hydroxypropyl methacrylate (HPMA), hydroxypropyl methacrylamide, and 3-trimethylsilylpropyl methacrylate (TMSPMA)), polyalkylene oxides, polyoxyethylated polyols (e.g., glycerol), poly(ethylene glycol) (PEG), poly(propylene glycol), mono-$C_1$-$C_{10}$ alkoxy-PEGs (e.g., monomethoxy-PEG), tresyl monomethoxy-PEG, aryloxy-PEGs, PEG acrylate (PEGA), PEG methacrylate, PEG propionaldehyde, bis-succinimidyl carbonate PEG, copolymers of 2-methacryloyloxyethyl-phosphorylcholine (MPC) and N-vinyl pyrrolidone (VP), hydroxy functional poly(N-vinyl pyrrolidone) (PVP), SIS-PEG (SIS is polystyrene-polyisobutylene-polystyrene block copolymer), polystyrene-PEG, polyisobutylene-PEG, PCL-PEG (PCL is polycaprolactone), PLA-PEG (PLA is polylactic acid), PMMA-PEG (PMMA is poly(methyl methacrylate)), PDMS-PEG (PDMS is polydimethyloxanone), PVDF-PEG (PVDF is polyvinylidene fluoride), PLURONIC™ surfactants (polypropylene oxide-co-polyethylene glycol), poly(tetramethylene glycol), poly(L-lysine-g-ethylene glycol) (PLL-g-PEG), poly(L-lysine-g-hyaluronic acid) (PLL-g-HA), poly(L-lysine-g-phosphoryl choline) (PLL-g-PC), poly(L-lysine-g-vinyl pyrrolidone) (PLL-g-PVP), poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), poly(ethylimine-g-vinyl pyrrolidone) (PEI-g-PVP), PLL-co-HA, PLL-co-PC, PLL-co-PVP, PEI-co-PEG, PEI-co-HA, PEI-co-PC, PEI-co-PVP, cellulose and derivatives thereof (e.g., hydroxyethyl cellulose), dextran, dextrins, hyaluronic acid and derivatives thereof (e.g., sodium hyaluronate), elastin, chitosan, acrylic sulfate, acrylic sulfonate, acrylic sulfamate, methacrylic sulfate, methacrylic sulfonate, methacrylic sulfamate, polymers and copolymers thereof, and polymers and copolymers of combinations thereof.

In a particular embodiment, the hydrophilic polymer is poly(ethylene glycol) (PEG), also called poly(ethylene oxide) (PEO). As used herein, the term "PEG" or "PEO" encompasses all the forms of PEG, branched and unbranched, which can be used to derivatize polypeptides, including without limitation mono-$(C_1-C_{10})$ alkoxy-PEGs and aryloxy-PEGs.

In one embodiment, the PEG-CNP conjugates comprise a PEG (or PEO) polymer of the formula $(CH_2CH_2O)_n$, wherein n is an integer from about 6 to about 100, and the PEG polymer is from about 0.3 kDa to about 5 kDa. In another embodiment, n is an integer from about 12 to about 50, and the PEG polymer is from about 0.6 kDa to about 2.5 kDa. In yet another embodiment, n is from about 12 to about 24, and the PEG polymer is from about 0.6 kDa to about 1.2 kDa. In a further embodiment, the terminal hydroxyl group of the PEG polymer is capped with a non-reactive group. In a particular embodiment, the end-capping group is an alkyl group, e.g., a lower alkyl group such as methyl, so that the PEG polymer terminates in an alkoxy group. In an embodiment, the PEG polymer is not branched. In another embodiment, CNP22 or variants thereof are conjugated to a PEG polymer only at the N-terminus.

PEGs and PEOs potentially include molecules with a distribution of molecular weights, i.e., they are potentially polydispersed, depending on the manner in which they are prepared. The size/mass distribution of a polymeric preparation can be characterized statistically by its weight average molecular weight ($M_w$) and its number average molecular weight ($M_n$), the ratio of which is called the polydispersity index ($M_w/M_n$). $M_w$ and $M_n$ can be measured by mass spectroscopy. PEG-CNP variants conjugated to a PEG moiety larger than 1.5 kDa may exhibit a range of molecular weights due to the polydispersed nature of the parent PEG molecule. For example, in the case of mPEG2K (Sunbright ME-020HS, NOF Co.), the molecular masses of the PEG molecules are distributed over a range from about 1.5 kDa to about 3 kDa, with a polydispersity index of 1.036. By contrast, the PEGs conjugated to CNP22 or variants thereof using MS $(PEG)_n$ reagents (n=4, 8, 12 or 24, denoted as, e.g., "PEO12" or "PEO24") from Pierce Biotechnology (Rockford, Ill.) are monodispersed, having discrete chain length and defined molecular weight.

Methods for generating polypeptides comprising a PEG moiety are known in the art (see, e.g., U.S. Pat. No. 5,824,784). Methods for preparing PEGylated CNP peptides generally comprise the steps of (a) reacting CNP22 or a variant thereof with a PEGylation reagent under conditions suitable for attaching PEG to the CNP peptide (e.g., at the N-terminus), and (b) obtaining the reaction product(s). Because PEGylating a CNP peptide might significantly alter its binding to NPR-B, depending on the size of the PEG moiety and the location of PEGylation, different kinds of PEG and PEGylation reaction conditions can be explored. The chemistry that can be used for PEGylation of a CNP peptide includes acylation of reactive primary amine(s) of the peptide using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates any charge of the original primary amine. PEG-CNP peptides designated with the symbol "PEO12" or "PEO24", as well as those designated with the symbol "PEG1K", "PEG2K", "PEG5K" or "PEG20K", are PEGylated via reaction of a primary amino group on the peptide with an NHS ester-activated, methoxy-end capped PEG reagent. PEG-CNP variants can also be prepared by other methods, e.g., via reductive amination involving a primary amino group on the peptide and a PEG aldehyde, such as, e.g., PEG-propionaldehyde, or mono-$C_1$-$C_{10}$ alkoxy or aryloxy derivatives thereof (see U.S. Pat. No. 5,252,714).

Unlike ribosome protein synthesis, synthetic peptide synthesis proceeds from the C-terminus to the N-terminus. Accordingly, Boc-PEG (containing tert-butyloxycarbonyl (Boc)) is one method to attach PEG to the C-terminus of a peptide (R. B. Merrifield, J. Am. Chem. Soc., 85(14): 2149-2154 (1963)). Alternatively, Fmoc (fluorenylmethoxycarbonyl) chemistry can be employed (E. Atherton and R. C. Sheppard, *Solid Phase Peptide Synthesis: a Practical Approach*, IRL Press (Oxford, England (1989)).

The present methods for preparing PEG-CNP variants provide a substantially homogenous mixture of polymer-protein conjugates. After purification, discrete PEG-CNP preparations are sufficiently pure for in vitro and in vivo testing of biological properties. As demonstrated herein, certain PEG-CNP variants exhibit reduced susceptibility to NEP cleavage and substantially similar or better functionality (e.g., stimulation of cGMP production).

As described herein, PEGylation reactions of CNP22 or variants thereof, using appropriate PEGylation reagent/CNP peptide ratios and reaction conditions, provide PEG-CNP derivatives. The nature and extent of PEGylation can be determined using, e.g., PAGE and HPLC analysis. In certain embodiments, at least about 50%, 60%, 70%, 80%, 90%, 95% or 99% of CNP22 or variants thereof are mono-PEGylated at the N-terminus. To optimize the beneficial effects of PEGylation on the biological properties of a CNP peptide, the polymer length, conformation (e.g., branched or linear), and/or functionalization (e.g., adding a negatively charged group) of a PEG moiety can be varied. PEGylated CNP variants are tested for NEP resistance, pharmacokinetics and bioactivity (e.g., the ability to bind to NPR-B and stimulate the generation of cGMP). PEGylated CNP variants that show improved NEP resistance and at least about 50% of the cGMP-stimulating activity of CNP22 can be further tested, e.g., in vitro in a rat chondrosarcoma cell-based achondroplasia model and in vivo in a murine achondroplasia animal model.

E. Methods of Using CNP Variants, Pharmaceutical Compositions of CNP Variants, and Routes of Administration Methods of Using CNP Variants
Bone-Related Disorders
Fibroblast growth factors (FGFs) play important roles in bone formation, and mutations in FGF receptor genes (FGFR 1, 2 and 3) give rise to a variety of inherited skeletal malformations (Curr. Biol., 5: 500-507 (1995)). In particular, activating mutations in FGFR-3 are responsible for disorders of the long bones, including achondroplasia, the most common form of human genetic dwarfism (Nature, 371: 252-254 (1994); Cell, 78: 335-342 (1994)), the milder disorder hypochondroplasia (Ann. N.Y. Acad. Sci., 785: 182-187 (1996)), and the more severe and neonatal lethal thanatophoric dysplasia (TD) types I and II (Hum. Mol. Genet., 5: 509-512 (1996); Nat. Genet., 9: 321-328 (1995)). Mouse models overexpressing FGF-2, and consequentially activating FGFR-3, show shortened long bones and macrocephaly (Mol. Biol. Cell, 6: 1861-73 (1995)). Consistent with this model, mice deficient in FGFR-3 show remarkable skeletal overgrowth with wider growth plates (Nature Genet., 12: 390-397 (1996)).

Complementary experiments with CNP, NPR-B and NPR-C suggest a link between the peptide ligand, the corresponding receptors, and bone growth. Activation of NPR-B by elevated plasma concentrations of CNP in transgenic mice causes skeletal overgrowth (Nat. Med., 10: 80-86 (2004)) histologically similar to that of the growth plate cartilage of FGFR-3 knockout mice (Nat. Genet., 4: 390-397 (1996)). In NPR-C knockout mice, NPR-C-mediated clearance of CNP should be eliminated; consistent with this prediction, the knockout animals show elongated long bones and elongated vertebrae with kyphosis (Proc. Natl. Acad. Sci. USA 96: 7403-08 (1999)). Conversely, CNP knockout mice are dwarfed with shorter long bones and vertebrae, a phenotype histologically similar to that of achondroplasia, and have increased mortality as a result of malocclusion and pulmonary restriction from the small rib cage (Proc. Natl. Acad. Sci. USA, 98: 4016-4021 (2001)). Consistent with the proposed role of CNP as an activator of NPR-B, the NPR-B knockout mouse has the same dwarfed skeletal phenotype and increased mortality as the CNP knockout mouse (Proc. Natl. Acad. Sci. USA, 101: 17300-05 (2004)). Furthermore, in a mouse model of achondroplasia with activated FGFR-3 in the cartilage, targeted overexpression of CNP in chondrocytes counteracts dwarfism (Yasoda et al., Nat. Med., 10: 80-86 (2004)). Additionally, CNP has been show to play a role in regulating endochondral bone growth and chondrocyte activity, including but not limited to chondrocyte proliferation and differentiation, inhibition of the mitogen activated protein (MAP) kinase/MEK (Raf-1) kinase signaling pathway, and promotion of endochondral ossification (Yasoda et al., Nat. Med., 10: 80-86 (2004)). These results suggest that activation of the CNP/NPR-B system is a potential therapeutic strategy for treatment of human achondroplasia.

By stimulating matrix production, proliferation and differentiation of chondrocytes and increasing long bone growth, the CNP variants of the disclosure are useful for treating mammals, including humans, suffering from a bone-related disorder, such as a skeletal dysplasia. Non-limiting examples of CNP-responsive bone-related disorders and skeletal dysplasias include achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, chondrodysplasia punctata, camptomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Further, the CNP variants are useful as an adjunct or alternative to growth hormone for treating idiopathic short stature and other skeletal dysplasias.

In addition, the CNP variants are useful for treating other bone-related conditions and disorders, such as rickets, hypophosphatemic rickets [including X-linked hypophosphatemic rickets (also called vitamin D-resistant rickets) and autosomal dominant hypophosphatemic rickets], and osteomalacia [including tumor-induced osteomalacia (also called oncogenic osteomalacia or oncogenic hypophosphatemic osteomalacia)].

The CNP variants of the disclosure can also be used to treat osteoarthritis. Osteoarthritis is a degenerative disease of the articular cartilage and occurs frequently in the elderly. Osteoarthritis involves destruction of the cartilage and proliferative change in the bone and cartilage resulting from degeneration of articular components, with the change resulting in a secondary arthritis (e.g., synovitis). The extracellular matrix proteins, which are the functional entity of the cartilage, are reduced, and the number of chondrocytes decreases in osteoarthritis (Arth. Rheum. 46(8): 1986-1996 (2002)). By promoting the matrix production, growth and differentiation of chondrocytes, the CNP variants are useful for countering the undesired effects of FGF-2 and increasing matrix synthesis in subjects suffering from arthritis, including osteoarthritis, thereby treating arthritis, including osteoarthritis.

Vascular Smooth Muscle Disorders

CNP and other vasoactive peptides (including ANP, BNP and urodilatin) have vasodilator and diuretic properties and play an important role in cardiovascular homeostasis (J. Cardiovasc. Pharmacol., 117: 1600-06 (1998); Kidney Int., 49: 1732-37 (1996); Am. J. Physiol., 275: H1826-1833 (1998)). CNP is widely distributed in the cardiovascular system, especially in high concentration in vascular endothelial cells (J. Cardiovasc. Pharmacol., 117: 1600-06 (1998)). CNP is a potent relaxant of vascular smooth muscle, particularly in the coronary circulation (Biochem. Biophys. Res. Commun., 205: 765-771 (1994)), and is an inhibitor of smooth muscle cell proliferation (Biochem. Biophys. Res. Commun., 177: 927-931 (1991)). Although the vasodilator effect of CNP is less potent than that of ANP (about 1:100) (Hypertens. Res., 21: 7-13 (1998); Am. J. Physiol., 275: L645-L652 (1998)), CNP mRNA is increased in response to shear stress (FEBS Lett., 373: 108-110 (1995)) and plasma levels of CNP are elevated in inflammatory cardiovascular pathologies (Biochem. Biophys. Res. Commun., 198: 1177-1182 (1994)). CNP has been shown to suppress inflammation through inhibition of macrophage infiltration in injured carotid arteries of rabbits (Circ. Res., 91: 1063-1069 (2002)) and to directly inhibit cardiac fibroblast proliferation through an NPR-B/cGMP-dependent pathway (Endocrinology, 144: 2279-2284 (2003)).

The cardiovascular actions of CNP are mediated via activation of the NPR subtypes, NPR-B and NPR-C (Endocrinology, 130: 229-239 (1992)), the latter accounting for 95% of NPRs expressed in vivo (Science, 293: 1657-1662 (2001)). The CNP/NPR-B pathway leads to elevation of cGMP, a well-established secondary messenger in the cardiovascular system. NPR-C's 37-amino acid portion from the C-terminus has a consensus sequence that interacts with the heterotrimeric G protein $G_i$ (J. Biol. Chem., 274: 17587-17592 (1999)), which has been shown to regulate adenylate cyclase and phospholipase C activity (J. Biol. Chem., 276: 22064-70 (2001); Am. J. Physiol., 278: G974-980 (2000); J. Biol.

Chem., 271: 19324-19329 (1996)). CNP mediates smooth muscle hyperpolarization and relaxation via activation of NPR-C and the opening of a G protein-regulated, inwardly rectifying $K^+$ channels (Proc. Natl. Acad. Sci. USA, 100: 1426-1431 (2003)). Likewise, CNP has important anti-proliferative effects in cardiac fibroblasts and, through interaction with NPR-C, regulates local blood flow and systemic blood pressure by hyperpolarizing smooth muscle cells (R. Rose and W. Giles, J. Physiol. 586: 353-366 (2008)).

By binding to NPR-B on vascular smooth muscle cells, CNP22 stimulates the production of cGMP, which acts as an intracellular secondary messenger to cause ultimately the relaxation of blood vessels. Based on the hypotensive actions of CNP, the CNP variants of the disclosure are useful for treating hypertension, congestive heart failure, cardiac edema, nephredema, hepatic edema, acute and chronic renal insufficiency, and so on. In addition, activation of cGMP signaling suppresses the growth of vascular smooth muscle cells. Accordingly, the CNP variants of the disclosure can be used to treat conditions or diseases caused by the abnormal growth of vascular smooth muscle cells, including but not limited to restenosis and arteriosclerosis.

The studies described above suggest that CNP may be a potential therapeutic candidate for vascular smooth muscle relaxation and remodeling. Pharmacological effects of CNP concerning certain disorders have been attributed, in part, to vasoprotective effects rather than to vasodilator activity (Am. J. Respir. Crit. Care Med., 170: 1204-1211 (2004)). Therefore, the CNP variants of the present disclosure are useful for treating conditions, e.g., vascular smooth muscle disorders, in which CNP may have a vasoprotective effect, including without limitation inducing smooth muscle relaxation and inhibiting infiltration of macrophages into cardiac tissue. In one embodiment, the CNP variants are used to treat heart failure, including but not limited to acute decompensated heart failure and acute congestive heart failure. In another embodiment, the CNP variants are used to treat asthma, cardiomyopathy, and restenosis of coronary arteries (by increasing smooth muscle cell relaxation and decreasing proliferation of smooth muscle cells).

Pharmaceutical Compositions of CNP Variants

In additional embodiments, the disclosure provides pharmaceutical compositions comprising a CNP variant, and one or more pharmaceutically acceptable excipients, carriers and/or diluents. In certain embodiments, the compositions further comprise one or more other biologically active agents (e.g., inhibitors of proteases, receptor tyrosine kinases, and/or the clearance receptor NPR-C).

In some embodiments, the compositions comprise the desired CNP variant in at least about 70%, 75%, 80%, 85%, 90%, 95%, 96%, 97%, 98% or 99% purity. In certain embodiments, the compositions contain less than about 10%, 5%, 4%, 3%, 2%, 1% or 0.5% of macromolecular contaminants, such as other mammalian (e.g., human) proteins and other CNP variants.

Non-limiting examples of excipients, carriers and diluents include vehicles, liquids, buffers, isotonicity agents, additives, stabilizers, preservatives, solubilizers, surfactants, emulsifiers, wetting agents, adjuvants, and so on. The compositions can contain liquids (e.g., water, ethanol); diluents of various buffer content (e.g., Tris-HCl, phosphate, acetate buffers, citrate buffers), pH and ionic strength; detergents and solubilizing agents (e.g., Polysorbate 20, Polysorbate 80); anti-oxidants (e.g., methionine, ascorbic acid, sodium metabisulfite); preservatives (e.g., Thimerosol, benzyl alcohol, m-cresol); and bulking substances (e.g., lactose, mannitol, sucrose). The use of excipients, diluents and carriers in the formulation of pharmaceutical compositions is known in the art; see, e.g., Remington's Pharmaceutical Sciences, 18th Edition, pages 1435-1712, Mack Publishing Co. (Easton, Pa. (1990)), which is incorporated herein by reference in its entirety.

For example, carriers include without limitation diluents, vehicles and adjuvants, as well as implant carriers, and inert, non-toxic solid or liquid fillers and encapsulating materials that do not react with the active ingredient(s). Non-limiting examples of carriers include phosphate buffered saline, physiological saline, water, and emulsions (e.g., oil/water emulsions). A carrier can be a solvent or dispersing medium containing, e.g., ethanol, a polyol (e.g., glycerol, propylene glycol, liquid polyethylene glycol, and the like), a vegetable oil, and mixtures thereof.

In some embodiments, the compositions are liquid formulations. In certain embodiments, the formulations comprise a CNP variant in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

In further embodiments, the compositions comprise a buffer solution or buffering agent to maintain the pH of a CNP-containing solution or suspension within a desired range. Non-limiting examples of buffer solutions include phosphate buffered saline, Tris buffered saline, and Hank's buffered saline. Buffering agents include without limitation sodium acetate, sodium phosphate, and sodium citrate. Mixtures of buffering agents can also be used. In certain embodiments, the buffering agent is acetic acid/acetate or citric acid/citrate. The amount of buffering agent suitable in a composition depends in part on the particular buffer used and the desired pH of the solution or suspension. For example, acetate is a more efficient pH buffer at pH 5 than pH 6, so less acetate may be used in a solution at pH 5 than at pH 6. In some embodiments, the buffering agent has a concentration of about 10 mM±5 mM. In certain embodiments, the pH of a composition is from about pH 3 to about pH 7.5, or from about pH 3.5 to about pH 7, or from about pH 3.5 to about pH 6.5, or from about pH 4 to about pH 6, or from about pH 4 to about pH 5, or is at about pH 5.0±1.0.

In other embodiments, the compositions contain an isotonicity-adjusting agent to render the solution or suspension isotonic and more compatible for injection. Non-limiting examples of isotonicity agents include NaCl, dextrose, glucose, glycerin, sorbitol, xylitol, and ethanol. In certain embodiments, the isotonicity agent is NaCl. In certain embodiments, NaCl is in a concentration of about 160±20 mM, or about 140 mM±20 mM, or about 120±20 mM, or about 100 mM±20 mM, or about 80 mM±20 mM, or about 60 mM±20 mM.

In yet other embodiments, the compositions comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%.

In still other embodiments, the compositions contain an anti-adsorbent (e.g., to mitigate adsorption of a CNP variant to glass or plastic). Anti-adsorbents include without limitation benzyl alcohol, Polysorbate 20, and Polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%.

In additional embodiments, the compositions comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%. In other embodiments, when the stabilizer is methionine, the stabilizer is in a concentration from about 0.01% to about 0.5%, or from about 0.01% to about 0.2%. In still other embodiments, when the stabilizer is glycerin, the stabilizer is in a concentration from about 5% to about 100% (neat).

In further embodiments, the compositions contain an antioxidant. Exemplary anti-oxidants include without limitation methionine and ascorbic acid. In certain embodiments, the molar ratio of antioxidant to CNP variant is from about 0.1:1 to about 15:1, or from about 1:1 to about 15:1, or from about 0.5:1 to about 10:1, or from about 1:1 to about 10:1 or from about 3:1 to about 10:1.

Pharmaceutically acceptable salts can be used in the compositions, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in *Remington's Pharmaceutical Sciences, 18th* Edition, Mack Publishing Company, (Easton, Pa. (1990)).

The pharmaceutical compositions can be administered in various forms, such as tablets, capsules, granules, powders, solutions, suspensions, emulsions, ointments, and transdermal patches. The dosage forms of the compositions can be tailored to the desired mode of administration of the compositions. For oral administration, the compositions can take the form of, e.g., a tablet or capsule (including softgel capsule), or can be, e.g., an aqueous or nonaqueous solution, suspension or syrup. Tablets and capsules for oral administration can include one or more commonly used excipieints, diluents and carriers, such as mannitol, lactose, glucose, sucrose, starch, corn starch, sodium saccharin, talc, cellulose, magnesium carbonate, and lubricating agents (e.g., magnesium stearate, sodium stearyl fumarate). If desired, flavoring, coloring and/or sweetening agents can be added to the solid and liquid formulations. Other optional ingredients for oral formulations include without limitation preservatives, suspending agents, and thickening agents. Oral formulations can also have an enteric coating to protect the CNP variant from the acidic environment of the stomach. Methods of preparing solid and liquid dosage forms are known, or will be apparent, to those skilled in this art (see, e.g., Remington's Pharmaceutical Sciences, referenced above).

Formulations for parenteral administration can be prepared, e.g., as liquid solutions or suspensions, as solid forms suitable for solubilization or suspension in a liquid medium prior to injection, or as emulsions. For example, sterile injectable solutions and suspensions can be formulated according to techniques known in the art using suitable diluents, carriers, solvents (e.g., buffered aqueous solution, Ringer's solution, isotonic sodium chloride solution), dispersing agents, wetting agents, emulsifying agents, suspending agents, and the like. In addition, sterile fixed oils, fatty esters, polyols and/or other inactive ingredients can be used. As further examples, formulations for parenteral administration include aqueous sterile injectable solutions, which can contain antioxidants, buffers, bacteriostats, and solutes that render the formulation isotonic with the blood of the intended recipient; and aqueous and nonaqueous sterile suspensions, which can contain suspending agents and thickening agents.

Compositions comprising a CNP variant can also be lyophilized formulations. In certain embodiments, the lyophilized formulations comprise a buffer and bulking agent, and optionally an antioxidant. Exemplary buffers include without limitation acetate buffers and citrate buffers. Exemplary bulking agents include without limitation mannitol, sucrose, dexran, lactose, trehalose, and povidone (PVP K24). In certain embodiments, mannitol is in an amount from about 3% to about 10%, or from about 4% to about 8%, or from about 4% to about 6%. In certain embodiments, sucrose is in an amount from about 6% to about 20%, or from about 6% to about 15%, or from about 8% to about 12%. Exemplary anti-oxidants include, but are not limited to, methionine and ascorbic acid.

The disclosure also provides kits containing, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a CNP-containing composition. The kits can also include dispensing devices, such as aerosol or injection dispensing devices, pen injectors, autoinjectors, needleless injectors, syringes, and/or needles.

As a non-limiting example, a kit can include syringes having a single chamber or dual chambers. For single-chamber syringes, the single chamber can contain a liquid CNP formulation ready for injection, or a solid (e.g., lyophilized) CNP formulation or a liquid formulation of a CNP variant in a relatively small amount of a suitable solvent system (e.g., glycerin) that can be reconstituted into a solution or suspension for injection. For dual-chamber syringes, one chamber can contain a pharmaceutically acceptable vehicle or carrier (e.g., solvent system, solution or buffer), and the other chamber can contain a solid (e.g., lyophilized) CNP formulation or a liquid formulation of a CNP variant in a relatively small amount of a suitable solvent system (e.g., glycerin) which can be reconstituted into a solution or suspension, using the vehicle or carrier from the first chamber, for injection.

As a further example, a kit can include one or more pen injector or autoinjector devices, and dual-chamber cartridges. One chamber of a cartridge can contain a pharmaceutically acceptable vehicle or carrier (e.g., solvent system, solution or buffer), and the other chamber can contain a solid (e.g., lyophilized) CNP formulation or a liquid formulation of a CNP variant in a relatively small amount of a suitable solvent system (e.g., glycerin) which can be reconstituted into a solution or suspension, using the vehicle or carrier from the first chamber, for injection. A cartridge can comprise an amount of the CNP variant that is sufficient for dosing over a desired time period (e.g., 1 day, 2 days, 3 days, 1 week, 2 weeks, 3 weeks, 4 weeks, etc.). The pen injector or autoinjector can be adjusted to administer a desired amount of the CNP formulation from a cartridge.

In addition, pharmaceutical compositions comprising a CNP variant can be formulated as a slow release, controlled release or sustained release system for maintaining a relatively constant level of dosage over a desired time period, such as 1 week, 2 weeks, 3 weeks, 1 month, 2 months, or 3 months. Slow release, controlled release and sustained release formulations can be prepared using, e.g., biodegradable polymeric systems {which can comprise, e.g., hydrophilic polymers [e.g., polylactide, polyglycolide, poly(lactide-glycolide)]}, and can take the form of, e.g., microparticles, microspheres or liposomes, as is known in the art.

Dosages and Frequency of Dosing

As used herein, the term "therapeutically effective amount" of an active agent (e.g., a CNP variant) refers to an amount that provides therapeutic benefit to a patient. The amount may vary from one individual to another and may depend upon a number of factors, including the overall physical condition of the patient. A therapeutically effective amount of a CNP variant can be readily ascertained by one skilled in the art, using publicly available materials and procedures. For example, the amount of a CNP variant used for therapy should give an acceptable rate of growth based on growth charts for children ages 0-17 years with achondroplasia (214 females and 189 males), which list height for age, head circumference, and segmental growth (Horton W A et al., Standard growth curves for achondroplasia, J. Pediatr., 93: 435-8 (1978)). CDC charts can be used to assess weight for age and weight for height or BMI for age. Secondary outcomes with courses that are more chronic in nature can also be measured.

Having a longer serum half-life than wild-type CNP22, the CNP variants can potentially be administered less frequently than CNP22. The dosing frequency for a particular individual may vary depending upon various factors, including the disorder being treated and the condition and response of the individual to the therapy. In certain embodiments, a pharmaceutical composition containing a CNP variant is administered to a subject about one time per day, one time per two days, one time per three days, or one time per week. In one embodiment, for treatment of bone-related disorders (e.g., skeletal dysplasias, including achondroplasia), a daily or weekly dose of a CNP variant is administered to patients until and/or through adulthood.

The CNP variants described herein can be administered to patients at therapeutically effective doses to treat, ameliorate or prevent bone-related disorders (e.g., skeletal dysplasias, including achondroplasia) and conditions (e.g., vascular smooth muscle disorders) in which CNP can provide a vasoprotective effect. The safety and therapeutic efficacy of the CNP variants can be determined by standard pharmacological procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Active agents exhibiting a large therapeutic index are normally preferred.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the CNP variants described herein are administered at a dose in the range from about 5 or 10 nmol/kg to about 300 nmol/kg, or from about 20 nmol/kg to about 200 nmol/kg. In some embodiments, the CNP variants are administered at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variants are administered at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 ug/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses of CNP variants described herein can be administered according to the dosing frequency/frequency of administration described herein, including without limitation daily, 2 or 3 times per week, weekly, every 2 weeks, every 3 weeks, monthly, etc.

The frequency of dosing/administration of a CNP variant for a particular subject may vary depending upon various factors, including the disorder being treated and the condition and response of the subject to the therapy. The CNP variant can be administered in a single dose or in multiple doses per dosing. In certain embodiments, the CNP variant is administered, in a single dose or in multiple doses, daily, every other day, every 3 days, 2 times per week, 3 times per week, weekly, bi-weekly, every 3 weeks, monthly, every 6 weeks, every 2 months, every 3 months, or as deemed appropriate by the treating physician.

In some embodiments, a CNP variant is administered so as to allow for periods of growth (e.g., chondrogenesis), followed by a recovery period (e.g., osteogenesis). For example, the CNP variant may be administered intravenously, subcutaneously or by another mode daily or multiple times per week for a period of time, followed by a period of no treatment, then the cycle is repeated. In some embodiments, the initial period of treatment (e.g., administration of the CNP variant daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Modes of Administration

The CNP variants, or pharmaceutical compositions comprising them, can be administered to subjects in various ways such as, e.g., by injection subcutaneously, intravenously, intra-arterially, intraperitoneally, intramuscularly, intradermally, or intrathecally. In an embodiment, the CNP variants are administered by a single subcutaneous, intravenous, intra-arterial, intraperitoneal, intramuscular, intradermal or intrathecal injection once a day.

The CNP variants can also be administered by direct injection at or near the site of disease. Further, the CNP variants can be administered by implantation of a depot at the target site of action (e.g., an abnormal or dysplasic bone). Alternatively, the CNP variants can be administered sublingually under the tongue (e.g., sublingual tablet) or by inhalation into the lungs (e.g., inhaler or aerosol spray), by delivery into the nasal cavity (e.g., intranasal spray), by delivery into the eye (e.g., eye drop), or by transdermal delivery (e.g., by means of a patch on the skin). The CNP variants may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the CNP variant or pharmaceutical composition over a pre-determined period. The osmotic pump or mini-pump can be implanted subcutaneously, or near the target site (e.g., the long bones of limbs, the epiphyses, etc.).

As explained above, the CNP variants can be used to treat conditions or diseases caused by the abnormal growth of vascular smooth muscle cells, including but not limited to restenosis and arteriosclerosis. For local delivery of a CNP variant to the diseased bodily vessel (e.g., blood vessel), the CNP variant can be delivered by means of a medical device (e.g., a stent) implanted at the diseased site. In one embodiment, the CNP variant is impregnated in a polymeric matrix or polymeric coating disposed over a stent. In another embodiment, the CNP variant is contained in reservoirs or channels formed in the body of a stent and covered by a porous polymeric membrane or layer through which the CNP variant can diffuse. The polymeric matrix, coating, membrane or layer can comprise at least one biodegradable (e.g., hydrophilic) polymer, as is known in the art. In a further embodiment, the CNP variant can be contained in micropores in the body of a stent. The CNP variant can be delivered from a stent by burst release, pulse release, controlled release or sustained release, or a combination thereof. For example, the stent can locally deliver the CNP variant to the diseased site in a burst release followed by a sustained release. Sustained release can be over a period up to about 2 weeks, 1 month, 2 months, 3 months, 6 months or 1 year.

It will be apparent to one skilled in the art that the CNP variants or compositions thereof can also be administered by other modes. Determination of the most effective mode of administration of the CNP variants or compositions thereof is within the skill of the skilled artisan.

The CNP variants can be administered as pharmaceutical formulations suitable for, e.g., oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a CNP variant, and one or more pharmaceutically acceptable excipients, carriers and/or diluents, and optionally one or more other biologically active agents.

Combination Therapy

In one embodiment, a CNP variant can be used in combination with one or more other active agents useful for treating, ameliorating or preventing CNP-responsive conditions or disorders such as, e.g., bone-related disorders (e.g., skeletal dysplasias) and vascular smooth muscle disorders. The other active agent(s) can enhance the effects of the CNP variant and/or exert other pharmacological effects in addition to those of the CNP variant. Non-limiting examples of active agents that can be used in combination with the CNP variants described herein are other natriuretic peptides (e.g., BNP) and inhibitors (e.g., antagonists) of peptidases and proteases (e.g., NEP and furin), NPR-C and tyrosine kinases (e.g., FGFR-3). By preventing NEP cleavage of the CNP variant, an NEP inhibitor can prolong the half-life of the variant. Examples of NEP inhibitors include, without limitation, thiorphan and candoxatril. Co-use of an NPR-C inhibitor can also prolong the half-life of the CNP variant via inhibition of the variant's clearance by NPR-C. A non-limiting example of an NPR-C inhibitor is the fragment FGIPMDRIGRNPR (SEQ ID NO: 82), which would be released at the target site (e.g., bone growth plate) upon proteolytic cleavage of the FGIPMDRI-GRNPR-CNP22 chimera (Analog CZ) (SEQ ID NO: 82) or similar chimeras comprising variants of CNP22 (e.g., those containing amino acid substitution(s), addition(s), and/or deletion(s) relative to CNP22). Co-use of a tyrosine kinase inhibitor can accentuate the effects of a CNP therapy by inhibiting the tyrosine kinase receptor FGFR-3, a negative regulator of chondrocyte and bone growth. Non-limiting examples of tyrosine kinase inhibitors include those disclosed in U.S. Pat. Nos. 6,329,375 and 6,344,459.

To achieve the appropriate therapeutic outcome in the combination therapies, one would generally administer to the subject the CNP composition and other therapeutic(s) in a combined amount effective to produce the desired therapeutic outcome (e.g., restored bone growth). This process may involve administering the CNP composition and other therapeutic agent(s) at the same time. Simultaneous administration can be achieved by administering a single composition or pharmacological protein formulation that includes both the CNP variant and other therapeutic agent(s). Alternatively, the other therapeutic agent(s) can be taken separately at about the same time as a pharmacological formulation (e.g., tablet, injection or drink) of the CNP variant. The CNP variant can also be formulated into a foodstuff such as brownies, pancakes, or cake, suitable for ingestion.

In other alternatives, administration of the CNP variant can precede or follow administration of the other therapeutic agent(s) by intervals ranging from minutes to hours. In embodiments where the other therapeutic agent(s) and the CNP composition are administered separately, one would generally ensure that the CNP variant and the other therapeutic agent(s) are administered within an appropriate time of one another so that both the CNP variant and the other therapeutic agent(s) can exert, synergistically or additively, a beneficial effect on the patient. For example, one can administer the CNP composition within about 0.5-6 hours (before or after) of the other therapeutic agent(s). In one embodiment, the CNP composition is administered within about 1 hour (before or after) of the other therapeutic agent(s).

Identifying and Monitoring Patient Populations

Protocols can be established to identify subjects suitable for CNP therapy and to determine whether a given patient is responsive to CNP therapy. For example, for treatment of bone-related disorders, indicators of growth can be measured, such as long bone growth measurements in utero and neonatal and measurements of bone growth biomarkers such as CNP, cGMP, Collagen II, osteocalcin, and Proliferating Cell Nuclear Antigen (PCNA).

One CNP signaling marker is cGMP (guanosine 3',5' cyclic monophosphate). The level of this intracellular signaling molecule increases after CNP binds to and activates its cognate receptor NPR-B. Elevated levels of cGMP can be measured from cell culture extracts (in vitro) after CNP exposure, conditioned media from bone ex-plant studies (ex vivo) after CNP exposure, and in the plasma (in vivo) within minutes of CNP administration subcutaneously, intravenously, or via other routes of administration known in the art.

Cartilage and bone-specific analytes (or cartilage- and bone-associated markers) can also be measured to assess CNP efficacy. For example, fragments of cleaved collagen type II are a cartilage-specific marker for cartilage turnover.

Type II collagen is the major organic constituent of cartilage and fragments of type II collagen (cleaved collagen) are released into circulation, and subsequently secreted into the urine, following cartilage turnover. Cartilage turnover preceeds new bone formation.

A bone-specific biomarker for bone formation which can be measured is N-terminal propeptides of type I procollagen (PINP). The synthesis of type I collagen is an important step in bone formation, as type I collagen is the major organic component in bone matrix. During collagen synthesis, propeptides are released from the procollagen molecule and can be detected in serum. In addition, fragments of collagen type I can be measured as a marker for bone resorption.

Other potential biomarkers for cartilage and bone formation and growth include aggrecan chondroitin sulfate (cartilage-specific marker for cartilage turnover), propeptides of type TT collagen (cartilage-specific marker for cartilage formation), alkaline phosphatase (bone-specific) and osteocalcin (bone-specific marker for bone formation). Cartilage- and bone-associated biomarkers can be measured, e.g., in serum from efficacy/pharmacodynamic in vivo studies and from the conditioned media of ex vivo studies, using commercially available kits.

In one embodiment, the level of at least one bone- or cartilage-associated biomarker is assayed or measured in a subject that has been administered a CNP variant in order to monitor the effects of the CNP variant on bone and cartilage formation and growth in vivo. For example, an increase in the level of at least one bone- or cartilage-associated biomarker may indicate that administration of a CNP variant has a positive effect on bone growth and is a useful treatment for skeletal dysplasias and other bone- or cartilage-related diseases or disorders associated with decreased CNP activity. Exemplary bone- or cartilage-associated biomarkers include, but are not limited to, CNP (e.g, endogenous levels of CNP), cGMP, propeptides of collagen type II and fragments thereof, collagen type II and fragments thereof, osteocalcin, proliferating cell nuclear antigen (PCNA), propeptides of type I procollagen (PINP) and fragments thereof, collagen type I and fragments thereof, aggrecan chondroitin sulfate, and alkaline phosphatase.

In an embodiment, biomarkers are measured by obtaining a biological sample from a subject who will be administered, is being administered or has been administered a CNP variant. Biomarkers can be measured using techniques known in the art, including, but not limited to, Western Blot, enzyme linked immunosorbant assay (ELISA), and enzymatic activity assay. The biological sample can be blood, serum, urine, or other biological fluids.

Additional aspects and details of the disclosure will be apparent from the following examples, which are intended to be illustrative rather than limiting.

F. Examples

Example 1

Synthesis of CNP Variants

CNP variants were prepared using the methods described herein. Substitutions with natural or unnatural amino acids or peptidomimetics were made, as indicated in Tables 1-3 (shown in Example 3), at the respective amino acid residues in the wild-type sequence of CNP22. In certain variants, additional amino acids were added to the N-terminal and/or C-terminal ends of the whole or a portion of the wild-type CNP22 sequence (see Table 3).

Also prepared were CNP variants in which a PEG (or PEO) moiety was conjugated to the N-terminus of CNP22 or variants thereof (see Table 4, shown in Example 3). PEGylation reagents can be obtained from the commercial sources shown in Table 5.

TABLE 5

| Vendor | Product Name | Name | MW (Da) | PEGylation Reagent |
|---|---|---|---|---|
| NOF | Sunbright ME-200CS | mPEG20K | 20,000 | CH3(CH2CH2O)450-(CH2)5COO—NHS |
| NOF | Sunbright ME-050CS | mPEG5K | 5,000 | CH3(CH2CH2O)110-(CH2)5COO—NHS |
| Pierce | (Methyl-PEG12)3-PEG4-NHS Ester | (mPEG12)3-PEG4 | 2,400 | [CH3(CH2CH2O)12]3-(CH2CH2O)4-NHCO(CH2)3-COO—NHS |
| NOF | Sunbright ME-020HS | mPEG2K | 2,000 | CH3(CH2CH2O)45-(CH2)5COO—NHS |
| NOF | Sunbright ME-020CS | mPEG2K | 2,000 | CH3(CH2CH2O)45-(CH2)5COO—NHS |
| NOF | Sunbright ME-010HS | mPEG1K | 1,000 | CH3(CH2CH2O)23-CO(CH2)2COO—NHS |
| Pierce | Methyl PEG24-NHS Ester | MS(PEG)24 | 1,200 | CH3(CH2CH2O)24-(CH2)2COO—NHS |
| Pierce | EZ-Link NHS-PEG12-Biotin | PEO12-Biotin | 940 | Biotin-(CH2CH2O)12-(CH2)2COO—NHS |
| Pierce | Methyl PEG12-NHS Ester | MS(PEG)12 | 690 | CH3(CH2CH2O)12-(CH2)2COO—NHS |
| Pierce | EZ-Link NHS-PEG4-Biotin | PEO4-biotin | 590 | Biotin-(CH2CH2O)4-(CH2)2COO—NHS |
| Pierce | Mono(lactosylamido)mono(succinimidyl)suberate | LSS | 590 | |
| Pierce | EZ-link NHS-LC-LC-Biotin | LC-LC-Biotin | 570 | |
| Pierce | EZ-link NHS-LC-Biotin | LC-Biotin (LC = long chain) | 450 | |
| Pierce | EZ-link NHS-Biotin | Biotin | 340 | |

The PEG (also called PEO) polymers purchased from Pierce Biotechnology (Rockford, Ill.) are monodispersed—i.e., they contain a single discrete polymer of a particular molecular weight. By contrast, the PEG polymers purchased from NOF (Nippon Oil and Fat) are polydispersed—i.e., they contain a mixture of polymers having a distribution of molecular weights.

To PEGylate CNP22 or variants thereof, reaction and purification conditions are optimized for each PEG-CNP conjugate. According to a general PEGylation procedure, reaction mixtures contain about 1 mM CNP22 or a variant thereof, and about 1 to 5 mM NHS-activated PEG in potassium phosphate buffer, pH between about 5.0 and 6.5. To mono-PEGylate selectively at the peptide N-terminus and minimize PEGylation at an internal site (e.g., Lys4 of CNP22), the PEGylation reaction can be conducted under more acidic conditions (e.g., at a pH between about 5.5 and 6.5) to protonate selectively and hence deactivate the more basic primary amino group on the lysine side chain. After about 1 to 3 hours of incubation at room temperature, the PEGylation reaction is quenched by addition of aqueous glycine buffer. Reaction products are then separated by reverse-phase HPLC, optimized for each PEG-CNP conjugate. Fractionation samples are speedvacced to dryness, and reconstituted/formulated in 1 mM HCl. Identification and purity of each PEG-CNP product are determined by liquid chromatography-mass spectrometry (LC/MS).

Example 2A

Recombinant Production of CNP Variants

CNP variants can be produced using recombinant technology. In certain embodiments, the CNP variants are produced as fusion proteins comprising a cleavable peptide, carrier protein or tag. Exemplary methods for recombinantly producing CNP fusion proteins are disclosed below.
Materials and Methods
Cloning of CNP Fusion Proteins into Expression Vectors CNP DNA fragments were amplified using polymerase chain reaction (PCR) and the amplified PCR fragments were digested with Nde I and BamHI and cloned into pET21a vector (Novagen, Gibbstown, N.J.). CNP fusion protein DNA was synthesized by DNA2.0 and cloned into different expression vectors (Table 6).

containing 100 ug/ml of carbeniciline or 50 ug/ml kanamycin at 37° C. with shaking. When an $OD_{600}$ of bacterial culture reached 0.6, 1 mM isopropyl β-D-1-thiogalactopyranoside (IPTG) was added to the cell media and the media was incubated at 37° C. for 3 hours with shaking. For cell harvest, bacterial cells were centrifuged at 4000 rpm for 10 minutes and the cell pellets were stored at −80° C. Cell pellets were lysed with B-PER II Bacterial Extraction Reagent (PIERCE, 0.4 ml per 4 ml of bacterial culture) and Benzonase Nuclease (Novagen, 0.025 U/ml) at room temperature for 10 minutes. Bacterial crude extract was reserved and centrifuged to obtain supernatant. Supernatant and crude extract were assayed for CNP fusion protein expression and solubility by SDS-PAGE and Western Blot.

Detection of CNP Fusion Protein Expression with SDS-PAGE and Western Blot

Ten uL of cell lysates or soluble supernatants was run on sodium dodecyl sulfate-polyacrylimide gel electrophoresis (SDS-PAGE) (Invitrogen, Carlsbad, Calif., NuPAGE 4-12% Bis-tris Gel, MES SDS buffer). The gel was stained using 20 ml Imperial Protein Stain (Thermo Fisher, Rockford, Ill.) at room temperature for 1 hour and de-stained with water. For Western blot, the protein was transferred to membrane with Gel blot (Invitrogen). The membrane was blocked in TBS buffer with 5% milk at room temperature for 1 hour. Rabbit anti-CNP22 antibody (1:2500 dilution) (Bachem, Torrance, Calif.) was added to the membrane, which was then incubated at room temperature with shaking for 2 hours, and then the membrane was washed 3 times with TBS buffer.

Alkaline phosphate (AP) conjugated anti-rabbit IgG (1:5000 dilution) was added to the membrane, which was then incubated at room temperature with shaking for 1 hour, and then the membrane was washed 3 times with TBS buffer. Ten ml WESTERN BLUE®Stabilized Substrate (Promega, Madison, Wis.) was added to the membrane, which was then incubated at room temperature with shaking for 1 to 5 min, and then the membrane was washed with TBS buffer to remove excess stain.

TABLE 6

| Construct | Vector | Product | Chemical cleavage | Final product | Expression E. coli strain |
|---|---|---|---|---|---|
| pJexpress-TAF-CNP | pJexpress401 | TAF-CNP inclusion bodies | Formic acid (Asp-Pro) | Pro-CNP | BL21; BL21(DE3) |
| pJexpress-KSI-CNP(M/N) | pJexpress404 | KSI-CNP(M/N) inclusion bodies | CNBr (Met-X) | CNP(M/N) | BL21 |
| pET-31b-KSI-CNP | pET-31b | KSI-CNP inclusion bodies | Formic acid (Asp-Pro) | Pro-CNP | BL21(DE3) |
| pET-32a-Trx-CNP | pET-32a | Trx-CNP fusion protein (soluble) | Formic acid (Asp-Pro) | Pro-CNP | BL21(DE3) |
| pMAL-CNP | pMAL-c2X | MBP-CNP fusion protein (soluble) | Formic acid (Asp-Pro) | Pro-CNP | BL21(DE3) |

CNP: GQEHPNARKYKGANKKGLSKGCFGLKLDRIGSMSGLGC [Gly-CNP37 (SEQ ID NO: 75);
TAF: human transcription factor TAF12;
KSI: ketosteroid isomerase;
MBP: maltose-binding protein;
Trx: thioredoxin Expression of CNP Fusion Proteins in E. coli CNP fusion protein expression plasmids were transformed into E. coli BL21 or BL21(DE3). Transformed cells were plated on LB plates containing 100 ug/ml carbeniciline or 50 ug/ml kanamycin and incubated overnight at 37° C. One single colony was picked and cultured in 4 ml LB medium Expression of TAF-CNP Fusion Protein in E. coli BL21

Cells (E. coli strain BL21) expressing TAF-CNP fusion protein were obtained from glycerol stock stored at −80° C. and were grown in 4 ml LB medium containing 50 ug/ml of kanamycin at 37° C. overnight with shaking (250 rpm). Four ml of overnight grown cell culture was transferred to 200 ml LB medium containing 50 ug/ml of kanamycin and was grown at 37° C. with shaking (250 rpm). When the OD$_{600}$ reached 0.6, IPTG was then added to a final concentration of 1 mM to induce protein expression at 37° C. with shaking (250 rpm) for 3 hours. Cells were then spun down at 3000 rpm for 10 minutes and the resulting cell pellet was frozen at −80° C.

Purification of TAF-CNP Inclusion Bodies and Formic Acid Cleavage

The cell pellet (from 200 ml culture) was resuspended in 25 ml of B-PER II buffer (PIERCE), the pellet was sonicated for 10 minutes (50%, 1 second, pause 2 seconds) on ice, centrifuged at 12000 rpm for 20 minutes at 4° C., and then the pellet was resuspended in 25 ml 20× diluted B-PER II buffer. This was repeated until the supernatant became clear (3-5 times). One mL of resuspended TAF-CNP inclusion bodies was transferred to a 1.5 ml tube and centrifuged at 14000 rpm for 15 min. The supernatant was discarded and the pellet was dissolved with 10 ul of 88% formic acid, and then 490 ul of Millipore filtered water was added immediately. The pellet was mixed well by vortex and incubated at 55° C. for 20 to 24 hours (70° C./6 hours are alternative conditions). The products of the formic acid cleavage were assayed by SDS-PAGE and LC/MS (C4RP).

LC/MS Sample Preparation

Inclusion bodies were isolated from about 8 mL of culture (about 1.5 OD) and the pellet was solubilized in 10 uL nt formate. Resolubilized pellet was immediately diluted to 2% or 10% final formate concentration (0.5 mL) and incubated at 55° C. for 21 hours (pH 2) (cloudiness was more evident in the 2% formate sample the next day). Both samples were centrifuged at 15000 rpm for 2 minutes. Twenty uL of supernatant was injected into an LC/MS (C4 RP) apparatus.

Results

CNP Fusion Proteins were Expressed in *E. coli*

Figure 1:
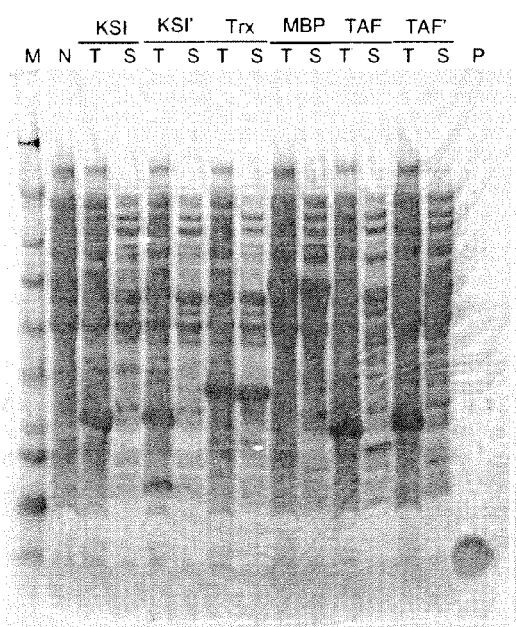
FIG. 1 shows expression of CNP fusion proteins in E. coli (FIG. 1A: Coomassie blue stain, FIG. 1B: Western blot). M: protein marker; T: total cell lysates; S: soluble supernatants; P: 2 ug CNP22; KSI: KSI-CNP(M/N) fusion protein expression (insoluble); N: Un-induced KSI-CNP fusion protein total lysates; KSI': KSI-P-CNP fusion protein expression (insoluble); Trx: Trx-P-CNP fusion protein expression (soluble); MBP: MBP-P-CNP fusion protein expression (soluble); TAF: TAF-P-CNP fusion protein expression (insoluble) (BL21); TAF': TAF-P-CNP fusion protein expression (insoluble) BL21(DE3), where CNP is Gly-CNP37.
Figure 1:

All CNP fusion proteins were expressed in *E. coli* induced with 1 mM IPTG at 37° C. for 3 hours (FIG. 1). The constructs pJexpress-TAF-CNP, pJexpress-KSI-CNP(M/N) and pET-31b-KSI-CNP were expressed as inclusion bodies, while the constructs pET-32a-Trx-CNP and pMAL-CNP were expressed as soluble fusion proteins. Western blot using anti-CNP22 antibody confirmed the expression of the CNP fusion proteins (FIG. 1).

CNP was Produced from TAF-CNP Inclusion Bodies by Formic Acid Cleavage

Figure 2:
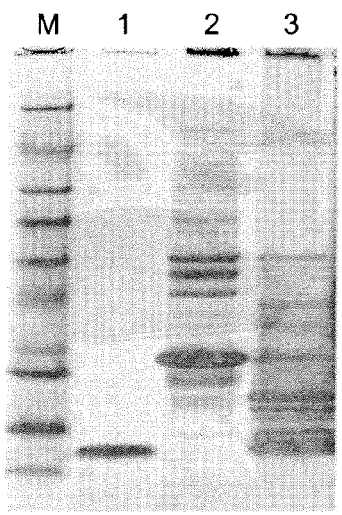
FIG. 2 shows formic acid cleavage of TAF-CNP inclusion bodies. M: protein marker; 1: Gly-CNP37 positive control; 2: uncleaved TAF-CNP inclusion bodies; 3: 2% formic acid cleaved TAF-CNP inclusion bodies, where CNP is Gly-CNP37.

TAF-CNP inclusion bodies were partially purified and treated with 2% formic acid at 55° C. for 20 to 24 hours (70° C./6 hours are alternative conditions). The majority of TAF-CNP was cleaved and one extra band having similar size as Gly-CNP37 peptide appeared on SDS-PAGE (FIG. 2). The cleaved sample was further analyzed by LC/MS (C4 RP). The LC/MS results showed that CNP was released in soluble form from TAF-CNP inclusion bodies after formic acid cleavage. LC/MS analysis indicated that formic acid cleavage of the CNP fusion proteins resulted in formation of cyclized Pro-Gly-CNP37 (MW=4102). Calculation of protein amounts based on analysis suggested that about 60 ug of formic acid-generated CNP was produced from 8 mL of very low OD culture. From a small scale (e.g., about 8 mL) of low OD (e.g., 1.2 OD) cell culture, approximately 8 ug/ml CNP was produced, while fermentation of a larger scale (e.g., about 8 L) of higher OD (e.g., 380D) cell culture can produce approximately 1 mg/ml CNP.

Conclusion

Five expression constructs were generated to express CNP fusion proteins. Expression of all five constructs produced soluble (Trx and MBP) or insoluble (TAF and KSI) CNP fusion proteins. Approximately 1 mg/ml soluble CNP can be produced from TAF-CNP inclusion bodies by a simple formic acid cleavage procedure.

Example 2B

Production of Additional CNP Variants in *E. coli*

Recombinant production of CNP variants was carried out as described in Example 2A. In this example, additional CNP constructs were generated with a QuikChange II XL site-directed mutagenesis kit (Stratagene) or were synthesized by DNA2.0. Additional CNP constructs and expression vectors are listed in Table 7.

TABLE 7

| Construct | Vector | Product | Chemical cleavage | Final product | Expression *E. coli* strain |
|---|---|---|---|---|---|
| pJexpress-TAF(C/A)-Pro-CNP38 | pJexpress401 | TAF(C/A)-Pro-CNP38 inclusion bodies | Formic acid (Asp-Pro) | Pro-CNP38 | BL21(DE3) |
| pJexpress-TAF(4D/4E)-Pro-CNP38 | pJexpress401 | TAF(4D/4E)-Pro-CNP38 inclusion bodies | Formic acid (Asp-Pro) | Pro-CNP38 | BL21(DE3) |
| pJexpress-TAF(C/A&4D/4E)-Pro-CNP38 | pJexpress401 | TAF(C/A&4D/4E)-Pro-CNP38 inclusion bodies | Formic acid (Asp-Pro) | Pro-CNP38 | BL21(DE3) |
| pJexpress-TAF(C/A&10D/10E)-Pro-CNP38 | pJexpress401 | TAF(C/A&10D/10E)-Pro-CNP38 inclusion bodies | Formic acid (Asp-Pro) | Pro-CNP38 | BL21(DE3) |
| pJexpress-TAF-NL-(C/A & 6D/6E)-Pro-CNP38 | pJexpress401 | TAF-NL-(C/A & 6D/6E)-Pro-CNP38 inclusion bodies | Formic acid (Asp-Pro) | Pro-CNP38 | BL21(DE3) |
| pJexpress-BMP-Pro-CNP38 | pJexpress401 | BMP-Pro-CNP38 inclusion bodies | Formic acid (Asp-Pro) | Pro-CNP38 | BL21; BL21(DE3) |

TABLE 7-continued

| Construct | Vector | Product | Chemical cleavage | Final product | Expression E. coli strain |
|---|---|---|---|---|---|
| pJexpress-TAF-Pro-CNP37 | pJexpress401 | TAF-Pro-CNP37 inclusion bodies | Formic acid (Asp-Pro) | Pro-CNP37 | BL21; BL21(DE3) |
| pJexpress-BMP-Pro-CNP37 | pJexpress401 | BMP-Pro-CNP37 inclusion bodies | Formic acid (Asp-Pro) | Pro-CNP37 | BL21; BL21(DE3) |
| pJexpress-TAF Pro-HSA-CNP | pJexpress401 | TAF-Pro-HSA-CNP inclusion bodies | Formic acid (Asp-Pro) | Pro-HSA-CNP | BL21 |
| pJexpress-TAF | pJexpress401 | TAF inclusion bodies | N/A | N/A | BL21(DE3) |
| pJexpress-BMP | pJexpress401 | BMP inclusion bodies | N/A | N/A | BL21(DE3) |
| pJexpress-TAF(C/A) | pJexpress401 | TAF(C/A) inclusion bodies | N/A | N/A | BL21(DE3) |
| pJexpress-TAF(4D/4E) | pJexpress401 | TAF(4D/4E) inclusion bodies | N/A | N/A | BL21(DE3) |
| pJexpress-TAF(C/A&4D/4E) | pJexpress401 | TAF(C/A&4D/4E) inclusion bodies | N/A | N/A | BL21(DE3) |
| pJexpress-TAF(C/A&10D/10E) | pJexpress401 | TAF(C/A&10D/10E) inclusion bodies | N/A | N/A | BL21(DE3) |
| pJexpress-TAF-NL-(C/A & 6D/6E) | pJexpress401 | TAF-NL-(C/A&6D/6E) inclusion bodies | N/A | N/A | BL21(DE3) |
| pJexpress-TAF-Pro-CNP53 | pJexpress401 | TAF-Pro-CNP53 inclusion bodies | Formic acid (Asp-Pro) | Pro-CNP53 | BL21(DE3) |
| pJexpress-TAF-CNP34 | pJexpress401 | TAF-CNP34 inclusion bodies | Formic acid (Asp-Pro) | CNP34 | BL21(DE3) |

Figure 3:
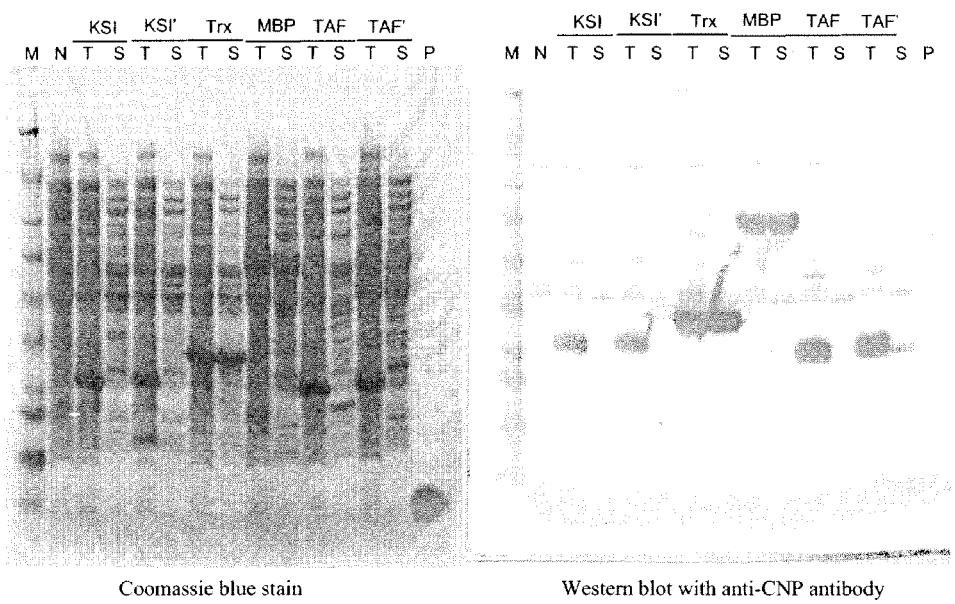
FIGS. 3A-E depict expression of CNP fusion proteins in E. coli. M: protein marker; Tu: total un-induced cell lysates; Su: un-induced soluble supernatants; T: total induced cell lysates; S: soluble supernatants; C1: CNP22; C: Gly-wtCNP37 ("CNP38"); P: insoluble pellets. A: KSI: KSI-CNP38(M/N) fusion protein expression (Insoluble); KSI': KSI-Pro-CNP38 (Pro-Gly-wtCNP37 is designated "Pro-CNP38") fusion protein expression (Insoluble); Trx: Trx-Pro-CNP38 fusion expression (Soluble); MBP: MBP-Pro-CNP38 fusion protein expression (Soluble); TAF: TAF-Pro-CNP38 fusion protein expression (Insoluble) from BL21 cell; TAF': TAF-Pro-CNP38 fusion protein expression (Insoluble) from BL21 (DE3) cell. B: TAF-Pro-CNP37 and BMP-Pro-CNP37 fusion protein expression. C: BMP-Pro-CNP38 fusion protein and BMP protein expression. D: TAF-Pro-HSA-CNP ("Pro-GH-KSEVAHRFK-wtCNP27 (SEQ ID NO: 188) is designated "Pro-HSA-CNP") fusion protein expression. E: TAF-Pro-CNP38 fusion protein and TAF protein expression.
Figure 3:
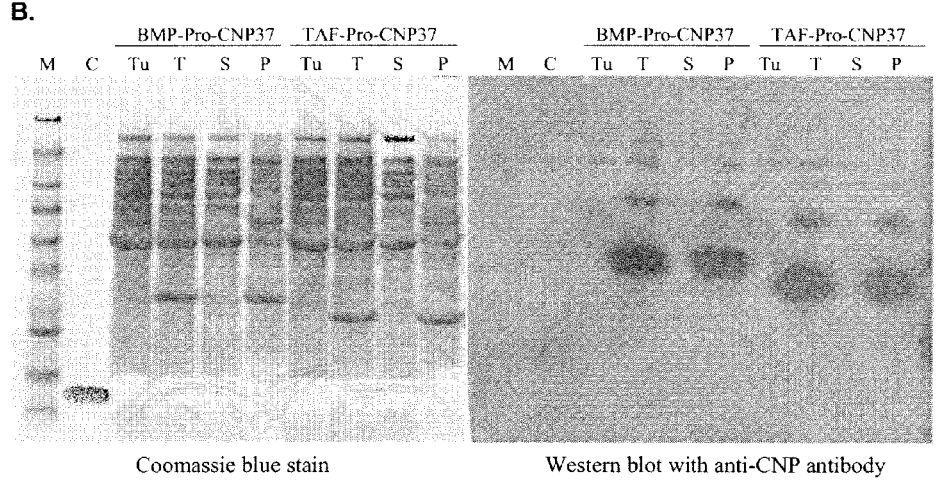
Figure 3:
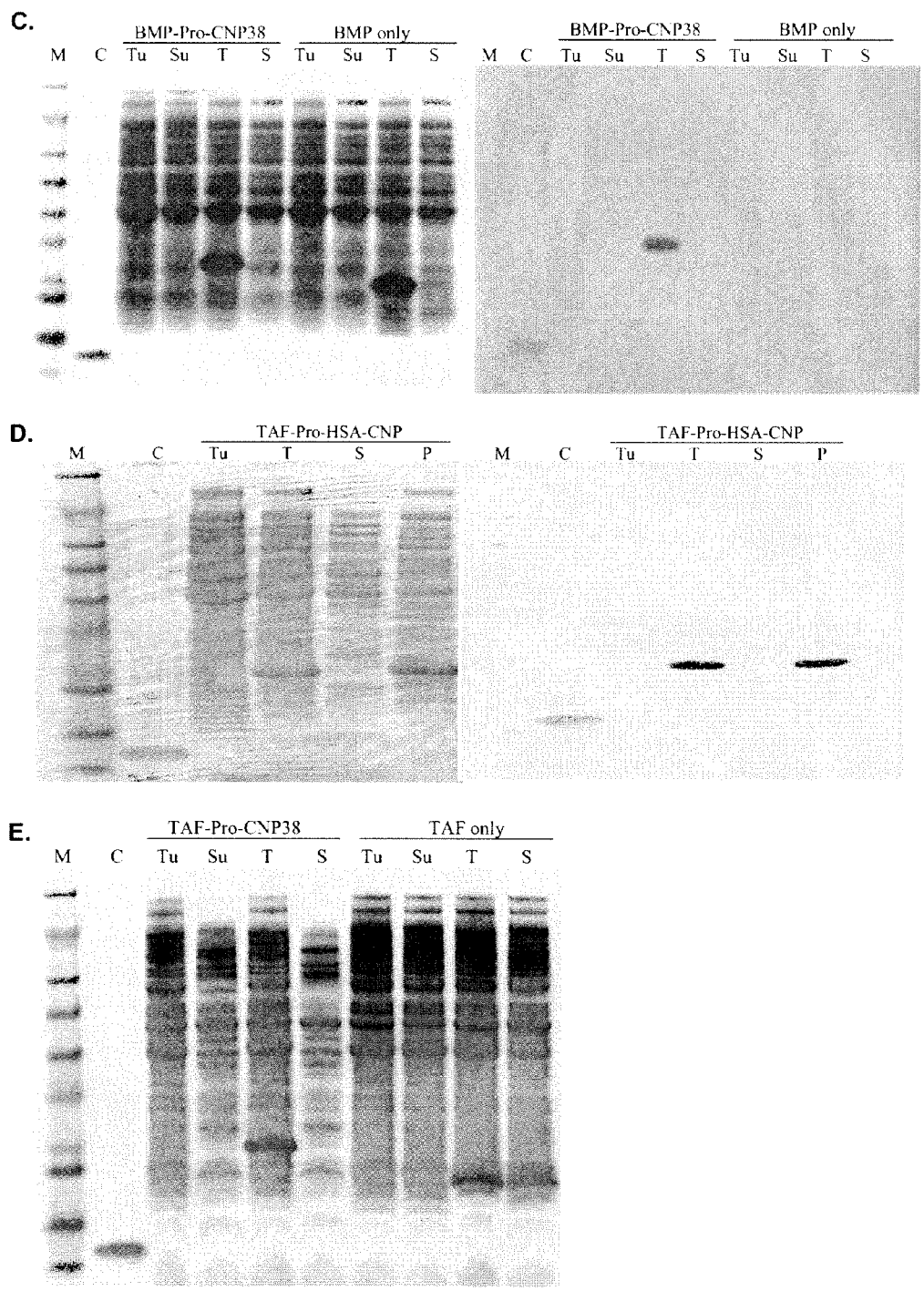

CNP38: GQEHPNARKYKGANKKGLSKGCFGLKLDRIGSMSGLGC [Gly-CNP37 (SEQ ID NO: 75)];
Pro-CNP38: PGQEHPNARKYKGANKKGLSKGCFGLKLDRIGSMSGLGC [Pro-Gly-CNP37] (SEQ ID NO: 145);
CNP37: QEHPNARKYKGANKKGLSKGCFGLKLDRIGSMSGLGC (SEQ ID NO: 60);
HSA-CNP: GHKSEVAHRFKGANKKGLSKGCFGLKLDRIGSMSGLGC [HSA-CNP27 (SEQ ID NO: 144)];
Pro-CNP53: PDLRVDTKSRAAWARLLQEHPNARKYKGANKKGLSKGCFGLKLDRIG-SMSGLGC (SEQ ID NO: 185);
CNP34: PNARKYKGANKKGLSKGCFGLKLDRIGSMSGLGC (SEQ ID NO: 163);
TAF-Pro-CNP38: MVLTKKKLQDLVREVCPNEQLDEDVEEMLLQIADDFIESVVTAA-CQLARHRKSSTLEVKDVQLHLERQWNM-WIMGSSHHHHHHSSGLVPRGSHT-GDDDDKHMDPGQEHPNARKYKGANKKGLSKGCFGLKLDRIGSMSGLGC (SEQ ID NO: 196);
TAF: human transcription factor TAF12 histone fold domain (HFD) and linker from pET-15b vector;
TAF-NL: TAF12 HFD without a linker;
TAF12 HFD: VLTKKKLQDLVREVCPNEQLDEDVEEMLLQIADDFIESVVTAACQLA-RHRKSSTLEVKDVQLHLERQWNMWI (SEQ ID NO: 197);
pET-15b linker: MGSSHHHHHHSSGLVPRGSHTGDDDDKHMD (SEQ ID NO: 195);
TAF(C/A): cysteine in TAF is changed to alanine;
TAF(D/E): aspartic acid in TAF is changed to glutamic acid (number indicates which amino acid residue is changed);
TAF(C/A & D/E): cysteine and aspartic acid in TAF are changed to alanine and glutamic acid, respectively;
BMP: bone morphogenetic protein 2 with seven C/A (cysteine to alanine) mutations;
KSI: ketosteroid isomerase;
MBP: maltose-binding protein;
TRX: thioredoxin Results All CNP fusion proteins were expressed in E. coli induced with 1 mM IPTG at 37° C. for 3 hours. Constructs pJexpress-BMP-Pro-CNP38, pJexpress-TAF-Pro-CNP37, pJexpress-BMP-Pro-CNP37, pJexpress-Pro-HSA-CNP, pJexpress-TAF and pJexpress-BMP were expressed as inclusion bodies. A Western Blot with anti-CNP antibody was used to confirm the expression (FIG. 3).

Figure 4:
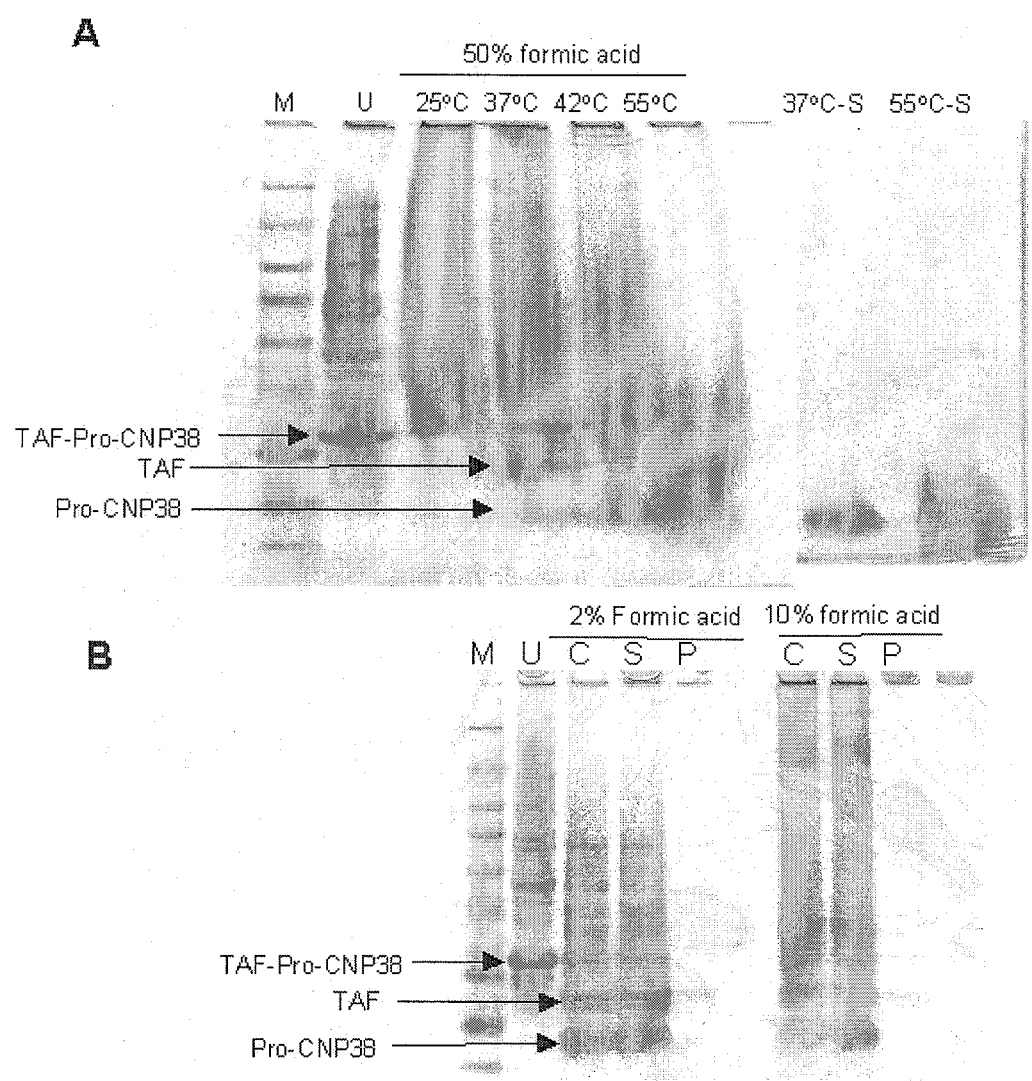
FIGS. 4A-C depict formic acid cleavage of TAF-Pro-CNP38 inclusion bodies. A: 50% formic acid cleavage of TAF-Pro-CNP38 inclusion bodies. M: protein marker; U: un-cleaved TAF-Pro-CNP38 inclusion bodies; 25° C., 37° C., 42° C., 55° C.: TAF-Pro-CNP38 inclusion bodies were cleaved in 50% formic acid at 25° C., 37° C., 42° C. or 55° C. for 24 hours. 37° C.-S and 55° C.-S: soluble supernatants from the cleavage reactions at 37° C. and 55° C. neutralized with 10N NaOH and centrifuged at 14,000 rpm for 15 minutes. B: 10% and 2% formic acid cleavage of TAF-Pro-CNP38 inclusion bodies. M: protein marker; U: un-cleaved TAF-Pro-CNP38 inclusion bodies; C: formic acid cleaved TAF-Pro-CNP38; S: soluble supernatant after centrifuged at 14,000 rpm for 5 minutes without neutralization; P: insoluble pellet after centrifuged at 14,000 rpm for 5 minutes without neutralization. C: LC/MS analysis of 2% and 10% formic acid cleaved products from TAF-Pro-CNP38 inclusion bodies.

Pro-Gly-CNP37 ("Pro-CNP38") was Produced from TAF-Pro-CNP38 Inclusion Bodies by Formic Acid Cleavage Formic acid is used as a denaturant for inclusion body proteins and can specifically cleave the peptide bond between Asp and Pro under optimized conditions. TAF-Pro-CNP inclusion bodies were partially purified as described above and treated with 50% formic acid at 25° C., 37° C., 42° C. and 55° C. for 24 hours. Most of the TAF-Pro-CNP38 was cleaved and one extra band with a similar size as the Gly-CNP37 ("CNP38") peptide showed on SDS-PAGE from the 37° C., 42° C. and 55° C. cleavages (FIG. 4A). The cleavage reactions at 37° C. and 55° C. were neutralized with 10 M NaOH and centrifuged at 14,000 rpm for 15 minutes. The un-cleaved TAF-Pro-CNP38, TAF and other inclusion bodies precipitated in the pellets. The supernatants contained soluble Pro-CNP38 and were further analyzed by LC/MS. The LC/MS result showed the supernatants contained a mixture of non-specific cleaved peptides generated by excess acidic hydrolysis.

Figure 4C:
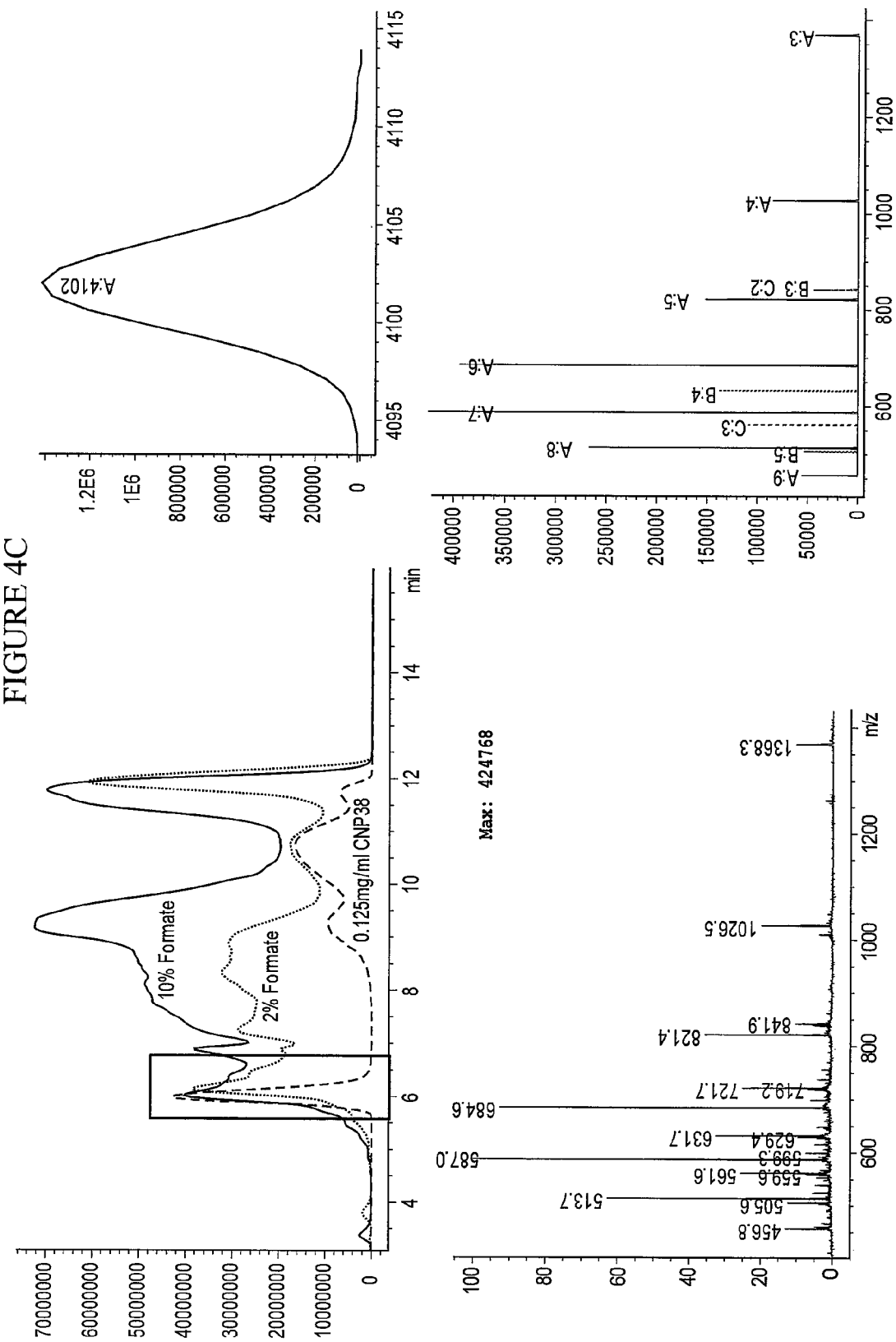

When TAF-Pro-CNP inclusion bodies were treated with 2% and 10% formic acid at 55° C. for 20 hours, the majority of TAF-Pro-CNP38 was cleaved and one extra band having a similar size as Gly-CNP37 was observed on SDS-PAGE (FIG. 4B). The cleaved sample was further analyzed by LC/MS. The LC/MS analysis showed that correct Pro-CNP38 was released in soluble form from TAF-Pro-CNP38 inclusion bodies after formic acid cleavage. The yields of Pro-CNP38 from 2% and 10% formic acid cleavages were similar (FIG. 4C).

Formic Acid Cleavage and Neutralization for Pro-Gly-CNP37 ("Pro-CNP38") Production and Purification Formic acid can dissolve and cleave TAF-Pro-CNP38, BMP-Pro-CNP38 and other inclusion bodies. The pH neutralization results in precipitation of insoluble contaminating proteins/peptides (un-cleaved TAF-Pro-CNP38 and BMP-Pro-CNP38, TAF, BMP and others). The soluble Pro-CNP38 stays in the supernatant after centrifugation. TAF-Pro-CNP38 and BMP-Pro-CNP38 were cleaved in 2% formic acid at 55° C. or 70° C. for 24 hours. The cleavage reactions were neutralized with 1:1 ratio of 0.5 M Tris buffer and centrifuged at 14,000 rpm for 15 minutes. Results showed that the supernatants contained almost pure peptides and there was no observed recovery loss of Pro-CNP38 upon neutralization. This is a simple and efficient step for Pro-CNP38 purification.

Figure 5:
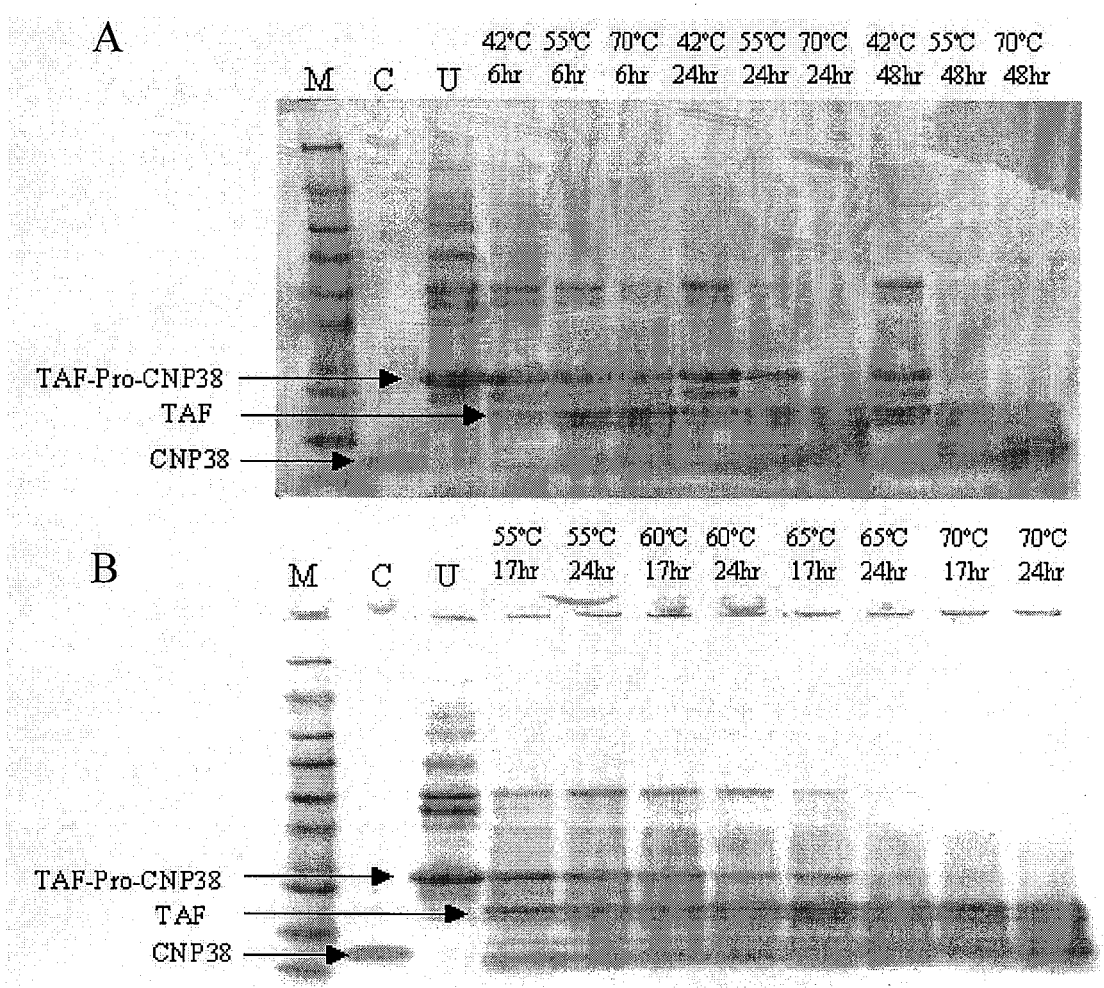
FIGS. 5A-C depict formic acid cleavage of TAF-Pro-CNP38 inclusion bodies at different temperature and time of formic acid cleavage. M: protein marker; C: Gly-wtCNP37 ("CNP38") positive control; U: un-cleaved TAF-Pro-CNP38 inclusion bodies. A: 2% formic acid cleaved TAF-Pro-CNP38 at 42° C., 55° C. or 70° C. for 6, 24 or 48 hours. B: 2% formic acid cleaved TAF-Pro-CNP38 at 55° C., 60° C., 65° C. or 70° C. for 17 or 24 hours. C: LC/MS analysis of 2% formic acid cleaved products from TAF-Pro-CNP38 inclusion bodies.
Figure 5C:
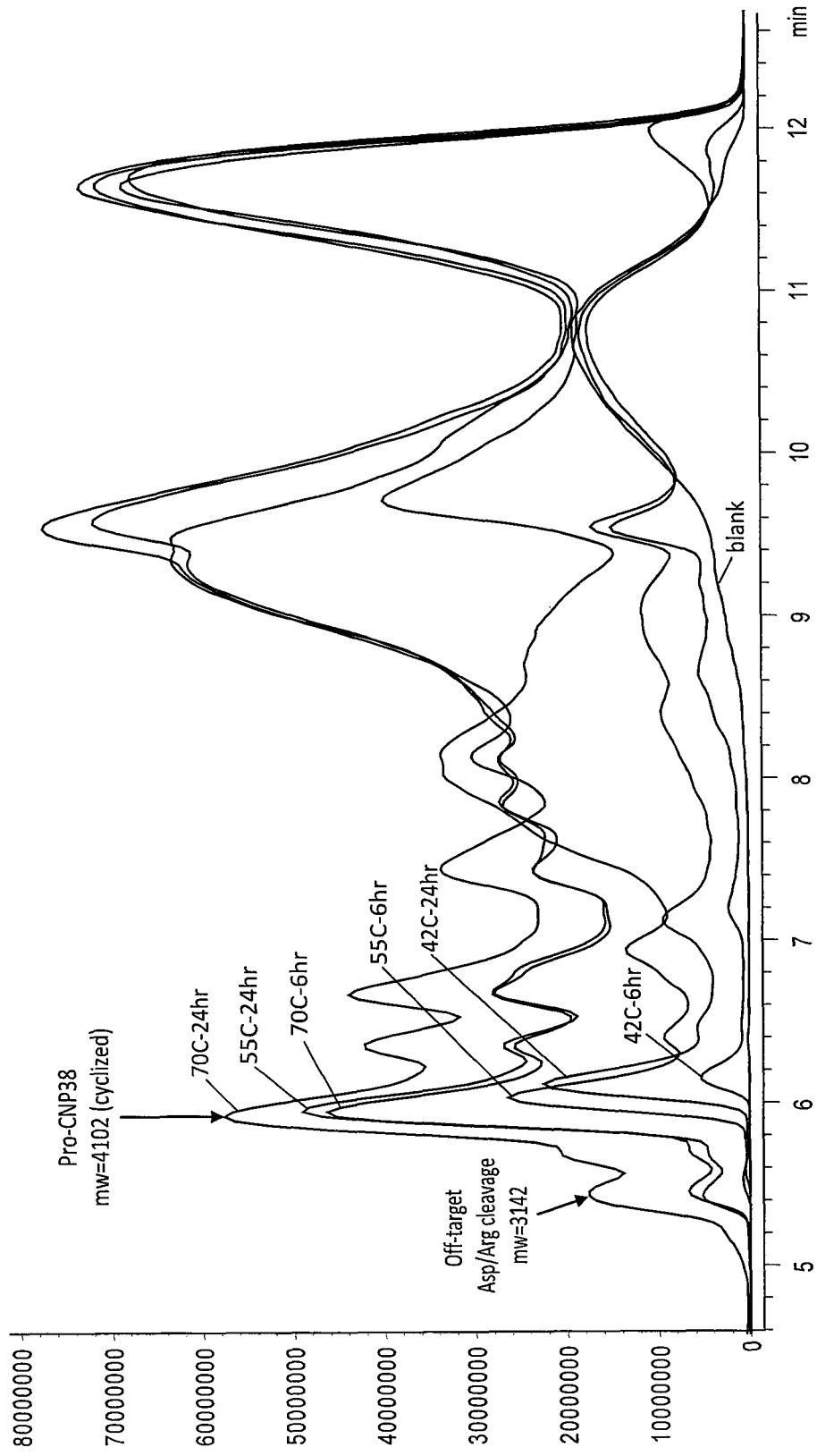

Analysis of Varying Conditions for Formic Acid Cleavage of TAF-Pro-CNP38 Inclusion Bodies for Pro-Gly-CNP37 ("Pro-CNP38") Production Formic acid can specifically cleave the peptide bond between Asp and Pro under optimized conditions. Non-specific cleavage of peptide bonds between Asp and any other amino acids or even non-specific cleavage of any peptide bond may occur if the formic acid cleavage conditions are not optimized. TAF-Pro-CNP38 inclusion bodies were cleaved with 2% formic acid at 42° C., 55° C. or 70° C. for 6, 24 or 48 hours. FIG. 5A shows that TAF-Pro-CNP38 was cleaved completely at 70° C. for 24 hours or at 55° C. for 48 hours. The 70° C. cleavage could be completed within 17 hours (FIG. 5B). Although the 70° C./24 h cleavage gave the highest yield, the non-specific cleavage products (for example, the peptide with molecular weight of 3142 generated from Pro-CNP38 by cleaving between peptide bond Asp and Arg) increased dramatically (FIG. 5C).

The yield and purity of Pro-CNP38 production were improved when TAF-Pro-CNP38 inclusion bodies were purified or treated with B-PER II buffer before formic acid cleavage. Because B-PER II buffer contains detergent octylthioglucoside and is relatively expensive, other commonly used detergents or buffers were tested for large-scale Pro-CNP38 production. TAF-Pro-CNP38 inclusion bodies were re-suspended in different detergents (Octylsucrose; Triton x-100; Tween-20; NP-40; CA-630) or buffers (B-PER II; B-PER II 1/20 dilution; B-PER; B-PER phosphate buffer; 25 mM tris, 150 mM NaCl, pH 7.9; 25 mM tris, pH 7.5; filtered water; PBS) and incubated at room temperature (RT) for 24 hours. All detergents were 1% in 25 mM tris buffer, pH 7.5. After incubation in detergent or buffer, TAF-Pro-CNP38 inclusion bodies were cleaved by 2% formic acid at 55° C. for 22 hours. Results showed that BPER II continued to exhibit good yield, and positive results were also obtained with CA630 and Triton X-100.

Pro-Gly-CNP37 ("Pro-CNP38") Proteolytic Cleavage Products

One unidentified protease, possibly a membrane associated protease, cleaved the Pro-CNP38 peptide (produced from BL21 strain, MW 4102) into two peptides during Pro-CNP38 purification, resulting in peptides PGQEHPNAR (MW 1004) (SEQ ID NO: 198) and KYKGANKKGL-SKGCFGLKLDRIGSMSGLGC (MW 3115) (SEQ ID NO: 199). Not to be bound by theory, one possible reason why detergents may improve the yield and purity of Pro-CNP38 is that detergents can remove most, but possibly not all, of the unidentified protease. High temperature, basic pH and EDTA were tested to identify if these agents could inhibit the protease cleavage. TAF-Pro-CNP38 inclusion bodies were incubated at RT or 120° C. for 2 hrs and centrifuged at 14000 rpm for 15 min. The pellets were re-suspended in 2% formic acid and incubated at 55° C. or 70° C. for 18 hours. A 1:1 ratio of 0.5 M Tris was added to neutralize the cleavage. The neutralized samples were centrifuged at 14000 rpm for 5 min and the supernatants were left at RT for 6 hrs or 22 hrs with or without 10 mM EDTA, pH 10. The proteolytic cleavage was assayed by LC/MS (Table 8).

TABLE 8

LC/MS result of Pro-CNP38 proteolytic cleavage

| Sample | | A210 Peak Area | Protein Conc. (mg/mL) | | Percent MW4102 | Percent MW3115 |
|---|---|---|---|---|---|---|
| 1 | H 55 C. | 942 | 0.04 | * | 91.8 | 8.2 |
| 2 | H 70 0 | 2878 | 0.11 | * | 79.2 | 20.7 |
| 3 | H 70 6H | 2675 | 0.10 | * | 80.6 | 19.4 |
| 4 | H 70 24 | 2741 | 0.11 | * | 79.2 | 20.7 |
| 5 | H 70 EDTA | 2385 | 0.09 | * | 80.8 | 19.2 |
| 6 | H 70 pH 10 | 1917 | 0.07 | * | 81.2 | 18.8 |
| 7 | 55 C. | 1291 | 0.05 | | 61.1 | 38.9 |
| 8 | 70 C. 0 | 4533 | 0.18 | | 96.8 | 3.2 |
| 9 | 70 C. 6H | 4120 | 0.16 | | 97.5 | 2.5 |
| 10 | 70 C. 24 | 4108 | 0.16 | | 96.5 | 3.5 |
| 11 | 70 C. EDTA | 4336 | 0.17 | | 96.9 | 3.1 |
| 12 | 70 C. pH 10 | 3425 | 0.13 | | 97.5 | 2.4 |

All samples (8-12) cleaved at 70° C. showed limited proteolytic cleavage (less than 4% cleavage of Pro-CNP38). Almost 40% of Pro-CNP38 was cleaved by protease when cleavage was carried out at 55° C. (sample 7). Basic pH and EDTA did not influence the non-specific proteolytic cleavage. High temperature (120° C. for 2 hrs) non-specifically cleaved Pro-CNP38.

It should be noted that the BL21(DE3) strain from Stratagene does not have the unidentified protease.

Figure 6:
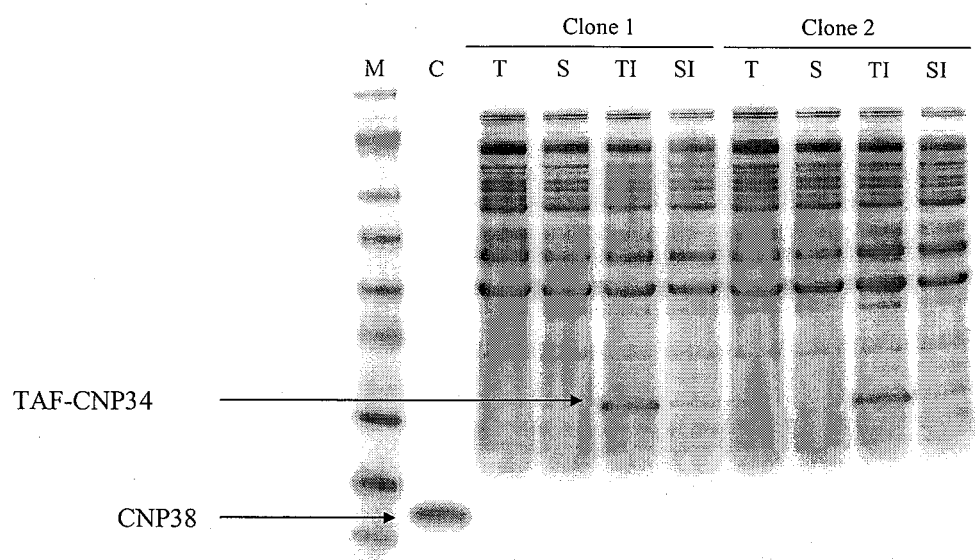
FIG. 6 is an SDS-PAGE (Coomassie blue stain) for the expression of a TAF-CNP34 fusion protein. M: protein marker; C: control [Gly-CNP37 ("CNP38")]; T: total cell lysates; S: supernatant; TI: total cell lysates induced; SI: supernatant induced.
Figure 8:
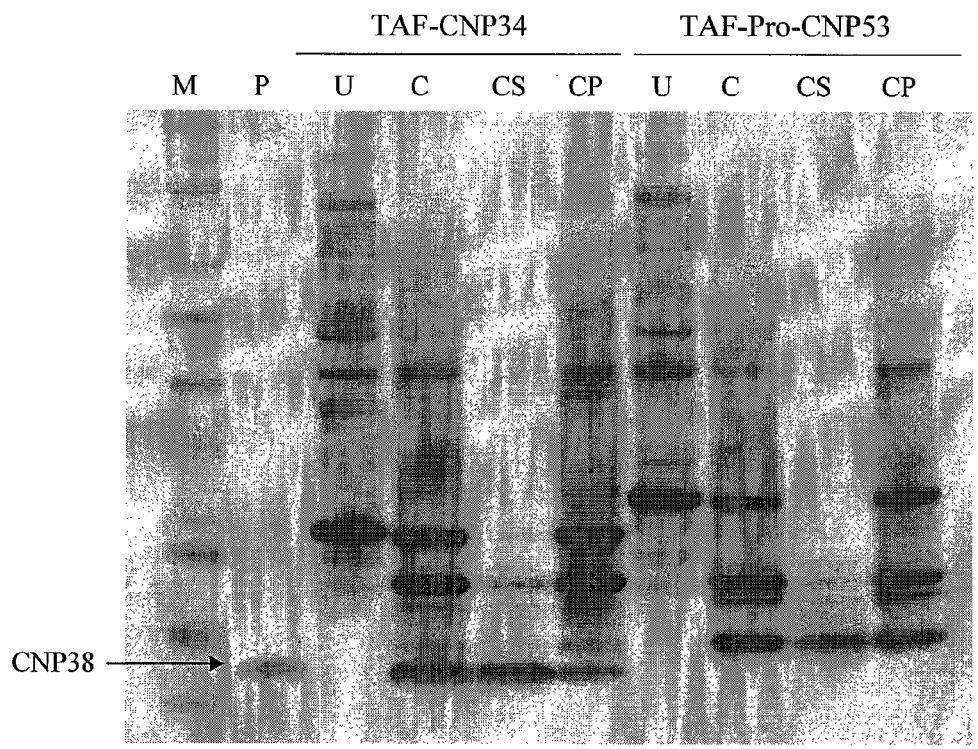
FIG. 8 is an SDS-PAGE (Coomassie blue stain) of the products of formic acid cleavage of the fusion proteins TAF-CNP34 and TAF-Pro-CNP53. M: protein marker; P: positive control [Gly-CNP37 ("CNP38")]; U: uncleaved; C: cleaved; CS: cleaved supernatant; CP: cleaved pellet.
Figure 9:
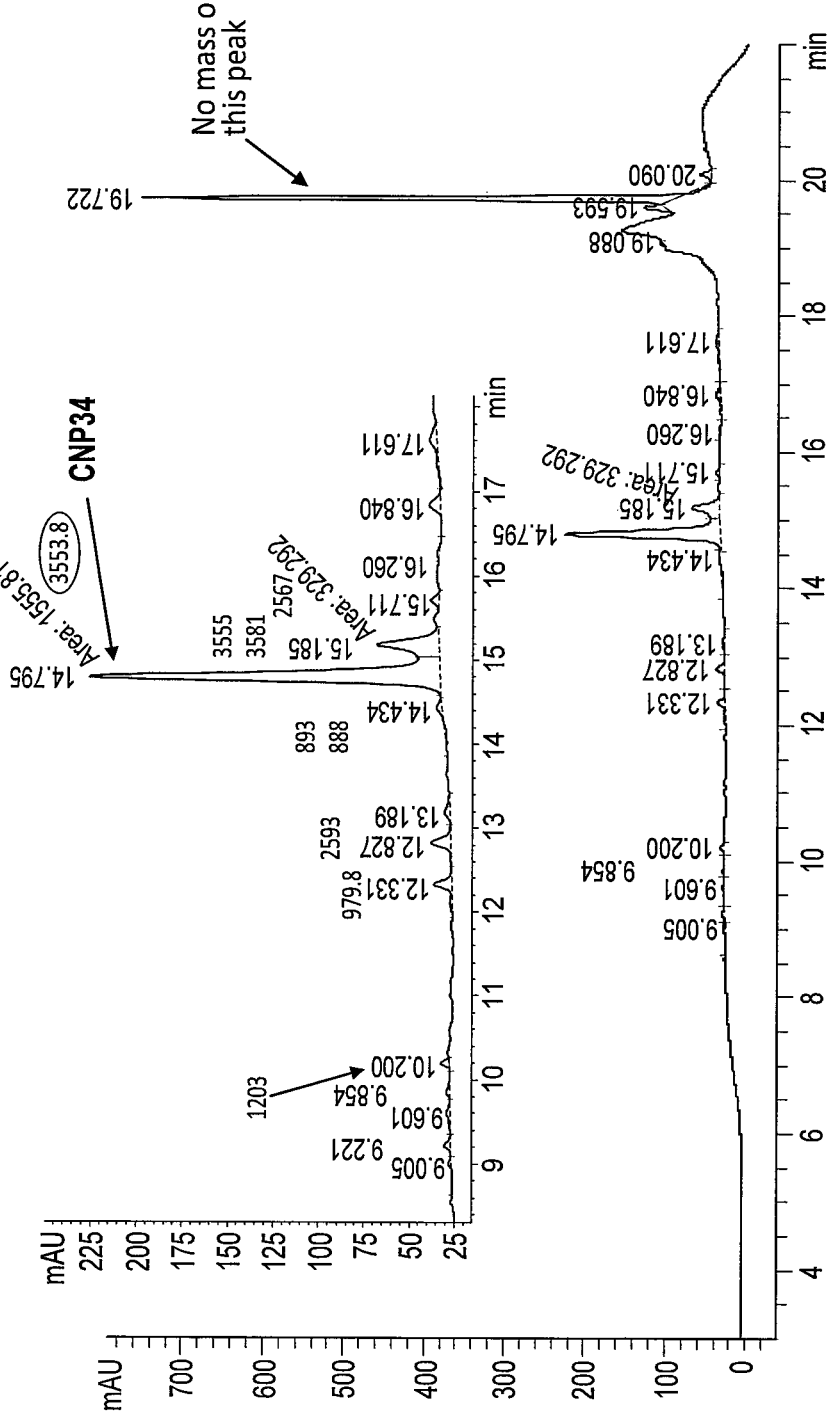
FIG. 9 is an LC/MS chromatogram showing the peak for CNP-34 after formic acid cleavage of TAF-CNP34.
Figure 10:
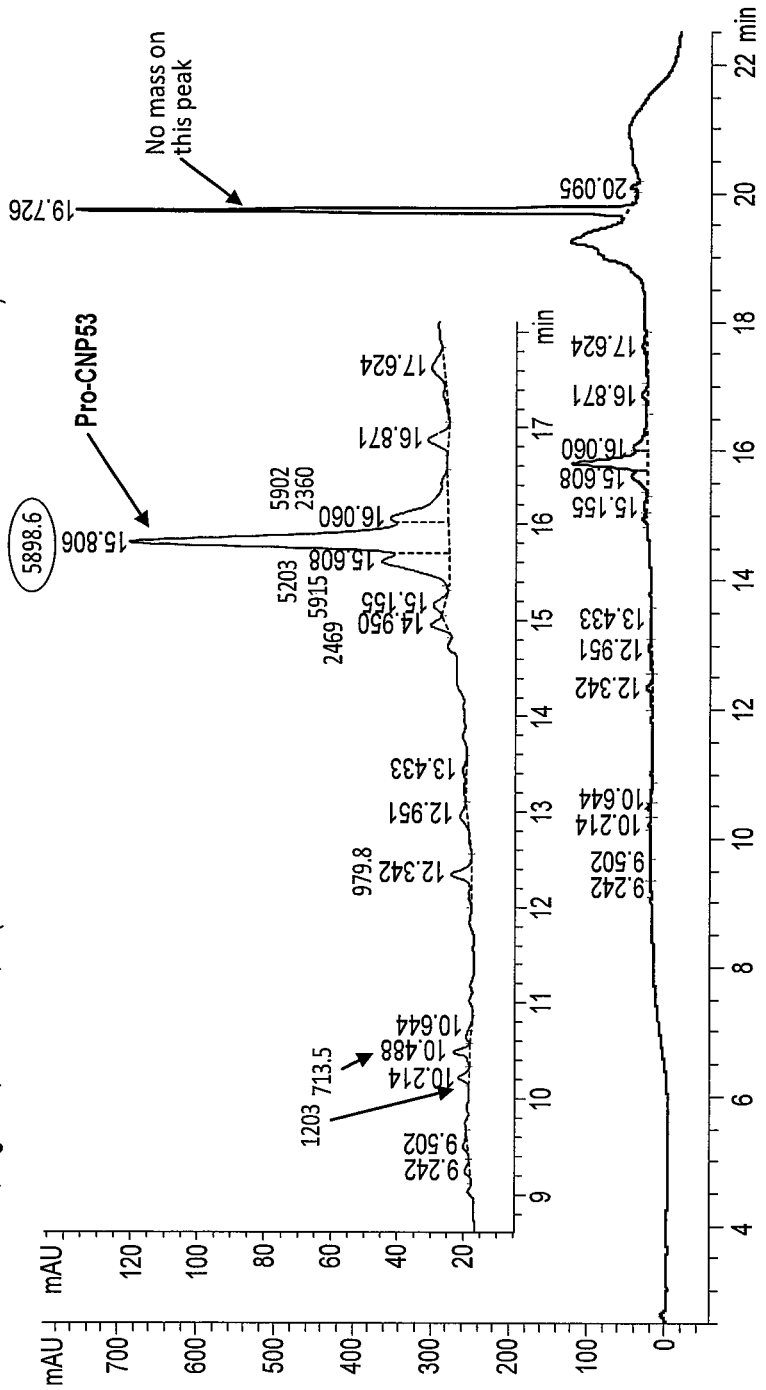
FIG. 10 is an LC/MS chromatogram showing the peak for Pro-CNP53 after formic acid cleavage of TAF-Pro-CNP53.

Production of Pro-Gly-CNP37 ("Pro-CNP38") and Other CNP Variants from Different Constructs:

Pro-CNP38 can be produced in large scale in *E. coli* by means of overexpression of a TAF-Pro-CNP38 fusion protein as inclusion bodies followed by formic acid cleavage of the fusion protein. Following the methods described herein, other TAF-CNP fusion proteins (TAF-CNP34 and TAF-Pro-CNP53) were expressed as inclusion bodies and then cleaved with formic acid to generate the CNP variants CNP34 and Pro-CNP53. FIG. 6 depicts the expression of TAF-CNP34, FIG. 7 the expression of TAF-Pro-CNP53, FIG. 8 the products of formic acid cleavage of TAF-CNP34 and TAF-Pro-CNP53, FIG. 9 the peak for CNP-34 in an LC/MS chromatogram, and FIG. 10 the peak for Pro-CNP53 in an LC/MS chromatogram.

Figure 7:
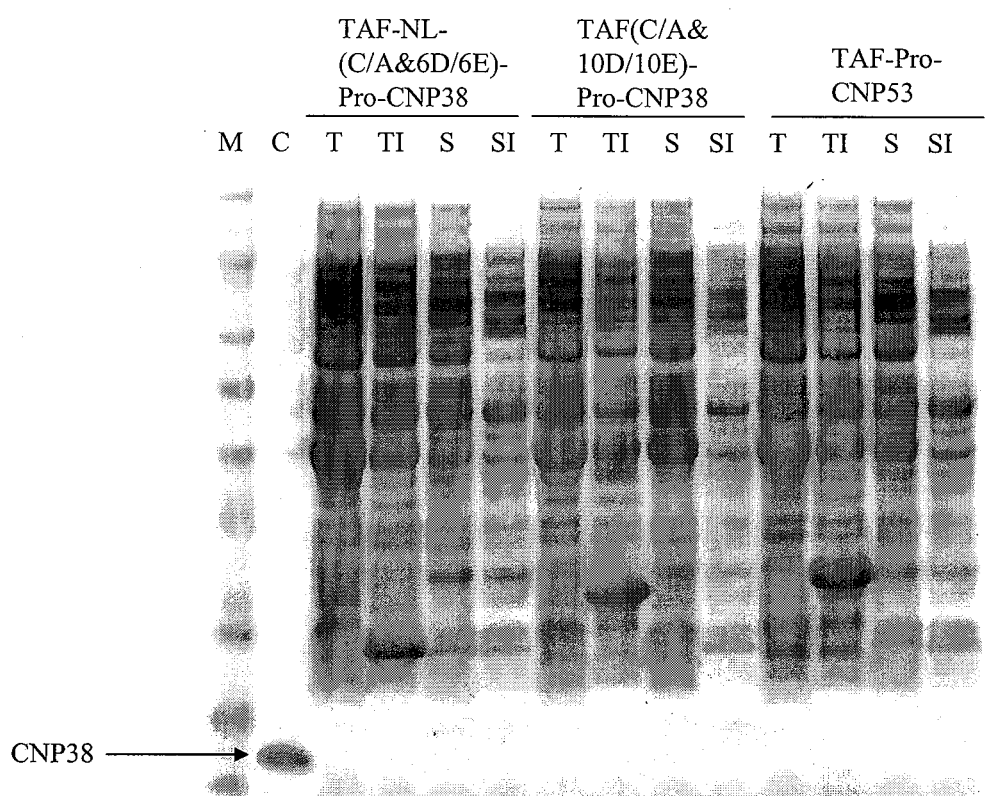
FIG. 7 is an SDS-PAGE (Coomassie blue stain) for the expression of fusion proteins TAF-NL-(C/A & 6D/6E)-Pro-CNP38, TAF(C/A & 10D/10E)-Pro-CNP38, and TAF-Pro-CNP53, where "Pro-CNP38" denotes Pro-Gly-CNP37. M: protein marker; C: control [Gly-CNP37 ("CNP38")]; T: total cell lysates; TI: total cell lysates induced; S: supernatant; SI: supernatant induced.
Figure 11:
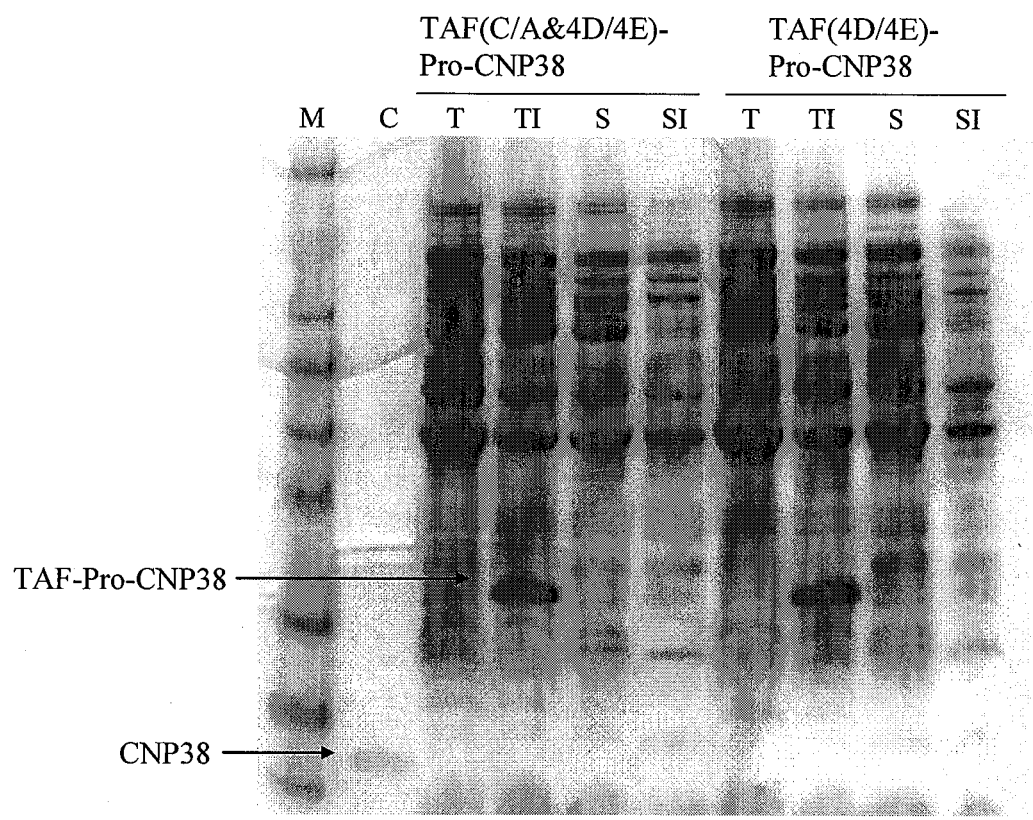
FIG. 11 is an SDS-PAGE (Coomassie blue stain) for the expression of fusion proteins TAF(C/A & 4D/4E)-Pro-CNP38 and TAF(4D/4E)-Pro-CNP38, where "Pro-CNP38" denotes Pro-Gly-CNP37. M: protein marker; C: control [Gly- CNP37 ("CNP38")]; T: total cell lysates; TI: total cell lysates induced; S: supernatant; SI: supernatant induced.
Figure 12:
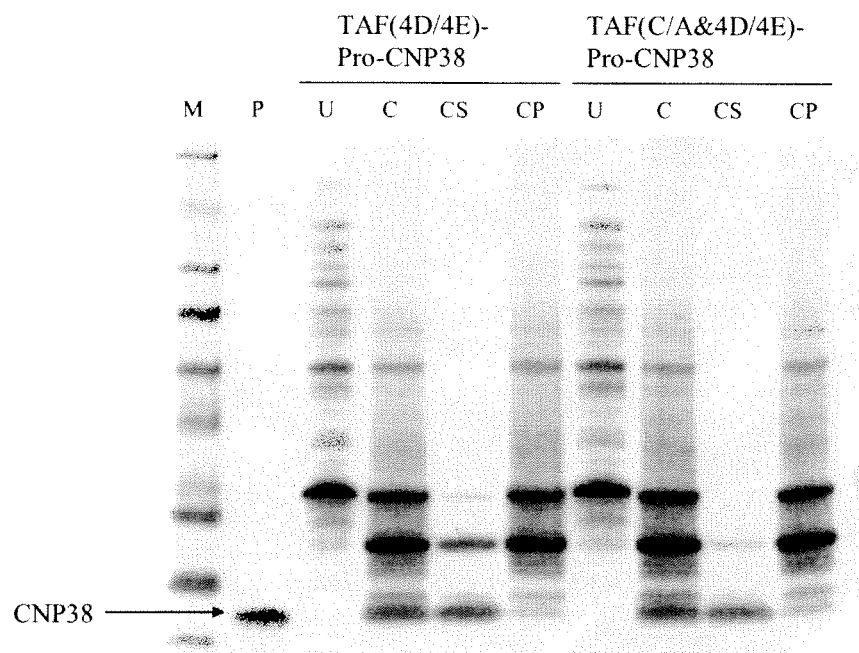
FIG. 12 is an SDS-PAGE (Coomassie blue stain) of the products of formic acid cleavage of the fusion proteins TAF (4D/4E)-Pro-CNP38 and TAF(C/A & 4D/4E)-Pro-CNP38, where "Pro-CNP38" denotes Pro-Gly-CNP37. M: protein marker; P: positive control [Gly-CNP37 ("CNP38")]; U: uncleaved; C: cleaved; CS: cleaved supernatant; CP: cleaved pellet.
Figure 13:
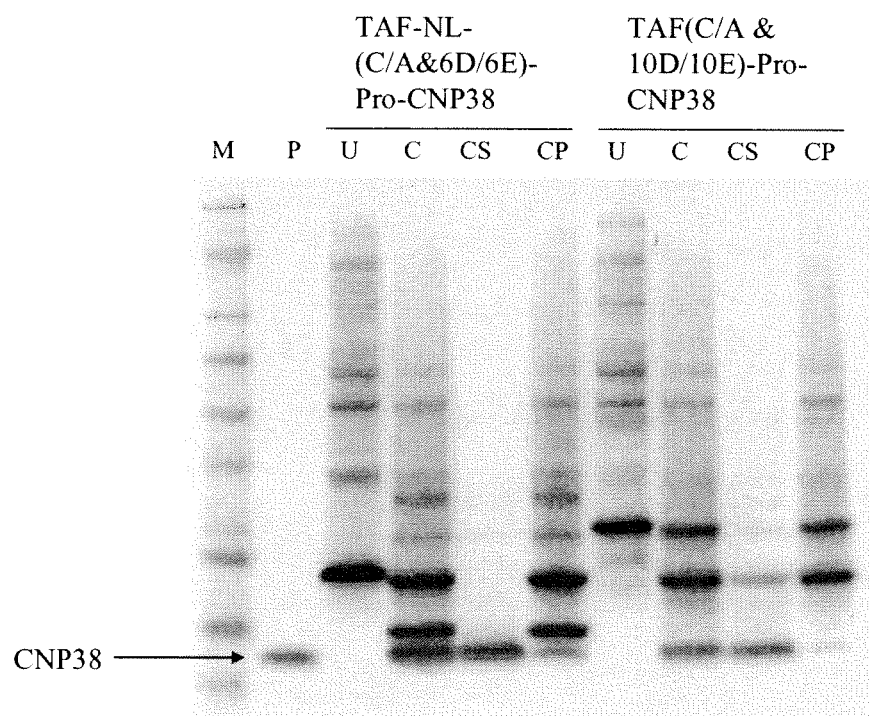
FIG. 13 is an SDS-PAGE (Coomassie blue stain) of the products of formic acid cleavage of the fusion proteins TAF-NL-(C/A & 6D/6E)-Pro-CNP38 and TAF(C/A & 10D/10E)-Pro-CNP38, where "Pro-CNP38" denotes Pro-Gly-CNP37. M: protein marker; P: positive control [Gly-CNP37 ("CNP38")]; U: uncleaved; C: cleaved; CS: cleaved supernatant; CP: cleaved pellet.

Use of formic acid may result in unspecific cleavage(s) at peptide bond(s) other than the targeted Asp-Pro bond. To improve the purity and overall titer of the desired formic acid cleavage product, different residues of aspartic acid in TAF12 or fragments thereof were changed to glutamic acid. Moreover, one or more cysteine residues in TAF12 or fragments thereof were changed to alanine to prevent unspecific disulfide bond formation. All TAF-Pro-CNP38 fusion proteins having such mutations in TAF12 were expressed as inclusion bodies and cleaved with formic acid to produce Pro-CNP38. FIG. 7 shows the expression of TAF-NL-(C/A & 6D/6E)-Pro-CNP38 and TAF(C/A & 10D/10E)-Pro-CNP38, FIG. 11 the expression of TAF(C/A & 4D/4E)-Pro-CNP38 and TAF(4D/4E)-Pro-CNP38, FIG. 12 the products of formic acid cleavage of TAF(4D/4E)-Pro-CNP38 and TAF(C/A & 4D/4E)-Pro-CNP38, and FIG. 13 the products of formic acid cleavage of TAF-NL-(C/A & 6D/6E)-Pro-CNP38 and TAF(C/A & 10D/10E)-Pro-CNP38. Table 9 summarizes the purity (prior to purification) and titer of Pro-CNP38 obtained from the various TAF-Pro-CNP38 constructs.

TABLE 9

| Construct | Purity | Titer (ug/mL) |
| --- | --- | --- |
| pJexpress-TAF-Pro-CNP38 | 32% | 44 |
| pJexpress-TAF(C/A)-Pro-CNP38 | 41% | 50 |
| pJexpress-TAF(4D/4E)-Pro-CNP38 | 36% | 52 |
| pJexpress-TAF(C/A & 4D/4E)-Pro-CNP38 | 42% | 58 |
| pJexpress-TAF(C/A & 10D/10E)-Pro-CNP38* | 32% | 26 |
| pJexpress-TAF-NL-(C/A & 6D/6E)-Pro-CNP38 | 50% | 55 |

*Cells with pJexpress-TAF(C/A&10D/10E)-Pro-CNP38 growed more slowly and the final cell density ($OD_{600}$) was lower compared to other TAF-Pro-CNP38 constructs.

Figure 14:
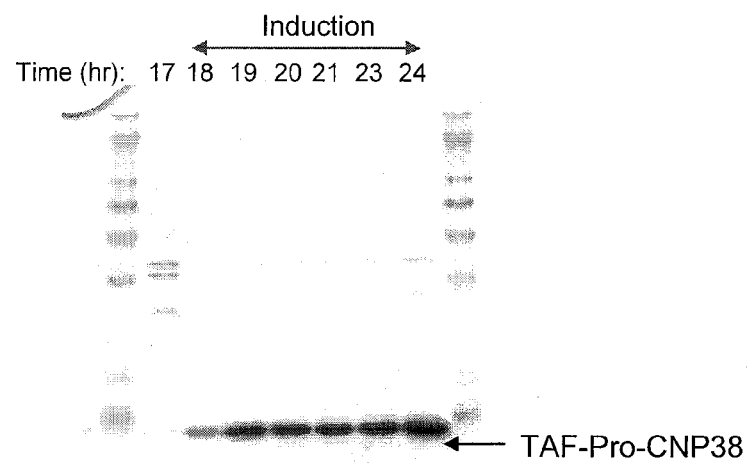
FIG. 14 is a Western blot, using an anti-CNP antibody, of a TAF-Pro-CNP38 fusion protein produced in a 10 L fermentation of BL21(DE3) cells, where the cells were induced at $OD_{600}=64$ and hour 17 and "Pro-CNP38" denotes Pro-Gly-CNP37.

Large-scale Production of Pro-Gly-CNP37 ("Pro-CNP38") by Fermentation and Formic Acid Cleavage BL21(DE3) cells comprising the pJexpress-TAF-CNP construct were grown in a 10 liter fermenter at 37° C. for about 16-17 hours until $OD_{600}$ reached 64. The cells were then grown/cultured in the presence of 1 mM IPTG at about 35-37° C., to induce expression of the TAF-Pro-CNP38 fusion protein, for about 7-8 hours until $OD_{600}$ reached 160. The fermentation produced a titer of 9 g/L TAF-Pro-CNP38. FIG. 14 displays a Western blot of the TAF-Pro-CNP38 fusion protein produced in the fermentation.

A cell pellet recovered from 750 mL cell culture from the 10 L fermentation was resuspended in phosphate-buffered saline, pH 7.4 (PBS) and lysed by three passes through a pressure homogenizer (10,000 bar). The resulting lysate was centrifuged at 6,500 g for 10 minutes and the supernatant was discarded. The pellet fraction containing insoluble TAF-Pro-CNP38 fusion protein inclusion bodies was resuspended in 500 mL PBS with a rotostator. The suspension was centrifuged at 6,500 g for 10 minutes and the supernatant was discarded. The resulting inclusion body pellet was resuspended in 500 mL water with a rotostator and incubated at 55° C. for 30 minutes. 250 mL 6% formic acid was added to the warmed inclusion body suspension for a final concentration of 2% formic acid and incubated at 55° C. for 20-24 hours. 50 mL of 400 mM $Na_2HPO_4$ was added after 20-24 hours to begin the neutralization of the formic acid cleavage reaction, and the resulting mixture was titrated with 50% w/v NaOH to pH 6.9-7.4 and left at room temperature for 30 minutes. Upon neutralization, a heavy precipitate formed and was removed by centrifugation at 6,500 g for 10 minutes. The supernatant was retained and contained on average 1.3 g/L culture of 80% pure Pro-CNP38. The majority of the *E. coli* and TAF-related proteins and peptides remained in the pellet.

Figure 15:
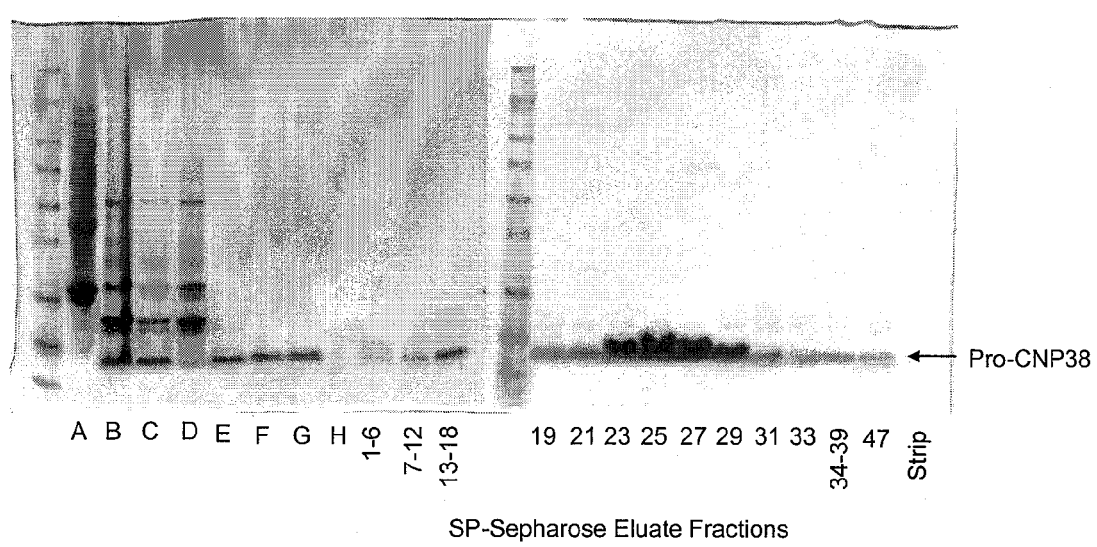
FIG. 15 is an SDS-PAGE (Coomassie blue stain) of eluate fractions from SP-Sepharose cation-exchange column chromatography of a cruder Pro-Gly-CNP37 ("Pro-CNP38") product. A: TAF-Pro-CNP38 inclusion body (IB) in water; B: IB in formate; C: IB in formate, neutralized; D: neutralized pellet; E: neutralized supernatant; F: TMAE Hi-CAP load; G: TMAE Hi-CAP flow through/SP-Sepharose load; H: SP-Sepharose flow through; SP-Sepharose eluate fractions 1-47: 10 uL/lane.

The soluble Pro-CNP38 resulting from the formic acid cleavage and neutralized supernatant was 80% pure and contained a mixture of linear and cyclized Pro-CNP38 peptides along with other product-related impurities. The pH neutral supernatant containing Pro-CNP38 was sterile-filtered. Further purification by anion-exchange chromatography using a Fractogel TMAE Hi-CAP column (EMD Biosciences) to remove DNA, endotoxins, and peptide contaminants, which should bind to the column, was performed at pH 7-7.4. The flow-through fraction contained partially cyclized Pro-CNP38. Cupric sulfate was added to the flow-through fraction to a final concentration of 10 uM and incubated at room temperature for 1 hour. The addition of $Cu^{++}$ at neutral pH catalyzed the oxidation of free cysteine sulfhydryl groups on the peptide to form an intramolecular disulfide bond, resulting in 100% cyclized Pro-CNP38 and no detectable linear peptide. The conductivity of the solution was adjusted to <15 mS/cm by the addition of water. Cation-exchange chromatography using an SP-Sepharose column (GE Healthcare) and a sodium phosphate buffer (pH 7) was then performed to remove any remaining DNA and endotoxins in the flow-through and further purify Pro-CNP38 to about 95-96% purity with <0.5% non-product related impurities. FIG. 15 is an SDS-PAGE of eluate fractions from the SP-Sepharose column; the highest concentrations of Pro-CNP38 were found in fractions 22 to 30. Reverse-phase HPLC/MS analysis of non-pooled fraction 24 indicated the presence of 90% Pro-CNP38, 5% Pro-CNP38 with an oxidized methionine residue, 3% Pro-CNP38 cleaved at the Gly-Cys bond to form CNP-17, and 1.6% Pro-CNP38 cleaved at the Asp-Arg bond in the cyclic domain. The yield of pure Pro-CNP38 peptide upon final purification was 0.9 g/L cell culture (36% total recovery).

Pro-CNP38 collected from five separate purifications was pooled for formulation. The pooled product contained 93.5% Pro-CNP38, 3.3% Pro-CNP38 with an oxidized methionine residue, 1.3% deamidated Pro-CNP38, and 1% Pro-CNP38 cleaved at the Gly-Cys bond to form CNP-17. Samples were diluted with 50 mM sodium phosphate (pH 7) to a conductivity of 10 mS/cm and loaded onto a CM-Sepharose column (GE-Healthcare) for concentration and buffer exchange. The weak cation-exchange property of the CM-Sepharose resin allows peptides to dissociate from the column with weak acid solutions rather than typical salt gradients. Acid concentrations required for dissociation of Pro-CNP38 from the CM-Sepharose column depended upon column loading. At 50 mg Pro-CNP38 per mL of resin, 10 mM HCl was sufficient for Pro-CNP38 elution. At 9 mg Pro-CNP38 per mL of resin, 50 mM HCl was required for elution. When the loading was 9 mg Pro-CNP38 per mL of resin, Pro-CNP38 eluted in less than one column volume, which significantly concentrated the peptide. The eluate fraction contained 20.3 mg/mL of 95% pure Pro-CNP38, along with 3% Pro-CNP38 with an oxidized methionine residue, 1% deamidated Pro-CNP38, and <1% Pro-CNP38 cleaved at the Gly-Cys bond to form CNP-17. The concentrated solution of Pro-CNP38 in weak acid is suitable for dilution into appropriate buffers for either liquid or lyophilized formulations.

Example 3

Cleavage of CNP Variants by Neutral Endopeptidase In Vitro

To determine the effects of amino acid substitutions, amino acid extensions, backbone modifications, side chain modifications and PEGylation on the susceptibility of CNP variants to neutral endopeptidase (NEP) cleavage, peptide cleavage assays were carried out using an in vitro assay that monitored disappearance of the non-cleaved CNP variant.

Recombinant human NEP (1 ug/mL final concentration) was added to 100 uM CNP variant diluted in 0.1 M Tris, pH 7. The reaction mixture was incubated at 37° C. for various periods of time, and the reaction was quenched with EDTA (10 mM final) followed by heat denaturation. The reaction mixture was reduced and then the reaction products were analyzed using HPLC and mass spectroscopy. The half-life of the CNP variant was calculated based on the disappearance of intact CNP variant over time. The results for digested CNP variants were compared to a parallel wtCNP22 digestion and normalized to the results for 100 uM CNP22 digested by 1 mg/mL NEP ($t_{1/2}$=80 min).

Table 1 lists the half-lives, based on the in vitro NEP cleavage assay, of various CNP variants having backbone or side chain modifications. Removal of three of the six NEP cleavage sites in Analog L nevertheless resulted in a substantially shorter half-life. Of tested CNP variants, the greatest resistance to NEP cleavage was exhibited by Analog N, which contains the D-enantiomer of all 22 amino acids of CNP22, and by Analog M, which has an N-methylated amide bond at both Leu9 and Leu11. However, both Analogs N and M failed to stimulate production of cGMP (see below).

Comparing the half-lives of Analogs A, B, E, F, G and H to one another, half-lives were determined to be about 1.5- to about 2.5-fold longer for Analogs E and G compared to those for Analogs A, B, F and H. All of these six analogs showed resistance or improved resistance to cleavage at the Cys6-Phe7 bond relative to wtCNP22 (data not shown). The rank order of analog resistance to NEP at 1 ug/ml, based on half-life, is Analog G (3-Cl-Phe)≥Analog E (D-Phe)>Analog H ("beta-2 Phe"), Analog B (N-Me-Phe), and Analog F (t-Bu-Gly)=wtCNP22>Analog A (Cys-$CH_2$—NH). Analogs E and G have about 1.5 times longer half-life in comparison to wtCNP22. Besides resistance to cleavage of the Cys6-Phe7 bond, Analogs B, E, F, G and H also exhibited resistance to cleavage of the Gly8-Leu9 bond in the presence of 1 ug/mL NEP (data not shown). These results indicate that CNP variants having backbone or side chain modifications between Cys6 and Gly8 can be resistant to NEP cleavage of the Cys6-Phe7 bond and/or Gly8-Leu9 bond, but do not necessarily have improved overall resistance to NEP or a longer half-life than CNP22. The results seem to be contrary to reports in the literature that NEP first cleaves at the Cys6-Phe7 bond of CNP22 and then elsewhere.

TABLE 1

| Analog | Backbone and Side Chain Modifications Natriuretic Peptide | cGMP Response rel. to 1 uM CNP22[1] 10 nM | 1 uM | NEP Cleavage ($t_{1/2}$, min) |
|---|---|---|---|---|
|  | CNP22 (SEQ ID NO: 1) | 46 ± 10 | 100 ± 13 | 80[2] |
| N | D-CNP22 (all D-amino acids) (SEQ ID NO: 115) | 2 | 1 | >>160 |
| A | CNP22, C6—CH2—NH (reduced carbonyl) (SEQ ID NO: 56) | 6 | 66 | 55 |
| B | CNP22, N-methyl-F7 (methylated amide) (SEQ ID NO: 57) | 2 | 38 | 80 |
| BD | CNP22, N-methyl-L9 (SEQ ID NO: 116) | 2 | 8 | ND |
| BN | CNP22, N-methyl-L11 (SEQ ID NO: 117) | 10 | 51 | ND |
| BE | CNP22, N-methyl-L20 (SEQ ID NO: 118) | 2 | 5 | ND |
| M | CNP22, N-methyl-L9, N-methyl-L11 (SEQ ID NO: 94) | 1 | 11 | >>160 |
| K | CNP22, N-methyl-L9, N-methyl-L20 (SEQ ID NO: 92) | 1 | 1 | 80 |
| L | CNP22, N-methyl-L9, N-methyl-L11, N-methyl-L20 (SEQ ID NO: 93) | 18 | 10 | 30 |
| J | CNP22, C6—CH2—NH, N-methyl-L9, N-methyl-L20 (SEQ ID NO: 91) | ND | ND | 50 |
| E | CNP22, D-F7 (D-Phe) (SEQ ID NO: 136) | 2 | 6 | 130 |
| H | CNP22, Beta-2-F7 (3-amino-2-phenylpropionyl) (SEQ ID NO: 57) | 2 | 2 | 80 |
| G | CNP22, 3-chloro-F7 (SEQ ID NO: 137) | 17 | 93 | 135 |
| F | CNP22, t-butyl-G8 (SEQ ID NO: 58) | 2 | 18 | 80 |
| V | CNP22, K4G, 3,4-dichloro-F7 (SEQ ID NO: 119) | ND | ND | 68 |
| X | CNP22, K4G, 3-methyl-F7 (SEQ ID NO: 120) | ND | ND | 68 |
|  | ANP | 10 | 23 | ND |

[1]Stimulation of cGMP production in NIH3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined Table 2 lists the half-lives, based on the in vitro NEP cleavage assay, of various CNP variants having substitutions with natural and/or unnatural amino acids. Of tested variants, the greatest resistance to NEP cleavage was shown by Analog BK, which has K4R and G15S substitutions, and Analog BJ, which has K4R and G15N substitutions.

TABLE 2

| Analog | Specificity Mutations Natriuretic Peptide | cGMP Response relative to 1 uM CNP22[1] 10 nM | cGMP Response relative to 1 uM CNP22[1] 1uM | NEP Cleavage ($t_{1/2}$, min) |
|---|---|---|---|---|
|  | CNP22 (SEQ ID NO: 1) | 46 ± 10 | 100 ± 13 | 80 |
| AH | CNP22, K4R (SEQ ID NO: 35) | 59 | 121 | 80 |
| BP | CNP22, K4R, G5S (SEQ ID NO: 121) | 45 | ND | ND |
| BO | CNP22, K4R, G5R (SEQ ID NO: 122) | 18 | 80 | ND |
| P | CNP22, K4G (SEQ ID NO: 123) | ND | ND | 68 |
| Z | CNP22, K4R, F7Y (SEQ ID NO: 95) | 2 | 18 | ND |
| AB | CNP22, K4R, G8S (SEQ ID NO: 97) | 26 ± 26 | 86 ± 17 | ND |
| AA | CNP22, K4R, G8V (SEQ ID NO: 96) | 3 | 25 | ND |
| AC | CNP22, K4R, G8T (SEQ ID NO: 98) | 11 ± 2 | 66 ± 16 | 80 |
| AD | CNP22, K4R, L9T (SEQ ID NO: 99) | 4 | 68 | ND |
| BH | CNP22, K4R, K10R (SEQ ID NO: 112) | 12 | 80 | ND |
| BF | CNP22, K4R, K10Cit (SEQ ID NO: 110) | 6 | 33 | ND |
| BG | CNP22, K4R, K10Q (SEQ ID NO: 111) | 9 | 45 | ND |
| BY | CNP22, K4R, K10S (SEQ ID NO: 124) | 16 | 53 | ND |
| BK | CNP22, K4R, G15S (SEQ ID NO: 114) | 13 ± 1 | 71 ± 11 | ≥160 |
| BJ | CNP22, K4R, G15N (SEQ ID NO: 113) | 4 | 41 | 150 |
| AE | CNP22, K4R, G15R (SEQ ID NO: 100) | 0.3 | 0.3 | ND |
| AF | CNP22, K4R, G15Cit (SEQ ID NO: 101) | 1.4 | 2 | ND |
| BZ | CNP22, K4R, S16Q (SEQ ID NO: 125) | 42 | 116 | ND |
| BX | CNP22, K4R, M17N (SEQ ID NO: 126) | 40 ± 2 | 103 ± 17 | ND |
| AG | CNP22, K4R, M17V (SEQ ID NO: 102) | 10 | 65 | ND |
| BQ | CNP22, K4R, G19S (SEQ ID NO: 127) | 21 | 63 | ND |
| BR | CNP22, K4R, G19R (SEQ ID NO: 128) | 22 ± 6 | 84 ± 10 | ND |
| AJ | CNP22, K4R, L20V (SEQ ID NO: 103) | 0.2 | 8 | ND |
| AK | CNP22, K4R, L20t-butyl-Ala (SEQ ID NO: 104) | 1 | 21 | ND |
| AT | CNP22, G1E, K4E (SEQ ID NO: 105) | 11 | 54 | 60 |
| BS | CNP22, K4R, L20R (SEQ ID NO: 129) | 11 | 8 | ND |
| BT | CNP22, K4R, G21S (SEQ ID NO: 130) | 7 | 39 | ND |
| BU | CNP22, K4R, G21T (SEQ ID NO: 131) | 6 | 21 | ND |
| BW | CNP22, K4R, G21R (SEQ ID NO: 132) | 20 | 21 | ND |
|  | ANP | 10 | 23 | ND |

[1]Stimulation of cGMP production in NIH3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined Table 3 lists the half-lives, based on the in vitro NEP cleavage assay, of CNP variants having N-terminal and/or C-terminal modifications, including amino acid extensions. Of the analogs tested, Analogs AZ, CC, CF, BL, CS, CK and CL, Pro-Gly-CNP37 and HSA-CNP27 were most resistant to NEP degradation.

TABLE 3

| | N- and C-Terminal Modifications Natriuretic Peptide | cGMP Response rel. to 1 uM CNP22[1] 10 nM | cGMP Response rel. to 1 uM CNP22[1] 1 uM | NEP Cleavage ($t_{1/2}$, min) |
|---|---|---|---|---|
|  | CNP22 | 46 ± 10 | 100 ± 13 | 80 |
| BC | Pentanoic acid (N-term.)-CNP22, G1E (SEQ ID NO: 109) | ND | ND | ND |
| BB | Heptanoic acid (N-term.)-CNP22, G1E (SEQ ID NO: 108) | 32 ± 4 | 84 ± 19 | 45-65 |
| AV | Pentanoic acid (N-term.)-CNP22, G1E, K4E (SEQ ID NO: 106) | ND | ND | 120 |
| AW | Heptanoic acid (N-term.)-CNP22, G1E, K4E (SEQ ID NO: 107) | ND | ND | <20 |
| AX | CNP17 (delta N-term) (SEQ ID NO: 2) | 18 | 69 | ND |
|  | R-CNP22 (SEQ ID NO: 40) | ND | ND | ND |
| AZ | R-CNP22, K4R (SEQ ID NO: 41) | 54 ± 11 | 106 ± 15 | ≥160 |
|  | ER-CNP22 (SEQ ID NO: 38) | ND | ND | ND |

TABLE 3-continued

| | N- and C-Terminal Modifications Natriuretic Peptide | cGMP Response rel. to 1 uM CNP22[1] | | NEP Cleavage |
|---|---|---|---|---|
| | | 10 nM | 1 uM | ($t_{1/2}$, min) |
| BA | ER-CNP22, K4R (SEQ ID NO: 39) | 38 ± 10 | 113 ± 10 | 90 |
| | GANRR-CNP22 (SEQ ID NO: 65) | ND | ND | ND |
| AY | GANRR-CNP22, K4R (SEQ ID NO: 36) | 59 ± 9 | 105 ± 20 | 65 |
| | GANQQ-CNP22 (SEQ ID NO: 64) | ND | ND | ND |
| CH | GANQQ-CNP22, K4R (SEQ ID NO: 69) | 44 ± 8 | 95 ± 11 | ND |
| | GANPR-CNP22 (SEQ ID NO: 66) | ND | ND | ND |
| CI | GANPR-CNP22, K4R (SEQ ID NO: 37) | 50 ± 1 | 105 ± 12 | ND |
| | GANSS-CNP22 (SEQ ID NO: 67) | ND | ND | ND |
| CG | GANSS-CNP22, K4R (SEQ ID NO: 70) | 27 ± 1 | 88 ± 1 | 95 |
| CA | AAWARLLQEHPNA-CNP22 (SEQ ID NO: 61) | 24 | 76 | ND |
| CB | AAWARLLQEHPNAR-CNP22 (SEQ ID NO: 62) | 36 | 84 | ND |
| CC | DLRVDTKSRAAWAR-CNP22 (SEQ ID NO: 63) | 34 | 101 | >160 |
| CF | GQPREPQVYTLPPS-CNP22 (IgG1(Fc) fragment) (SEQ ID NO: 79) | 23 ± 9 | 72 ± 19 | >160 |
| | PNARKYKGANKK-CNP22 (CNP34) | ND | ND | ND |
| BL | QEHPNARKYKGANKK-CNP22 (CNP37) (SEQ ID NO: 60) | 43 ± 15 | 97 ± 27 | >>160 |
| | PQEHPNARKYKGANKK-CNP22 (Pro-CNP37) | ND | ND | ND |
| CE | GERAFKAWAVARLSQ-CNP22 (HSA fragment) (SEQ ID NO: 81) | 15 | 87 | ND |
| CY | GQHKDDNPNLPRGANPR-CNP22 (HSA fragment) (SEQ ID NO: 80) | ND | ND | ND |
| CQ | GHHSHEQHPHGANQQ-CNP22 (HRGP fragment) (SEQ ID NO: 76) | 16 | 95 | ND |
| CX | GHHSHEQHPHGANPR-CNP22 (HRGP fragment) (SEQ ID NO: 78) | ND | ND | ND |
| CS | GQEHPNARKYKGANPK-CNP22 (modified CNP37) (SEQ ID NO: 129) | 19 | 61 | >>160 |
| CT | GQEHPNARKYKGANQK-CNP22 (modified CNP37) (SEQ ID NO: 130) | 60 | 121 | ND |
| CU | GQEHPNARKYKGANQQ-CNP22 (modified CNP37) (SEQ ID NO: 131) | 9 | 57 | ND |
| DB | GQEHPNARKYKGANKK-CNP22 (Gly-CNP37) (SEQ ID NO: 75) | 50 ± 14 | 98 ± 17 | >>160 |
| | PGQEHPNARKYKGANKK-CNP22 (Pro-Gly-CNP37) | 49 ± 6 | 103 ± 17 | >>160 |
| CW | GQEHPNARKYKGANKP-CNP22 (modified CNP37) (SEQ ID NO: 74) | ND | ND | ND |
| CR | GAHHPHEHDTHGANQQ-CNP22 (HRGP fragment) (SEQ ID NO: 128) | 14 ± 5 | 77 ± 12 | ND |
| CZ | FGIPMDRIGRNPR-CNP22 (osteocrin "NPR-C inhibitor") (SEQ ID NO: 82) | ND | ND | ND |
| DA | GKRTGQYKLGSKTGPGPK-CNP22 (FGF2 "heparin-binding domain" fragment) (SEQ ID NO: 83) | ND | ND | ND |
| CK | GQPREPQVYTGANQQ-CNP22, K4R (IgG1(Fc) fragment) (SEQ ID NO: 84) | 2 | 32 | ≥160 |
| CL | GVPQVSTSTGANQQ-CNP22, K4R (HSA fragment) (SEQ ID NO: 85) | 3 | 35 | >160 |

TABLE 3-continued

| N- and C-Terminal Modifications Natriuretic Peptide | cGMP Response rel. to 1 uM CNP22[1] | | NEP Cleavage ($t_{1/2}$, min) |
|---|---|---|---|
| | 10 nM | 1 uM | |
| GHKSEVAHRFKGANKK-CNP22 (HSA-CNP27) (SEQ ID NO: 144) | 51 ± 9 | 109 ± 15 | >>160 |
| PGHKSEVAHRFKGANKK-CNP22 (Pro-HSA-CNP27) | 32 | 107 | ND |
| CN GQTHSSGTQSGANQQ-CNP22, K4R (fibrinogen) (SEQ ID NO: 87) | 12 | 115 | ND |
| CM GQPSSSSQSTGANQQ-CNP22, K4R (fibronectin) (SEQ ID NO: 86) | ND | ND | ND |
| CO GSTGQWHSESGANQQ-CNP22, K4R (fibrinogen) (SEQ ID NO: 88) | 2 | 33 | ND |
| CP GSSSSSSSSSGANQQ-CNP22, K4R (zinc finger) (SEQ ID NO: 89) | ND | ND | ND |
| CD SPKMVQGSG-CNP17-KVLRRH ("BNP tails") (SEQ ID NO: 68) | 25 | 102 | ND |
| CJ RSSCFGGRIDRIGAC ("C-ANP4-23", ANP-derived) (SEQ ID NO: 133) | ND | ND | ND |
| CNP22, K4R, K10R, N.-term.--N-term. dimer/ disuccinimidyl glutarate (SEQ ID NO: 134) | 19 | 44 | ND |
| CNP22, K4R, K10R, N-term.--N.-term. dimer/Bis-PEO5 (SEQ ID NO: 135) | 19 | 41 | ND |
| BM CNP53 (SEQ ID NO: 4) | 61 | 101 | >>160 |
| ANP | 10 | 23 | ND |

[1]Stimulation of cGMP production in N1H3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined Table 4 lists the half-lives, based on the in vitro NEP cleavage assay, of CNP variants conjugated to PEG (or PEO) polymers at the N-terminus. All the PEGylated CNP variants tested and shown in Table 4 displayed resistance or enhanced resistance to NEP cleavage except for PEO12-GANPR-CNP22(K4R), which had the same half-life as wtCNP22. N-terminal PEGylation of CNP22 having a K4G substitution does not seem to confer substantial improvement in NEP resistance. For example, PEG2K-CNP22(K4G) was only slightly more resistant to NEP cleavage than CNP22 (data not shown), whereas PEG2K-CNP22 had a much longer half-life in vitro than CNP22.

TABLE 4

| | | cGMP Response rel. to 1 uM CNP22[1] | | NEP Cleavage |
|---|---|---|---|---|
| N-Terminal PEGylation | | | | |
| Natriuretic Peptide | PEG | 10 nM | 1uM | ($t_{1/2}$, min) |
| CNP22 | | 46 ± 10 | 100 ± 13 | 80 |
| CNP22 | PEG20K | 0 | 15 | >>160 |
| CNP22 | PEG5K | 8 ± 1 | 20 ± 7 | >>160 |
| CNP22 | PEG2K | 6 ± 2 | 32 ± 4 | >>160 |
| CNP22 | PEO4-(PEO12)$_3$ (branched) | 17 ± 1 | 52 ± 6 | >>160 |
| CNP22 | PEO24 (1.2 kDa) | 8 ± 5 | 46 ± 10 | >>160 |
| CNP22 | PEG1K | 15 ± 3 | 68 ± 17 | >160 |
| CNP22 | PEO12 (0.6 kDa) | 12 ± 7 | 57 ± 18 | 160 |
| CNP22 | (PEO12)-Biotin | 19 | 81 | 140 |
| CNP22, K4G | (PEO12)-Biotin | 10 | 27 | 100 |
| CNP22, K4R | PEO24 | 15 | 56 | ND |
| CNP22, K4R | PEO12 | 13 | 44 | ND |
| CNP-17 | PEG2K | 5 | 50 | >160 |
| R-CNP22, K4R (SEQ ID NO: 41) | PEO24 | 15 ± 2 | 75 ± 12 | ND |
| R-CNP22, K4R (SEQ ID NO: 41) | PEO12 | 23 ± 2 | 93 ± 19 | ≥160 |
| ER-CNP22, K4R (SEQ ID NO: 39) | PEO24 | 6 ± 2 | 60 ± 10 | ND |
| ER-CNP22, K4R (SEQ ID NO: 39) | PEO12 | 20 ± 1 | 92 ± 25 | ND |

TABLE 4-continued

| N-Terminal PEGylation | | cGMP Response rel. to 1 uM CNP22[1] | | NEP Cleavage |
| --- | --- | --- | --- | --- |
| Natriuretic Peptide | PEG | 10 nM | 1uM | ($t_{1/2}$, min) |
| GANRR-CNP22, K4R (SEQ ID NO: 36) | PEG2K | 15 ± 2 | 45 ± 18 | ND |
| GANRR-CNP22, K4R (SEQ ID NO: 36) | PEO24 | 28 ± 9 | 82 ± 18 | >>160 |
| GANRR-CNP22, K4R (SEQ ID NO: 36) | PEG1K | 15 ± 0.4 | 56 ± 23 | >160 |
| GANRR-CNP22, K4R (SEQ ID NO: 36) | PEO12 | 40 ± 2 | 99 ± 13 | >160 |
| GANQQ-CNP22, K4R (SEQ ID NO: 69) | PEO24 | 16 ± 13 | 73 ± 30 | ND |
| GANQQ-CNP22, K4R (SEQ ID NO: 69) | PEO12 | 30 | 78 | ND |
| GANPR-CNP22, K4R (SEQ ID NO: 37) | PEO24 | ND | ND | ND |
| GANPR-CNP22, K4R (SEQ ID NO: 37) | PEO12 | ND | ND | 80 |
| GANSS-CNP22, K4R (SEQ ID NO: 70) | PEO24 | 8 ± 5 | 46 ± 21 | ND |
| GANSS-CNP22, K4R (SEQ ID NO: 70) | PEO12 | 8 ± 0.3 | 52 ± 13 | ND |

Figure 16:
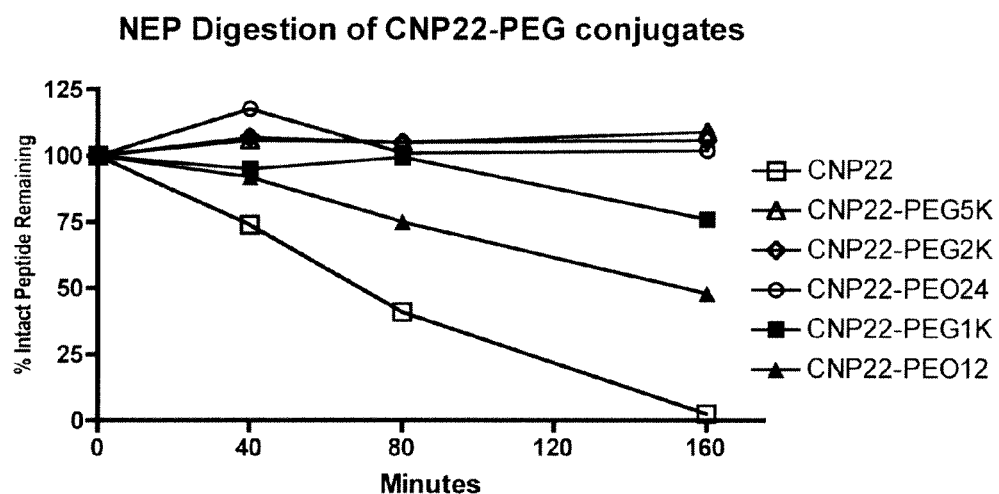
FIG. 16 shows the degree of resistance of N-terminal PEGylated CNP22 conjugates to neutral endopeptidase (NEP) in vitro.

[1]Stimulation of cGMP production in NIH3T3 cells by natriuretic peptide relative to cGMP production in the presence of 1 uM CNP22
[2]CNP22 NEP resistance $t_{1/2}$ averaged 80 min. Due to variations in NEP catalytic activity between experiments, all CNP22 $t_{1/2}$ digestions were normalized to 80 min and the difference coefficient was used to calculate analog $t_{1/2}$ in each experiment to obtain an adjusted $t_{1/2}$.
ND = Not Determined FIG. 16 shows the NEP resistance profile of five N-terminal PEGylated conjugates of CNP22. The CNP22 peptides conjugated to PEG (or PEO) polymers of increasing mass exhibited increasing resistance to NEP degradation. In particular, PEO24-CNP22, PEG2K-CNP22 and PEG5K-CNP22 were resistant to NEP degradation over the assay period of 160 minutes.

Figure 17:
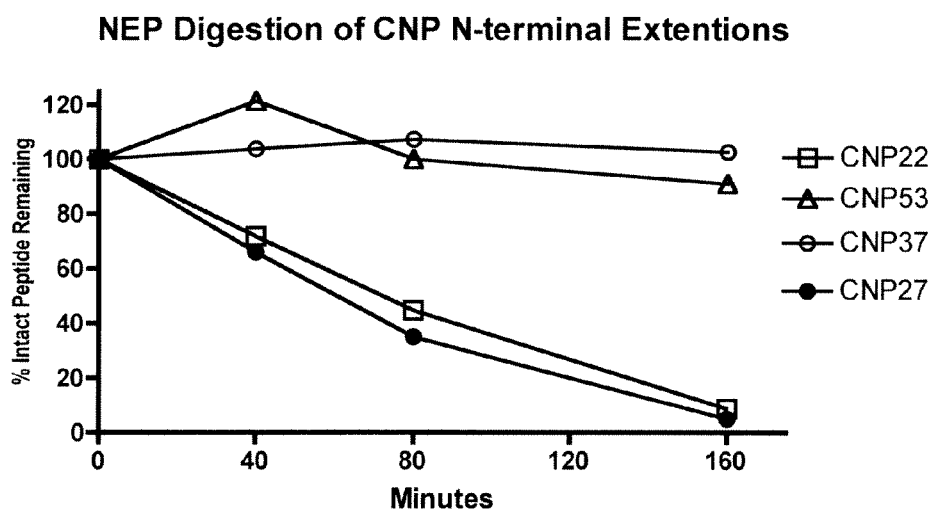
FIG. 17 depicts the degree of NEP resistance of CNP variants having an amino acid extension at the N-terminus ["CNP27" is GANRR-CNP22(K4R) (SEQ ID NO: 36)].

FIG. 17 displays the NEP resistance profile of CNP variants CNP37 (Analog BL), CNP53 and GANRR-CNP22 (K4R) (SEQ ID NO: 36) having an N-terminal amino acid extension. As can be clearly seen, both CNP37 and CNP53 were resistant to NEP degradation in this in vitro assay, whereas GANRR-CNP22(K4R) (SEQ ID NO: 36) had the same lability to NEP hydrolysis as CNP22.

Figure 18:
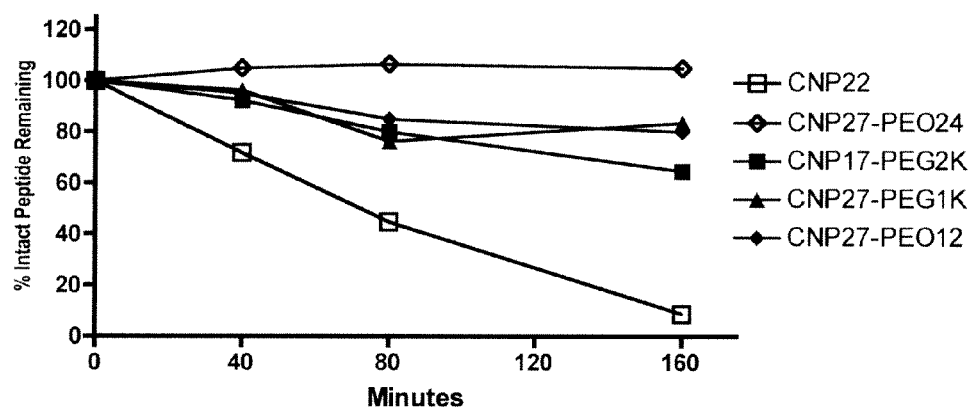
FIG. 18 illustrates the degree of NEP resistance of N-terminal PEGylated CNP17 and GANRR-CNP22(K4R) ("CNP27") (SEQ ID NO: 36).

FIG. 18 depicts the NEP resistance profile of CNP17 and GANRR-CNP22(K4R) (SEQ ID NO: 36) conjugated to a PEG (or PEO) moiety at the N-terminus. PEGylation of GANRR-CNP22(K4R) (SEQ ID NO: 36) greatly improved the NEP resistance of this CNP variant, with PEO24-GANRR-CNP22(K4R) (SEQ ID NO: 36) being completely resistant to NEP cleavage over the assay period of 160 minutes. Increasing the mass of the PEO moiety from about 0.6 kDa (PEO12) to about 1.2 kDa (PEO24) improved the NEP resistance of PEGylated GANRR-CNP22(K4R) (SEQ ID NO: 36). PEGylation of GANRR-CNP22(K4R) (SEQ ID NO: 36) to a monodispersed PEO24 moiety rather than a polydispersed PEG1K moiety also improved NEP resistance. Finally, although both PEO24-GANRR-CNP22(K4R) (SEQ ID NO: 36) and PEG2K-CNP17 have a similar total mass (keeping in mind that PEG2K is polydispersed), the former displayed substantially better NEP resistance.

Figure 19:
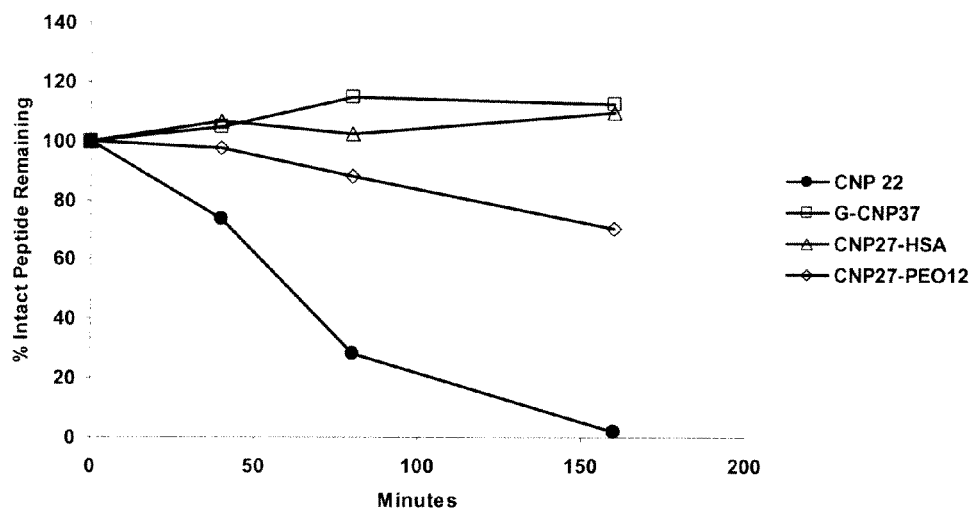
FIG. 19 illustrates the degree of NEP resistance of wtCNP22 and CNP variants Gly-CNP37, GHKSEVAHRFK-wtCNP27 ("CNP27-HSA" in the figures) (SEQ ID NO: 144) and PEO12-GANRR-CNP22(K4R) ("CNP27-PEO12" in the figures) (SEQ ID NO: 36).

NEP resistance assays were also performed on wtCNP22 and CNP variants G-CNP37, GHKSEVAHRFK-wtCNP27 ("CNP27-HSA", SEQ ID NO: 144) and PEO12-GANRR-CNP22(K4R) ("CNP27-PEO12") (SEQ ID NO: 36). FIG. 19 shows that G-CNP37 and CNP27-HSA were completely resistant to NEP cleavage, and CNP27-PEO12 exhibited much greater stability to NEP degradation compared to wtCNP22.

Example 4

CNP Variant Stimulation of cGMP Production in NIH3T3 Cells

To determine the functional activity of CNP variants, the production of cGMP was measured in NIH3T3 cells exposed to the CNP variants. Murine NIH3T3 cells express endogenously the CNP signaling receptor, NPR-B, which shares 98% protein sequence identity with human NPR-B. NIH3T3 cells were cultured in high glucose Dulbecco's Modified Eagle Medium supplemented with 10% fetal calf serum and antibiotics at 37° C. with 5% CO). Twenty four to 48 hours prior to signaling, cells were passaged to 12-well plates with a density of $2-5 \times 10^5$ cells per well at the time of the assay. CNP variants were resuspended in 1 mM HCl to a stock concentration of 1 mg/mL (455 uM for wtCNP22) and subsequently diluted to a 30 uM working stock solution with phosphate-buffered saline (PBS). Ten-fold serial dilutions were prepared in phosphate-buffered saline. Culture medium was removed from the cells and replaced with 0.4 mL PBS/Dulbecco's modified Eagle medium (50/50, v/v) containing 0.75 mM isobutylmethylxanine. Plates were incubated at 37° C., 5% $CO_2$ for 15 minutes before addition of 0.2 mL CNP variant in PBS and continued incubation at 37° C. for 15 minutes. Reactions were stopped by the addition of 0.2 mL lysis buffer supplied with the CatchPoint cGMP assay kit (Molecular Devices), and cGMP production was determined with the CatchPoint cGMP Assay (Molecular Devices). All stimulation experiments were performed in duplicate.

Tables 1-4 summarize the ability of CNP variants having backbone or side chain modifications, amino acid substitutions, N-terminal amino acid extensions, and/or N-terminal PEGylation, respectively, to stimulate cGMP production in NIH3T3 cells. In all four tables, the values for cGMP production in NIH3T3 cells exposed to 10 nM or 1 uM CNP variant are normalized to cell number and cGMP production in the presence of 1 uM wtCNP22.

Regarding the results in Table 1, only Analog G having 3-Cl-Phe at position 7 displayed substantially the same NPR-B stimulation activity at 1 uM as wtCNP22. With respect to Table 2, various CNP variants with amino acid substitutions, including Analogs AH, BO, AB, BH, BZ, BX and BR, showed substantially similar NPR-B stimulation activity as wtCNP22.

Figure 20:
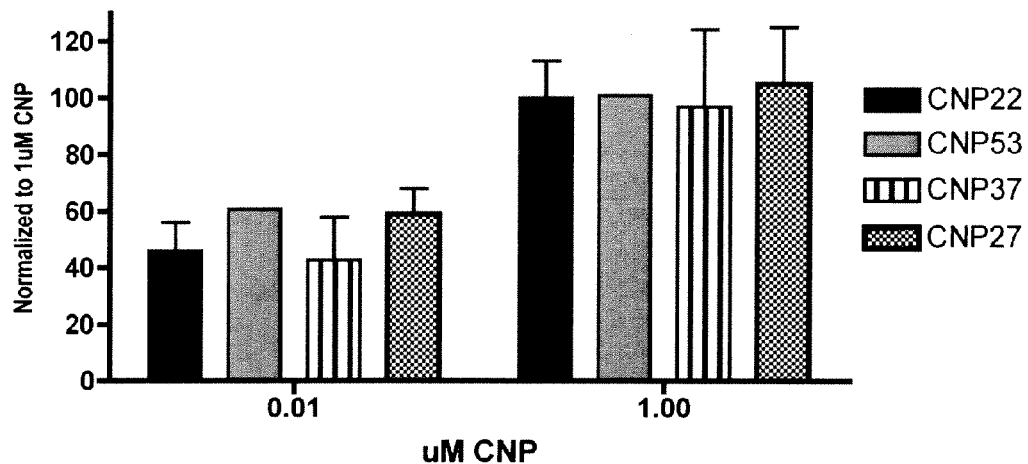
FIG. 20 shows the ability of CNP variants having an N-terminal amino acid extension to stimulate cGMP production in NIH3T3 cells in vitro. The results are relative to the level of cGMP produced in the presence of 1 uM CNP22. "CNP27" is GANRR-CNP22(K4R) (SEQ ID NO: 36)

Considering the results in Table 3, many CNP variants having N-terminal and/or C-terminal modifications, including amino acid extensions, exhibited comparable NPR-B stimulation activity as wtCNP22. The functional CNP variants include Analog BB, which is CNP22(G1E) attached to heptanoic acid at the N-terminus, and Analog CD, which is the cyclic domain of CNP22 ("CNP17" retaining the Cys6 to Cys22 sequence) conjugated to the N-terminal and C-terminal "tails" of BNP. FIG. 20 illustrates that GANRR-CNP22

(K4R) (SEQ ID NO: 36), CNP37 (Analog BL) and CNP53 all had similar NPR-B stimulation activity as wtCNP22 in the in vitro assay.

Of note from Table 3 is that among the CNP variants assayed for both CNP functionality and NEP resistance, Analog AZ (R-CNP22(K4R)), Analog CC, Analog CF, Analog BL (CNP37), Analog DB (Gly-CNP37) and GHKSEVAHRFK-CNP27 (HSA-CNP27) (SEQ ID NO: 144) all had substantially similar NPR-B stimulation activity as CNP22 while being substantially more resistant to NEP cleavage than CNP22.

Figure 21:
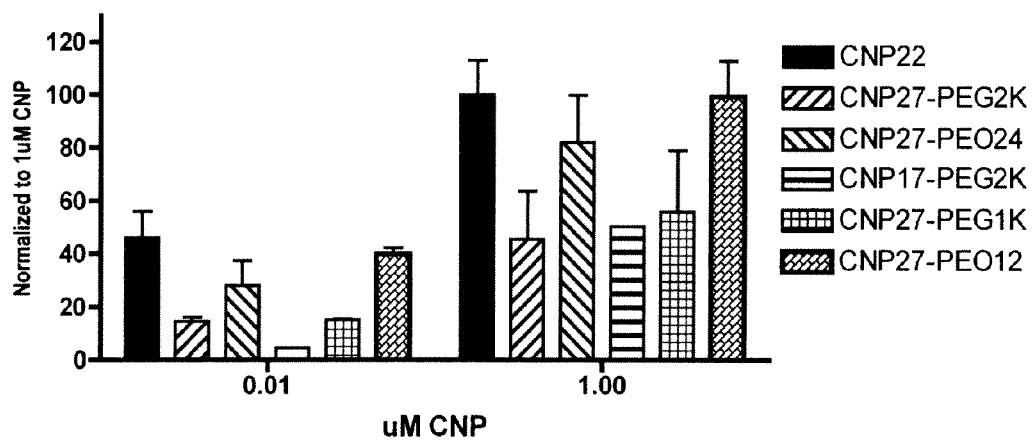
FIG. 21 displays the ability of N-terminal PEGylated CNP17 and GANRR-CNP22(K4R) ("CNP27") (SEQ ID NO: 36) to stimulate cGMP production in NIH3T3 cells.
Figure 22:
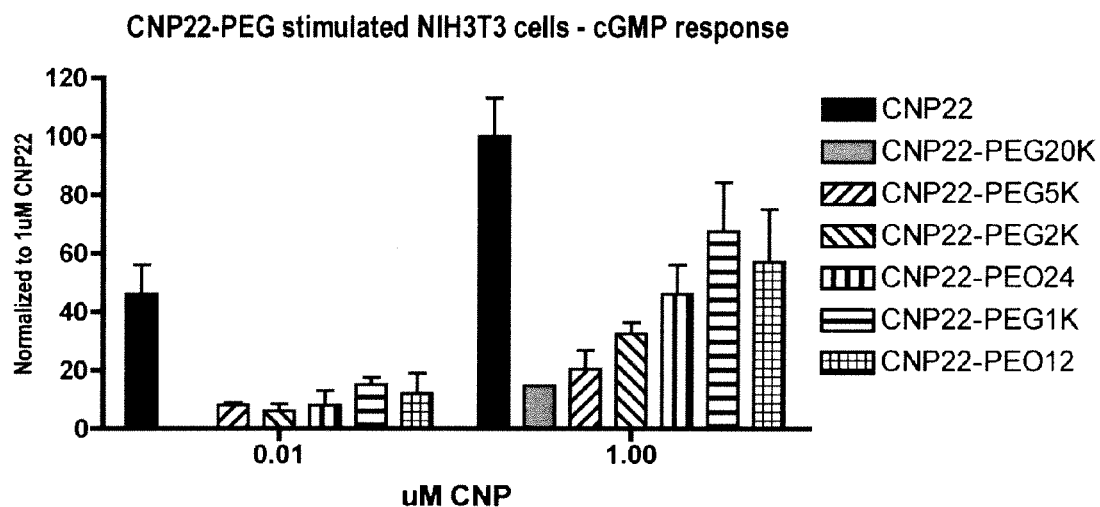
FIG. 22 illustrates the effects of N-terminal PEGylation of CNP22 on cGMP production.

With regard to the results in Table 4, nine N-terminal PEGylated CNP variants at 1 uM stimulated cGMP production to at least about 70% of the level achieved by wtCNP22. Several noteworthy aspects appear in Table 4. First, N-terminal PEGylation of GANRR-CNP22(K4R) (SEQ ID NO: 36) with a monodispersed PEO polymer (PEO12 is about 0.6 kDa, PEO24 about 1.2 kDa) resulted in better NPR-B functionality than that with a polydispersed PEG polymer (PEG1K has a polymer number average molecular weight ($M_n$) of around 1 kDa, PEG2K around 2 kDa) (see also FIG. 21). Second, N-terminal PEGylation of wtCNP22 with a polydispersed PEG polymer of increasing $M_n$ (PEG1K, PEG2K, PEG5K and PEG20K) or with a monodispersed PEO polymer of greater mass (PEO12 and PEO24) correspondingly decreased the NPR-B activation ability of the CNP variants (see also FIG. 22). Third, PEO24-GANRR-CNP22(K4R) (SEQ ID NO: 36), having the N-terminal GANRR (SEQ ID NO: 8) extension, stimulated greater cGMP production than PEO24-CNP22 and PEO24-CNP22 (K4R). Also of note is that among the N-terminal PEGylated CNP variants assayed for both CNP functionality and NEP resistance, PEO12-R-CNP22(K4R), PEO12-GANRR-CNP22(K4R) (SEQ ID NO: 36) and PEO24-GANRR-CNP22(K4R) (SEQ ID NO: 36) all had substantially similar NPR-B stimulation activity as CNP22 while being much more resistant to NEP degradation than CNP22.

Figure 23:
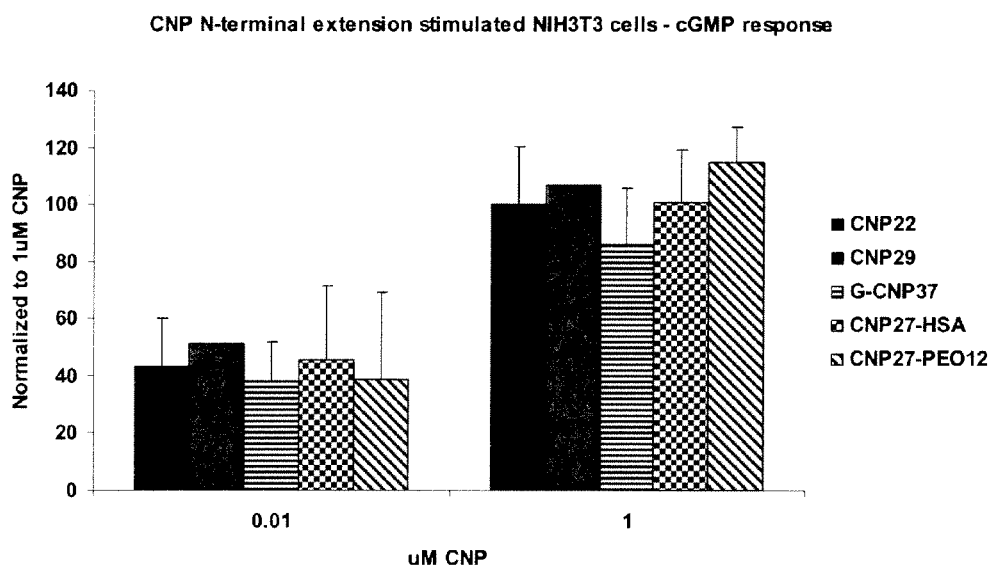
FIG. 23 illustrates the cGMP production induced by wtCNP22 and CNP variants Gly-CNP37, GHKSEVAHRFK-wtCNP27 ("CNP27-HSA") (SEQ ID NO: 144), wtCNP29 and PEO12-GANRR-CNP22(K4R) ("CNP27-PEO12") (SEQ ID NO: 36) in NIH3T3 cells.

Among the CNP variants listed in Tables 1-4 and assayed for both CNP functionality and NEP resistance, Analogs G, BK, AZ, CC, CF, BL and DB, Pro-Gly-CNP37, HSA-CNP27 (GHKSEVAHRFK-CNP27) (SEQ ID NO: 144), PEG1K-CNP22, (PEO12)-biotin-CNP22, PEO12-R-CNP22(K4R), PEO12-GANRR-CNP22(K4R) (SEQ ID NO: 36), and PEO24-GANRR-CNP22(K4R) (SEQ ID NO: 36) all had substantially similar NPR-B stimulation activity as wtCNP22 while being substantially more resistant to NEP cleavage than wtCNP22.

cGMP production assays were also carried out on wtCNP22 and CNP variants G-CNP37, GHKSEVAHRFK-wtCNP27 ("CNP27-HSA", SEQ ID NO: 144), wtCNP29 and PEO12-GANRR-CNP22(K4R) ("CNP27-PEO12") (SEQ ID NO: 36). FIG. 23 shows that CNP22 and all the CNP variants assayed induced production of similar cGMP levels at either low or high dose of CNP.

Example 5

Binding Specificity for NPR-A, NPR-B and NPR-C

Signaling Competition Assay

To determine the binding specificity of CNP variants for the clearance receptor NPR-C, a signaling competition assay is carried out. Expression plasmids for human NPR-B or NPR-C (each purchased from OriGene) are transiently transfected and receptors are expressed in HEK293T cells. Forty hours after transfection, NPR-B, NPR-C and native HEK293T cells are harvested, counted and plated at a ratio of 1:1 (NPR-B cells:competing cells (either NPR-C or native HEK293T cells)) in 12-well or 96-well plates. Twenty hours after plating, cells are processed for the NPR-B/cGMP stimulation assay described in Example 4. If present, the natriuretic clearance receptor, NPR-C, is expected to bind and internalize CNP, thereby reducing the overall CNP concentration available for signaling through NPR-B, resulting in decreased cGMP production and a shift in the dose-response curve to the right. A rightward shift in the dose-response curve has been verified for wtCNP22. CNP variants having reduced affinity for NPR-C are not expected to induce a shift, or are expected to induce a smaller shift, in the dose-response curve to the right. This signaling competition assay is similar to that previously described by Cunningham (U.S. Pat. No. 5,846,932; B. Cunningham, EMBO J. 13(11): 2508-2515 (1994); H. Jin et al., J. Clin. Invest. 98(4): 969-976 (1996)).

Figure 24:
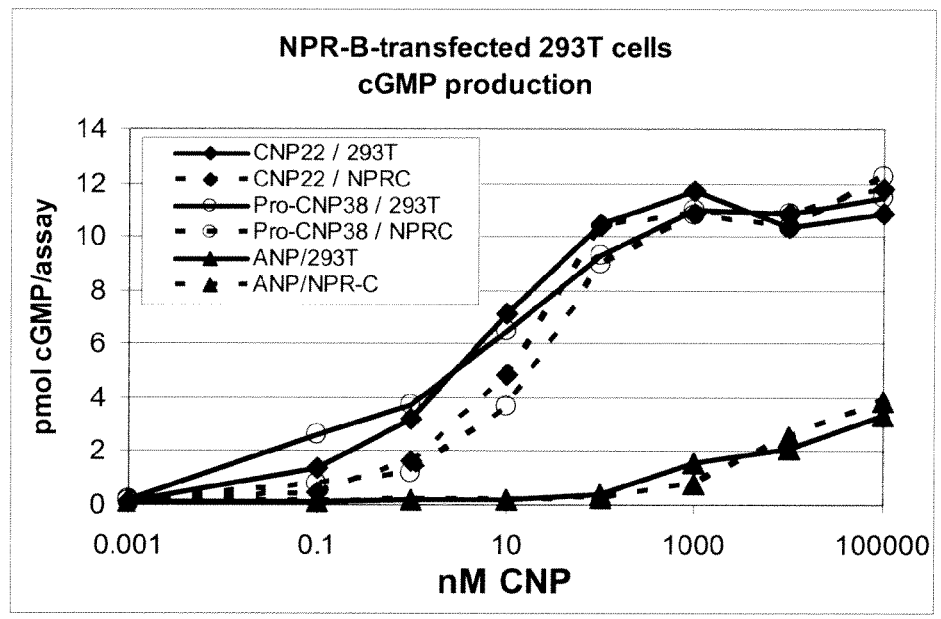
FIGS. 24A and B show that CNP-22 and Pro-Gly-CNP37 ("Pro-CNP38") stimulated cGMP production through NPR-B with similar dose-response curves, and to a much greater extent than through NPR-A, and exhibited a similar profile for NPR-B vs. NPR-C selectivity in in vitro signaling competition assays.
Figure 24:
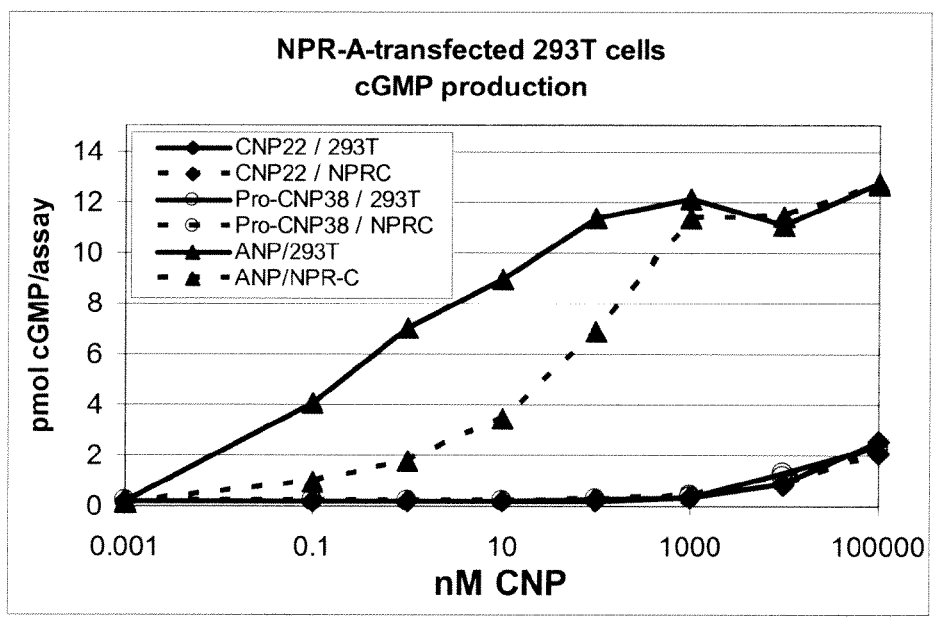

The cGMP stimulation activity of wtCNP-22, Pro-Gly-wtCNP37 and ANP through NPR-B and NPR-A, and their selectivity for NPR-B vs. NPR-C and for NPR-A vs. NPR-C, were evaluated in signaling competition assays. NPR-A, NPR-B and NPR-C individually were transiently tranfected into HEK293T cells. Thirty hours after transfection, the cells were plated into 96-well plates: (A) 20,000 NPR-B cells+20,000 mock transfected cells; (B) 20,000 NPR-B cells+20,000 NPR-C cells; (C) 20,000 NPR-A cells+20,000 mock transfected cells; and (D) 20,000 NPR-A cells+20,000 NPR-C cells. Twenty hours after plating, the culture media was removed and replaced with serum-free media:PBS (1:1)+0.75 uM IBMX for 15 minutes. For cGMP signaling through NPR-B, dose series for ANP, CNP-22 and Pro-Gly-CNP37 were added and incubated at 37° C. for 12 minutes before the assay was stopped by cell lysis. For cGMP signaling through NPR-A, dose series for CNP-22 and Pro-Gly-CNP37 were incubated at 37° C. for 12 minutes, while dose series for ANP were incubated at 37° C. for 6 minutes (because NPR-A appeared to be a "faster" guanylyl cyclase than NPR-B, the incubation time for ANP was shortened in order not to max out (use up all cellular GTP) too soon when signaling with ANP). FIGS. 24A and B show that CNP-22 and Pro-Gly-CNP37 ("Pro-CNP38") stimulated cGMP production through NPR-B with similar dose-response curves, and to a much greater extent than through NPR-A, and exhibited a similar profile for NPR-B vs. NPR-C selectivity in the signaling competition assays.

Determination of Binding Affinities ($K_i$) for NPR-A, NPR-B and NPR-C

The binding affinities ($K_i$) of CNP variants for NPR-A, NPR-B and NPR-C are determined in a heterologous competition binding assay (U.S. Pat. No. 5,846,932; B. Cunningham, EMBO J. 13(11): 2508-2515 (1994); H. Jin et al., J. Clin. Invest. 98(4): 969-976 (1996)). Membranes from HEK293 cells, or another suitably transfectable cell line (e.g., HeLa cells), expressing human NPR-A, NPR-B or NPR-C are prepared for radio-labeled ligand binding assays. Membrane preparations are diluted in an appropriate buffer and varying concentrations of wtCNP22 or CNP variant (competitor) are added with $I^{125}$-labeled wtCNP22 (Bachem). Samples are incubated at room temperature to allow for ligand/receptor equilibration and bound peptide is separated from free peptide by filtration through PVDF filter membranes. Filters are washed before the addition of scintillant and counting by a scintillation counter. Binding is measured in duplicate for each concentration of competitor peptide. CNP variant affinity ($K_i$, equilibrium dissociation constant) and $B_{max}$, (receptor number) are calculated by non-linear regression analysis and/or the Cheng-Prusoff equation.

CNP variants exhibiting reduced affinity to NPR-C are expected to have reduced susceptibility to clearance by NPR-C and thus a longer plasma or serum half-life. Increased half-life of the CNP variants in circulation would increase the availability of the variants for therapeutic activity.

Example 6

Effect of CNP Variants on the Growth of Rat Chondrosarcoma (RCS) Cells and cGMP Production in RCS Cells To assess the ability of CNP variants to stimulate bone growth, skeletal dysplasia is simulated in cell culture by treating rat chondrosarcoma (RCS) cells with fibroblast growth factor 2 (FGF-2), which activates fibroblast growth factor receptor 3 (FGFR-3) and induces growth arrest (Krejci et al., J. Cell Sci., 118(21):5089-5100 (2005)).

Optimal CNP treatment parameters are determined by varying CNP concentration (0.05, 0.1, 0.2 and 0.5 uM), and treatment duration and interval (continuous; 2.5 min, 10 min, 30 min, 1 hr, 2 hr, 4 hr and 8 hr once a day; 2.5 min, 10 min, 30 min, 1 hr, 2 hr and 4 hr twice a day). After 72 hours, cells are counted using an automated cell counter, and the amount of extracellular matrix is estimated using alcian blue staining.

RCS cells are then treated with a CNP variant using the optimal conditions determined from the growth experiments with wtCNP22. The concentration of cGMP is measured by competitive ELISA for untreated RCS cells, RCS cells treated with CNP, and RCS cells treated with the CNP variant. Cell growth and matrix synthesis resulting from treatment with the CNP variant are also monitored and compared to those resulting from CNP treatment.

To assess the effect of CNP variants in a human cell culture system, primary re-differentiated human chondrocytes in alignate beads are treated with wtCNP22 and CNP variants, and cGMP concentration is determined by competitive ELISA as a measure of effective CNP signaling.

The methods described herein can be employed to assess the ability of CNP variants to stimulate cGMP production in and growth of rat chondrosarcoma cells in vitro.

Example 7

Dose Response Study in Rat Chondrosarcoma Cells

The tyrosine kinase receptor fibroblast growth factor receptor 3 (FGFR-3), a negative regulator of chondrocyte growth, is contitutively on in achondroplasia subjects. Stimulation of the FGFR-3 receptor with FGF-2 causes growth arrest by prolonged activation of Erk MAPK, and causes decreased matrix synthesis and loss of matrix, as well as a change in cell shape. Continuous exposure of rat chondrosarcoma (RCS) cells to fibroblast growth factor 2 (FGF-2) simulates achondroplasia in cell culture by activating FGFR-3 and inducing growth arrest (Krejci et al., J. Cell Sci., 118(21): 5089-5100 (2005)). To determine the dose of CNP variant and frequency of dosing that stimulate sufficient growth of bone cells, a dose response study was performed using the RCS cell assay as described in Example 6.

RCS cells were seeded at $10 \times 10^3$ cells per well in 24-well plates, grown for 24 hr, treated for 72 hr, and then counted. RCS cells were continuously exposed to FGF-2 (5 ng/mL) to simulate a constitutively active FGFR-3, which induced cell growth arrest (see bar #5 in FIG. 25). Wild-type CNP22 (0.2 uM) was cultured continuously (72 hr), 1 hr daily or 2 hr daily. All stimulants were changed daily Continuous exposure of RCS cells to 0.2 uM CNP22 in the presence of 5.0 ng/mL FGF-2 partially reversed FGF2-induced growth arrest, leading to the growth of approximately $200 \times 10^3$ cells per well (bar #6 in FIG. 25), compared to approximately $100 \times 10^3$ cells per well in the absence of CNP22 (bar #5 in FIG. 25).

Figure 25:
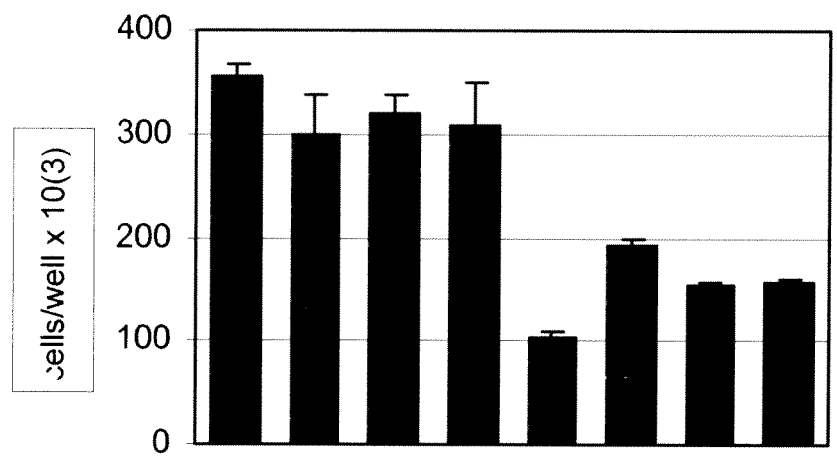
FIG. 25 demonstrates that exposure of rat chondrosarcoma cells to CNP22 1 hour once daily or 2 hours once daily has substantially similar effectiveness in reversing FGF2-induced arrest of chondrocyte growth as continuous exposure to CNP22.
Figure 26:
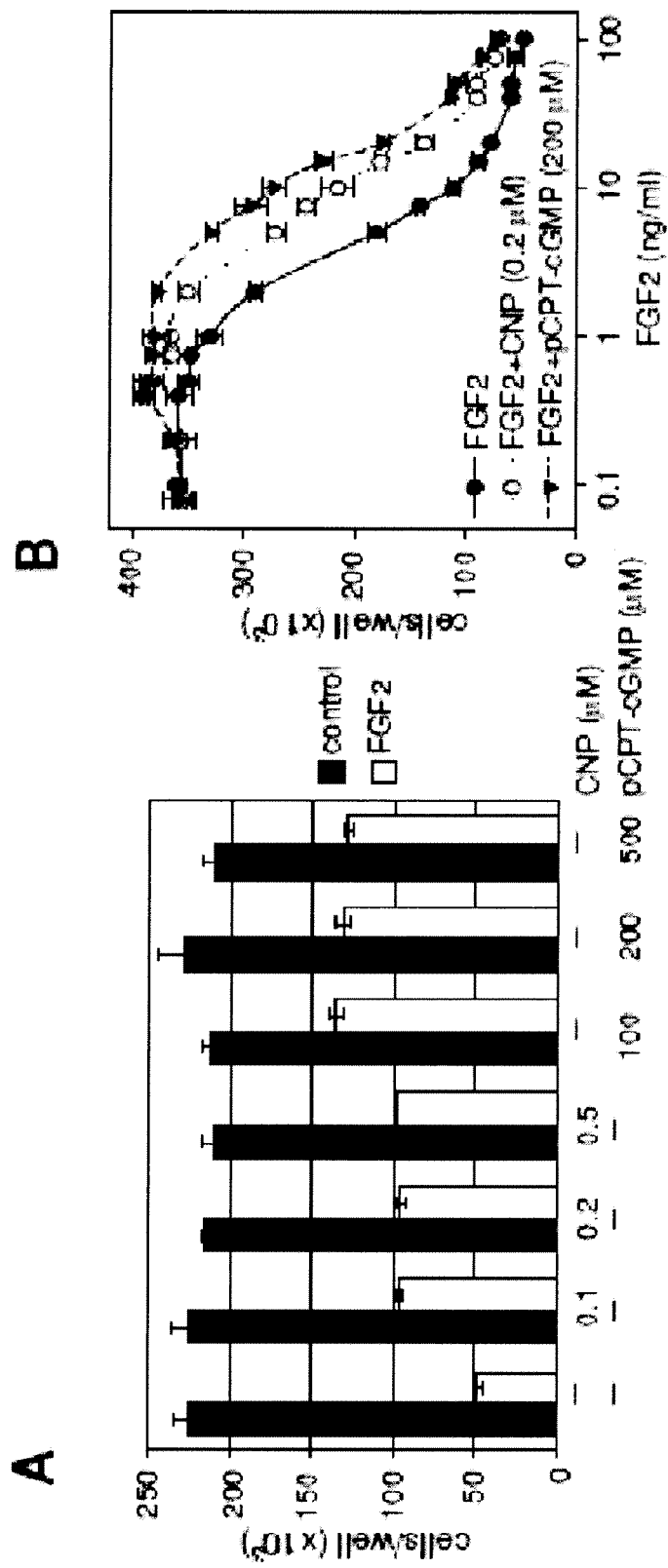
FIGS. 26A and B show results from a dose response study of CNP22 effects on FGF2-arrested rat chondrosarcoma (RCS) cells.
Figure 27:
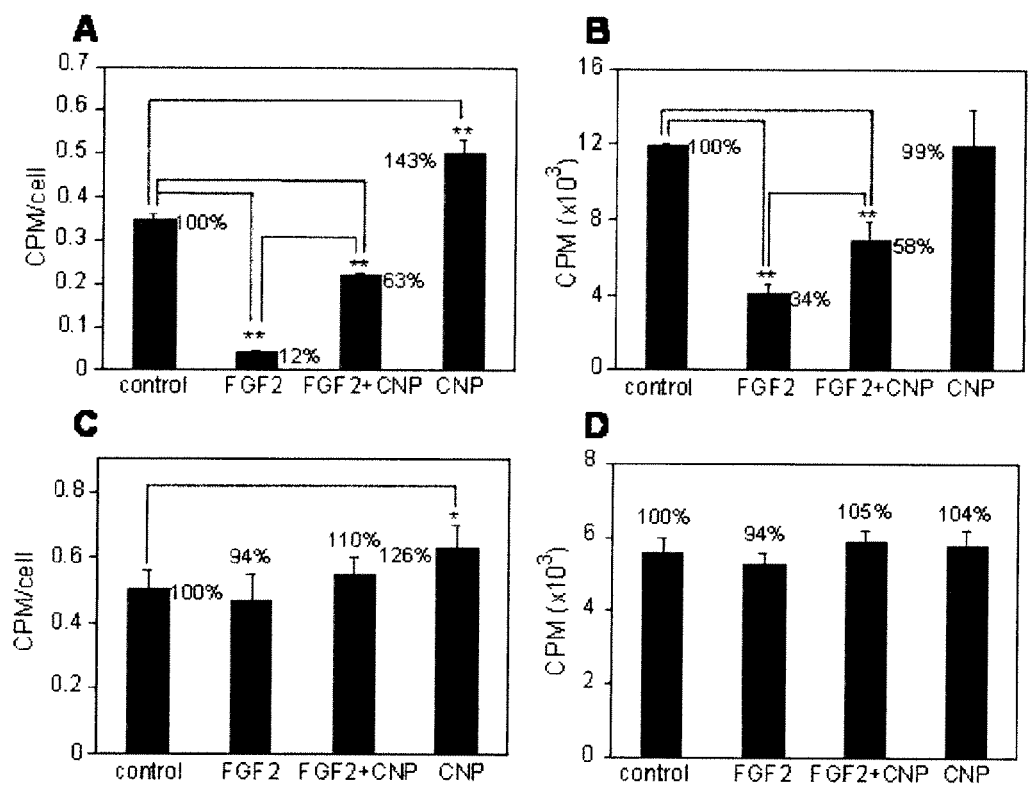
FIGS. 27A-D show that addition of CNP22 to RCS cells arrested by FGF2 increases matrix synthesis and partly inhibits FGF2, as assessed by $^{35}$S-sulfate and $^{3}$H-Pro incorporation into or decrease from matrix. Panels A and C, synthesis; B and D, degradation; A and B, $^{35}$S measurement; C and D, $^{3}$H measurement. Statistically significant differences are highlighted (ANOVA; *$p<0.05$, **$p<0.01$).

Both 1 hr exposure to CNP22 (0.2 uM) once a day and 2 hr exposure to CNP22 (0.2 uM) once a day achieved about 84% of the effect of continuous CNP22 (0.2 uM) exposure on chondrocyte growth (bars #7 and 8 in FIG. 25). These results demonstrate that continuous exposure of growth-arrested chondrocytes to CNP22 is not required for reversal of cell growth arrest. Additionally, dose response studies demonstrate that lower doses of CNP22 are capable of reversing growth arrest (FIG. 26A).

Figure 28:
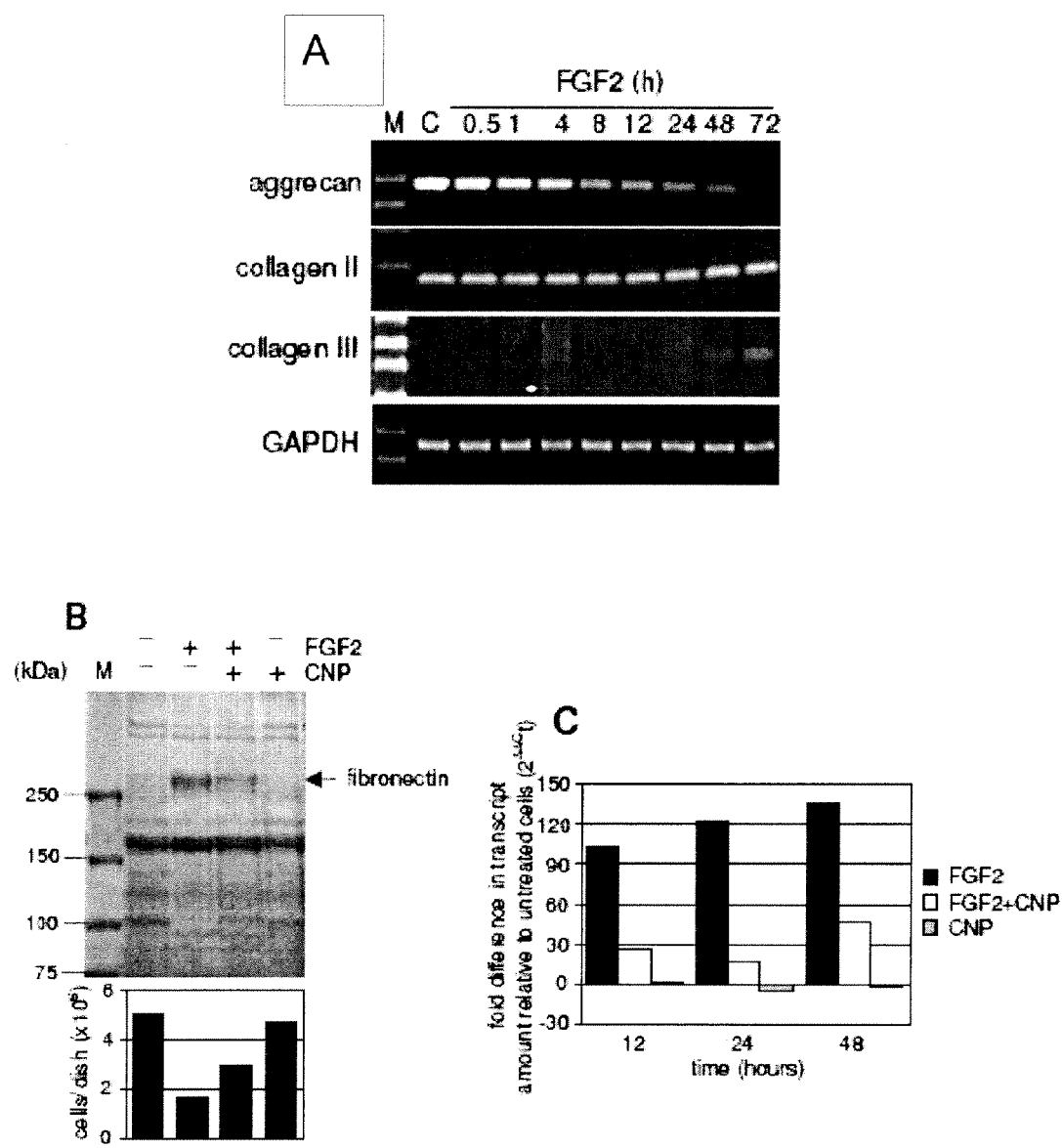
FIGS. 28A-C show the levels of aggrecan and fibronectin production (mRNA, panels A and C, and protein, panel B) in RCS cells cultured with FGF2 and CNP22.

Furthermore, histological and cell morphological analysis of the extracellular matrix showed that CNP22 treatment antagonized FGF2-mediated loss of chondrosarcoma extracellular matrix and increased matrix synthesis. Exposure to FGF-2 decreased matrix synthesis and increased degradation, while addition of CNP22 to the FGF-2 cell culture increased matrix synthesis and partially inhibited FGF-2, as assessed by $^{35}$S-sulfate and $^3$H-Pro incorporation into, or decrease from, matrix (FIGS. 27A-D). Analysis of aggrecan and fibronectin production (mRNA and protein) in RCS cells cultured with FGF-2 and CNP22 shows that FGF-2 decreased aggrecan level and increased fibronectin level, which was inhibited by addition of CNP22 (FIGS. 28A-C). FGF-2 induces and activates matrix-processing molecules predominantly via Erk, and addition of CNP22 shows some effect on this activation.

Additional high-throughput assays for measuring growth arrest, such as crystal violet staining, are useful for measuring the effects of CNP22 and variants thereof on RCS cells.

Similar dose response studies can be conducted with the CNP variants described herein to determine their effective dose for reversing FGF2-induced growth arrest of RCS cells.

Example 8A

Ex Vivo Stimulation of Growth of Tibia and Femur from Mice with Mild Achondroplasia Mouse tibial organ culture model has been used to demonstrate the efficacy of wild-type CNP22 in stimulating longitudinal bone growth. Treatment of wild-type tibiae with CNP22 at $10^{-8}$, $10^{-7}$ or $10^{-6}$ M for 6 days increased longitudinal growth by 31%, 40% and 42%, respectively. Histological evaluation also showed expansion of the hypertrophic zone, e.g., an increase in the number and size of hypertrophic chondrocytes in the growth plate (Agoston et al., BMC Dev. Biol. 7:18 (2007)). Similar findings were observed in tibiae isolated from FGFR3$^{Ach}$ mice (Yasoda et al., Nat. Med. 10: 80-86 (2004)).

To determine the efficacy of CNP variants in stimulating longitudinal bone growth, CNP variants were tested in a mouse organ culture model of endochondral bone growth in wild-type mice and transgenic mice having a G380R mutation in the human FGFR-3 gene (FGFR3$^{wt/Ach}$ heterozygote) which represent a mouse model of mild achondroplasia. In brief, the pharmacological activity of wild-type CNP22 and CNP variants was compared in an organ culture model of embryonic or neonatal mouse tibiae, isolated from wild-type and FGFR3$^{wt/Ach}$ littermates. Overall bone growth and histological changes within the growth plate were assessed. Conditioned culture medium is also assessed for biomarkers of intracellular signaling (cGMP), cartilage metabolism (type II collagen, other collagens, aggrecan chondroitin sulfate), bone metabolism (bone alkaline phosphatase, osteocalcin, type I collagen [C-telopeptide, N-telopeptide]), and inflammation (interleukin-1, interleukin 6, interleukin-11).

Effective CNP variants are identified by their ability, e.g., to stimulate production of cGMP, and bone growth as measured by increased longitudinal bone length and expansion of the cells in the hypertrophic zone of the growth plate.

Measurement of Bone Growth

The efficacy of wtCNP22, CNP37 and PEO24-GANRR-CNP22(K4R) (SEQ ID NO: 36) in stimulating longitudinal femoral growth was evaluated in the mouse organ culture model. For these experiments femora were isolated from 2-3 day old wild-type mice and cultured in alphaMEM supplemented with 0.2% BSA, 0.5 mM L-glutamine, 40 units penicillin/mL and 40 ug streptomycin/mL, for 8 days in the presence of vehicle, CNP22 or CNP variants. The treatment commenced at day 0 and was repeated every two days thereafter, as the medium was changed. Bones were measured prior to treatment and every two days thereafter, using a dissection microscope fitted with a 1 cm eye-piece reticule. Conditioned medium was used for biomarker analysis. At day 8 bones were fixed in 4% paraformaldehyde for 24 hr, decalcified in 5% formic acid for 24 hrs, dehydrated and embedded in paraffin. Bones were sectioned at 5 um (microns), which were then deparaffinized, rehydrated, and stained with Alcian Blue for 30 min (pH 2.5; MasterTech). Alcian Blue stains cartilage blue. Stained sections were visualized and photographed by brightfield microscopy. The thickness of the hypertrophic region of the growth plate cartilage was determined by image analysis.

Figure 29:
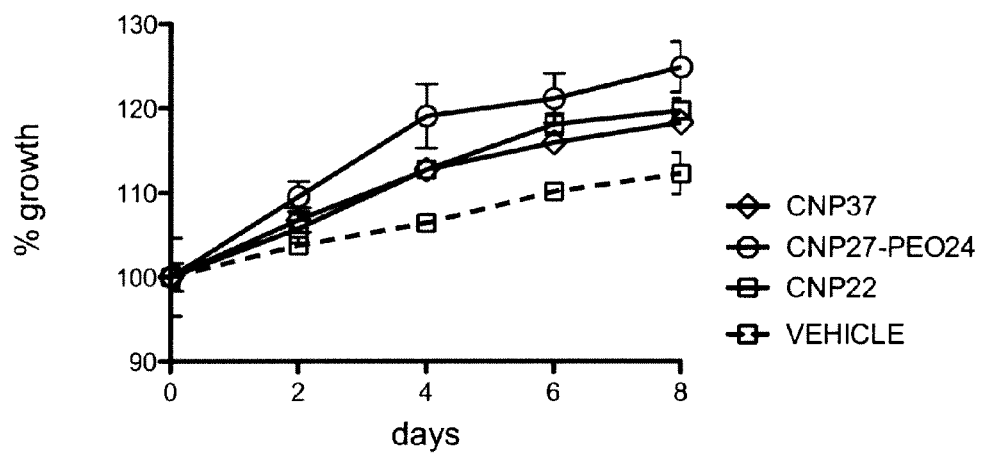
FIG. 29 shows the efficacy of CNP37 and PEO24-GANRR-CNP22(K4R) ("CNP27-PEO24" in the figures) (SEQ ID NO: 36) in stimulating longitudinal growth of wild-type femur in an ex vivo mouse organ model.

FIG. 29 illustrates the effect of wtCNP22, CNP37 and PEO24-GANRR-CNP22(K4R) (SEQ ID NO: 36) on longitudinal growth of 3-day old wild-type mouse femurs treated with the CNP peptides every two days. The results were normalized to measurements prior to treatment (day 0). The studies were performed in triplicate (vehicle) or quadruplicate (CNP peptides). As shown in FIG. 29, CNP37 and PEO24-GANRR-CNP22(K4R) (SEQ ID NO: 36), as well as CNP22, were effective in stimulating longitudinal femoral growth, with the N-terminal PEGylated CNP variant being the most effective.

Figure 30:
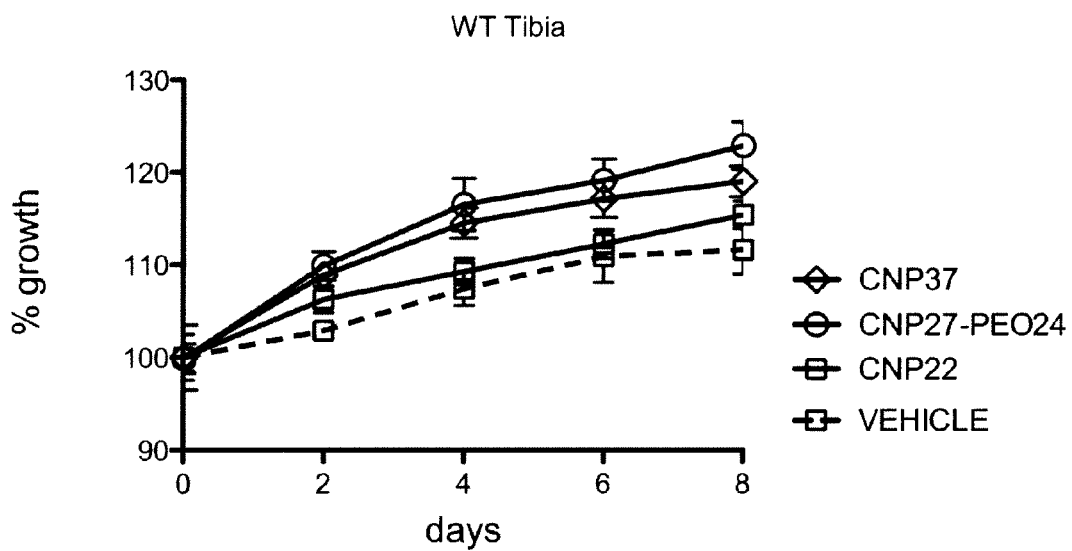
FIG. 30 shows longitudinal bone growth of 2-3 day-old wild-type mouse tibias treated with CNP22, CNP37 or PEO24-GANRR-CNP22(K4R) (SEQ ID NO: 36) every two days. Results are normalized to measurements prior to treatment (day 0). Data is represented as means±SEM (n=8).
Figure 31:
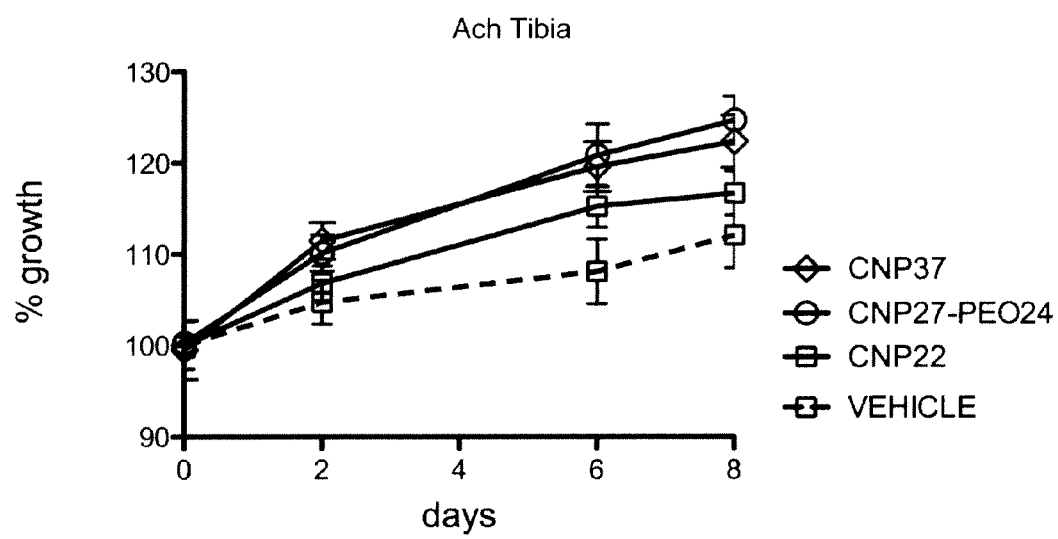
FIG. 31 shows longitudinal bone growth of 2-3 day old achondroplastic FGFR3$^{ach}$ mouse tibias treated with CNP22, CNP37 or PEO24-GANRR-CNP22(K4R) (SEQ ID NO: 36) every two days. Results are normalized to measurements prior to treatment (day 0). Data is represented as means±SEM (n=7-8).
Figure 32:
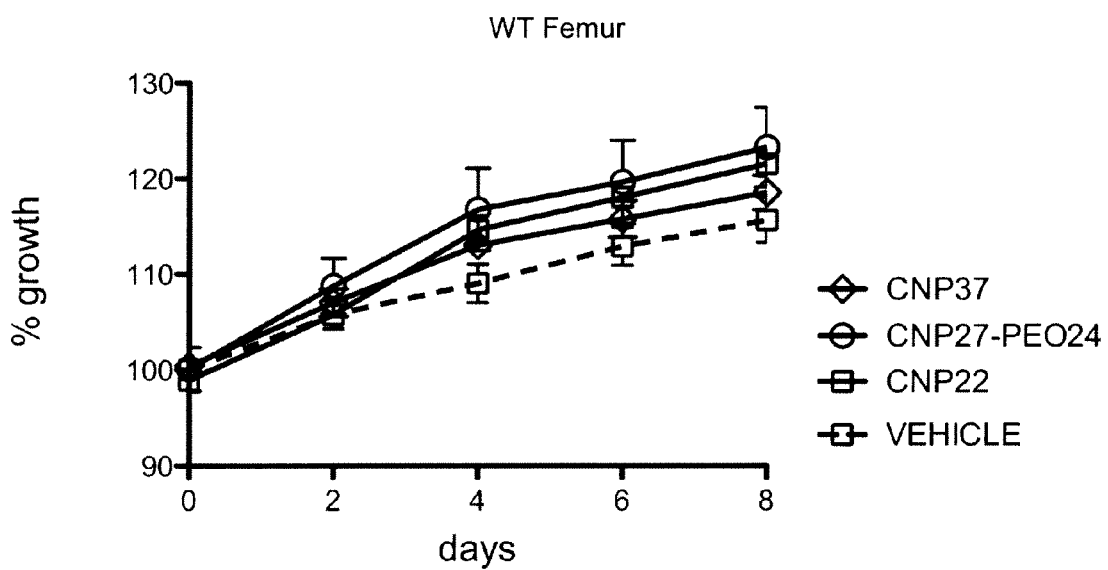
FIG. 32 shows longitudinal bone growth of 2-3 day-old wild-type mouse femurs treated with CNP22, CNP37 or PEO24-GANRR-CNP22(K4R) (SEQ ID NO: 36) every two days. Results are normalized to measurements prior to treatment (day 0). Data is represented as means±SEM (n=8).
Figure 33:
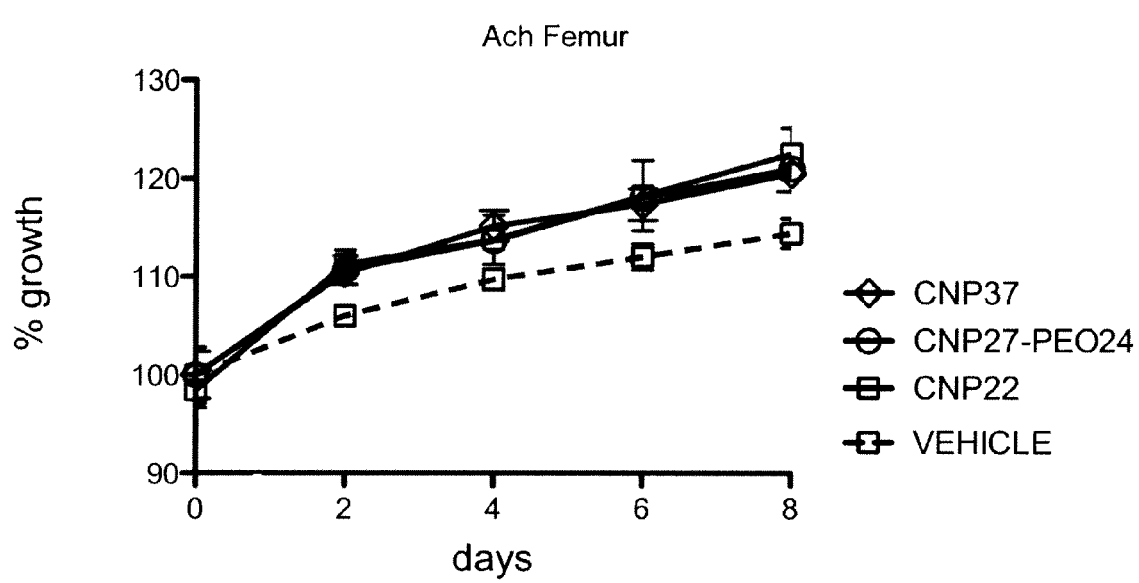
FIG. 33 shows longitudinal bone growth of 2-3 day-old FGFR3$^{ach}$ mouse femurs treated with CNP22, CNP37 or PEO24-GANRR-CNP22(K4R) (SEQ ID NO: 36) every two days. Results are normalized to measurements prior to treatment (day 0). Data is represented as means±SEM (n=3-7).

The growth of wild-type and FGFR3$^{ach}$ mouse femur and tibia in response to CNP22, CNP37 and PEO24-GANRR-CNP22(K4R) ("CNP27-PEO24") (SEQ ID NO: 36) was also assessed. Culture of either wild-type or achondroplastic (FGFR3$^{ach}$) mouse tibia showed that CNP37 and PEO24-GANRR-CNP22(K4R) (SEQ ID NO: 36) both increased the longitudinal growth of the tibia compared to vehicle or CNP22 (FIGS. 30 and 31). CNP22, CNP37 and PEO24-GANRR-CNP22(K4R) (SEQ ID NO: 36) also stimulated the growth of wild-type mouse femur (FIG. 32). Moreover, each of CNP22, PEO24-GANRR-CNP22(K4R) (SEQ ID NO: 36) and CNP37 increased the longitudinal growth of FGFR3$^{ach}$ mouse femur compared to vehicle (FIG. 33).

Figure 34:
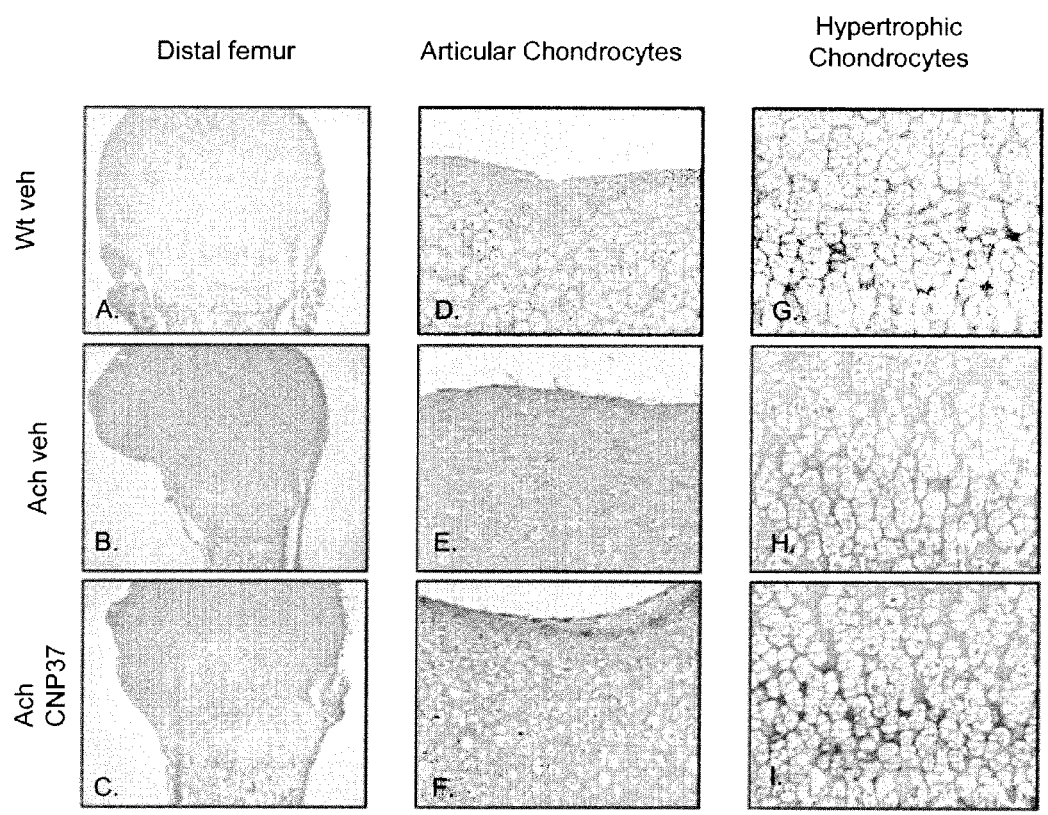
FIGS. 34A-I depict CNP37 biodistribution in FGFR3$^{ach}$ mouse femurs treated ex vivo every two days. Panels A-C illustrate distribution in distal femurs, panels D-F illustrate distribution in articular chondrocytes and panels G-I illustrate distribution in hypertrophic chondrocytes.

Furthermore, ex vivo distribution of CNP37 in the growth plate of FGFR3$^{ach}$ mouse tibia was evaluated. Bone samples were prepared as described above. Paraffin sections were cut and heat fixed for 1 hour at 60° C. Antigen retrieval with 1% hyaluronidase at 37° C. (30 minutes) was followed by a 1 hour serum block (10% Normal Goat Serum). CNP22 antibody (1:500 dilution; Peninsula Laboratories Inc., San Carlos, Calif.) was applied overnight at 4° C. For immunodetection, Vectastain ELITE ABC kit (Vector, Burlingame, Calif.) was used according to the manufacturer's recommendations. Specific bound peroxidase was visualized by incubation with DAB substrate kit (Vector) and the reaction was developed for 3 minutes. Slides were then dehydrated and mounted and photographed using a brightfield microscope. Staining for CNP in the growth plate of FGFR3$^{ach}$ mouse tibia showed that CNP immunoreactivity was increased in the regions of articular and hypertrophic chondrocytes (FIG. 34), indicating that CNP37 was delivered to the chondrocytes.

Figure 35:
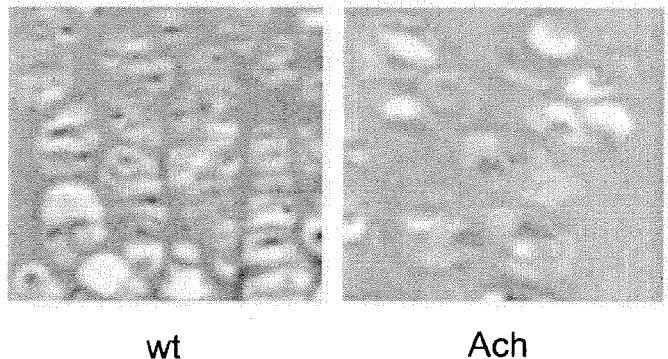
FIGS. 35A-C depict the cellularity of proliferating columns in growth plates after treatment of wild-type and FGFR3$^{ach}$ mouse femurs with CNP22 or CNP37 every two days for 8 days. (A) no treatment, (B) cell numbers per column after treatment, (C) morphological studies after treatment. The panels in FIGS. 35C(i) to C(vi). correspond to the sample order set out in FIG. 35B. Data is represented as means±SEM (n=4-8).
Figure 35:
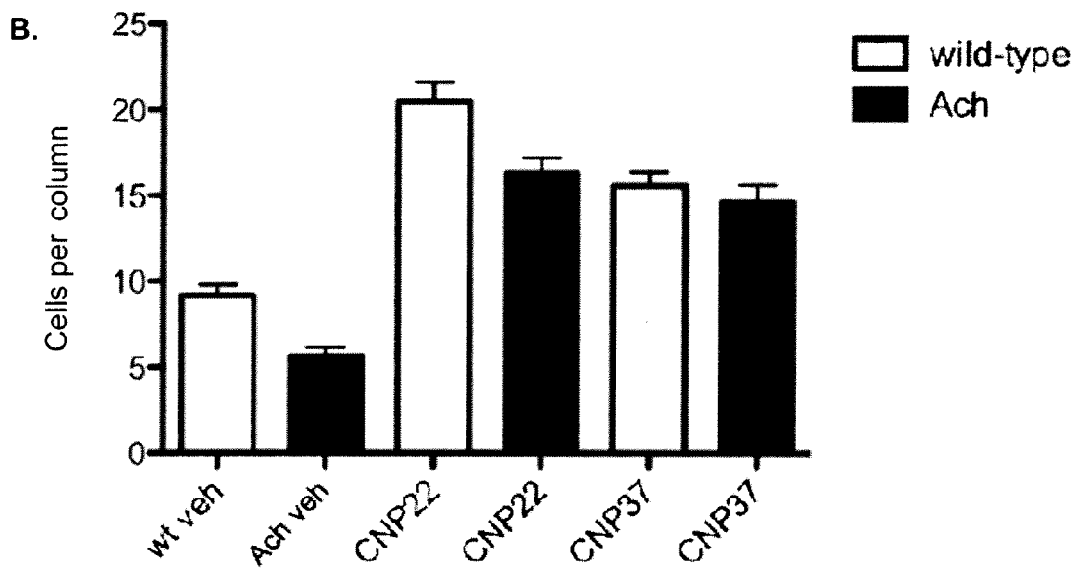
Figure 35:
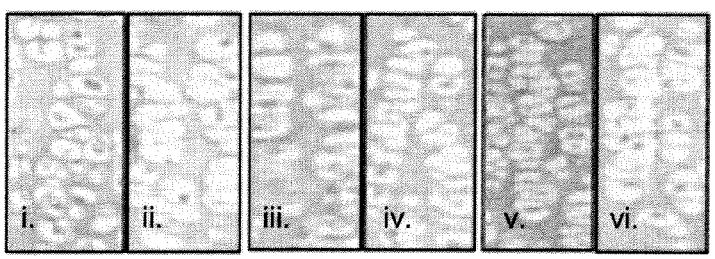
Figure 36:
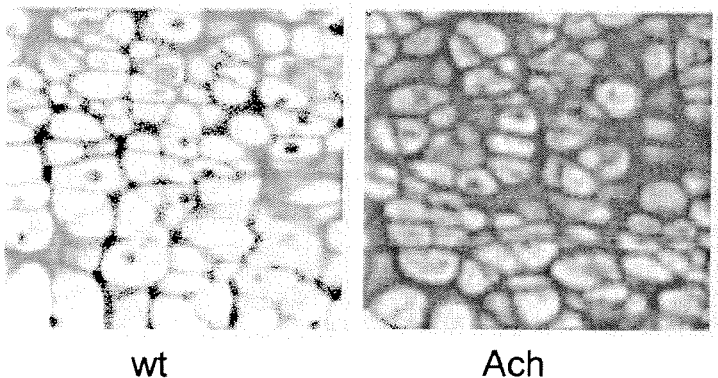
FIGS. 36A-C depict chondrocyte hypertrophy after ex vivo treatment of wild-type and FGFR3$^{ach}$ mouse femurs with CNP22 or CNP37 every two days for 8 days. (A) no treatment, (B) cell size after treatment, (C) morphological studies after treatment. The panels in FIGS. 36C(i) to C(vi) correspond to the sample order set out in FIG. 36B. Data is represented as means±SEM (n=4-9).
Figure 36:
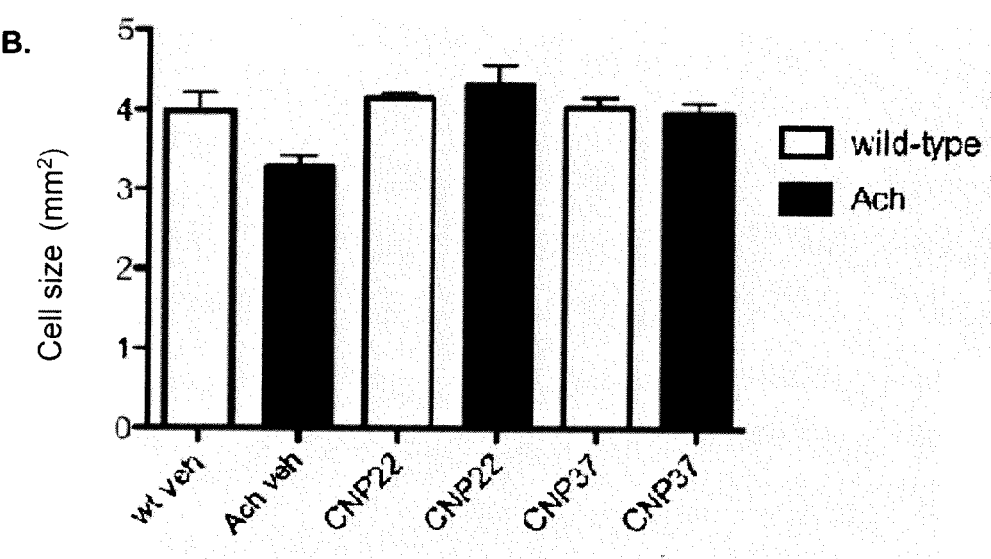
Figure 36:
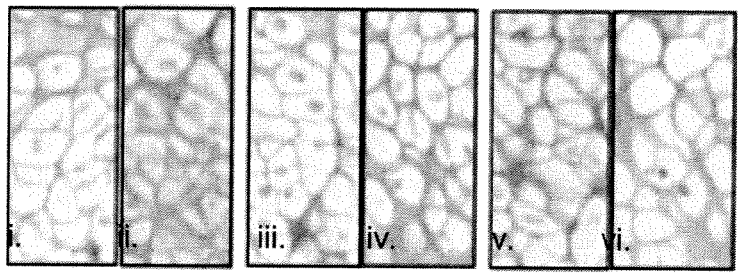

In addition to the distribution of CNP variants in the bone growth plate, the ex vivo effects of CNP37, CNP22 and vehicle on cells in the FGFR3$^{ach}$ and wild-type growth plate, e.g., hypertrophic cell size and cellularity of proliferating zone, were also evaluated. Bone samples were prepared, including Alcian Blue staining, as described above. Images of the entire proximal growth plate were taken at 4× magnification. The growth plate is divided into three zones, starting from the epiphyseal side of cartilage: the resting zone (individual small chondrocytes), proliferating zone (columns of stacked chondrocytes parallel to the long axis of the bone), and hypertrophic zone (large chondrocytes and thin septa between the chondrocytes). In these regions, measurements were made by ImageJ software, including the number of proliferating chondrocytes per column and the density of hypertrophic chondrocytes. A test square (4×4 mm$^2$) at five different regions of the hypertrophic zone was used to determine the density of hypertrophic chondrocytes. The cell size of hypertrophic chondrocytes was calculated by 1 over determined cell density. Cellularity of proliferating columns was increased by CNP37 and CNP22 in both wild-type and FGFR3$^{ach}$ mice (FIGS. 35B and C). Chondrocyte hypertrophy in FGFR3$^{ach}$ mice was also increased as a result of culture with CNP22 or CNP37 (FIGS. 36B and C).

Ex vivo studies of cultures of mouse bones indicated that CNP37 was delivered to the growth plate and was able to increase chondrocyte cellularity and hypertrophy, which are associated with growth plate expansion and longitudinal bone growth. To assess the biodistribution of CNP37 in the bone growth plate in vivo and the in vivo effects of CNP37 on the growth plate (including total growth plate thickness, hypertrophic zone thickness, and cellularity of proliferating zone), bone samples were obtained from FGFR3$^{ach}$ mice treated with vehicle or CNP37 as described above. For biodistribution and in vivo effects studies, tibias were fixed and stored in 70% ethanol. For immunohistochemistry, the samples were decalcified in 5% formic acid for 2 days, dehydrated and embedded in paraffin. Bones were sectioned at 5 um (microns), which were then deparaffinized, rehydrated, and used for CNP immunohistochemistry as described above. For cellular image analysis, bones were sectioned at 5 (microns), and then deparaffinized, rehydrated, and stained with Alcian Blue for 30 minutes (pH 2.5; MasterTech) and Hematoxylin & Eosin for 30 seconds. Stained sections were visualized and photographed by brightfield microscopy. Thicknesses of the growth plate and the proliferating and hypertrophic zones were measured using ImageJ software.

Figure 37:
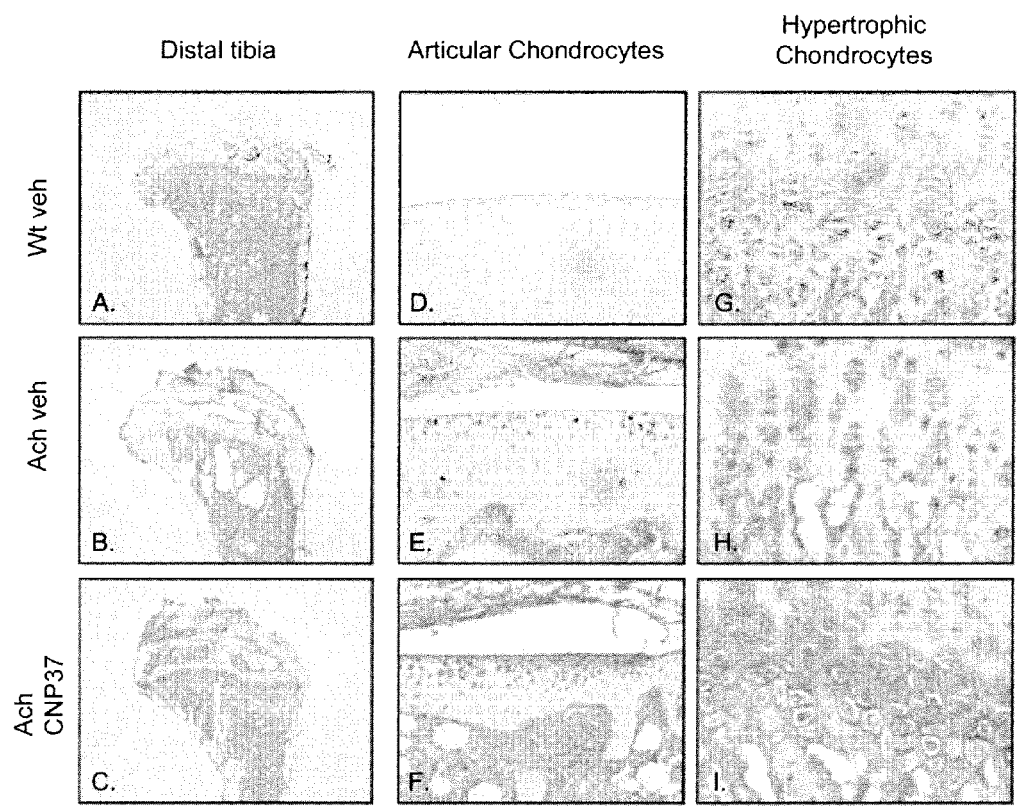
FIGS. 37A-I depict the biodistribution of CNP37 in FGFR3$^{ach}$ mouse tibias treated in vivo. Panels A-C show distribution in distal femurs, panels D-F illustrate distribution in articular chondrocytes and panels G-I illustrate distribution in hypertrophic chondrocytes.
Figure 38:
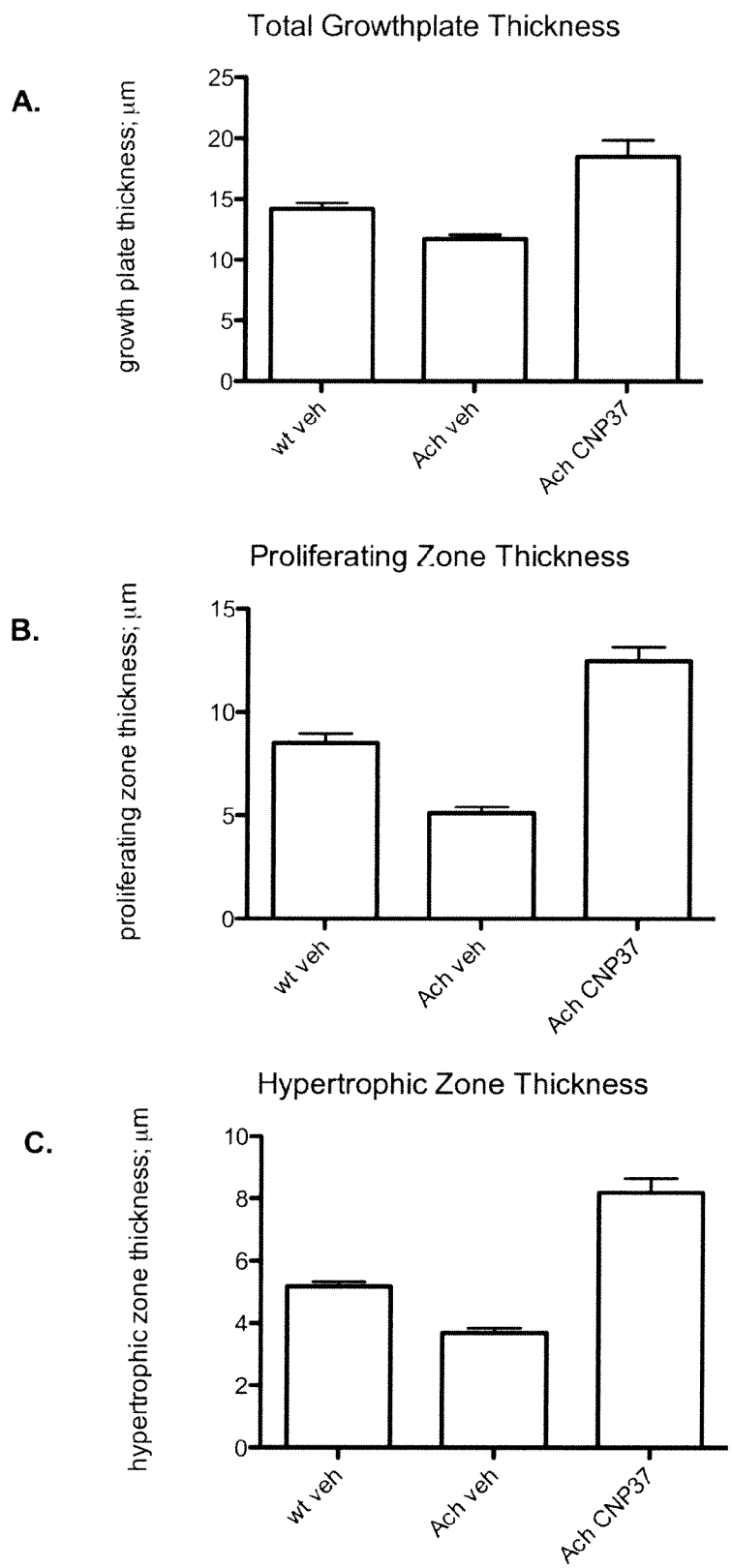
FIGS. 38A-C illustrate the in vivo effects of CNP37 on FGFR3$^{ach}$ mouse tibia growth plate: (A) total growth plate thickness, (B) proliferating zone thickness, and (C) hypertrophic zone thickness. Data is represented as means±SEM (n=7-15).
Figure 39:
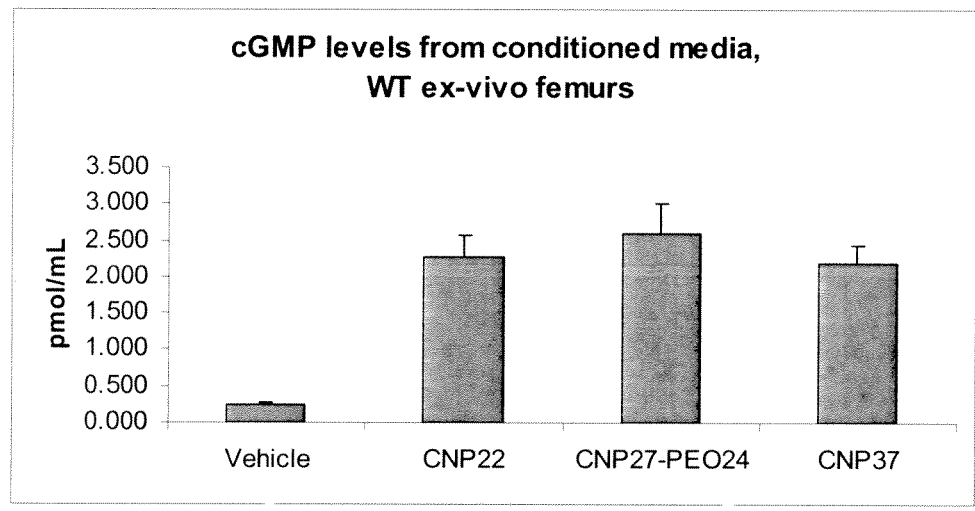
FIG. 39 shows cGMP levels in conditioned media from wild-type mouse femurs treated ex vivo with CNP22, CNP37 or PEO24-GANRR-CNP22(K4R) ("CNP27-PEO24") (SEQ ID NO: 36) (p<0.01).
Figure 40:
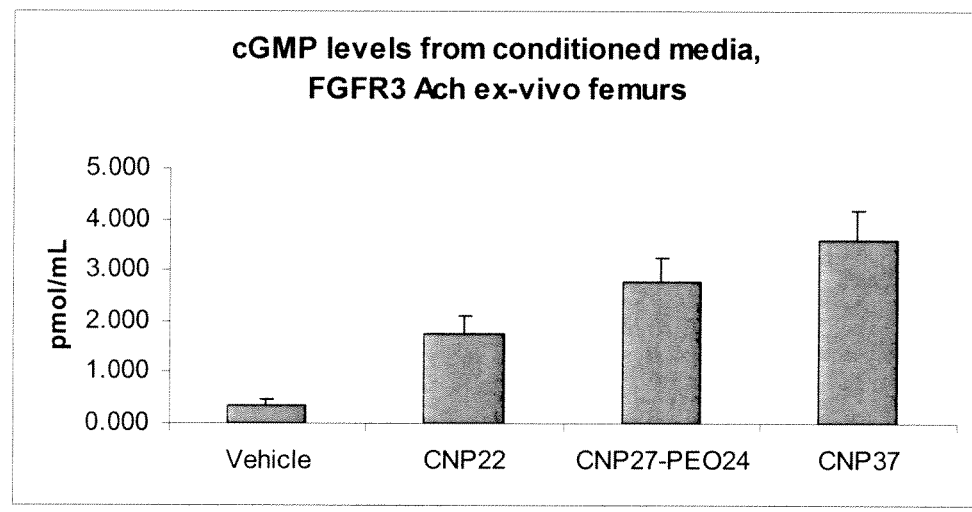
FIG. 40 shows cGMP levels in conditioned media from FGFR3$^{ach}$ mouse femurs treated ex vivo with CNP22, CNP37 or PEO24-GANRR-CNP22(K4R) (SEQ ID NO: 36) (p<0.01).
Figure 41:
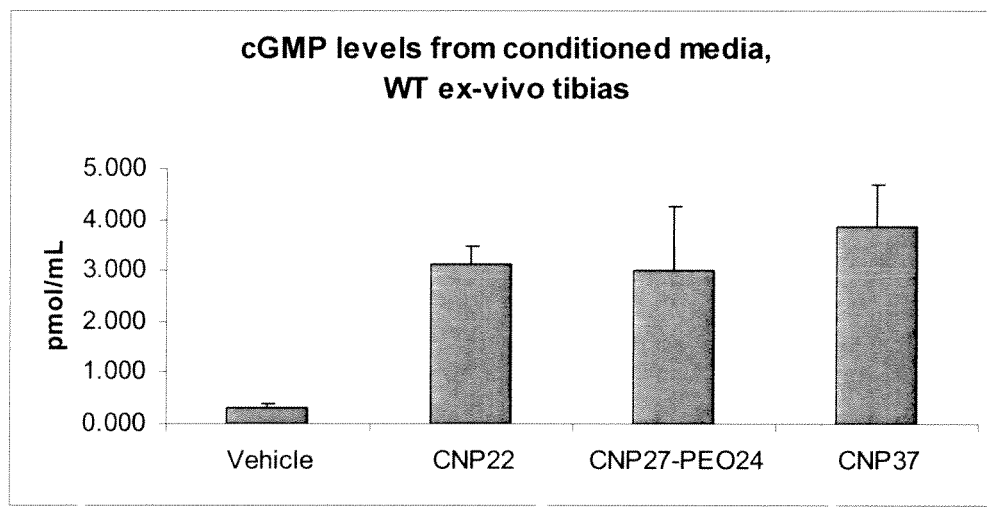
FIG. 41 depicts cGMP levels in conditioned media from wild-type mouse tibias treated ex vivo with CNP22, CNP37 or PEO24-GANRR-CNP22(K4R) (SEQ ID NO: 36) (p<0.01).
Figure 42:
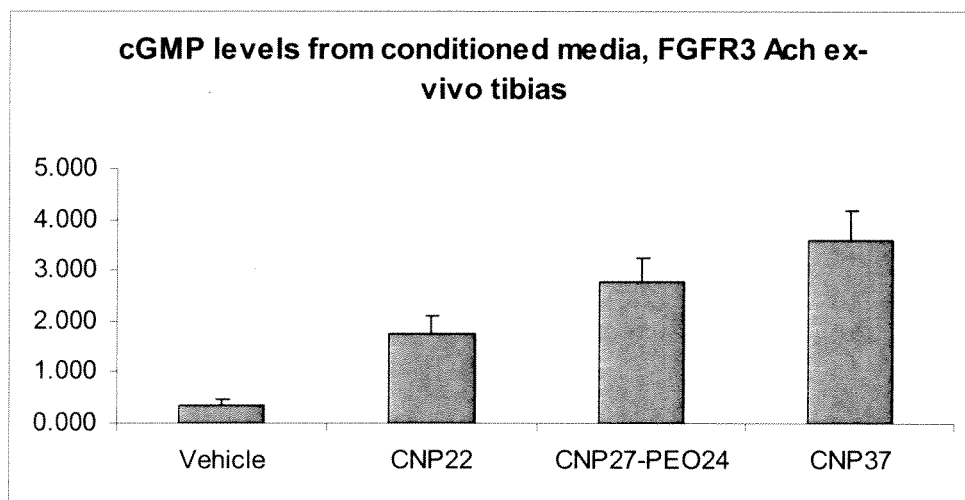
FIG. 42 shows cGMP levels in conditioned media from FGFR3$^{ach}$ mouse tibias treated ex vivo with CNP22, CNP37 or PEO24-GANRR-CNP22(K4R) (SEQ ID NO: 36) (p<0.01).

In vivo biodistribution studies demonstrated that, similar to the ex vivo studies, CNP immunoreactivity was increased in the regions of articular and hypertrophic chondrocytes in the tibia growth plate of FGFR3$^{ach}$ mice treated with CNP37, indicating that CNP37 was delivered in vivo to the growth plate of FGFR3$^{ach}$ mouse tibia (FIG. 37). Furthermore, CNP37 treatment significantly increased the total growth plate thickness, proliferating zone thickness and hypertrophic zone thickness of FGFR3$^{ach}$ mouse tibia in vivo (FIGS. 38A-C).

These results demonstrate that CNP variants of the disclosure penetrate into the growth plate of wild-type and achondroplastic animals, increase the number and size of chondrocytes, increase the thickness of the proliferating zone and the hypertrophic zone of the growth plate, and increase longitudinal bone growth in treated wild-type and achondroplasic animals. Therefore, the CNP variants are useful for stimulating bone growth in achondroplastic subjects.

Measurement of Biomarkers

In addition to measurement of bone growth in response to CNP variants, assay of the levels of biomarkers for cartilage and bone formation and growth induced in response to CNP variants is useful for evaluating the effect of CNP variants on bone growth.

Femurs and tibias were isolated from wild-type and FGFR3$^{ach}$ mice as described above. Bones were cultured with CNP22 or a variant thereof for eight days with the replacement of media every two days. On the eighth day, media was collected and analyzed for the biomarkers cGMP (cyclic guanosine 3', 5' cyclic monophosphate) and fragments of cleaved collagen type II, a cartilage-specific marker for cartilage turnover. Both markers were measured using commercially available enzyme-linked immunosorbent assays (ELISA) for cGMP (Cayman Chemical Co., Ann Arbor, Mich.) and cleaved collagen type II (Cartilaps) (Immunodiagnostic Systems, Fountain Hills, Ariz.), following the manufacturer's protocol.

Figure 43:
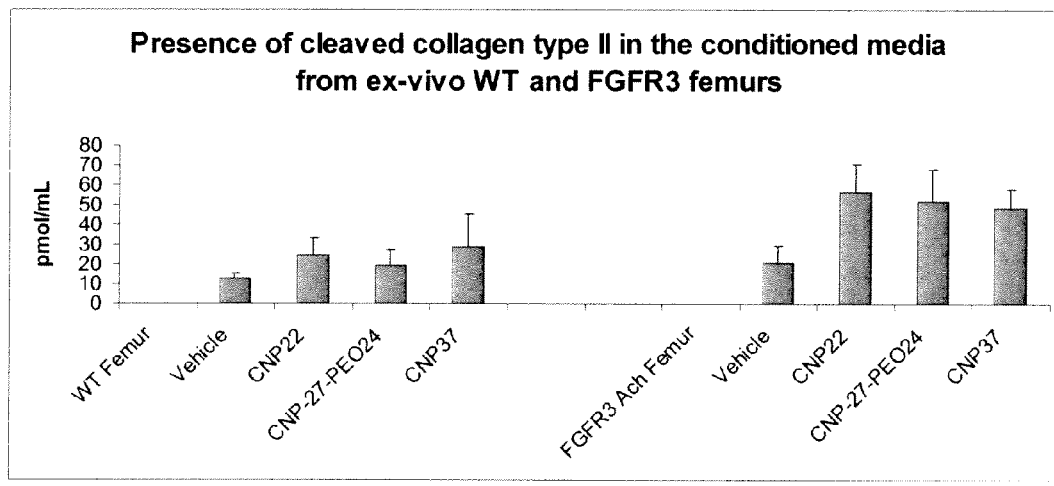
FIG. 43 demonstrates that ex vivo exposure of wild-type and FGFR3$^{ach}$ mouse femurs to CNP22, CNP37 or PEO24-GANRR-CNP22(K4R) (SEQ ID NO: 36) increased the levels of cleaved collagen type II in the conditioned media (p<0.05).

Levels of cGMP and collagen type II fragments were measured from cell culture extracts after exposure to CNP22, CNP37 or PEO24-GANRR-CNP22(K4R) ("CNP27-PEO24") (SEQ ID NO: 36). FIGS. 39-42 show a large increase (p<0.01) in the levels of cGMP in the media after exposure of ex-planted wild-type and FGFR3$^{ach}$ mouse femurs and tibias to CNP22, CNP37 or PEO24-GANRR-CNP22(K4R) (SEQ ID NO: 36). In addition, exposure of wild-type and FGFR3$^{ach}$ mouse femurs to CNP22, CNP37 or PEO24-GANRR-CNP22(K4R) (SEQ ID NO: 36) increased the levels of cleaved collagen type II, with the treated FGFR3$^{ach}$ mouse femurs showing significantly increased (p<0.05) levels of collagen type II fragments (FIG. 43). Elevated levels of collagen type II fragments indicate a turnover of the cartilage matrix, and cartilage turnover typically precedes new bone formation in growing bones.

Example 8B

Ex Vivo Stimulation of Growth of Femur from Mice with Severe Achondroplasia

Figure 44:
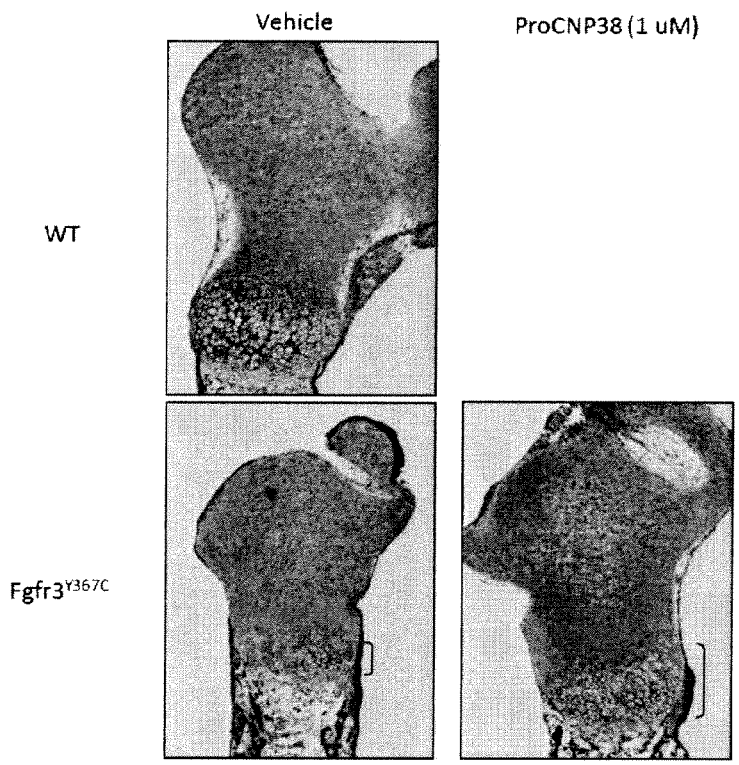
FIG. 44 depicts the hypertrophic region of femoral bones isolated from wild-type mice and FGFR3$^{Y367C}$ mice (a mouse model of severe achondroplasia) and treated ex vivo with vehicle or 1 uM Pro-Gly-CNP37 ("ProCNP38") for 6 days, demonstrating that Pro-Gly-CNP37 treatment resulted in increase in bone growth and expansion in the growth plate.

The effect of a CNP variant on the growth of bones from mice with severe achondroplasia was evaluated ex vivo. Used in the study were transgenic mice expressing a human FGFR-3 gene having a Y367C mutation (FGFR3$^{Y367C}$) [S. Pannier et al., Biochim. Biophys. Acta, 1792(2): 140-147 (2009)], which represent a mouse model of severe achondroplasia. Femurs were isolated at embryonic day 16.5 and cultured for 6 days in the presence of 1 uM Pro-Gly-CNP37. Bone lengths were measured at Day 1 and Day 7. The bones were then paraffin-embedded, sectioned and stained with hematoxylin and eosin to assess histological changes and cellular morphology. Treatment of bone explants isolated from FGFR3$^{Y367C}$ mice with Pro-Gly-CNP37 ("ProCNP38") resulted in increase in bone growth and expansion in the growth plate (FIG. 44). Femurs from FGFR3$^{Y367C}$ mice treated with vehicle for 6 days showed an 18% deficiency in growth length-wise compared to wild-type femurs treated with vehicle. Treatment of femurs from FGFR3$^{Y367c}$ mice with 1 uM Pro-Gly-CNP37 for 6 days reduced the growth deficiency to just 11%, i.e., reduced the growth defect by around 40%.

Example 9

Serum/Plasma Stability of CNP Variants In Vitro

In preparation for pharmacokinetics (PK) studies, the stability of CNP variants in serum and/or plasma is evaluated.

Briefly, the analyte is isolated by the removal of serum or plasma proteins by either a 2% trichloroacetic acid precipitation or a 1:3 serum:acetonitrile precipitation. The precipitation mixture is vortexed at 14,000 rpm for five minutes, and a portion of the supernatant is removed and diluted with water prior to transfer to a silanized autosampler vial for analysis. Serum extracts are then analyzed by reverse-phase high performance liquid chromatography (RP-HPLC) with electrospray ionization mass spectrometry (ESI-MS). A single mass (m/z), shown to be specific for the CNP variant, is monitored for quantitation purposes.

Initially, analytical stability and recovery is determined. Analytical (RP-HPLC and ESI-MS) parameters are optimized through the analysis of matrix standards (serum extracts fortified with analyte post-precipitation). After optimization, analytical recovery is determined by spiking serum samples at known concentrations and comparison of the analyte response to that of matrix standards prepared at similar concentrations. Analyte stability in serum extracts is also determined to assure no significant losses occur after serum precipitation and prior to actual analysis. To test the effect of freezing on serum stability, a two-cycle freeze/thaw study is also performed. In this study a serum sample is spiked with CNP variant and analyzed prior to freezing overnight at −20° C. The sample is then thawed at room temperature and re-analyzed. The process is repeated for a second freeze/thaw cycle.

Serum stability of CNP variant is determined by spiking of serum/plasma samples with CNP variant at a concentration of 10 ug/mL. The sample is placed in a 37° C. water bath for a period of three hours. At 30 minute intervals duplicate aliquots of serum are removed and analyzed. If rapid losses of analyte are evident (>50% in 30 minutes), the study may be repeated with 10 minute timepoints.

In an exemplary method for determining the stability of CNP variants in murine plasma, a mixture of CNP variant (10 uL of a stock solution of about 2.5-5.0 mg/mL), heparinized murine plasma (50 uL, Bioreclamation, CD-1 Lith Hep 62231), and 5 M NaCl (10 uL) is incubated at 37° C. and 5% $CO_2$ for 0-5 hr, and then quenched with 10× protease inhibitor cocktail (15 uL, Sigma P2714). For extraction, 150 uL of MeOH/0.1% FA is added to 85 uL of the reaction mixture, and the resulting mixture is vortexed for 1 min and then centrifuged at 15° C. for 15 min. 75 uL of the supernatant is added to 300 uL of aqueous 0.1% FA. A small portion of the resulting mixture is subjected to analysis by LC/MS.

Example 10

Pharmacokinetics and cGMP Production in Rats and Mice

Studies were conducted in normal rats to evaluate the pharmacokinetics (PK) profile of CNP22 and certain CNP variants and the time courses of plasma cGMP concentration after single intravenous (i.v.) or subcutaneous (s.c.) administration of the CNP peptides. Plasma CNP immunoreactivity was determined by using a competitive radioimmunoassay (RIA) with an anti-CNP rabbit polyclonal antibody. Plasma cGMP concentration was determined by RIA using a commercially available kit (YAMASA cyclic GMP Assay kit, YAMASA Corporation).

Normal male rats, 7-8 weeks of age, were used. Recombinant wild-type CNP22, CNP37 and PEO24-GANRR-CNP22 (K4R) (SEQ ID NO: 36) were evaluated. A dosage of 20 nmol/kg of each CNP peptide as a solution in 5% mannitol was intravenously injected once into the tail, or a dosage of 50 nmol/kg of each CNP peptide as a solution in 0.03 mol/L acetic acid buffer solution, pH 4.0, containing 1% (w/v) benzyl alcohol and 10% (w/v) sucrose, was subcutaneously injected once into the back.

Plasma CNP immunoreactivity was determined by the competitive RIA using anti-CNP rabbit polyclonal antibody. Standard and QC samples were prepared. Fifty uL of the standard, QC and assay samples were added, respectively, to test tubes containing 50 uL of RIA buffer. Diluted anti-CNP rabbit polyclonal antibody (100 uL) was added to the tubes. All tubes were kept at 4° C. overnight. $^{125}$I-[Tyr$^0$]-CNP22 solution (100 uL) and rabbit IgG solution (100 uL) were added and left at approximately 4° C. overnight. One milliliter of anti-rabbit IgG goat serum containing 10% polyethylene glycol was added, vortexed and left at approximately 4° C. for at least 1 hour, and then the insoluble fraction was precipitated by centrifugation. After aspiration of the supernatant, the amount of radiation (gamma line) in the sediment was measured by a gamma-counter. Each sample was measured in duplicate, and the mean was adopted as the value determined.

Plasma cGMP concentrations in the sample at 5, 30, 60 and 90 minutes after i.v. dosing, or at 5, 30, 60, 120 and 180 minutes after s.c. dosing, were determined by the competitive RIA using anti-cGMP monoclonal antibody. Standard samples were prepared. 100 uL of the assay samples (standard solutions for the calibration curve or the diluted plasma samples for cGMP determination) were transferred to test tubes. Then 100 uL of anti-cGMP monoclonal antibody solution and 100 uL of $^{125}$I-labeled succinyl cGMP tyrosine methyl ester solution were added to the tubes, respectively. All tubes were kept at 4° C. overnight. After the addition of 500 uL dextran charcoal solution, the tubes were vortexed and then placed on ice for 10 minutes. The reaction mixture was centrifuged and 500 uL of the supernatant was transferred from each sample to a new test tube. The amount of radiation (gamma line) in the supernatant was measured by a gamma-counter. Each sample was measured in duplicate, and the mean was adopted as the value determined.

Plasma CNP immunoreactivity was employed for pharmacokinetics (PK) analysis. PK analysis was performed using WINNONLIN® Professional (Pharsight Corporation). The PK profiles of CNP22, CNP37 and PEO24-GANRR-CNP22 (K4R) (SEQ ID NO: 36) after i.v. administration were calculated using PK parameters such as concentration at 0 hour ($C_0$: extrapolation, pmol/mL), total body clearance ($CL_{tot}$: mL/min/kg), distribution volume at steady state ($V_{dss}$: mL/kg), area under the plasma concentration-time curve (AUC: pmol·min/mL), mean residence time (MRT: min), and half-life ($T_{1/2}$: min). The PK profiles of the CNP peptides after s.c. administration were calculated using PK parameters such as maximum plasma concentration ($C_{max}$: pmol/mL), time to reach $C_{max}$ ($T_{max}$: min), area under the plasma concentration-time curve (AUC: pmol·min/mL), mean residence time (MRT: min), and half-life ($T_{1/2}$: min).

In plasma spike recovery experiments, the RIA detected CNP22, CNP37 and PEO24-GANRR-CNP22(K4R) (SEQ ID NO: 36) similarly (data not shown).

Procedures similar to those described above are employed to study in mice the PK profiles of CNP22 and variants thereof and their ability to stimulate cGMP production.

Figure 45:
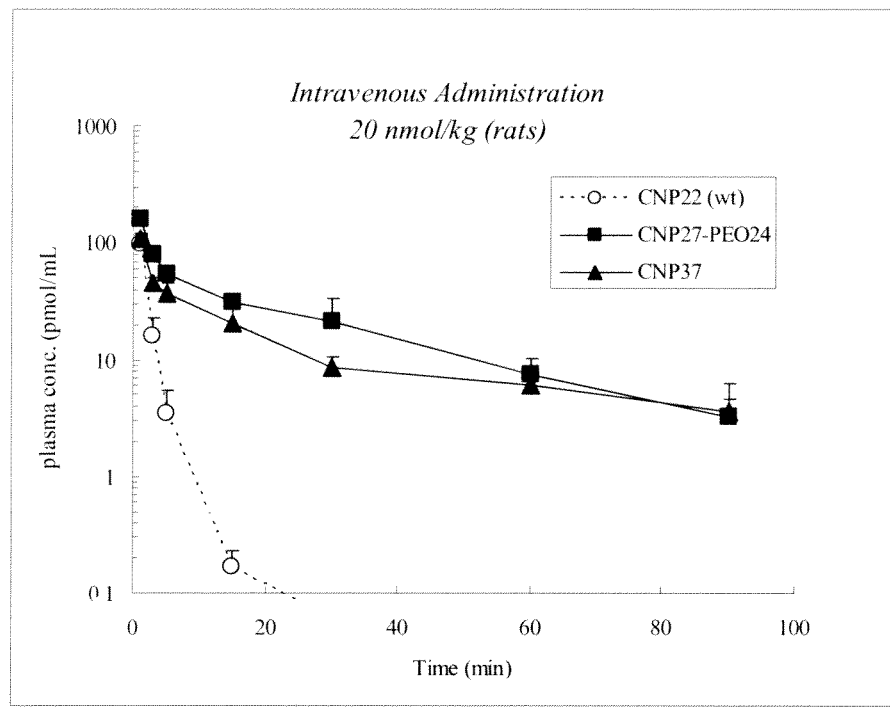
FIG. 45 shows that CNP37 and PEO24-GANRR-CNP22(K4R) (SEQ ID NO: 36) intravenously (i.v.) administered to rats have a much longer half-life and a much greater bioavailability in the plasma than CNP22.

The PK profiles of CNP22, CNP37 and PEO24-GANRR-CNP22(K4R) (SEQ ID NO: 36) after i.v. administration in three rats are illustrated in FIG. 45. As shown by FIG. 45, CNP37 and PEO24-GANRR-CNP22(K4R) (SEQ ID NO: 36) had a much longer half-life and a much greater bioavailability than CNP22. The half-life, $T_{1/2}$ (min), was 1.42 (±0.45) for CNP22, 22.3 (±1.5) for PEO24-GANRR-CNP22 (K4R) (SEQ ID NO: 36), and 49.5 (±28.0) for CNP37. The area under the curve, AUC (pmol·min/mL), was 320 (±54) for CNP22, 1559 (±568) for CNP37, and 2084 (±424) for PEO24-GANRR-CNP22(K4R) (SEQ ID NO: 36).

Figure 46:
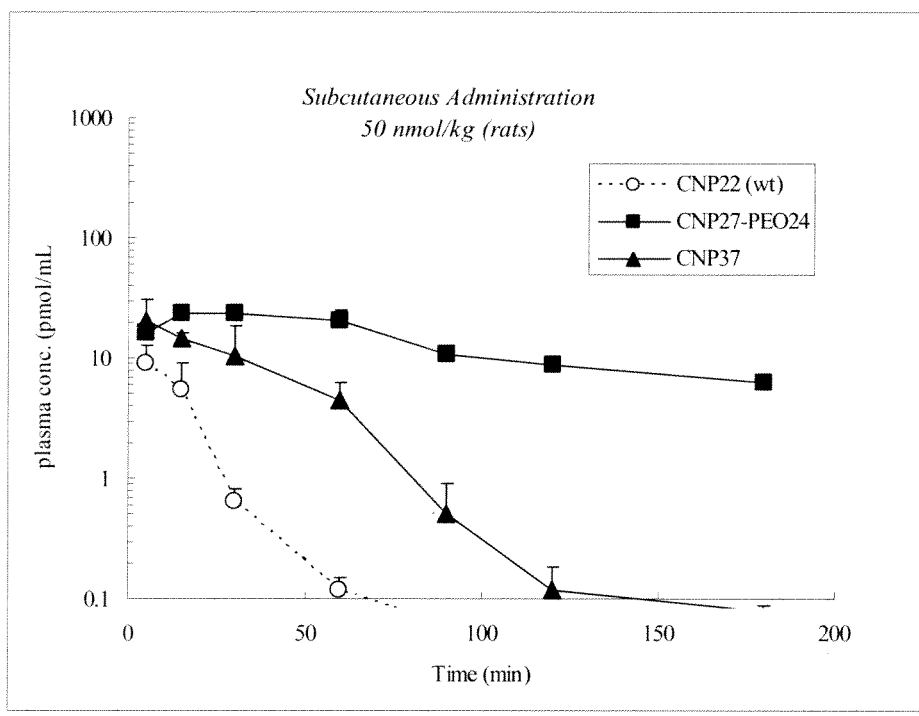
FIG. 46 illustrates that PEO24-GANRR-CNP22(K4R) (SEQ ID NO: 36) subcutaneously (s.c.) administered to rats also has a much longer half-life and a much greater bioavailability in the plasma than CNP22.

The PK profiles of the three CNP peptides after s.c. administration in three rats are depicted in FIG. 46. Compared to CNP22, PEO24-GANRR-CNP22(K4R) (SEQ ID NO: 36) had a much longer half-life (78.1 min (±16.4) vs. 10.0 (±5.0)) and a much greater bioavailability (60% (±6%) vs. 19% (±9%)).

Figure 47:
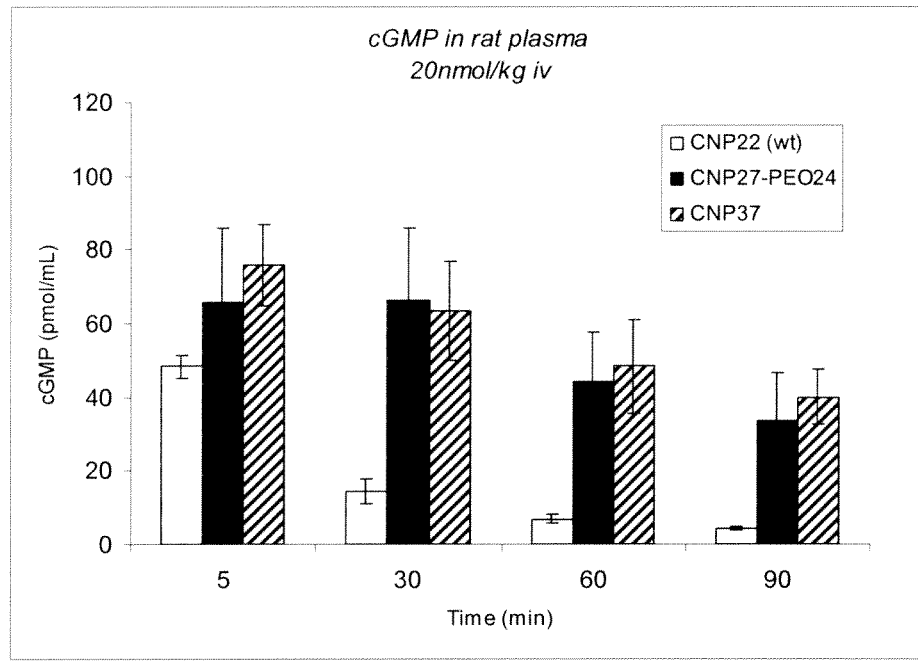
FIG. 47 demonstrates that i.v. administered CNP37 and PEO24-GANRR-CNP22(K4R) (SEQ ID NO: 36) stimulate a much greater level of cGMP production in rats than CNP22.

The time courses of plasma cGMP concentrations after i.v. administration of the three CNP peptides in three rats are displayed in FIG. 47. FIG. 47 clearly demonstrates that i.v. administration of CNP37 and PEO24-GANRR-CNP22 (K4R) (SEQ ID NO: 36) resulted in much higher plasma levels of cGMP at 30, 60 and 90 minutes than i.v. administration of CNP22.

Figure 48:
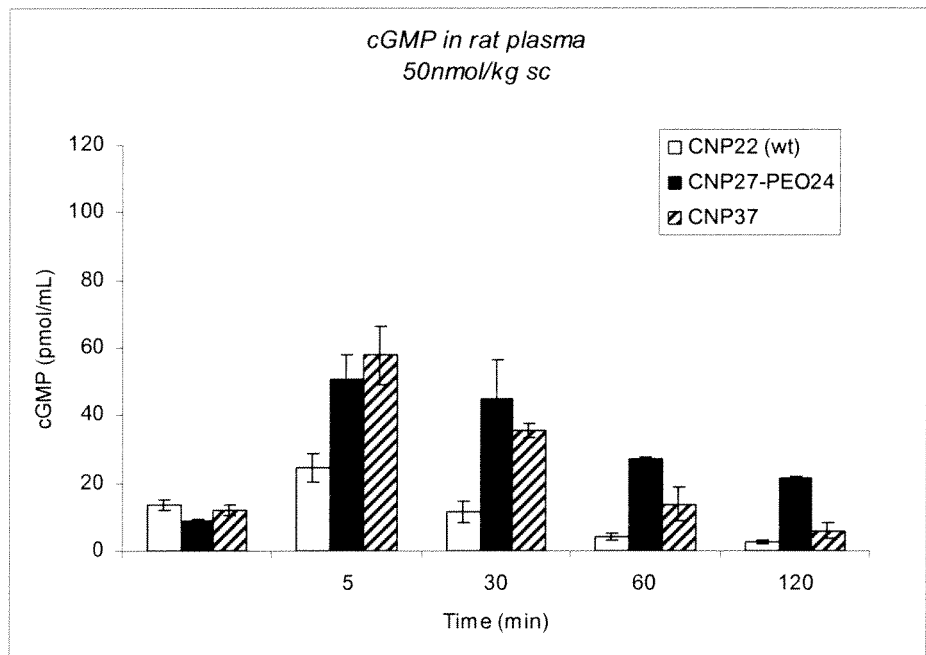
FIG. 48 shows that s.c. administered PEO24-GANRR-CNP22(K4R) (SEQ ID NO: 36) and, to a lesser extent, CNP37 are substantially more effective in stimulating cGMP production in rats than CNP22.

The time profiles of plasma cGMP concentrations after s.c. administration of the three CNP peptides in three rats are shown in FIG. 48. Subcutaneous administration of PEO24-GANRR-CNP22(K4R) (SEQ ID NO: 36) and CNP37 also resulted in substantially higher plasma concentrations of cGMP than s.c. administration of CNP22, with the difference relative to CNP22 increasing over time for PEO24-GANRR-CNP22(K4R) (SEQ ID NO: 36), but decreasing over time for CNP37.

The rat studies indicate that compared to wtCNP22, the CNP variants CNP37 and PEO24-GANRR-CNP22(K4R) (SEQ ID NO: 36) had a substantially longer half-life in vivo, had a substantially greater bioavailability in vivo, and stimulated substantially higher levels of cGMP production in vivo for an extended period of time. The resistance of CNP37 and PEO24-GANRR-CNP22(K4R) (SEQ ID NO: 36) to NEP degradation correlates to a longer plasma half-life in vivo, which in turn correlates to prolonged NPR-B/cGMP signaling in vivo. These results show that compared to CNP22, the CNP variants of the disclosure, administered by i.v. or s.c. injection (e.g., once daily), can be more effective in treating CNP-responsive conditions or disorders, such as bone-related disorders and vascular smooth muscle disorders.

Example 11

Pharmacokinetics Study in Mice

To determine CNP variants having increased NEP resistance, for efficacy study in FGFR3$^{ach}$ mice (see Example 13), a pharmacokinetics (PK) study is carried out that compares the pharmacokinetics properties of CNP variants to wild-type CNP22. The FGFR3$^{ach}$ mouse is a mutant mouse model of mild achondroplasia, containing a single transgene on a background of FVB mice.

Wild-type CNP22 or variant thereof is administered as a single intravenous (i.v.) dose in 6-week old wild-type FVB mice. Exemplary PK studies were conducted using wtCNP22. Six-week old FVB/N mice were intravenously administered wtCNP22 in a single dose at 100 nmol/kg. Mean plasma levels of CNP22 were calculated, and the estimated half-life of CNP22 was determined to be from 0.76 min to 1.03 min.

CNP variants displaying greater resistance to NEP degradation are expected to exhibit increased serum concentrations over time and a longer half-life in vivo.

Example 12

Efficacy of CNP Variants in Wild-Type Mice

The in vivo effects of CNP variants on bone growth were assessed in wild-type mice. Three week old FVB wild-type male mice received daily subcutaneous (s.c.) injection of either vehicle, G-CNP37 (200 nmol/kg) or PEO12-GANRR- CNP22(K4R) ("CNP27-PEO12") (SEQ ID NO: 36) (200 nmol/kg) for 5 weeks. Body weight was measured at least once weekly. Tail length was measured at least once weekly using digital caliper readings, and body length (naso-anal length), bone length (tibia, femur, ulna and humerus), skull length (anterior to posterior cranial segment) and lumbar vertebrae 5 (LV5) length were measured after 5 weeks of treatment using a caliper. X-rays were taken at baseline and after 5 weeks of treatment.

Figure 49:
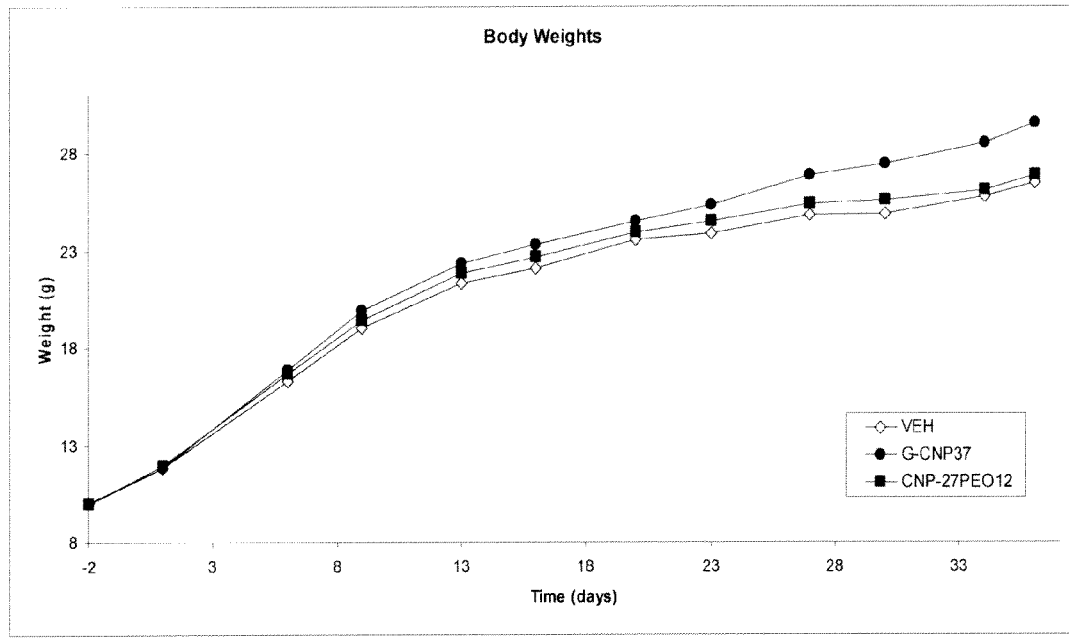
FIG. 49 shows body weight measurements of wild-type mice treated with Gly-CNP37 or PEO12-GANRR-CNP22(K4R) (SEQ ID NO: 36).
Figure 50:
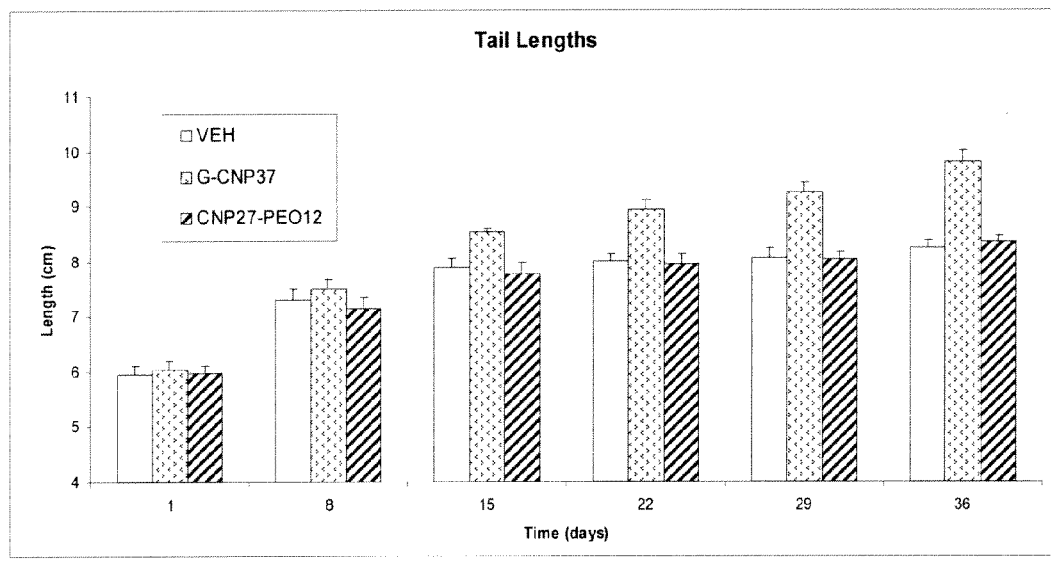
FIG. 50 shows tail length measurements of wild-type mice treated with Gly-CNP37 or PEO12-GANRR-CNP22(K4R) (SEQ ID NO: 36).

Five weeks of treatment of wild-type mice with G-CNP37 resulted in significant body weight gain, with increased body weight being observed beginning at Day 9 ($p<0.05$) (FIG. 49). Treatment with G-CNP37 also resulted in significantly increased tail length, beginning at the second week after treatment ($p<0.01$) (FIG. 50).

Table 10 shows the percentage change in tail length, body (naso-anal) length, skull (anterior to posterior cranial segment) length, bone (femur, tibia, humerus and ulna) lengths, and lumbar vertebrae 5 (LV5) length in wild-type mice injected s.c. once daily with 200 nmol/kg of either G-CNP37 or PEO12-GANRR-CNP22(K4R) ("CNP27-PEO12") (SEQ ID NO: 36) for 5 weeks, relative to a value of 100% for wild-type mice treated with vehicle only.

In another study, various dosing regimens of Pro-Gly-CNP37 were administered for nine weeks followed by one week of recovery. Wild-type FVB mice were dosed s.c. with:

(1) vehicle daily for nine weeks, followed by one week of recovery;
(2) 20 nmol/kg Pro-Gly-CNP37 daily for one week, followed by three doses per week for eight weeks and one week of recovery;
(3) 20 nmol/kg Pro-Gly-CNP37 on alternating weeks; or
(4) 5 nmol/kg Pro-Gly-CNP37 daily for nine weeks followed by one week of recovery.

Increased growth in tail length, body length, and bone lengths was observed in all treatment groups (Groups 2, 3 and 4) at the end of the study. Table 12 shows the percentage change in tail length, body (naso-anal) length, and bone (femur, tibia, humerus and ulna) lengths in wild-type mice administered Pro-Gly-CNP37 ("Pro-CNP38") under the dose regimens described above, relative to a value of 100% for wt mice treated with vehicle only.

TABLE 10

|  | Tail | Naso-Anal | Anterior to Posterior (Skull) | Femur | Tibia | Humerus | Ulna | LV5 |
|---|---|---|---|---|---|---|---|---|
| G-CNP37 | 119%** | 114%** | 104%* | 109%** | 105%** | 104%** | 101% | 108%* |
| CNP27-PEO12 | 101% | 104%** | 101% | 102%* | 100% | 102%* | 96%* | 103% |

**$p<0.01$,
*$p<0.05$

Treatment with G-CNP37 resulted in significantly increased tail length, body (naso-anal) length, skull length, proximal bone (femur and humerus) length, distal bone (tibia) length, and vertebral (lumbar vertebrae 5) length compared to treatment with vehicle.

Lower doses of Pro-Gly-CNP37 dosed daily s.c. at 5 nmol/kg, 20 nmol/kg or 70 nmol/kg for five weeks resulted in a dose-dependent increase in tail length, body (naso-anal) length, and bone lengths compared to vehicle. Table 11 shows the percentage change in tail length, body (naso-anal) length, and bone (femur, tibia, humerus and ulna) lengths in wild-type mice injected s.c. once daily with 5 nmol/kg, 20 nmol/kg or 70 nmol/kg Pro-Gly-CNP37 for 5 weeks, relative to a value of 100% for wild-type mice treated with vehicle only.

TABLE 11

|  | Tail | Naso-Anal | Femur | Tibia | Humerus | Ulna |
|---|---|---|---|---|---|---|
| 5 nmol/kg | 107.6%** | 102.7%** | 103.3%** | 101.7%** | 101.1% | 100.9%* |
| 20 nmol/kg | 107.8%** | 107.6%** | 107.1%** | 103.4%** | 102.3%** | 102.5%** |
| 70 nmol/kg | 113.6%** | 112.5%** | 109.3%** | 105.9%** | 103.6%** | 104.1%** |

**$p<0.01$,
*$p<0.05$

TABLE 12

|  | Total Pro-CNP38 received (nmol/kg) | Tail | Naso-Anal | Femur | Tibia | Humerus | Ulna |
|---|---|---|---|---|---|---|---|
| Group 2 | 620 | 104.8%** | 106.0%** | 105.3%** | 100.8% | 102.5% | 101.7% |
| Group 3 | 700 | 106.7%** | 106.5%** | 104.1%** | 102.5%** | 102.6%* | 102.8%* |
| Group 4 | 350 | 104.9%** | 105.1%** | 107.3%** | 102.7%** | 102.3%** | 103.6%** |

**$p < 0.01$,
*$p < 0.05$

While all dose regimens of Pro-Gly-CNP37 increased axial and appendicular growth parameters measured, daily dosing of Pro-Gly-CNP37 promoted appendicular growth (femur, tibia, humerus, and ulna) at a lower total dose level (Group 4) compared to regimens with less frequent dosing (Groups 2 and 3).

Example 13

Efficacy in Mouse Model of Mild Achondroplasia

The efficacy of CNP variants in enhancing growth and correcting achondroplasia was tested in a mouse model of mild achondroplasia, using a strain of transgenic mice expressing a human FGFR-3 gene having a G380R mutation (FGFR3$^{ach}$) (Wang et al., Proc. Natl. Acad. Sci. USA, 96(8): 4455-4460 (1999); Naski et al., Development USA, 125: 4977-4988 (1998); U.S. Pat. Nos. 6,265,632 and 6,136,040).

At 3 weeks of age, FGFR3$^{ach}$ mice and their wild-type littermates were anesthetized to have lateral whole-body X-ray images taken by Faxitron, and randomized by body weight into the following treatment groups (n=8/group): (1) wild-type/vehicle, (2) FGFR3$^{ach}$/vehicle, (3) FGFR3$^{ach}$/CNP37, and (4) FGFR3$^{ach}$/PEO24-GANRR-CNP22(K4R) (SEQ ID NO: 36). The mice received once daily subcutaneous (s.c.) administration of designated test article (vehicle or 200 nmol/kg CNP variant) for 5 weeks. Satellite groups (n=3) were used to confirm exposure of each test article following a single subcutaneous administration on Day 1. Wild-type male FVB mice that received daily s.c. injection of vehicle for 5 weeks were used as a control for normal growth.

X-ray measurements at baseline and at the end of the study were performed to determine change in the head length, area of the skull, and the external auditory meatus (EAM, the ear canal running from the outer ear to the middle ear). Body weight and tail length were measured at least once weekly, using a digital caliper to measure tail length, and body (naso-anal) length was measured after 5 weeks of treatment. Bone (tibia, femur, ulna and humerus) lengths were measured using a digital caliper at necropsy.

On Day 37, all mice were sacrificed by terminal anesthesia and whole-animal photographs and X-ray images by Faxitron were taken. Left and right tibia, femur, humerus, and ulna were collected and measured using a digital caliper. The left portions of each bone were processed for histology, and the right portions were snap-frozen for archival. Samples obtained from the bones were used to evaluate the effects of CNP variants on endochondral bone growth.

Figure 51:
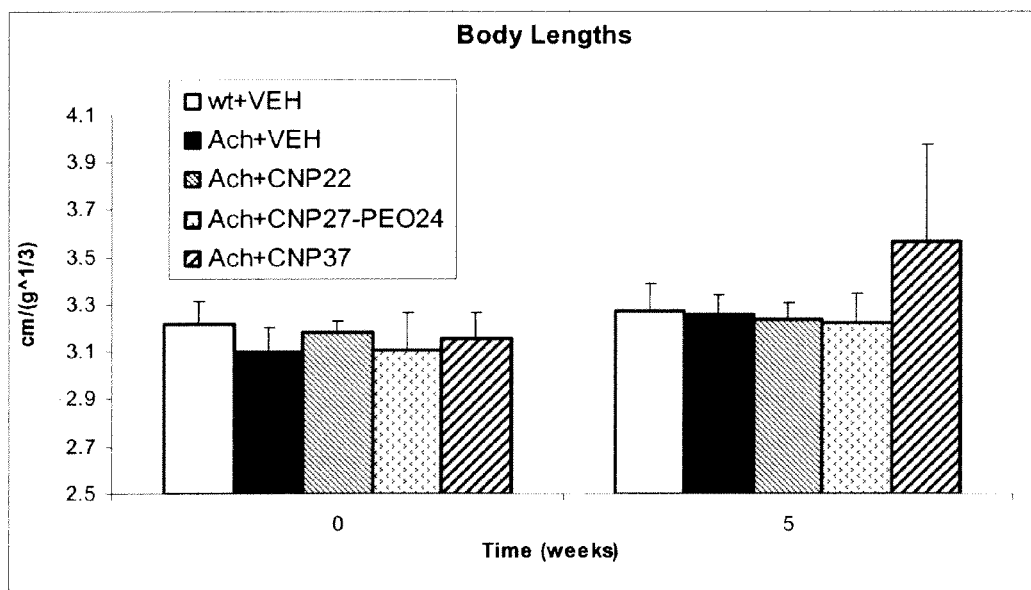
FIG. 51 illustrates the effect of treatment of FGFR3$^{ach}$ mice with CNP22, CNP37 or PEO24-GANRR-CNP22(K4R) (SEQ ID NO: 36) on body length (p=0.02, 1-tailed t-test, unequal variance).
Figure 52:
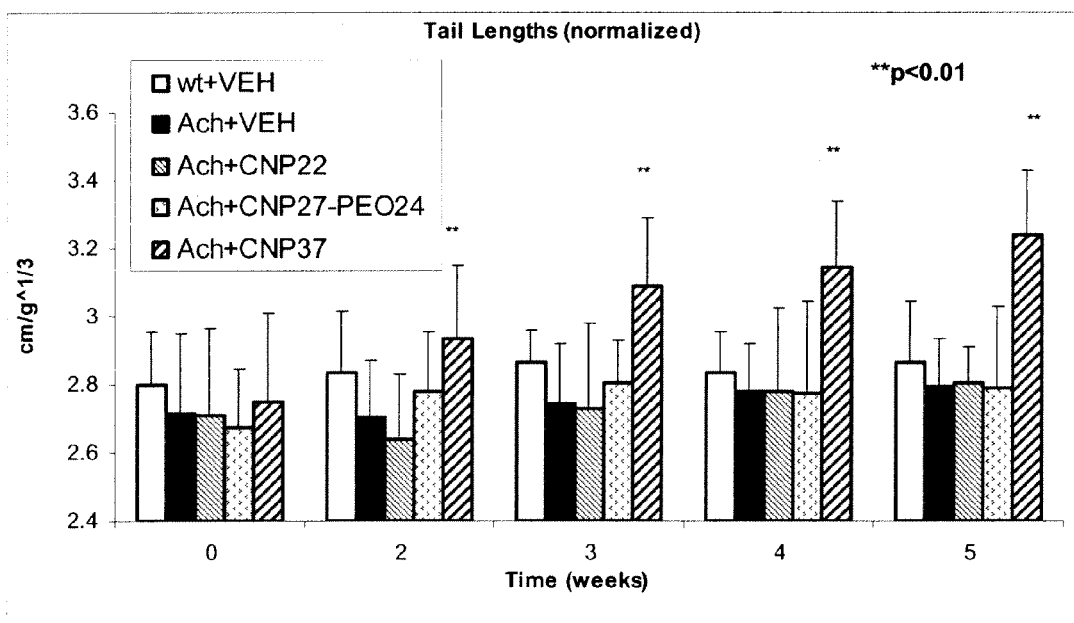
FIG. 52 shows the effect of CNP22, CNP37 and PEO24-GANRR-CNP22(K4R) (SEQ ID NO: 36) on tail length in FGFR3$^{ach}$ mice.
Figure 53:
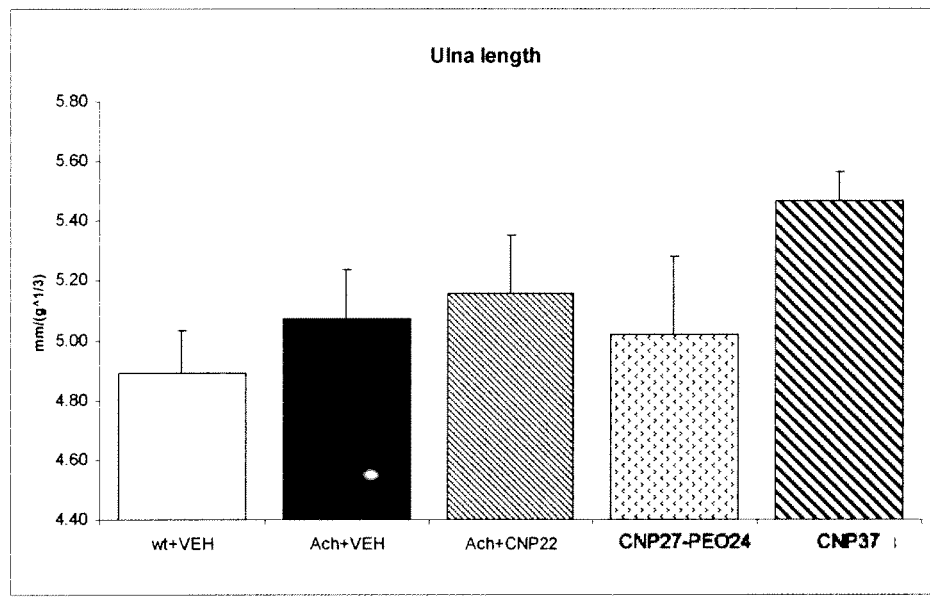
FIGS. 53A and B show the effect of CNP22, CNP37 and PEO24-GANRR-CNP22(K4R) (SEQ ID NO: 36) on the length of distal long bones (A, ulna; B, tibia) in FGFR3$^{ach}$ mice (p<0.01, one-tailed t-test, unequal variance).
Figure 53:
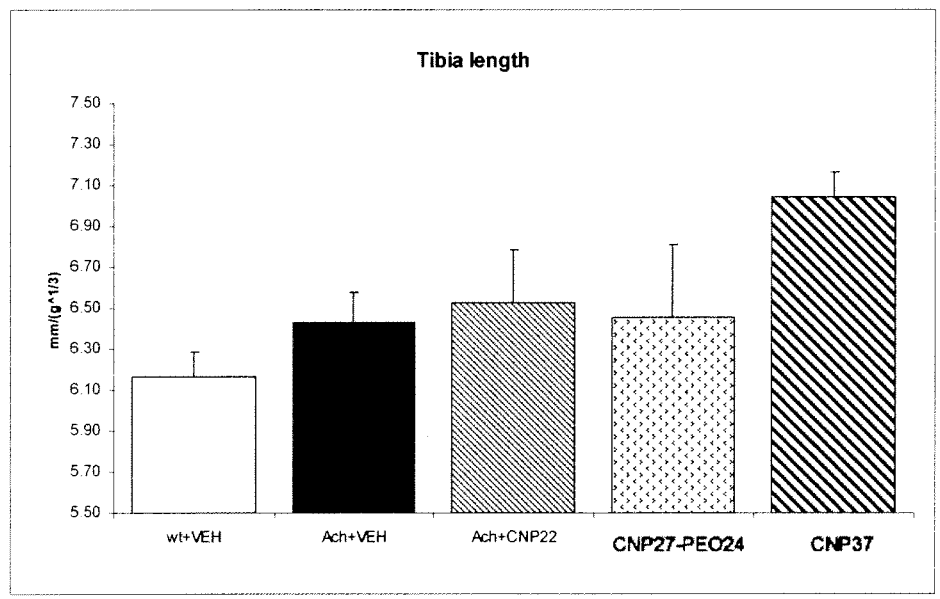
Figure 54:
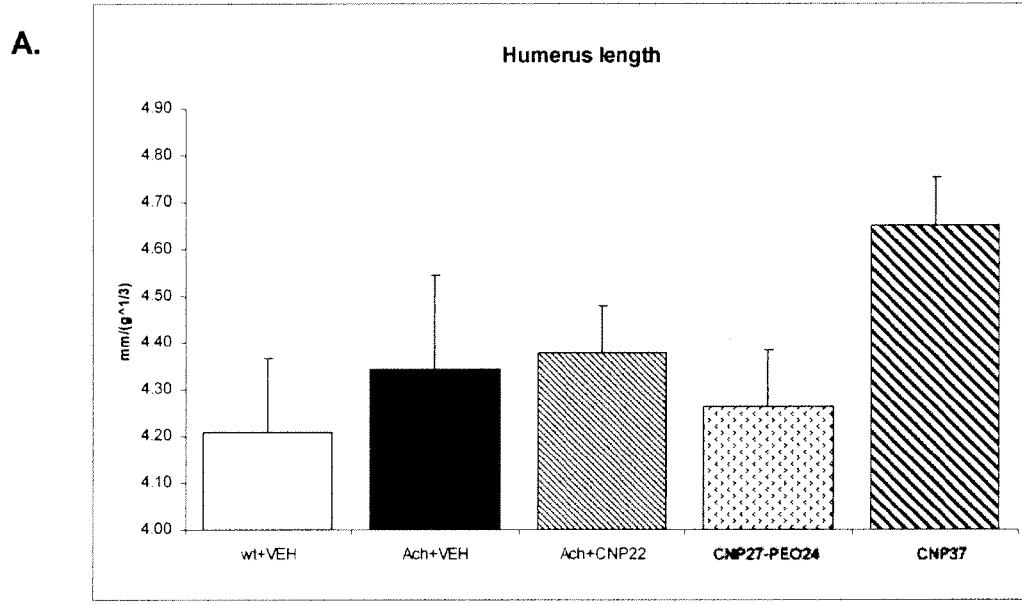
FIGS. 54A and B show the effect of CNP22, CNP37 and PEO24-GANRR-CNP22(K4R) (SEQ ID NO: 36) on the length of proximal bones (A, humerus; B, femur) in FGFR3$^{ach}$ mice (p<0.01, one-tailed t-test, unequal variance).
Figure 54:
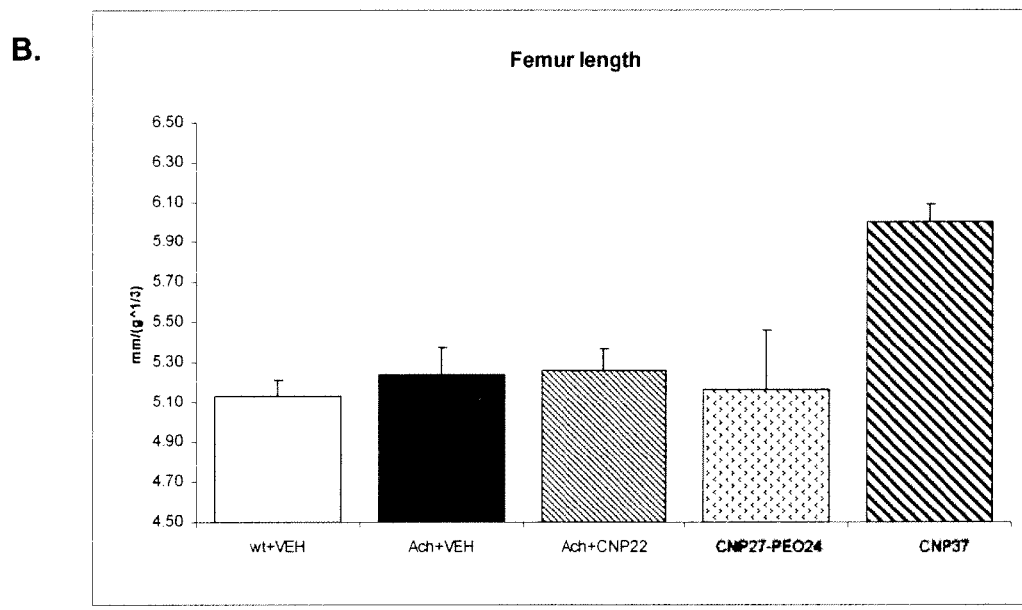
Figure 55:
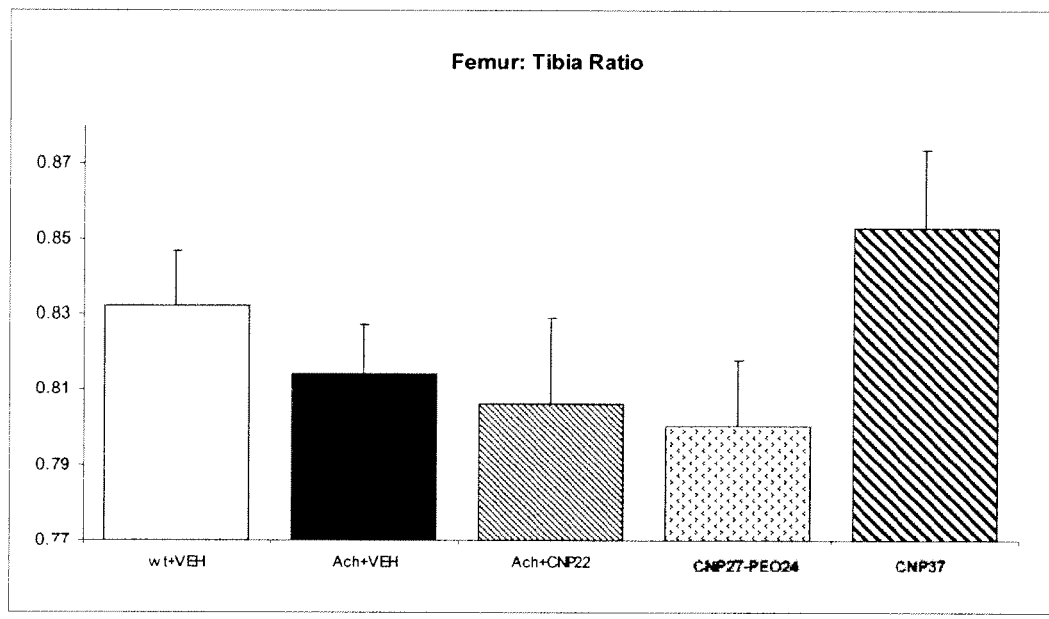
FIG. 55 illustrates that CNP37 administration corrects rhizomelia (disproportion of the length of the proximal limbs) as assessed by the femur:tibia ratio observed in FGFR3$^{ach}$ mice (p<0.01, one-tailed t-test, unequal variance).
Figure 56:
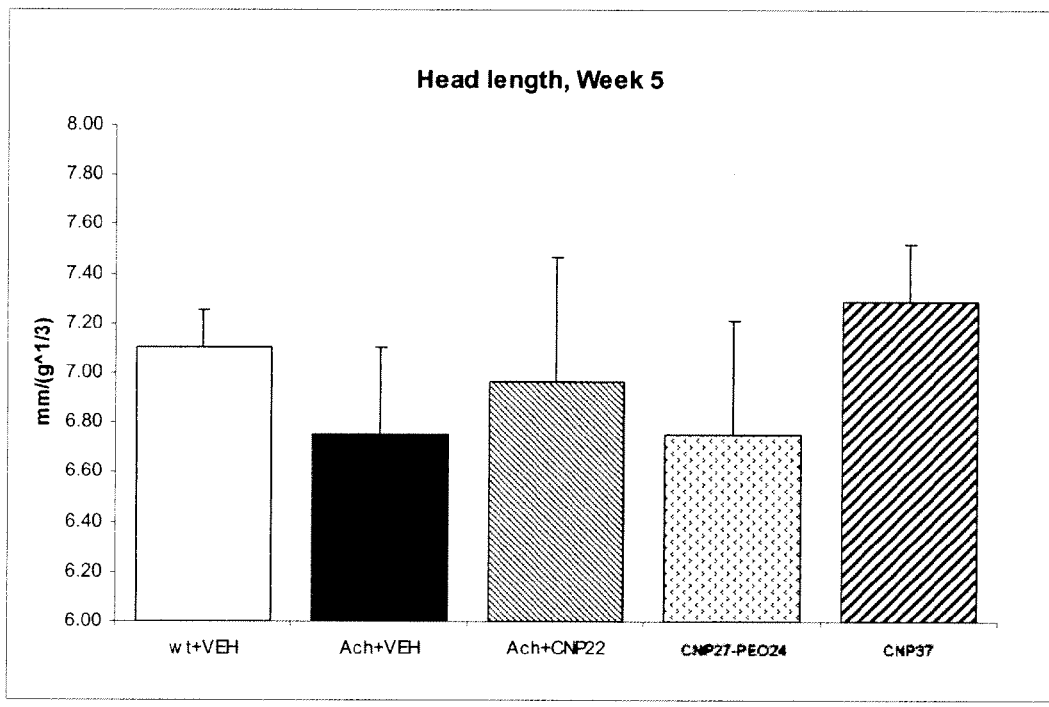
FIG. 56 shows the effect of CNP22, CNP37 and PEO24-GANRR-CNP22(K4R) (SEQ ID NO: 36) on head length in FGFR3$^{ach}$ mice (p<0.01 one-tailed t-test, unequal variance).
Figure 57:
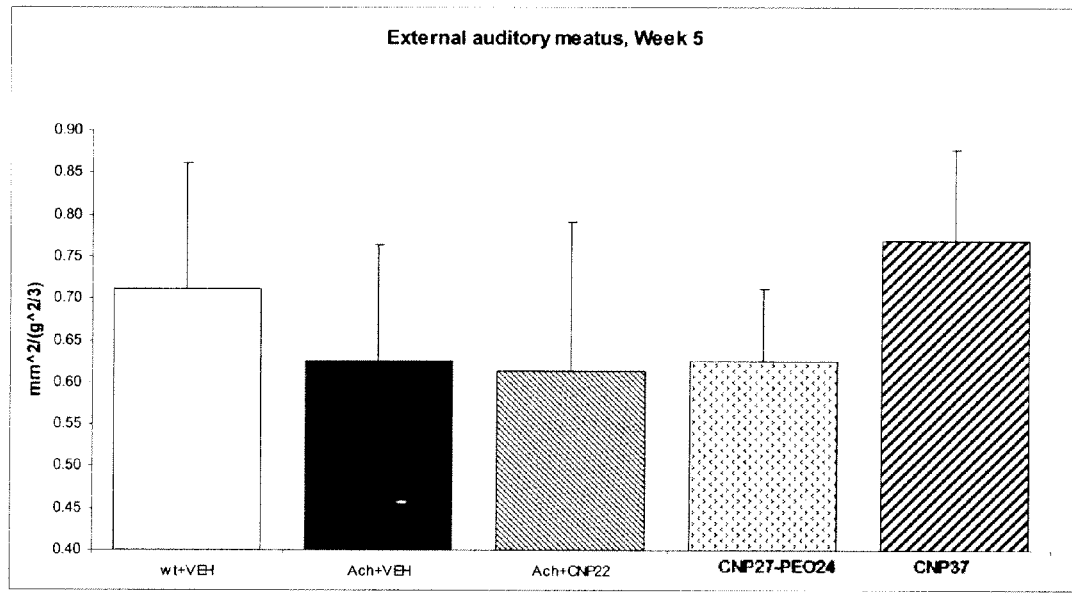
FIG. 57 shows that treatment of FGFR3$^{ach}$ mice with CNP37 increases the size of the external auditory meatus (EAM) (P=0.03, one-tailed t-test, unequal variance).
Figure 58:
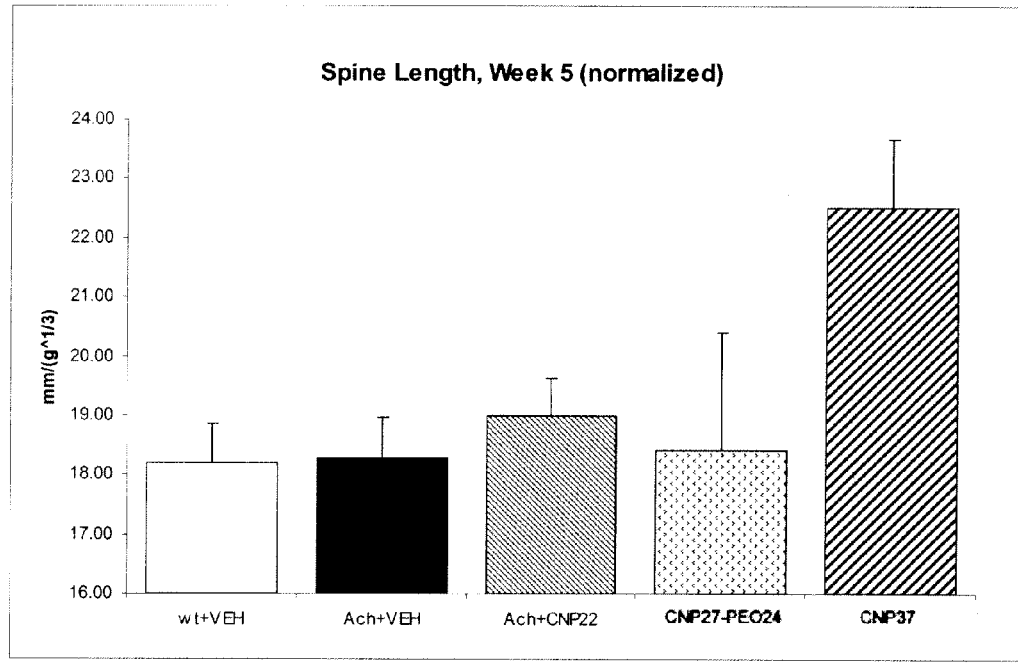
FIG. 58 shows the effect of CNP22, CNP37 and PEO24-GANRR-CNP22(K4R) (SEQ ID NO: 36) on spinal length in achondroplasic mice, expressed as extension of vertebral bodies (e.g., lumbar vertebra 5).

Treatment of FGFR3$^{ach}$ mice with CNP37 by once daily s.c. injection for 5 weeks resulted in significantly increased body length (FIG. 51), tail length (FIG. 52), distal bone (ulna and tibia) lengths (FIGS. 53A and B), and proximal bone (humerus and femur) lengths (FIGS. 54A and B). Moreover, treatment with CNP37 increased the head length (FIG. 56), area of the external auditory meatus (FIG. 57), and spine length (FIG. 58) via extension of the vertebral bodies. Additionally, treatment with CNP37 corrected rhizomelia (disproportion of the length of the proximal limbs) of FGFR3$^{ach}$ mice, i.e., restored proportional growth of proximal bones, as assessed by the femur:tibia ratio (FIG. 55). Table 13 summarizes the percentage change in tail length, body (naso-anal) length, and bone (femur, tibia, humerus and ulna) lengths in FGFR3$^{ach}$ mice injected s.c. once daily with 200 nmol/kg of either CNP37 or PEO24-GANRR-CNP22(K4R) ("CNP27-PEO24") (SEQ ID NO: 36) for 5 weeks, relative to a value of 100% for FGFR3$^{ach}$ mice treated with vehicle only.

TABLE 13

|  | Tail | Naso-Anal | Femur | Tibia | Humerus | Ulna |
|---|---|---|---|---|---|---|
| CNP37 | 115%** | 109%** | 112%** | 107%** | 105%* | 106%** |
| CNP27-PEO24 | 100% | 99% | 100% | 102% | 100% | 101% |

**$p < 0.01$,
*$p < 0.05$

The results of these studies show that CNP37 can stimulate spinal and long bone growth, help to correct rhizomelia by preferentially increasing the length of the femur over the tibia, and help to restore craniofacial proportions in FGFR3$^{ach}$ mice. These results indicate that CNP37 and potentially other CNP variants may be effective in correcting the symptoms of achondroplasia and treating subjects having defects in bone growth or in need of increased bone growth.

Example 14

Measurement of Biomarkers and Evaluation of Immunogenicity in Wild-Type and Achondroplastic Mice Measurement of Biomarkers After CNP Administration The levels of bone growth biomarkers were measured in wild-type and achondroplastic (FGFR3$^{ach}$) mice.

Transgenic FVB FGFR3$^{ach}$ mice (a mouse model of mild achondroplasia) were treated daily for 5 weeks by subcutaneous injection with either vehicle (30 mM acetic acid/acetate buffer, 1% benzyl alcohol, 10% sucrose, pH 4.0), CNP22, CNP37 or PEO24-GANRR-CNP22(K4R) ("CNP27-PEO24") (SEQ ID NO: 36) at 200 nmol/kg for each CNP compound, as described above. Plasma and serum were collected during the study. Harvested plasma was stored with 10× protease inhibitor at −80° C. until analysis. cGMP levels were measured 15 minutes post-injection on Day 36 from K2-ETDA plasma collection tubes. Fragments of cleaved collagen type II (cartilage-associated biomarkers), osteocalcin (bone-associated biomarker), and IgG (relating to immunogenicity) were measured from terminal bleed serum at the end of the study (Day 37). cGMP was measured using a commercially available ELISA kit (Cayman Chemical Co., Cat. No. 581021.1), cleaved collagen type II (Cartilaps) was measured using a commercially available kit from Immunodiagnostic Systems (Cat. No. 3CAL4000), and osteocalcin was measured using a commercially available kit from Biomedical Technologies Inc. (Stoughton, Mass.).

Figure 59:
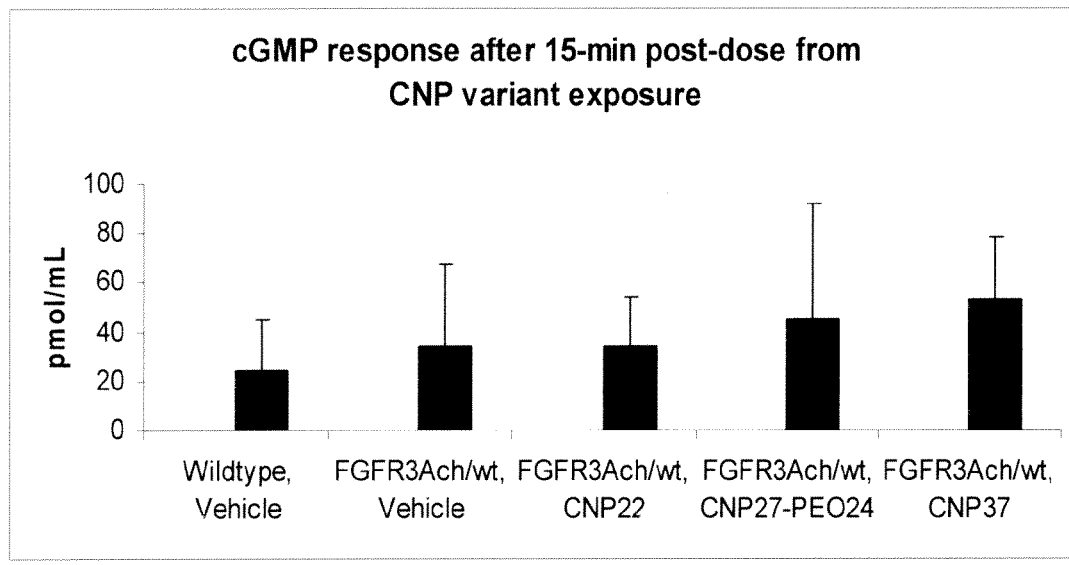
FIG. 59 shows that treatment of FGFR3$^{ach}$ mice with CNP37 or PEO24-GANRR-CNP22(K4R) (SEQ ID NO: 36) results in increased cGMP plasma levels 15-min post-dose.
Figure 60:
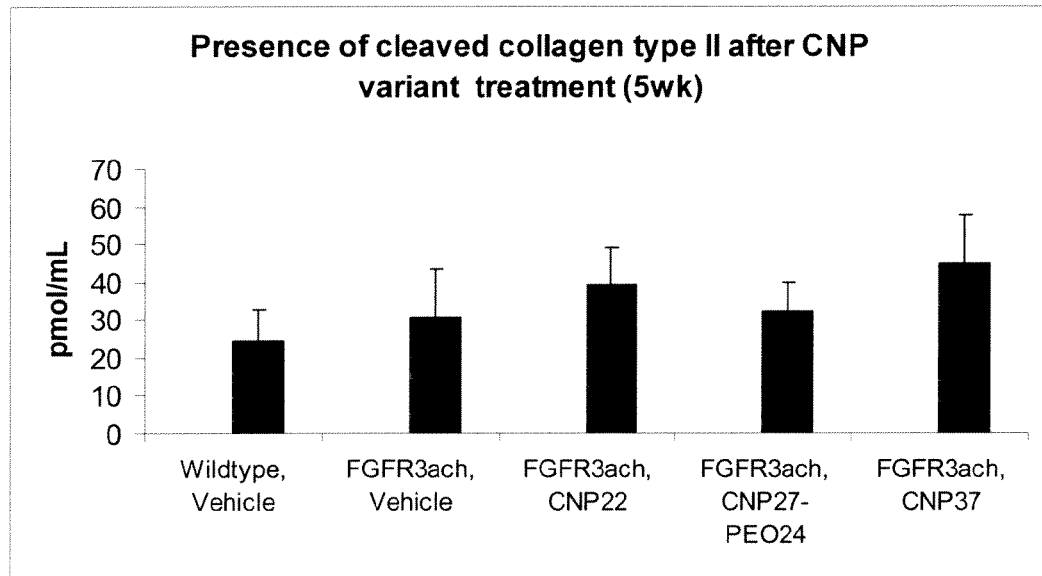
FIG. 60 illustrates the serum levels of cleaved collagen type II in FGFR3$^{ach}$ mice treated 5 weeks with CNP22, CNP37 or PEO24-GANRR-CNP22(K4R) (SEQ ID NO: 36).
Figure 61:
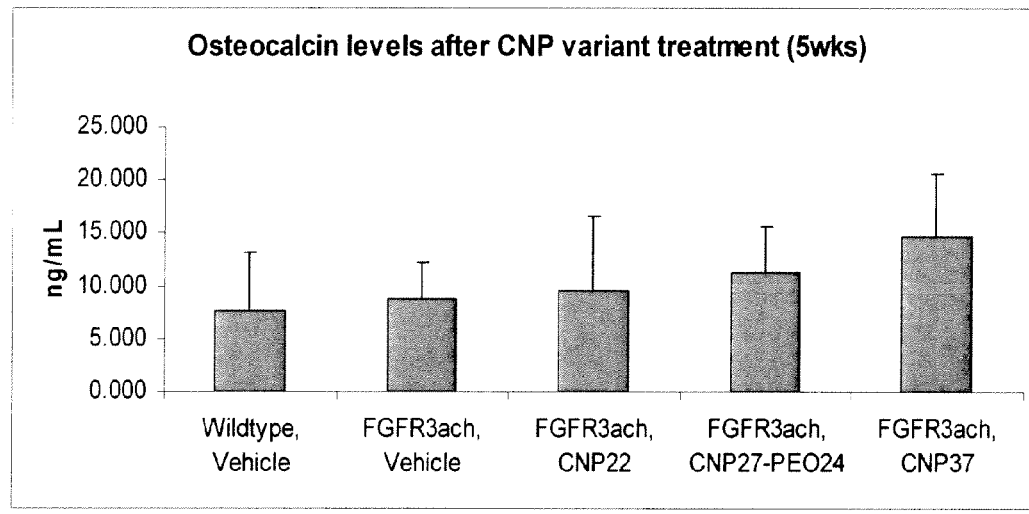
FIG. 61 shows the serum levels of osteocalcin in FGFR3$^{ach}$ mice treated 5 weeks with CNP22, CNP37 or PEO24-GANRR-CNP22(K4R) (SEQ ID NO: 36).

FIG. 59 shows an increase in cGMP plasma levels in FGFR3$^{ach}$ mice treated with CNP37 or PEO24-GANRR-CNP22(K4R) (SEQ ID NO: 36) compared to vehicle. FIGS. 60 and 61 show that administration of CNP37 resulted in the greatest elevation of serum levels of cleaved collagen type II and osteocalcin. These results indicate that administration of the CNP peptides, in particular CNP37, to FGFR3$^{ach}$ mice led to increased levels of bone growth markers, suggesting increased bone formation and growth in CNP peptide-treated FGFR3$^{ach}$ mice.

For evaluation of biomarkers in wild-type mice, wild-type FVB mice were treated daily for 5 weeks by subcutaneous injection with either vehicle (30 mM acetic acid/acetate buffer, 1% benzyl alcohol, 10% sucrose, pH 4.0), 200 nmol/kg G-CNP37, 200 nmol/kg PEO12-GANRR-CNP22(K4R) ("CNP27-PEO12") (SEQ ID NO: 36), or 20 nmol/kg or 70 nmol/kg Pro-Gly-CNP37. Plasma and serum were collected during the study. Harvested plasma was stored with 10× protease inhibitor at −80° C. until analysis. cGMP levels were measured 15 minutes post-injection on Day 36 from K2-ETDA plasma collection tubes. The levels of cleaved collagen type II, bone-specific alkaline phosphatase, and IgG (relating to immunogenicity) were measured from terminal bleed serum at the end of the study (Day 37). cGMP and cleaved collagen type II (Cartilaps) were measured as described above. Bone-specific alkaline phosphatase was measured using a commercially available kit (Cusabio, Cat. No. CSB-E11914m).

Figure 62:
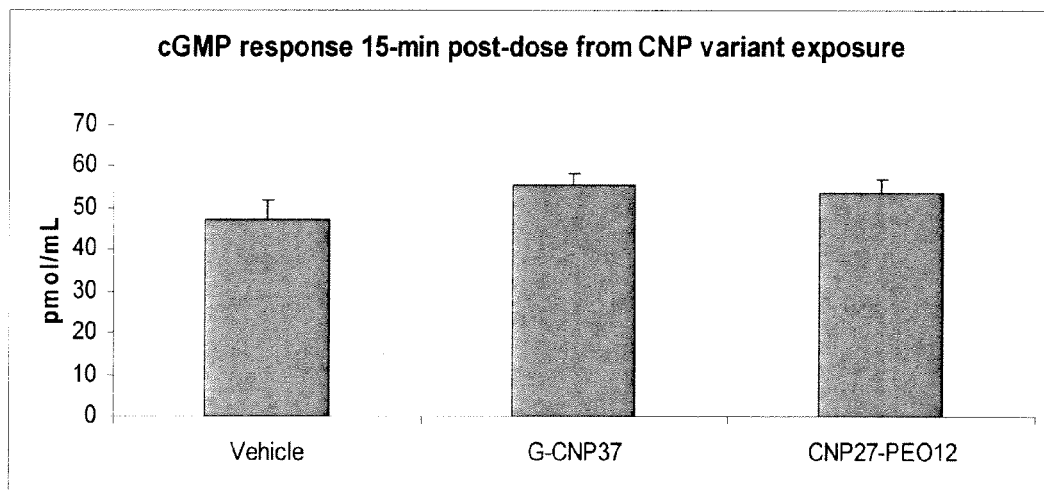
FIG. 62 shows cGMP plasma levels 15-min post-dose from wild-type mice treated with Gly-CNP37 or PEO12-GANRR-CNP22(K4R) (SEQ ID NO: 36) (p<0.05).
Figure 63:
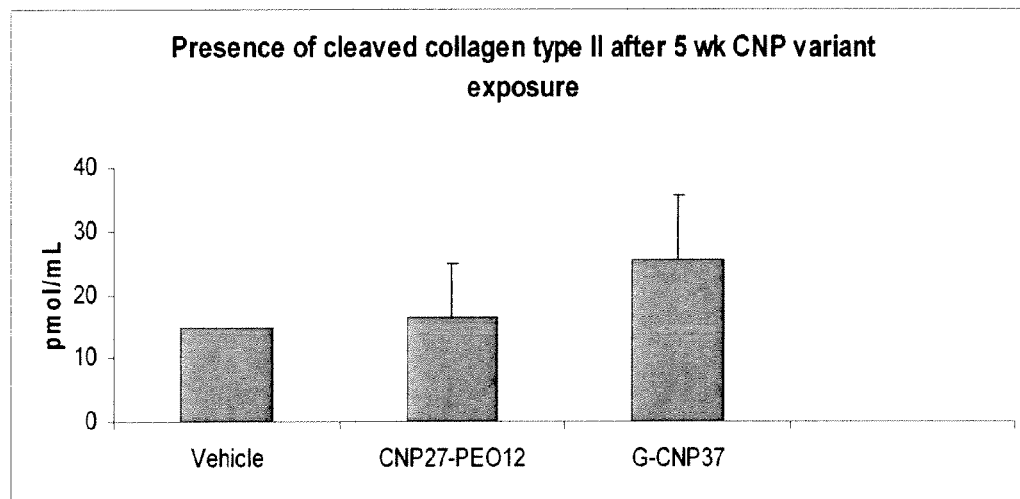
FIG. 63 shows the serum levels of cleaved collagen type II in wild-type mice treated 5 weeks with Gly-CNP37 or PEO12-GANRR-CNP22(K4R) (SEQ ID NO: 36).

Administration of G-CNP37 significantly increased (p<0.05) the level of cGMP (FIG. 62) and particularly the level of fragments of cleaved collagen type II (FIG. 63) in wild-type mice compared to vehicle. The significantly higher level of collagen type II fragments resulting from administration of G-CNP37 indicates turnover of the cartilage matrix, suggesting that G-CNP37 stimulated new bone formation in growing bones in wild-type mice.

Figure 64:
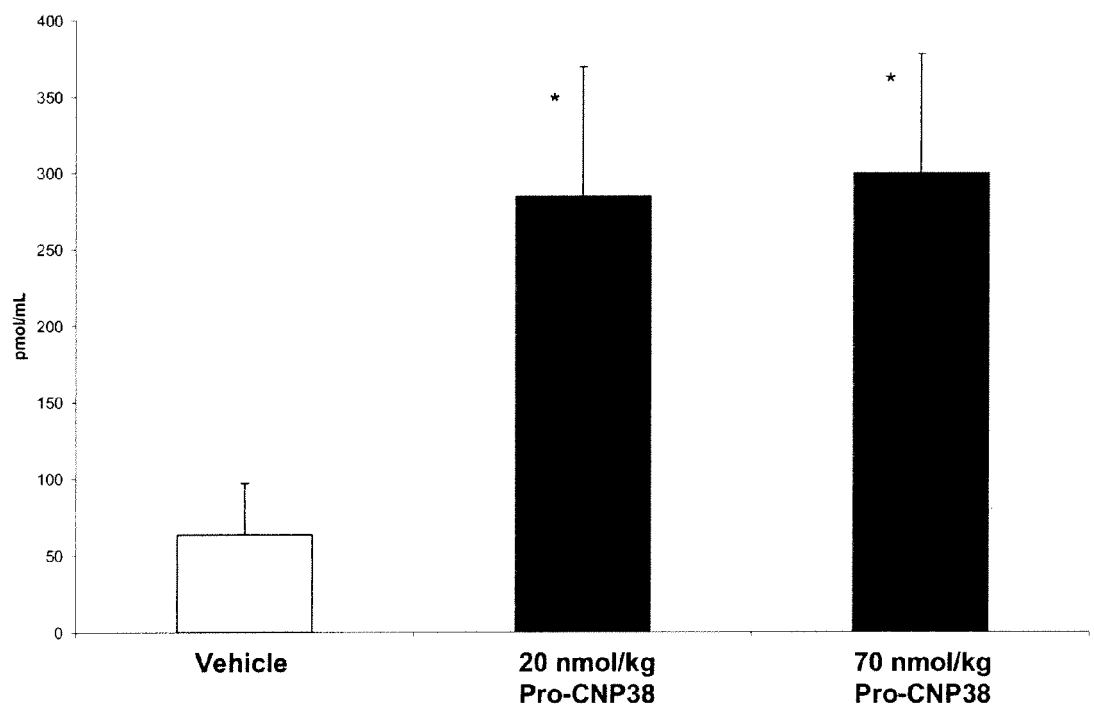
FIGS. 64-66 display the levels of cGMP, cleaved collagen type II and alkaline phosphatase after administration of vehicle or 20 nmol/kg or 70 nmol/kg Pro-Gly-CNP37 ("Pro-CNP38") to wild-type mice.
Figure 65:
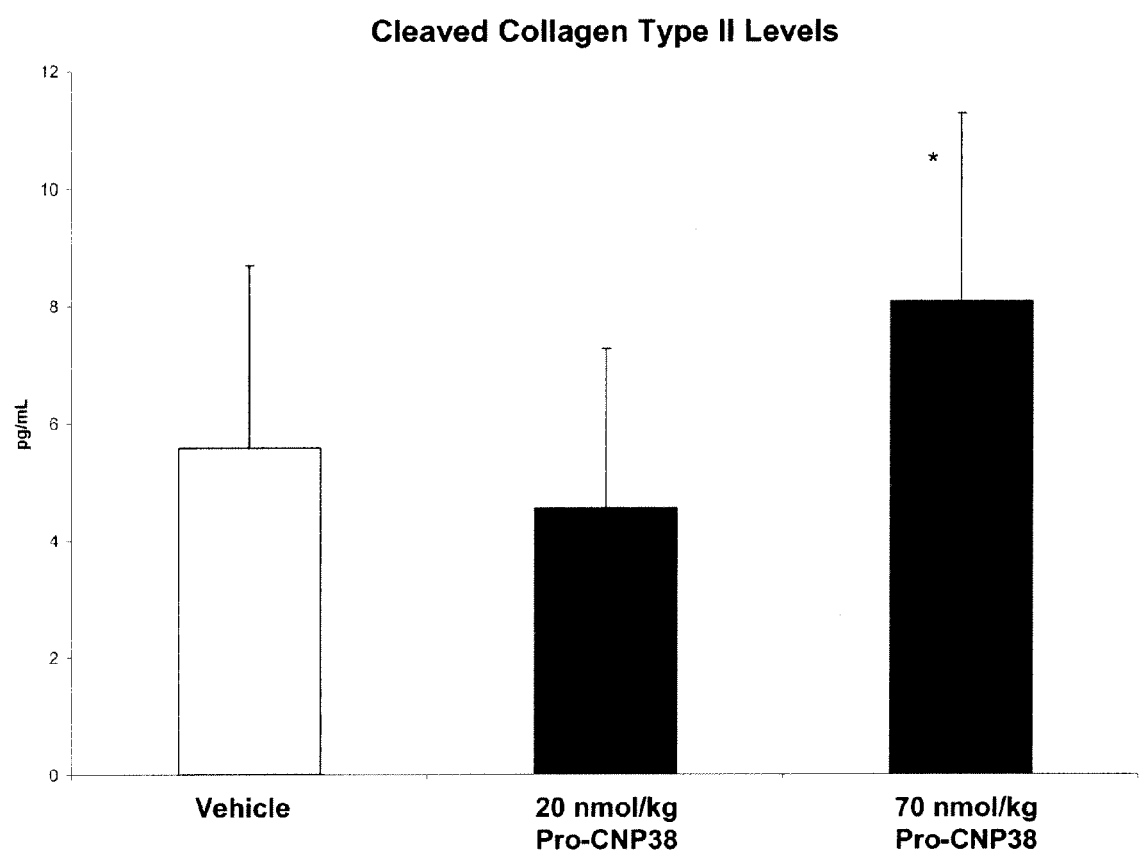
Figure 66:
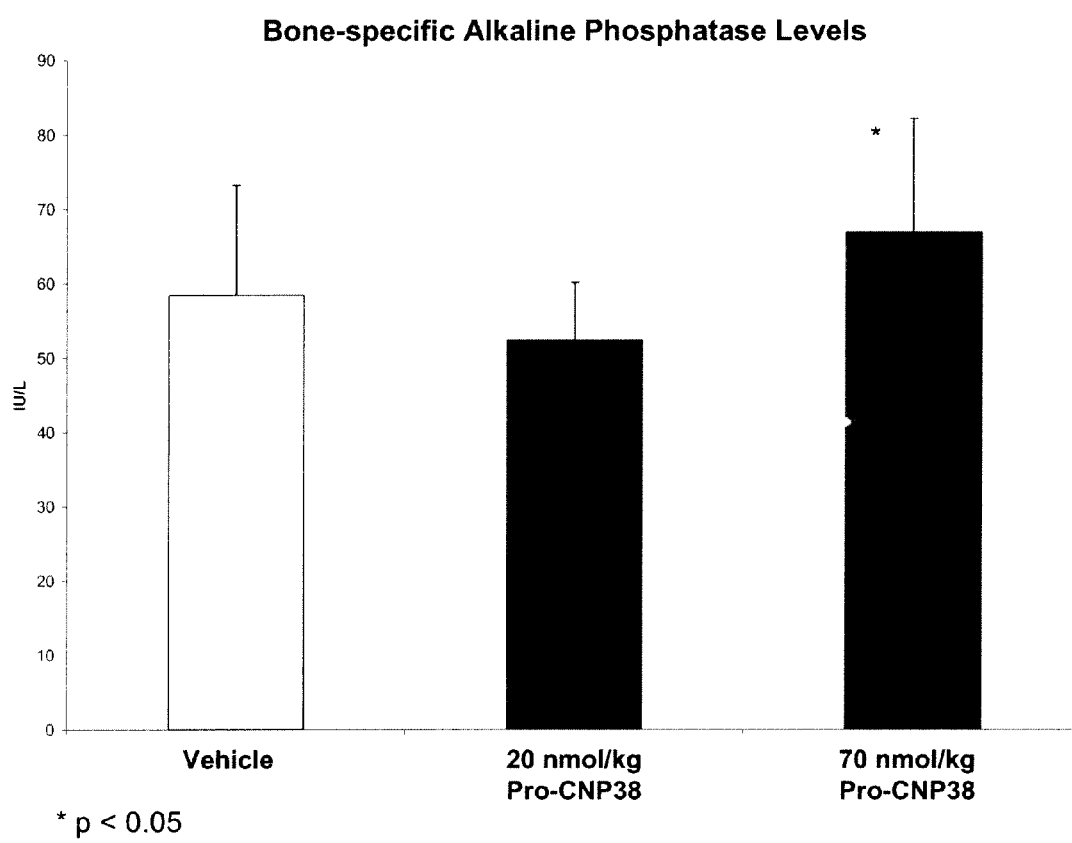

Both doses of Pro-Gly-CNP37 ("Pro-CNP38"), 20 and 70 nmol/kg, significantly increased (p<0.05) plasma cGMP level 15 minutes after administration compared to wild-type mice treated with vehicle (FIG. 64). Administration of the higher dose (70 nmol/kg) of Pro-Gly-CNP37 also significantly increased (p<0.05) the level of cleaved collagen type II compared to vehicle-treated mice (FIG. 65), suggesting that the higher dose of Pro-Gly-CNP37 stimulated cartilage matrix turnover prior to new bone formation in wild-type mice. Furthermore, administration of the higher dose (70 nmol/kg) of Pro-Gly-CNP37 increased (p<0.05) the level of bone-specific alkaline phosphatase compared to vehicle-treated mice (FIG. 66), suggesting that the higher dose of Pro-Gly-CNP37 increased bone remodeling in wild-type mice.

Evaluation of Immunogenicity of CNP Variants

Because the CNP variants are peptide derivatives, it is possible that administration of the peptides may lead to an immunogenic response in vivo. To assess whether an immune response occurred after successive administrations of CNP variant, measurement of serum antibody levels was performed.

An IgG assay was performed to assess whether an IgG immune response was triggered by 5 week exposure of achondroplastic FGFR3$^{ach}$ mice to CNP22, CNP37 or PEO24-GANRR-CNP22(K4R) ("CNP27-PEO24") (SEQ ID NO: 36). IgG is the most predominant immunoglobulin in mouse and human serum and is produced as part of the secondary immune response to an antigen. The IgG response to administration of the CNP peptides was determined as follows. 96-well plates were coated with 100 ng/mL CNP22, CNP37 or PEO24-GANRR-CNP22(K4R) (SEQ ID NO: 36) in BupH PBS buffer (Pierce/Thermo, Cat. No. 28372, Rockford, Ill.). After overnight incubation, plates were blocked with Casein-PBS blocking buffer (Pierce/Thermo, Cat. No. 37528) for two hours at room temperature with shaking at 300 rpm. After washing with wash buffer (1×PBS with 0.05% Tween), diluted serum samples from a terminal bleed (diluted 1:25) were added to the plate. Positive and negative controls were also loaded onto the plate. Positive control was 1:25 diluted serum (pooled from 6 individual FVB mice) with anti-CNP22 antibody added (Bachem rabbit anti-CNP22 IgG, Cat. No. T-4222) at 1:1000 dilution. Negative control was the diluted pooled serum. After two hours of incubation, the plates were washed and secondary antibody diluted in blocking buffer was added to the wells. For the mouse serum samples, anti-mouse IgG Fcγ (peroxidase-conjugated affinipure goat anti-mouse IgG, Fcγ fragment, Cat. No. 115-035-071, Jackson Immunoresearch, West Grove, Pa.) was added at a 1:10,000 dilution. For the positive and negative controls, anti-rabbit IgG-HRP (Santa Cruz Biotechnology, Cat. No. SC-2004, Santa Cruz, Calif.) was added to blocking buffer. After two hours of incubation at room temperature with shaking at 300 rpm, plates were washed with wash buffer. 100 uL of TMB (One-step TMB, Pierce/Thermo, Cat. No. 34022) was added to all wells. Plates were incubated at room temperature for 15 minutes with shaking at 300 rpm. Colorimetric reactions were stopped by the addition of 100 uL of 2 N $H_2SO_4$. Plates were read at 450 nm (Spectramax, Molecular Devices, Sunnyvale, Calif.) and data was analyzed using SoftMax Pro software (Molecular Devices).

Serum samples from FGFR3$^{ach}$ mice treated with CNP22 or PEO24-GANRR-CNP22(K4R) (SEQ ID NO: 36) indicated no positive IgG immune response in any of the mice. Only one out of nine CNP37-treated FGFR3$^{ach}$ mice showed a slightly positive IgG response.

The immunogenic response of wild-type mice administered G-CNP37, PEO12-GANRR-CNP22(K4R) (SEQ ID NO: 36) or Pro-Gly-CNP37, as measured by an increase in serum IgG level, was also assessed by examining terminal bleed serum samples as described above. None of the wild-type mice treated with PEO12-GANRR-CNP22(K4R) (SEQ ID NO: 36) or Pro-Gly-CNP37 (20 or 70 nmol/kg) showed a positive IgG immune response, and only one out of six wild-type mice administered G-CNP37 showed a slightly positive IgG response.

Measurement of Biomarkers Under Different CNP Dosing Regimens

Wild-type FVB mice were treated daily for 9 weeks by subcutaneous (s.c.) injection of vehicle (30 mM acetic acid/acetate buffer, 1% benzyl alcohol, 10% sucrose, pH 4.0) or Pro-Gly-CNP37 ("Pro-CNP38") under different dosing regimens. Group 1 included vehicle-treated mice injected s.c. daily for 9 weeks followed by 1 week of no treatment. Group 2 included mice treated with Pro-Gly-CNP37 (20 nmol/kg) once daily for 1 week, followed by three doses per week for 8 weeks, followed by 1 week of no treatment. Group 3 contained mice treated with Pro-Gly-CNP37 (20 nmol/kg) once daily in alternate weeks (weeks 1, 3, 5, 7 and 9), with 1 week of no treatment following each week of treatment. Group 4 contained mice treated with Pro-Gly-CNP37 (5 nmol/kg)

once daily for 9 weeks followed by 1 week of no treatment. Finally, Group 5 included mice treated with Pro-Gly-CNP37 (5 nmol/kg) once daily for 5 weeks without any week of no treatment. Terminal bleed serum was collected from the mice, and cleaved collagen type II, total alkaline phosphatase and total antibody levels were measured therefrom. Cleaved collagen type II levels were measured as described above. Total alkaline phosphatase levels, predominantly from the liver and bones, were measured with the assistance of a veterinary diagnostic laboratory testing facility (Antech).

A total antibody assay was developed to evaluate potential immune response. The platform used for the total antibody assay was an electrochemiluminescent assay (ECLA). The ECLA platform utilizes a biotin-labeled drug (here, biotin-Pro-Gly-CNP37) and a ruthenium-labeled drug (here, Ru—Pro-Gly-CNP37). The biotin-labeled drug binds to a streptavidin-coated plate that contains electrodes, and the ruthenium-labeled drug functions as the detection component of the assay, as ruthenium can be electrochemically stimulated. A drug-specific antibody (here, a CNP-specific antibody) binds to the biotin-labeled drug and the ruthenium-labeled drug and "bridges" the two labeled drugs. Among the advantages of the ECLA platform, any isotype of antibody (IgG, IgM, etc.) can be detected, and the ECLA assay is species-independent.

The total antibody assay was performed as follows. Pro-Gly-CNP37 was labeled with biotin in a 4:1 challenge ratio, and Pro-Gly-CNP37 was also labeled separately with ruthenium in a 10:1 challenge ratio. Both separate labeling reactions were quenched by the addition of glycine, and the samples from both reactions were buffer-exchanged to PBS. Low and high QCs were prepared by using commercially available anti-CNP22 antibody (Bachem rabbit anti-CNP22 IgG, Cat. No. T-4222) added at low and high concentrations to 5% diluted FVB mouse serum. Mouse serum samples were diluted to 5% using assay diluent (5% BSA in PBS, MSD Cat. No. R93AA-1). A working solution was prepared by adding biotin-labeled Pro-Gly-CNP37 to assay diluent, then adding ruthenium-labeled Pro-Gly-CNP37 to assay diluent, and then combining the two solutions together. Twenty-five uL of low and high QCs were loaded onto the plate as controls. Then 25 uL of sample was added to a non-binding 96-well plate, followed by the addition of 50 uL of working solution to all wells. Samples and QCs were incubated with the working solution at room temperature for 2 hours with shaking at 350 rpm. In the meantime, an MSD streptavidin plate (MSD Cat. No. L13SA-1) was blocked with blocking buffer (MSD Cat. No. R93AA-1) at room temperature for 2 hours with shaking at 350 rpm. At the end of the two hour incubation, the MSD streptavidin plate was washed, and then 50 uL of sample or QC was transferred to the MSD plate. The plate was then incubated at room temperature for 1 hour with shaking at 350 rpm. At the end of the 1 hour incubation, the MSD plate was washed and 150 uL of 2× read buffer (MSD Cat. No. R92TC-2) was added to the plate. The plate was read using an MSD PR400 machine.

Figure 67:
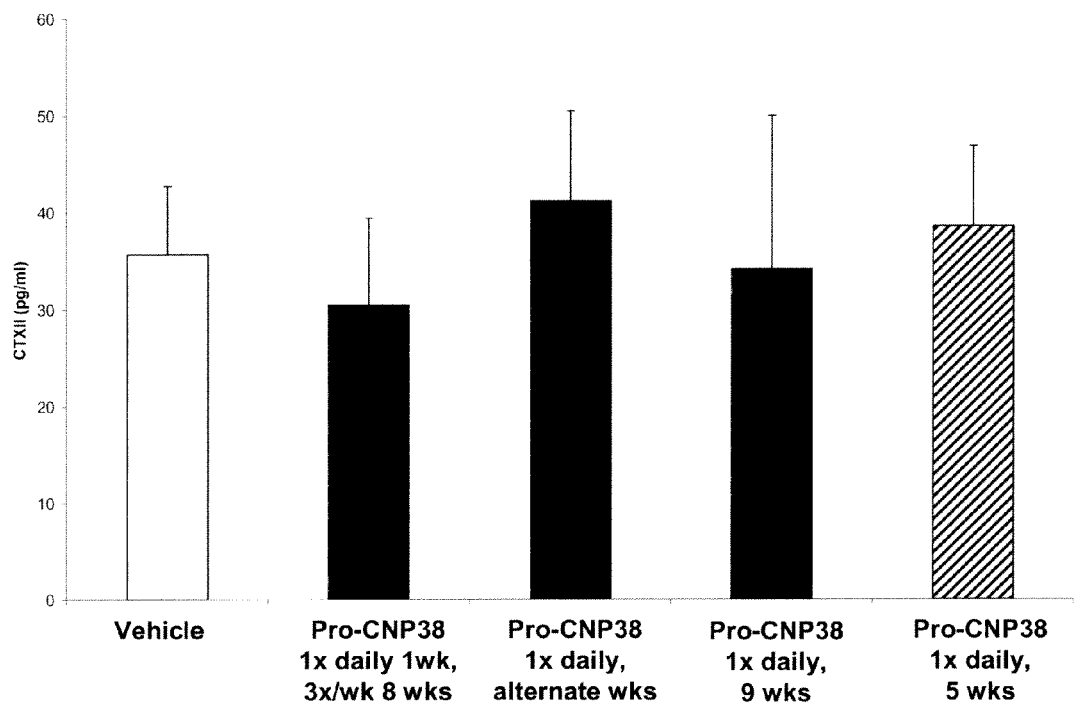
FIGS. 67 and 68 depict cleaved collagen type II and total alkaline phosphatase levels after administration of vehicle or Pro-Gly-CNP37 ("Pro-CNP38") under different dosing regimens.
Figure 68:
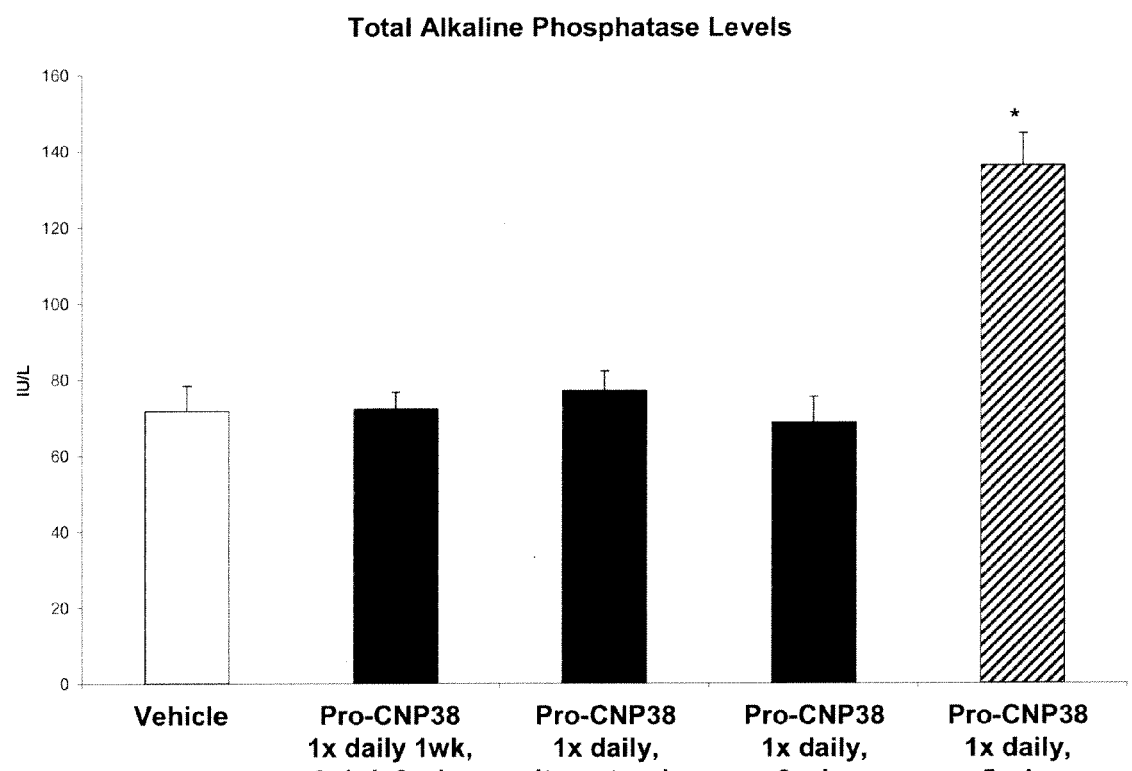

All five groups of mice exhibited substantially comparable levels of cleaved collagen type II (FIG. 67). Treatment of the mice in Group 5 with 5 nmol/kg Pro-Gly-CNP37 once daily for 5 weeks significantly increased ($p<0.001$) total alkaline phosphatase level (FIG. 68), which is indicative of bone remodeling. Serum samples from each of the four groups of mice treated with Pro-Gly-CNP37 did not show a positive antibody response in the total antibody assay.

Not to be bound by any theory, there are possible explanations as to why the four groups of CNP-treated mice did not exhibit statistically significant difference in cleaved collagen type II level compared to vehicle-treated mice, and why only the CNP-treated mice in Group 5 exhibited a statistically significant increase in total alkaline phosphatase level compared to vehicle-treated mice. It is possible that because the vehicle-treated mice in the study were also growing, cleaved collagen type II and alkaline phosphatase, which are biomarkers of growth, were also produced in the vehicle-treated mice. In addition, there was a one week period of no treatment for the mice in each of Groups 1 to 4, which possibly diluted out any changes in the cleaved collagen type II and total alkaline phosphatase levels between the CNP-treated mice in Groups 1-3 and the vehicle-treated mice. There was no period of no treatment for the CNP-treated mice in Group 5, and those mice exhibited significantly ($p<0.001$) greater total alkaline phosphatase level compared to vehicle-treated mice.

Example 15

Dose Responses of CNP Variants in Mice

The effects of varying doses of CNP variants were assessed in wild type FVB mice.

For the dose study, in two separate studies (S1 and S2), groups of 10 mice were administered Pro-Gly-wtCNP37 ("Pro-CNP38") at 20 and 70 nmol/kg subcutaneously once daily for 36 injections. Tail length and body weight were measured over the course of treatment. Animals were sacrificed at the end of the experiment and bone length assessed.

Figure 69:
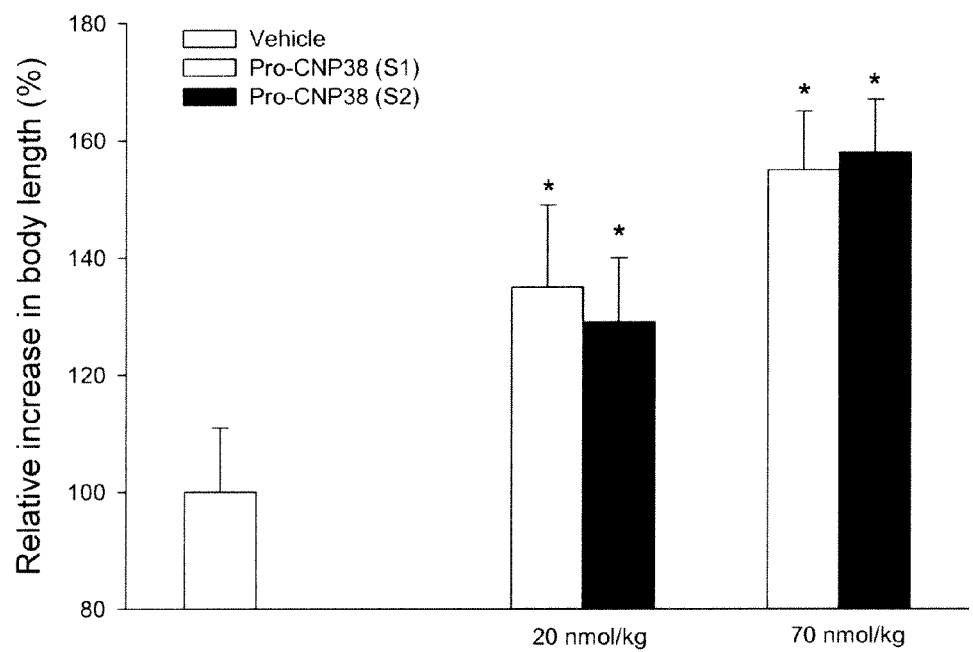
FIG. 69 illustrates the relative increase in body length of Pro-Gly-CNP37 ("Pro-CNP38") and vehicle treated animals in two separate studies (S1 and S2) at Day 37 vs Day 1.

Tail length of vehicle treated animals was approximately 8 cm at day 36, whereas animals treated with 20 nmol/kg Pro-CNP38 exhibited tail length of approximately 8.75 cm and 70 nmol/kg Pro-CNP38 increased tail length to approximately 9.5 cm. Administration of Pro-CNP38 in either dose induces a significant ($p<0.05$) relative increase in total body length compared to control treated animals, demonstrating approximately a 130% increase in growth velocity at 20 nmol/kg and approximately a 160% increase in growth velocity at 70 nmol/kg Pro-CNP38 (FIG. 69).

Treatment with Pro-CNP 38 also significantly increased bone length in most of the long bones assessed as well as total naso-anal (body length) of the animal. Table 14 is representative of the relative % increase in bone length in treated animals in comparison to vehicle treated animals.

TABLE 14

| Pro-CNP38 | Tail | Naso-Anal | LV4-6 | Femur | Tibia | Humerus | Ulna |
|---|---|---|---|---|---|---|---|
| 20 nmol/kg | 8%* | 7%* | 10%* | 7%* | 4%* | 3%* | 3% |
| 70 nmol/kg | 16%* | 13%* | 13%* | 10%* | 7%* | 4%* | 5%* |

Relative % increase,
*$p < 0.05$ ANNOVA (Dunnett's) v vehicle

Figure 70:
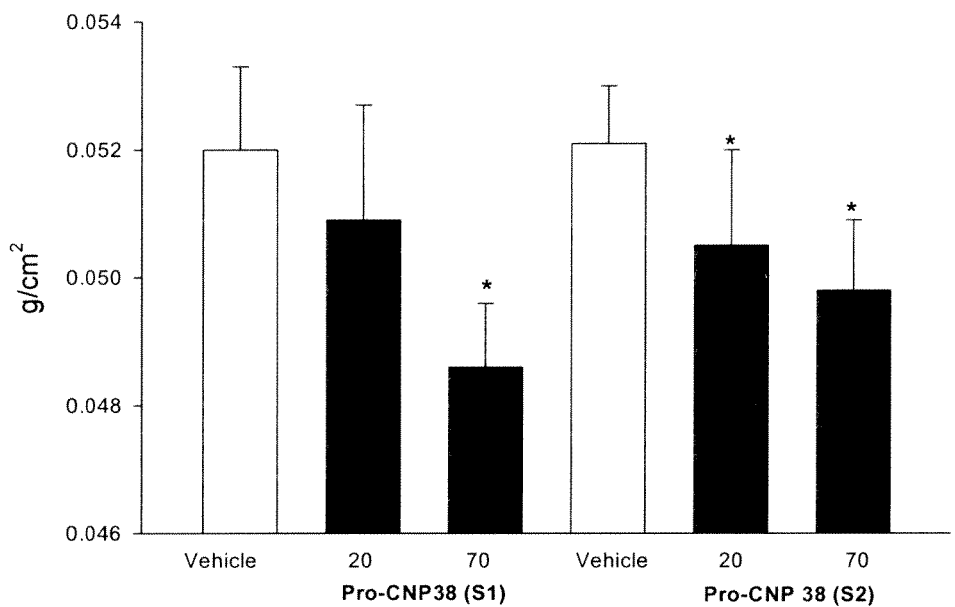
FIGS. 70A and B show changes in bone mineral density (A) and bone mineral content (B) after administration of Pro-Gly-CNP37 ("Pro-CNP38").
Figure 70:
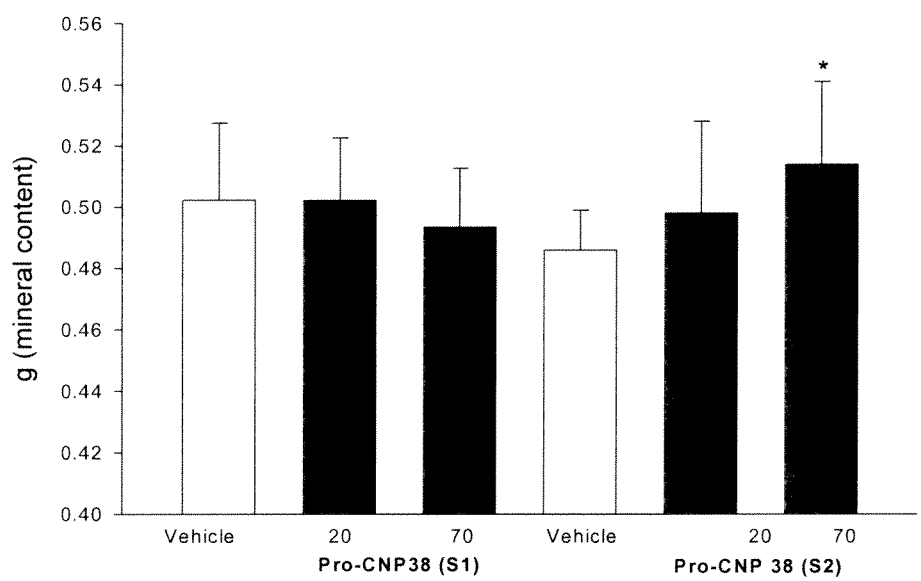

Bone mineral density (BMD) and bone mineral content (BMC) were also evaluated after administration of Pro-CNP38 at different doses. Results (FIG. 70) showed that administration of Pro-CNP38 at 70 nmol/kg significantly decreased bone mineral density (FIG. 70A) and increased bone mineral content (FIG. 70B), suggesting there is a delay in bone mineralization in treated animals, but the mineralization process itself is not adversely affected by treatment with CNP.

There were no significant changes in organ weight between Pro-CNP38 or vehicle treated animals.

Bioanalytical Studies of Dose Response in Mice

Bioanalytical studies were carried out to measure markers of CNP activity after in vivo administration of varying doses of Pro-CNP38. Plasma cGMP levels, serum levels of collagen type II and serum levels of alkaline phosphatase from in vivo samples were analyzed. Wild type mice were administered 20 and 70 nmol/kg Gly-wtCNP37 ("CNP38"), 20 and 70 nmol/kg Pro-Gly-wtCNP37 ("Pro-CNP38") and 70 and 200 nmol/kg of GHKSEVAHRFK-wtCNP27 ("HSA-CNP27") (SEQ ID NO: 144) subcutaneously once daily for 36 days. Plasma was collected 15 minutes after the last injection on day 36 and mice were sacrified 24 hr later. At sacrifice, terminal bleed serum was collected and used for biomarker analysis as described previously.

Figure 71:
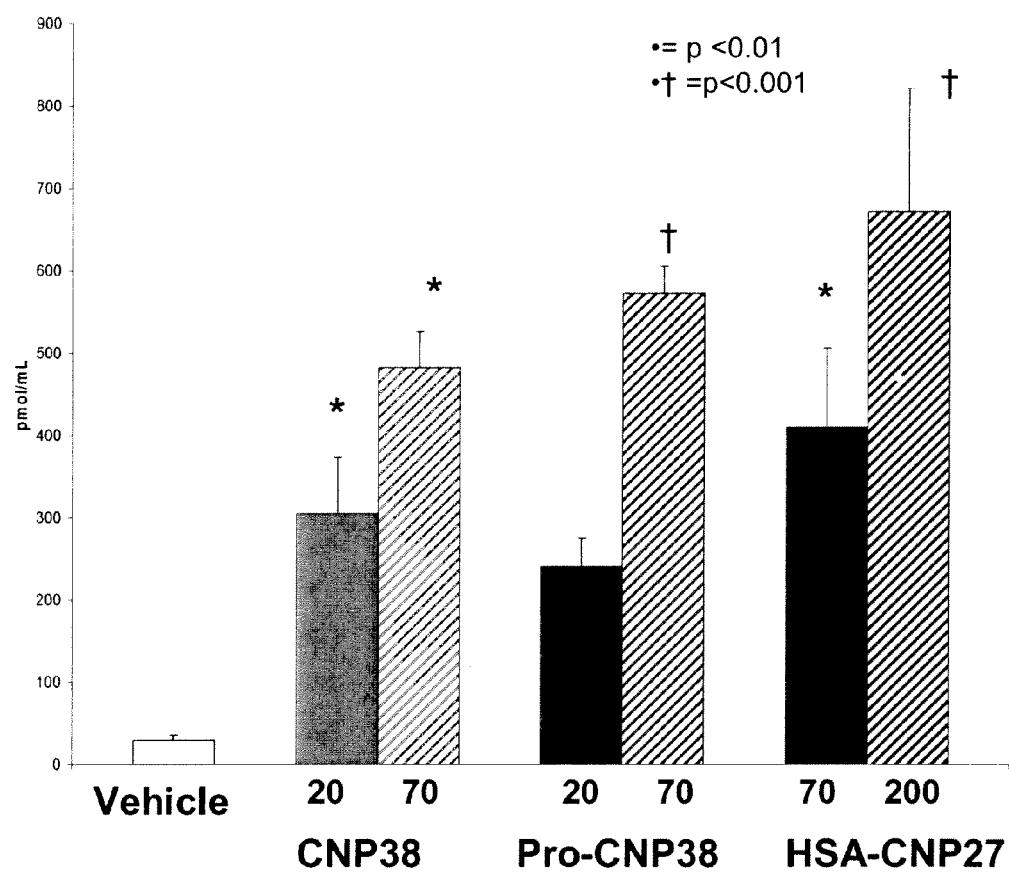
FIG. 71 shows plasma cGMP levels 15 min after the last subcutaneous dose of CNP variant, Day 36, where Gly-wtCNP37 is "CNP38", Pro-Gly-wtCNP37 is "Pro-CNP38", and GHKSEVAHRFK-wtCNP27 (SEQ ID NO: 144) is "HSA-CNP27" in FIGS. 71-73.

FIG. 71 shows that 20 nmol/kg CNP38 and 70 nmol/kg HSA-CNP27 signficantly increased plasma cGMP ($p<0.01$), raising plasma cGMP levels to approximately 300 pmol and 400 pmol, respectively. Adminsitration of 70 nmol/kg CNP38 increased cGMP to approximately 500 pmol ($p<0.01$), while administration of 70 nmol/kg Pro-CNP38 increased cGMP to approximately 575 pmol ($p<0.001$). Administration of 200 nmol/kg HSA-CNP27 increased cGMP to approximately 675 pmol ($p<0.001$).

Figure 72:
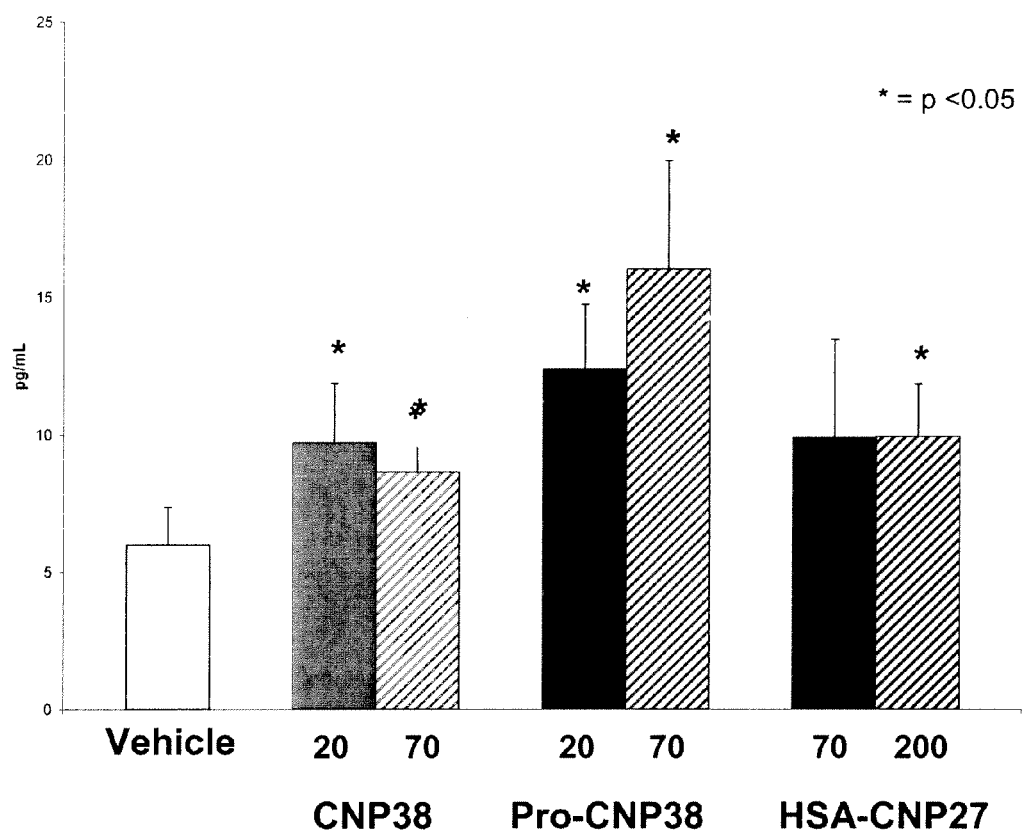
FIG. 72 shows serum levels of cleaved collagen type II from mice treated with Gly-CNP37, Pro-Gly-CNP37 or GHKSEVAHRFK-CNP27 (SEQ ID NO: 144).

CNP variants also significantly increased serum levels of cleaved collagen type II (FIG. 72). CNP38 at 20 nmol/kg increased collagen to approximately 9 pg/ml ($p<0.05$), CNP38 at 70 nmol/kg increased collagen to approximately 8 pg/ml ($p<0.05$), Pro-CNP38 at 20 nmol/kg increased collagen to approximately 12 pg/ml ($p<0.05$), Pro-CNP38 at 70 nmol/kg increased collagen to approximately 16 pg/ml ($p<0.05$), HSA-CNP27 at 70 nmol/kg increased collagen to approximately 10 pg/ml, and HSA-CNP27 at 200 nmol/kg increased collagen to approximately 10 pg/ml ($p<0.05$).

Figure 73:
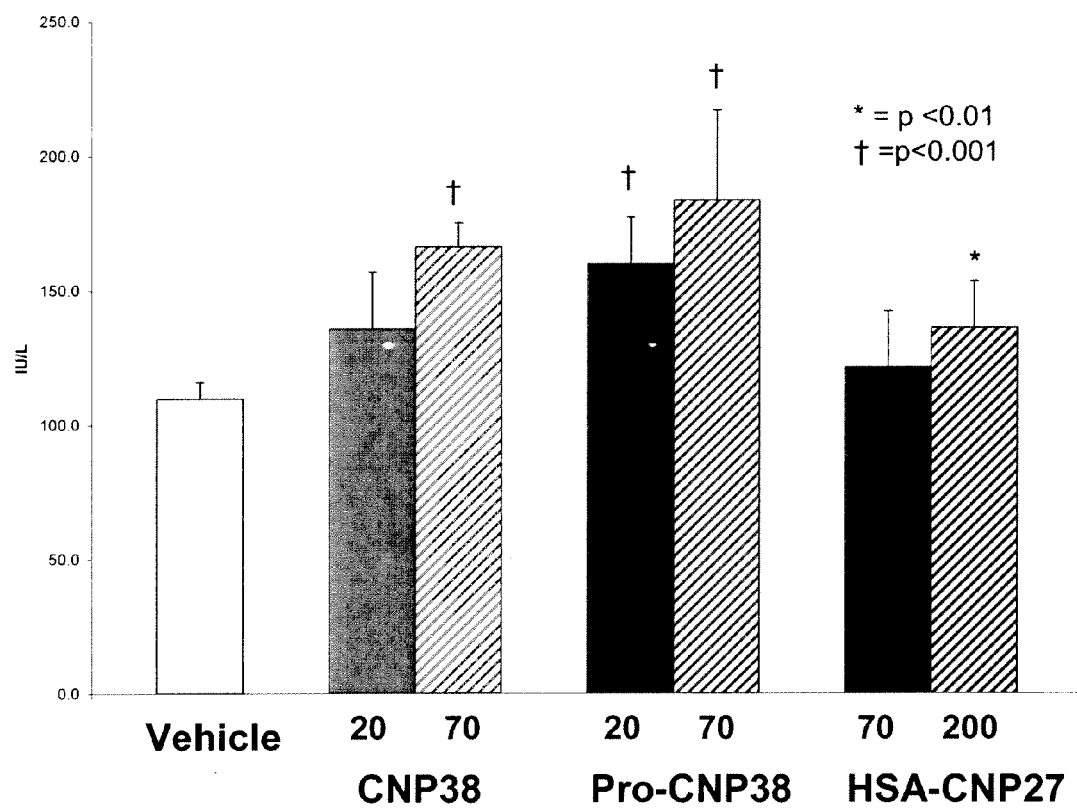
FIG. 73 shows serum levels of alkaline phosphatase from mice treated with Gly-CNP37, Pro-Gly-CNP37 or GHKSEVAHRFK-CNP27 (SEQ ID NO: 144).

Serum alkaline phosphatase (AP) levels also increased after administration of CNP variants (FIG. 73). CNP38 at 20 nmol/kg increased AP to approximately 130 IU/L, CNP38 at 70 nmol/kg increased AP to approximately 160 IU/L ($p<0.001$), Pro-CNP38 at 20 nmol/kg increased AP to approximately 155 IU/L ($p<0.001$), Pro-CNP38 at 70 nmol/kg increased AP to approximately 180 IU/L ($p<0.001$), HSA-CNP27 at 70 nmol/kg increased AP to approximately 120 IU/L, and HSA-CNP27 at 200 nmol/kg increased AP to approximately 140 IU/L ($p<0.01$). Table 15 illustrates the percent of total AP that is bone specific.

TABLE 15

|  | Total AP IU/L | Bone-specific AP IU/L | % of Total Alk Phos |
|---|---|---|---|
| Vehicle | 109.8 | 24.7 | 22.5 |
| CNP38 (20 nmol/kg) | 135.9 | 47.9 | 35.2 |
| CNP38 (70 nmol/kg) | 166.3 | 63.5 | 38.2 |
| Pro-CNP38 (20 nmol/kg) | 159.9 | 65.9 | 41.2 |
| Pro-CNP38 (70 nmol/kg) | 183.6 | 78.4 | 42.7 |
| HSA-CNP27 (20 nmol/kg) | 121.4 | 51.7 | 42.6 |
| HSA-CNP27 (70 nmol/kg) | 136.1 | 76.5 | 56.2 |

Analysis of anti-CNP antibodies showed that only HSA-CNP27 elicited an IgG antibody response in mice.

The results above illustrate that administration of CNP variants increases the concentration of collagen type II and alkaline phosphatase in serum, indicating that CNP increases factors relevant for increased bone growth, and suggest that administration of CNP variants at doses as low as 20 nmol/kg are effective in increasing bone growth in vivo.

cGMP Response After Different Dose Regimens

Bioanalytical analysis was also assessed at different times after administration of Pro-Gly-wtCNP37 ("Pro-CNP38") to wild type CD-1 mice, 8-10 weeks old, (n=3 per treatment group). Pro-CNP38 was given in a single subcutaneous dose of 200 nmol/kg and levels of cGMP measured at 15 minutes, 3 hours, 1 day, 2 days and 3 days post injection in the plasma, epiphysis, cortical bone (marrow removed), lung and brain. Blood was collected on K2EDTA. Tibial and femoral epiphysis and cortical bone, ear pinna, brains, kidneys and lungs were harvested, placed in boiling water for 5 minutes, then frozen to −70° C. Both plasma and tissue were assayed for cGMP (Cayman Chemical cyclic GMP ELISA kit).

Results showed that cGMP levels increased at 15 minutes post injection in plasma (approximately 1300 pmol/ml) and epiphysis (approximately 2.5 pmol/ml/mg). By 3 hours, plasma levels had decreased approximately to control levels, while levels in the epiphysis were approximately 3 fold lower than cGMP levels at 15 minutes post injection, but higher than control levels. Levels of cortical bone increased to approximately 0.5 pmol/ml/mg at 15 minutes and remained at this level at 3 hours. Levels of cGMP at all timepoints were back to control levels by 1 day after injection. Little to no cGMP was detected in lung or brain at any timepoint.

cGMP levels were also measured in mice administered multiple injections of Pro-CNP38. Groups of mice (n=3) were given Pro-CNP38 as follows: 20 nmol/kg single dose, subcutaneously; 200 nmol/kg single dose, subcutaneously; 20 nmol/kg subcutaneously on days 0 and 1; 200 nmol/kg subcutaneously on days 0 and 1; 20 nmol/kg subcutaneously on days 0 and 3; 200 nmol/kg subcutaneously on days 0 and 3. Mice were sacrificed 15 minutes after the final dose of Pro-CNP38 and plasma levels of cGMP analyzed. There does not appear to be a modulation of the plasma cGMP signal due to the different dose regimens. cGMP responses in the cartilage are also investigated.

Evaluation of Potential Desensitization of NPR-B Receptor

Histological analysis shows that CNP, when administered daily at 200 nmol/kg, accumulates in the growth plate of animals, based on increased CNP immunoreactivity. It is possible that this accumulation, or daily stimulation of the CNP receptor, in the growth plate could desensitize the CNP receptor.

To determine if multiple dosing desensitizes the NPR-B receptor in vitro, normal human articular chondrocytes were cultured with Pro-Gly-wtCNP37 ("Pro-CNP38") for varying times and cGMP secretion measured.

Primary normal human chondrocytes isolated from articular cartilage were cultured as recommended by the supplier (Lonza). At 60-80% confluence the chondrocytes were treated with 1 uM Pro-CNP38 twice, with increasing amounts of time between treatments (first treatment at time 0, then at 15 min, 30 min, 60 min, 2 hrs, 3 hrs, 4 hrs, 6 hrs after the initial treatment). In the following experiment the treatments were either applied twice, with increasing amounts of time between treatment (first treatment at time 0, then at 6, 16, 24, 48 hrs after initial treatment) or only once, in parallel to the second treatment (only at 6, 16, 24 and 48 hrs-naïve responses). Treatments were either applied for 15 min only (acute treatment), or for the duration of the experiment (chronic treatment when CNP was left in the medium). Cell lysates and conditioned medium were collected and analyzed for total cGMP secretion (Molecular Devices ELISA).

In a short term experiment, cells were stimulated with Gly-wtCNP37 ("CNP38") 1 uM two times for 15 minutes (acute treatment), or two times with CNP38 throughout culture (chronic treatment). The periods between treatments were 15 min, 30 min, 60 min, 2 hrs, 3 hrs, 4 hrs, and 6 hrs. Peak cGMP stimulation was obtained by treating cells once only, at the last time point of the experiment, (6 hours; >0.1 pmol/well in the acute experiment and 0.2 pmol/well in the chronic experiment). In the acute experiment, when the cells are treated twice, the response decreases to 0.1 pmol/well if the cells are treated at time 0 and then again at 15 minutes. In the acute experiment, when the cells are treated twice, the response decreases to approximately 0.5 pmol/well if the cells are treated at time 0 and again at 30 min, 60 min, 2, 3, and 4 hours. In the chronic experiment, when the cells are treated twice, the response decreases to approximately 0.16 pmol/well if the cells are treated at time 0 and at 15 minutes. In the chronic experiment, when the cells are treated twice, the response decreases to approximately 0.6 pmol/well if the cells are treated at time 0 and again at 30 min, 60 min, or 2 hours. In the chronic experiment, when the cells are treated twice, the response decreases to <0.5 pmol/well if the cells are treated at time 0 and again at 2, 4 or 6 hours.

Figure 74:
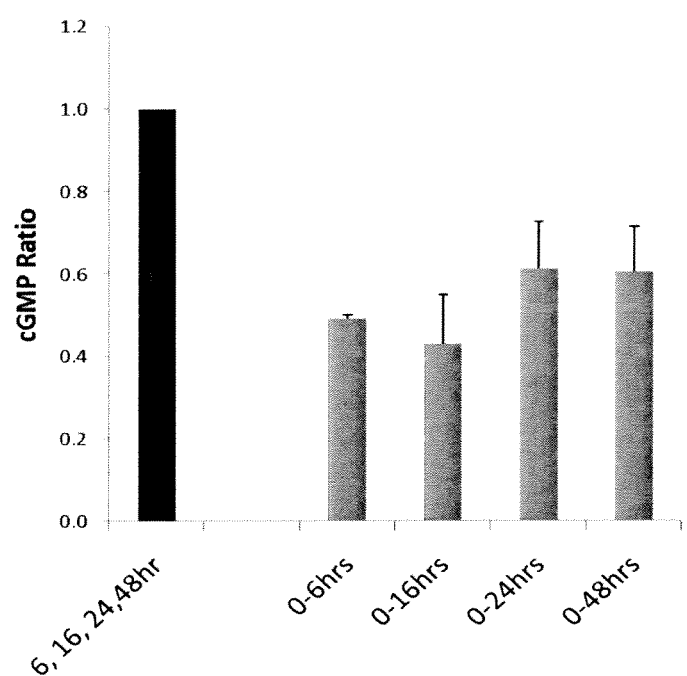
FIGS. 74A and B depict desensitization of the cGMP response after acute (A) or chronic (B) treatment with 1 uM Gly-CNP37.
Figure 74:
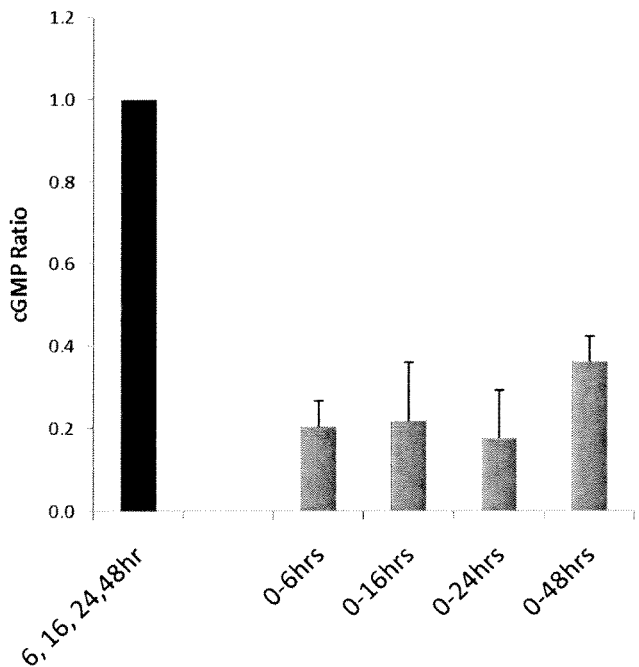

Long term studies were also carried out. For acute treatment, 1 uM CNP38 was added to cell culture as described above. For chronic treatment, 1 uM CNP38 was added to cell culture throughout the experiment duration as described above. Results indicate that the NPR-B receptor can desensitize after repeated, daily CNP administration in vitro, and 48 hours between doses is sufficient to recover to 60% of the maximial NPR-B response to CNP38, if the CNP is removed after the first dose, and to <40% if the CNP is incubated throughout the experiment (FIG. 74).

To evaluate whether treatment with a CNP variant desensitizes the NPR-B receptor in vivo, experiments were conducted with wild-type mice. CD-1 male mice 8-10 weeks of age were injected subcutaneously with vehicle control or Pro-Gly-wtCNP37 ("Pro-CNP38") at 200 nmol/kg on the appropriate days. The mice were either injected with Pro-CNP38 daily for up to 8 days, or were injected with Pro-CNP38 on the first day, the first and second days, or the first and third days of the study. Fifteen minutes following the final injection, the mice (n=3 per treatment group) were deeply anesthetized and ex-sanguinated via thoracotomy and aortic cannulation. Circulating blood was flushed from the body with PBS via an aortic cannula. The kidneys and right tibias, right femurs and left femurs were collected, boiled in water for 5 minutes and/or snap frozen in liquid nitrogen and stored on dry ice or in a −70° C. freezer until cGMP assay. For estimation of cGMP production in cartilage, distal femurs and/or proximal tibias were dissected, weighed and pulverized using Covaris Cryoprep CP02. Powdered samples were homogenized using a Covaris E210 sonicator in 5% perchloric acid, and neutralized in 60% KOH. Samples were then centrifuged at 10,000 rpm at 4° C. for 5 minutes, and the supernatant was used for the cGMP assay (Cyclic GMP Enzyme Immunoassay Kit, Cayman, Mich.). Additionally, left tibias were collected, fixed in 10% normal buffered formalin, and saved for further immunohistochemical analysis.

Figure 75:
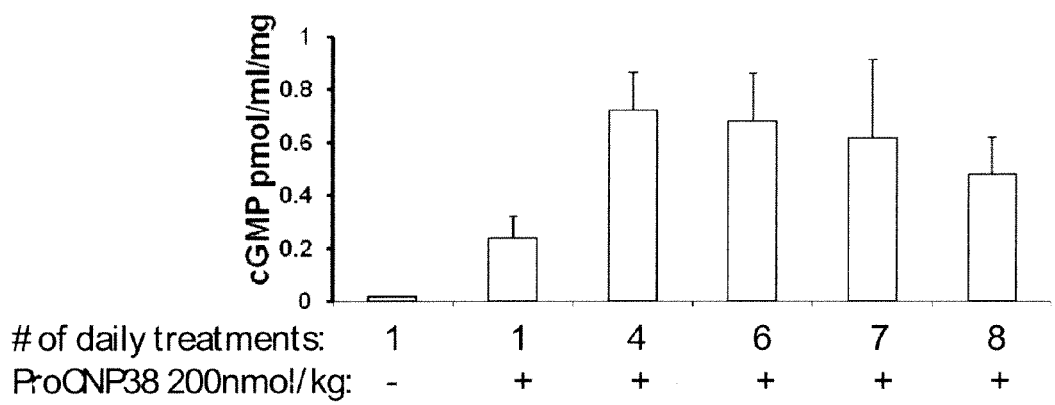
FIG. 75A demonstrates that daily treatment of wild-type mice with 200 nmol/kg of Pro-Gly-CNP37 ("Pro-CNP38") for 8 days did not desensitize the cGMP response.
FIG. 75B shows that treatment of the mice with 200 nmol/kg of Pro-Gly-CNP37 once a day for two consecutive days potentiated the cGMP response.
Figure 75:
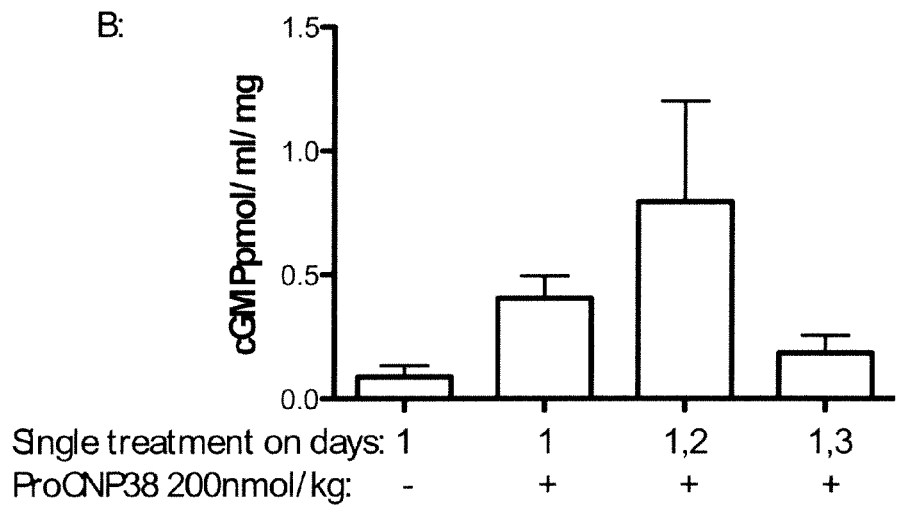
Figure 76:
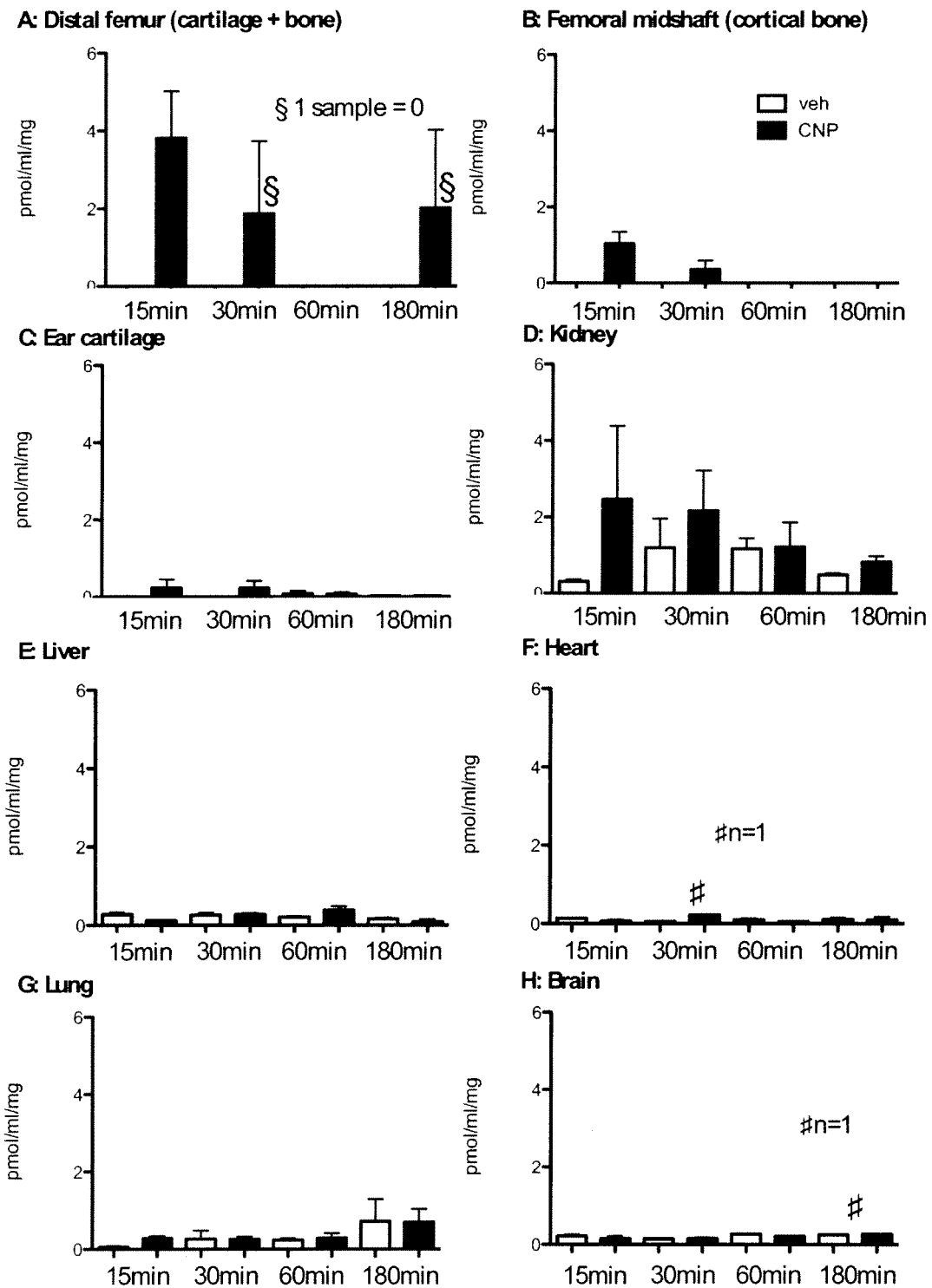
FIGS. 76A-D show that treatment of wild-type mice with 200 nmol/kg of Gly-CNP37 stimulated cGMP secretion in distal femurs (cartilage and bone) (A), femoral cortices (bone) (B), ear pinna (cartilage) (C), and kidney (D). FIGS.
Figure 77:
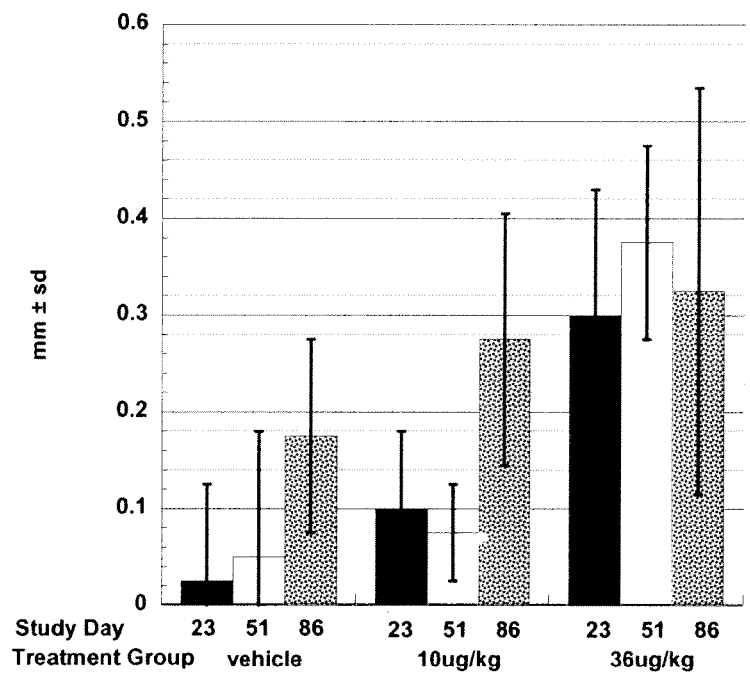
Figure 79:
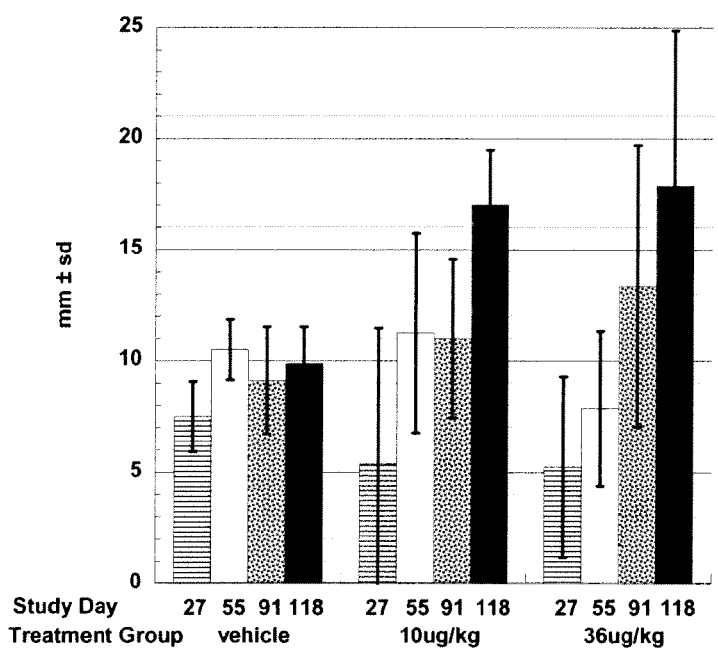
Figure 78:
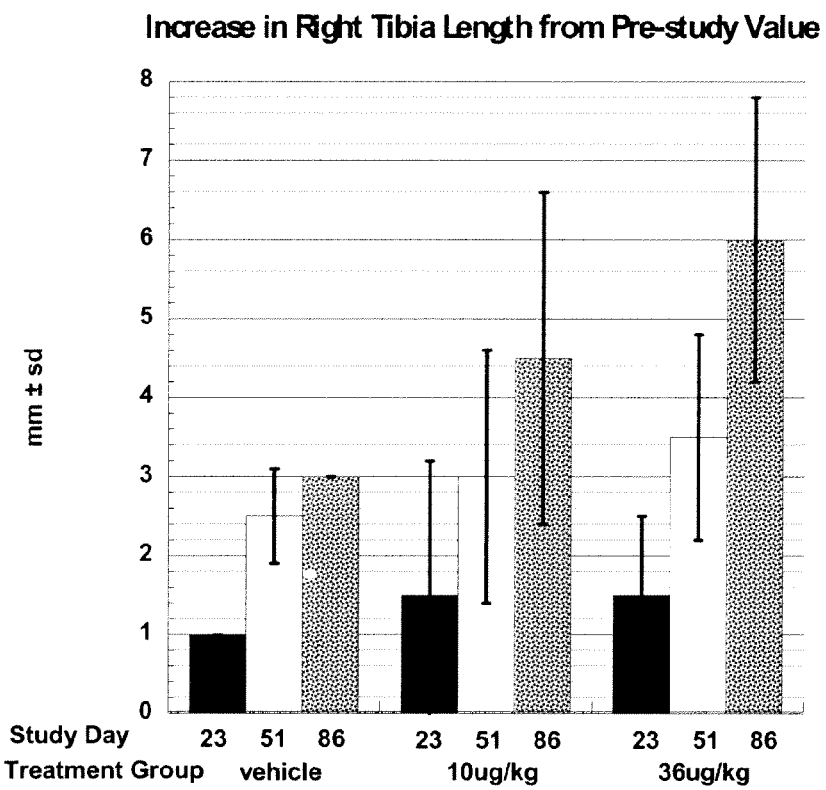
Figure 78:
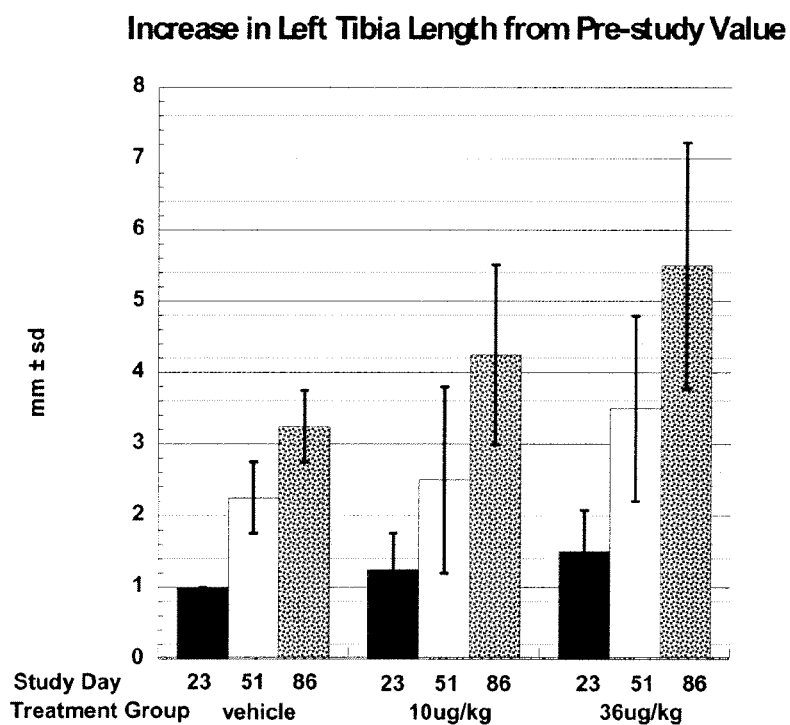
Figure 80:
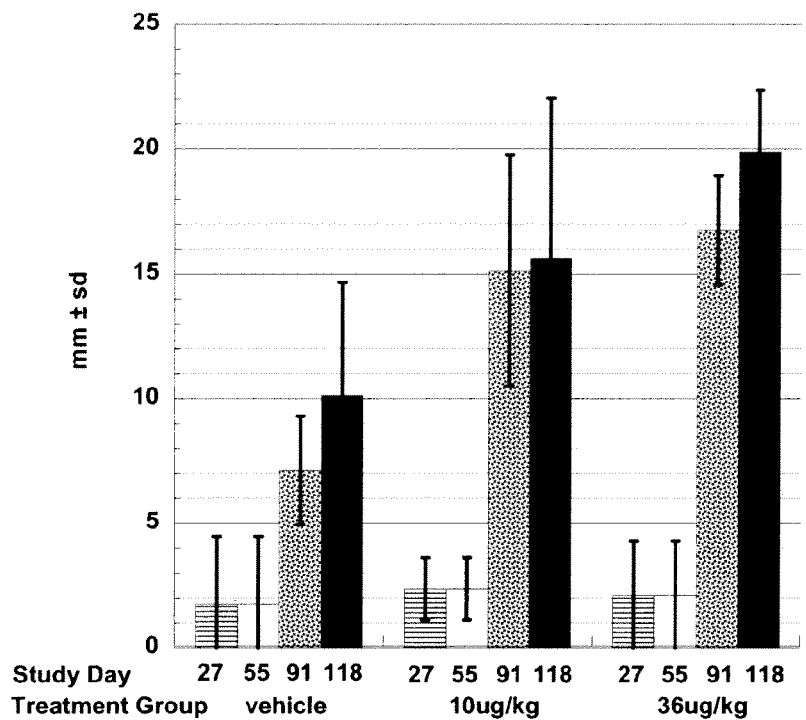
Figure 81:
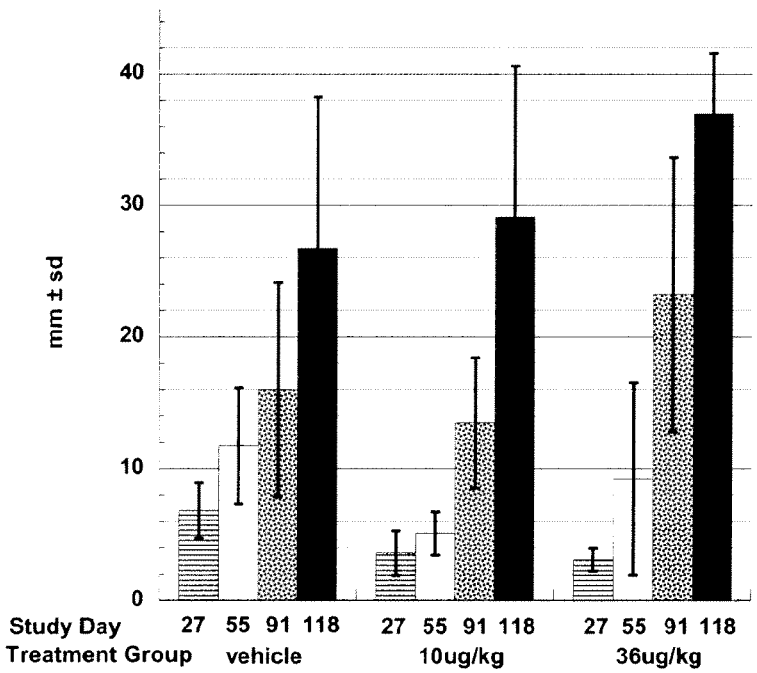

FIG. 75A shows that repeated daily treatment of wild-type mice with 200 nmol/kg of Pro-CNP38 for 1, 4, 6, 7 and 8 days did not result in desensitization of the cGMP response. To the contrary, potentiation of the cGMP response was observed after 4 days of daily treatment. Further daily treatment resulted in a plateau of the cGMP reponse, up to 8 days. The results indicate that daily treatment of wild-type mice with 200 nmol/kg of Pro-CNP38 for up to 8 days do not desensitize the cGMP response.

The kinetics of the cGMP response in distal femoral cartilage after treatment of the wild-type mice with Pro-CNP38 was also investigated. Treatment of the mice once a day for two days potentiated the cGMP response to Pro-CNP38, compared with the cGMP response to a single treatment (FIG. 75B). When the mice were treated on the first and third days, but not on the first and second days, the cGMP response after the second treatment (on the third day) was substantially similar to the cGMP response observed after a single treatment on day one (FIG. 75B). The results suggest that dosing on consecutive days is beneficial for potentiating the cGMP response to Pro-CNP38 in this mouse study.

Activation of NPR-B in Different Tissues

To evaluate potential activation of NPR-B in different tissues by a CNP variant, wild-type male CD-1 mice were injected with 200 nmol/kg of Gly-CNP37, and the cGMP response was measured in certain tissues at different time points. Two mice were used for each treatment group. Each mouse received one subcutaneous injection of Gly-CNP37 or vehicle control. Fifteen, 30 or 60 minutes or 3 hours following the injection, the mice were deeply anesthetized and ex-sanguinated via thoracotomy and aortic cannulation. Circulating blood was removed by a PBS flush with an aortic cannula. Heart, liver, lung, kidney, ear pinna, aorta and brain were collected. All tissues were boiled in water for 5 minutes, finely dissected (including flushing of marrow from femoral cortices with PBS), weighed, cooled in liquid nitrogen, and pulverized in a BioPulverizer. The resulting powdered samples were homogenized with a Polytron in 6% pre-chilled perchloric acid and neutralized with 60% KOH. Samples were then centrifuged at 10,000 rpm and 4° C. for 5 minutes, and the supernatant was used for the assay of cGMP (Cyclic GMP Enzyme Immunoassay Kit, Cayman Chemical Company, Ann Arbor, Mich.). The results were normalized for tissue weight.

Secretion of cGMP in response to treatment with Gly-CNP37 ("CNP" in FIG. 76) was detectable in distal femurs (cartilage and bone), femoral cortices (bone), ear pinna (cartilage), and kidney (FIGS. 76A-D). Maximal cGMP responses in those tissues were observed 15 min after treatment. Liver, heart, lung and brain tissues did not exhibit appreciable cGMP secretion in response to Gly-CNP37 relative to vehicle control at the studied time points (FIGS. 76E-H). The results indicate that treatment with 200 nmol/kg of Gly-CNP37 stimulated cGMP secretion in cartilage, bone and renal tissues.

Example 16

Dose Responses of CNP Variants in Monkeys

The effects of the CNP variant Pro-Gly-CNP37 on bone growth and the levels of bone growth-related biomarkers are evaluated in cynomolgus monkeys. Eight normal juvenile cynomolgus monkeys (about 2.5 years of age at the start of the on-going study) are subcutaneously injected daily with 10 or 36 μg/kg/day of Pro-Gly-CNP37 (n=4 per dose group). Four such monkeys are administered vehicle as control. The total length of treatment is 6 months. Various measures of growth plate expansion and bone growth are made by digital X-ray and magnetic resonance imaging, and by measurement of limb and body lengths externally. Blood and urine samples are collected periodically for clinical pathology and measurement of levels of Pro-Gly-CNP37 and biomarkers. Following termination of the study, gross pathology is performed and tissue samples are evaluated histologically for assessment of efficacy and safety.

Data obtained thus far in the on-going study show that both doses of Pro-Gly-CNP37 have increased growth plate width by digital X-ray (FIG. 77), increased right and left tibia lengths by digital X-ray (FIGS. 78A and B), increased leg length by external measurement (FIG. 79), increased arm length by external measurement (FIG. 80), increased body length by external measurement (FIG. 81), and increased the serum level of alkaline phosphatase, a biomarker for bone formation (FIG. 82). The data demonstrate that Pro-Gly-CNP37 can stimulate bone growth in normal juvenile cynomolgus monkeys at hemodynamically acceptable doses.

Example 17

Effects of CNP Variants on Cardiovascular System in Mice

Natriuretic peptides such as CNP have been reported to affect the cardiovascular system. Wang et al. (Eur J Heart Fail. 9:548-57. 2007) describe that CNP has been shown to have a cardioprotective effect in preventing myocardial ischaemia/reperfusion injury and improving cardiac remodelling after myocardial infarction in rats. Wang demonstrated that mice overexpressing CNP have reduced incidence of cardiac hypertrophy caused by myocardial infarction. Additionally, CNP has been shown to cause endothelium-independent vasodilation (M. Honing et al., Hypertension, 37:1179-1183 (2001)) and therefore may transiently decrease blood pressure in vivo.

To assess the effects of CNP variants on the cardiovascular system, the blood pressure and heart rate in anesthetized wild-type FVB mice is studied following subcutaneous injection of the variants.

After a pilot study to define a broad dose range of cardiovascular activity, a dose-response study is conducted to examine the effects of three different dose levels of each CNP variant. Three male FVB mice aged 8 weeks comprise each treatment group. Doses are administered subcutaneously to anesthetized mice, and systolic, diastolic and mean arterial pressure (MAP), as well as heart rate, are monitored via implanted intraarterial pressure transducers.

Example 18

Formulation of CNP Variants

CNP preformulation studies were carried out to assess the stability of CNP variant Gly-wtCNP37 ("CNP38") at different pH's (pH 3, 4, 5, 6, 7 and 8) and temperatures (5° C., 25° C., and 40° C.) over time. CNP38 exhibited greater stability at pH 4-6 than at the other pH's in the studies. CNP38 was stable at 5° C. at pH 4-6, with ≥about 95% of CNP38 remaining after 15 weeks. When the temperature was raised to 25° C., at pH 4 about 85% of CNP38 remained after 15 weeks, at pH 5 about 85% remained after 15 weeks, and at pH 6 about 80% remained after 15 weeks. When the temperature was raised to 40° C., at pH 4 about 55-60% of CNP38 remained after 15 weeks, at pH 5 about 65% remained after 15 weeks, and at pH 6 about 40% remained after 15 weeks. FIG. 83 illustrates the observed plot of pseudo-first order degradation rate constant ($K_{obs}$) vs. pH from pH 3 to 8 and at 5° C., 25° C. and 40° C. The stability data for CNP38 in the preformulation studies suggests CNP formulations having a pH in the range from about 4 to about 6. An acidic pH (e.g., pH≤about 6) can promote the stability of a CNP variant by, e.g., minimizing or avoiding deamidation of asparagine and/or glutamine residue(s), isomerization of aspartic acid residue(s), or degradation of the CNP variant by other pathways.

CNP variants can be formulated in pharmaceutical carriers for administration to subjects affected by, e.g., bone growth conditions. In some embodiments, liquid formulations of CNP variants are formulated according to any combinations of the ingredients and their amounts or concentrations in Table 16.

TABLE 16

| Ingredient Class | Ingredient | Concentration Range |
|---|---|---|
| Active ingredient | CNP variant | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent | NaCl | 140 mM ± 20 mM |
| Isotonicity-adjusting agent | Sucrose | 10% ± 5% |
| Preservative | m-Cresol | 0.4% ± 0.1% or 0.2% |
| Preservative/anti-adsorbent | Benzyl alcohol | 1.5% ± 0.5% |
| Stabilizer | Glycerin (glycerol) | 5%-100% (neat)[1] |
| Stabilizer | Methionine | 0.01%-0.2% |
| Stabilizer | Ascorbic acid/ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

[1]Glycerin is used to minimize or prevent water-driven hydrolysis, deamidation, isomerization or cleavage of CNP variants. For lyophilized formulations, 4-6% or 6-20% mannitol or sucrose can be substituted for NaCl.

In certain embodiments, lyophilized formulations of CNP variants are prepared from formulations formulated according to any combinations of the ingredients and their amounts or concentrations in Table 17.

TABLE 17

| Ingredient Class | Ingredient | Concentration Range |
|---|---|---|
| Active ingredient | CNP variant | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent/bulking agent | Sorbitol | 5% ± 3% |
| Isotonicity-adjusting agent/bulking agent | Mannitol | 5% ± 3% |
| Isotonicity-adjusting agent/bulking agent | Sucrose | 10% ± 5% |
| Preservative | m-Cresol | 0.4% ± 0.2% |
| Preservative/anti-adsorbent | Benzyl alcohol | 1.5% ± 0.5% |
| Stabilizer | Glycerin (glycerol) | 5%-100% (neat)[1] |
| Stabilizer | Methionine | 0.01%-0.2% |
| Stabilizer | Ascorbic acid/ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

[1]Glycerin is used to minimize or prevent water-driven hydrolysis, deamidation, isomerization or cleavage of CNP variants.

In certain embodiments, a formulation comprising a CNP variant has a pH of about 3-7, or about 3-6, or about 3.5-6.5, or about 4-6, or about 4-5, or about 4.5-5.5. In some embodiments, for pH 4-5.5 a suitable buffering agent is acetic acid/acetate (e.g., sodium acetate), and for pH 5.5-6 a suitable buffering agent is citric acid/citrate. Citric acid/citrate (e.g., sodium citrate) is also a suitable buffering agent in the range of pH 3-6 or pH 4-6. In certain embodiments, the buffering agent has a concentration in the formulation of about 2-50 mM, or about 2-40 mM, or about 2-30 mM, or about 5-30 mM, or about 2-20 mM, or about 5-20 mM, or about 5-15 mM.

To minimize or avoid deamidation of a CNP variant, the variant can be formulated in pharmaceutically acceptable organic cosolvents, such as glycerin, ethanol, and propylene glycol. Because deamidation occurs by hydrolysis, substitution of an organic cosolvent for water minimizes contact of the CNP variant with water. The concentration of one or more organic solvents in an organic-aqueous solvent system can be, e.g., from about 10% to about 99%, or about 100% if water is not used.

Also to minimize or avoid deamidation of a CNP variant, water can be removed from the formulation by lyophilization. In some embodiments, lyophilized formulations contain any combinations of the following components:
  buffer: sodium acetate and acetic acid, or sodium citrate and citric acid;
  isotonicity/bulking agent: mannitol (e.g., 3-10%, 2-8% or 4-6%);
    sucrose (e.g., 6-20%, 5-15% or 8-12%);
  antioxidants: methionine and/or ascorbic acid with molal ratio of each antioxidant to CNP variant from about 0.1:1 to about 1:1, or from about 0.5:1 to about 5:1, or from about 1:1 to about 15:1, or from about 1:1 to about 10:1, or from about 3:1 to about 10:1.

Deamidation can also be minimized or avoided by storing a CNP composition (e.g., a liquid formulation or a lyophilized formulation) at lower temperature, such as at about 5° C., 0° C., −10° C., −20° C., −30° C., −40° C., −50° C., −60° C., −70° C., −80° C., −90° C., or −100° C.

To minimize or avoid oxidation of oxidizable residues (e.g., methionine) in a CNP variant, the variant can be formulated with one or more antioxidants. Exemplary antioxidants include, but are not limited to, methionine, ascorbic acid, and thioglycerol. Oxidation of, e.g., methionine residues can also be minimized or prevented by purging oxygen from a liquid medium (if a liquid formulation) with nitrogen or argon, and/or by purging oxygen from a container or packaging with nitrogen or argon.

In some embodiments, to minimize or prevent adsorption (e.g., adsorption of a CNP variant to plastic or glass), Polysorbate 20, Polysorbate 80 or benzyl alcohol, or a combination thereof, is added to a CNP formulation. In certain embodiments, each of the anti-adsorbent(s) is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%. Exemplary range(s) of anti-adsorbent(s) in the formulation include without limitation from about 0.001% to about 0.5% of Polysorbate 20, from about 0.001% to about 0.5% of Polysorbate 80, and/or from about 0.5% to about 1.5% of benzyl alcohol.

In certain embodiments, a liquid CNP formulation comprises, or a lyophilized CNP formulation is prepared from a formulation that comprises, (1) an acetic acid/acetate (e.g., sodium acetate) buffer having a concentration of about 30 mM±5 or 10 mM buffering agent and a pH of about 4±0.5 or 1, and (2) benzyl alcohol (e.g., as a preservative and/or anti-adsorbent) at a concentration of about 1%±0.5%, and optionally (3) sucrose at a concentration of about 10%±5%.

Example 19

Clinical Evaluation of CNP Variants

The following example provides guidance on the parameters to be used for the clinical evaluation of compositions comprising CNP22 or variants thereof in the therapeutic methods of the present disclosure. As discussed herein, CNP22 or variants thereof will be used in the treatment of disorders responsive to CNP, including disorders of the bone and vascular smooth muscle. Clinical trials will be conducted which will provide an assessment of doses of CNP22 or variants thereof for safety, pharmacokinetics, and initial response of both surrogate and defined clinical endpoints. The trial will be conducted for a minimum, but not necessarily limited to, 24 weeks to collect sufficient safety information on about 100 evaluable patients. The initial dose for the trials will vary from about 0.001 to about 1.0 mg/kg/week, or any of the doses described herein. In the event that the initial dose in this range does not produce a significant direct clinical benefit, the dose should be increased within this range or beyond this range as necessary, and maintained for an additional minimal period of, but not necessarily limited to, 24 weeks to establish safety and to evaluate efficacy further.

Measurements of safety will include adverse events, allergic reactions, complete clinical chemistry panel (including kidney and liver functions), urinalysis, and CBC with differential. In addition, other parameters relevant to clinical benefit will be monitored. The present example also includes the determination of pharmacokinetic parameters of CNP22 or variants thereof, including absorption, distribution, metabolism, excretion, and half-life and bioavailability in the blood. It is anticipated that such analyses will help relate dose to clinical response.

Methods

Patients will undergo a baseline medical history and physical exam, and a standard set of clinical laboratory tests (including CBC, Panel 20, CH50, and UA). The patients will be followed closely with weekly visits to the clinic. The patients will return to the clinic for a complete evaluation one week after completing the treatment period. Should dose escalation be required, the patients will follow the same schedule outlined above. Safety will be monitored throughout the trial.

Diagnosis and Inclusion Criteria

The patients may be male or female, with a documented diagnosis of a potentially CNP-responsive disorder. A specific example of a potentially CNP-responsive, bone-related disorder is achondroplasia, which may be confirmed by genetic testing and other evidence of an FGFR-3 mutation or dysfunction. The ideal age range of achondroplasia patients will be from infant (<1 year of age) to pre-adolescent (<13 years of age). A patient will be excluded from this study if the patient is pregnant or lactating; has received an investigational drug within 30 days prior to study enrollment; or has a medical condition, serious intercurrent illness, or other extenuating circumstance that may significantly decrease study compliance.

Safety

Therapy with CNP22 or variants thereof will be determined to be safe if no significant acute or chronic drug reactions occur during the course of the study. The longer-term administration of the drug will be determined to be safe if no significant abnormalities are observed in the clinical examinations, clinical labs, or other appropriate studies.

It has been shown that compared to wild-type CNP22, certain CNP variants of the disclosure are much more resistant to NEP degradation in vitro, have a much longer plasma half-life and bioavailability in rats, stimulate a much higher level of cGMP production in rats, and/or induce a significantly greater increase in long bone length and body length in achondroplastic mice. Furthermore, it has been shown that short duration dose regimen treatments with CNP22 are nearly as effective as continuous CNP22 treatment in reversing FGF2-induced arrest of chondrocyte growth in vitro. These results, among others described herein, demonstrate the utility of CNP variants of the disclosure in treating CNP-responsive conditions or disorders such as, e.g., bone-related disorders and vascular smooth muscle disorders.

It is understood that every embodiment of the disclosure described herein may optionally be combined with any one or more of the other embodiments described herein. Every patent literature and every non-patent literature cited herein are incorporated herein by reference in their entirety.

Numerous modifications and variations to the disclosure, as set forth in the embodiments and illustrative examples described herein, are expected to occur to those skilled in the art. Consequently only such limitations as appear in the appended claims should be placed on the disclosure.

What is claimed is:

1. A variant of C-type natriuretic peptide (CNP) selected from the group consisting of:

(SEQ ID NO: 179)
GDLRVDTKSRAAWARLLQEHPNARKYKGANKKGLSKGCFGLKLDRIGSMS
GLGC (Gly-CNP53);

(SEQ ID NO: 185)
PDLRVDTKSRAAWARLLQEHPNARKYKGANKKGLSKGCFGLKLDRIGSMS
GLGC (Pro-CNP53);

(SEQ ID NO: 190)
MDLRVDTKSRAAWARLLQEHPNARKYKGANKKGLSKGCFGLKLDRIGSMS
GLGC (Met-CNP53)

(SEQ ID NO: 180)
DLRVDTKSRAAWARLLQEHPNARKYKGANKKGLSKGCFGLKLDRIGSNS
GLGC [CNP-53(M48N)].

2. A pharmaceutical composition comprising a CNP variant of claim 1, and a pharmaceutically acceptable excipient, carrier or diluent.

3. The composition of claim 2, which is a lyophilized formulation prepared from a formulation that comprises a citric acid/citrate buffer or an acetic acid/acetate buffer having a pH from about 4 to about 6.

4. The composition of claim 3, wherein the lyophilized formulation is prepared from a formulation that further comprises (a) an isotonicity-adjusting agent or a bulking agent or (b) an antioxidant.

5. A method of treating a bone-related disorder or skeletal dysplasia, comprising administering a CNP variant to a subject in need thereof, wherein the CNP variant is a CNP variant according to claim 1, and wherein the bone-related disorder or skeletal dysplasia is selected from the group consisting of achondroplasia, hypochondroplasia, short stature, dwarfism and homozygous achondroplasia.

6. A method for recombinant production of a CNP variant, comprising culturing in a medium a host cell comprising a first polynucleotide encoding a CNP variant polypeptide linked to a second polynucleotide encoding a cleavable peptide or protein under conditions that result in expression of a fusion polypeptide encoded by the polynucleotides, wherein the fusion polypeptide comprises the CNP variant polypeptide directly linked to the cleavable peptide or protein or indirectly linked thereto via a linker, wherein the CNP variant is selected from the group consisting of:

(SEQ ID NO: 179)
GDLRVDTKSRAAWARLLQEHPNARKYKGANKKGLSKGCFGLKLDRIGSMS
GLGC (Gly-CNP53);

(SEQ ID NO: 185)
PDLRVDTKSRAAWARLLQEHPNARKYKGANKKGLSKGCFGLKLDRIGSMS
GLGC (Pro-CNP53);

(SEQ ID NO: 190)
MDLRVDTKSRAAWARLLQEHPNARKYKGANKKGLSKGCFGLKLDRIGSMS
GLGC (Met-CNP53);

(SEQ ID NO: 180)
DLRVDTKSRAAWARLLQEHPNARKYKGANKKGLSKGCFGLKLDRIGSNS
GLGC [CNP-53(M48N)].

7. The method of claim 6, wherein the cleavable peptide or protein is selected from the group consisting of histidine tags, human transcription factor TAF12, TAF12 fragments, TAF12 histone fold domain, mutants of TAF12 and fragments thereof, TAF12(C/A), TAF12(D/E), TAF12(4D/4E), TAF12 (6D/6E), TAF12(10D/10E), TAF12(C/A & D/E), TAF12 (C/A & 4D/4E), TAF12(C/A & 6D/6E), TAF12(C/A & 10D/10E), ketosteroid isomerase, maltose-binding protein, β-galactosidase, glutathione-S-transferase, thioredoxin, chitin-binding domain, BMP-2, BMP-2 mutants, BMP-2(C/A), and mutants and fragments thereof.

8. The method of claim 6, wherein the host cell is bacterial.

9. The method of claim 6, wherein the fusion polypeptide is expressed as a soluble protein or as an inclusion body.

10. The method of claim 6, further comprising isolating the expressed fusion polypeptide from the host cell or culture medium.

11. The method of claim 10, further comprising contacting the isolated fusion polypeptide with a cleaving agent selected from the group consisting of formic acid, cyanogen bromide (CNBr), hydroxylamine, protein self cleavage, Factor Xa, enterokinase, ProTEV, and SUMO protease.

12. A CNP variant produced according to the method of claim 6, wherein the CNP variant is selected from the group consisting of:

```
                                          (SEQ ID NO: 179)
GDLRVDTKSRAAWARLLQEHPNARKYKGANKKGLSKGCFGLKLDRIGSMS
GLGC (Gly-CNP53));

(SEQ ID NO: 185)
PDLRVDTKSRAAWARLLQEHPNARKYKGANKKGLSKGCFGLKLDRIGSMS
GLGC (Pro-CNP53));

(SEQ ID NO: 190)
MDLRVDTKSRAAWARLLQEHPNARKYKGANKKGLSKGCFGLKLDRIGSMS
GLGC (Met-CNP53));

(SEQ ID NO: 180)
DLRVDTKSRAAWARLLQEHPNARKYKGANKKGLSKGCFGLKLDRIGSNSG
LGC [CNP-53(M48N)]).
```

13. A method of increasing long bone growth, comprising administering a CNP variant according to claim 1 to a subject in need thereof, where the administration increases long bone growth.

14. A CNP variant according to claim 1 useful for increasing long bone growth or treating achondroplasia, hypochondroplasia, short stature, dwarfism, or homozygous achondroplasia in a subject in need thereof.

\* \* \* \* \*